US009283271B2

(12) United States Patent
Montrasio et al.

(10) Patent No.: US 9,283,271 B2
(45) Date of Patent: Mar. 15, 2016

(54) HUMAN ANTI-SOD1 ANTIBODIES

(75) Inventors: Fabio Montrasio, Schindellegi (CH); Maria Grazia Barenco Montrasio, Schindellegi (CH); Jan Grimm, Dubendorf (CH); Roger Nitsch, Zumikon (CH); Christoph Hock, Erlenbach (CH); Marcel Maier, Zurich (CH)

(73) Assignees: Neurimmune Holding AG (CH); University of Zurich (CH)

( * ) Notice: Subject to any disclaimer, the term of this patent is extended or adjusted under 35 U.S.C. 154(b) by 0 days.

(21) Appl. No.: 13/992,840

(22) PCT Filed: Dec. 19, 2011

(86) PCT No.: PCT/EP2011/073303
§ 371 (c)(1),
(2), (4) Date: Sep. 10, 2013

(87) PCT Pub. No.: WO2012/080518
PCT Pub. Date: Jun. 21, 2012

(65) Prior Publication Data
US 2014/0301945 A1 Oct. 9, 2014

Related U.S. Application Data

(60) Provisional application No. 61/424,451, filed on Dec. 17, 2010.

(30) Foreign Application Priority Data

Dec. 17, 2010 (EP) .................................... 10015767

(51) Int. Cl.
| | |
|---|---|
| *A61K 39/395* | (2006.01) |
| *A61K 39/00* | (2006.01) |
| *C07K 14/435* | (2006.01) |
| *C07K 16/40* | (2006.01) |
| *C12N 9/02* | (2006.01) |
| *A61K 45/06* | (2006.01) |
| *A61K 47/48* | (2006.01) |
| *A61K 49/08* | (2006.01) |
| *A61K 51/10* | (2006.01) |
| *G01N 33/573* | (2006.01) |

(52) U.S. Cl.
CPC ......... *A61K 39/3955* (2013.01); *A61K 39/0005* (2013.01); *A61K 45/06* (2013.01); *A61K 47/48646* (2013.01); *A61K 49/085* (2013.01); *A61K 51/10* (2013.01); *C07K 14/435* (2013.01); *C07K 16/40* (2013.01); *C12N 9/0089* (2013.01); *G01N 33/573* (2013.01); *A61K 2039/505* (2013.01); *C07K 2317/21* (2013.01); *C07K 2317/24* (2013.01); *C07K 2317/30* (2013.01); *C07K 2317/34* (2013.01); *C07K 2317/92* (2013.01); *G01N 2800/28* (2013.01)

(58) Field of Classification Search
None
See application file for complete search history.

(56) References Cited

U.S. PATENT DOCUMENTS

| 2005/0152894 A1* | 7/2005 | Krummen et al. | ......... 424/133.1 |
| 2008/0206251 A1* | 8/2008 | Cashman et al. | ......... 424/139.1 |
| 2010/0021470 A1 | 1/2010 | Lanzavecchia | |

FOREIGN PATENT DOCUMENTS

| JP | 2009-529498 | 8/2009 |
| JP | 2010-528601 | 8/2010 |
| JP | 2010-536907 | 12/2010 |
| WO | WO 2007/025385 | 3/2007 |

OTHER PUBLICATIONS

International Preliminary Report on Patentability for International (PCT) Patent Application No. PCT/EP2011/073303, issued Jun. 18, 2013, 10 pages.
Bond et al., "Contributions of CDR3 to $V_HH$ Domain Stability and the Design of Monobody Scaffolds for Naïve Antibody Libraries," Journal of Molecular Biology, 2003, vol. 332, Iss. 3, pp. 643-655.
Dorfman et al., "A Tyrosine-sulfated Peptide Derived from the Heavy-chain CDR3 Region of an HIV-1-neutralizing Antibody Binds gp120 and Inhibits HIV-1 Infection," The Journal of Biological Chemistry, 2006, vol. 281, No. 39, pp. 28529-28535.
Hosse et al., "A new generation of protein display scaffolds for molecular recognition," Protein Science, 2006, vol. 15, Iss. 1, pp. 14-27.
Igarashi et al., "Specific Binding of a Synthetic Peptide Derived from an Antibody Complementarity Determining Region to Phosphatidylserine," The Journal of Biochemistry, 1995, vol. 117, Iss. 2, pp. 452-457.
Levi et al., "A complementarity-determining region synthetic peptide acts as a miniantibody and neutralizes human immunodeficiency virus type 1 in vitro," Proceedings of the National Academy of Sciences of the United States of America, 1993, vol. 90, No. 10, pp. 4374-7378.

(Continued)

*Primary Examiner* — Christina Borgeest
(74) *Attorney, Agent, or Firm* — Sheridan Ross P.C.

(57) ABSTRACT

Provided are novel human copper-zinc superoxide dismutase, also known as superoxide dismutase 1 or SOD1, specific antibodies as well as fragments, derivatives and variants thereof as well as methods related thereto. Assays, kits, and solid supports related to antibodies specific for SOD1 are also disclosed. The antibody, immunoglobulin chain(s), as well as binding fragments, derivatives and variants thereof can be used in pharmaceutical and diagnostic compositions for SOD1 targeted immunotherapy and diagnosis, respectively.

21 Claims, 15 Drawing Sheets

(56) References Cited

OTHER PUBLICATIONS

Nicaise et al., "Affinity transfer by CDR grafting on a nonimmunoglobulin scaffold," Protein Science, 2004, vol. 13, Iss. 7, pp. 1882-1891.

International Search Report prepared by the European Patent Office on Feb. 23, 2012 for International Application No. PCT/EP2011/073303.

Fujiwara et al.: "Different immunoreactivity against monoclonal antibodies between wild-type and mutant copper/zinc superoxide dismutase linked to amyotrophic lateral sclerosis", Journal of Biological Chemistry; vol. 280, No. 6, Feb. 11, 2005, pp. 5061-5070.

Ni: "New technologies for the generation of human monoclonal antibodies", Trends in Bio/Pharmaceutical Industry, 2009, pp. 3-12.

Steinitz: "Three decades of human monoclonal antibodies: past, present and future developments", Human Antibodies 2009, vol. 18, No. 1-2, 2009, pp. 1-10.

Bosco et al.: "Wild-type and mutant SOD1 share an aberrant conformation and a common pathogenic pathway in ALS", Nature Neuroscience, Nov. 2010, vol. 13, No. 11, pp. 1396-1403.

Gros-Louis et al.: "Intracerebroventricular infusion of monoclonal antibody or its derived Fab fragment against misfolded forms of SOD1 mutant delays mortality in a mouse model of ALS." Journal of Neurochemistry, Jun. 2010, vol. 113, No. 5, pp. 1188-1199.

Forsberg et al."Novel antibodies reveal inclusions containing non-native SOD1 in sporadic ALS patients." PLOS One 2010 Public Library of Science, vol. 5, No. 7, Jul. 14, 2010.

Rakhit et al.: "An immunological epitope selective for pathological monomer-misfolded SOD1 in ALS." Nature Medicine, vol. 13, No. 6, Jun. 1, 2007, pp. 754-759.

Jonsson et al.: "Minute Quantities of Misfolded Mutant Superoxide Dismutase-1 Cause Amyotrophic Lateral Sclerosis." Brain, vol. 127, No. 1, Jan. 1, 2004, pp. 73-88.

Sekine, Susumu "Current Status and Issues of antibody drugs," Science&Technology Trends, Oct. 2009, No. 103, 30 pages (Machine Translation) [http://wvvw.nistep.go.jp/achiev/ftx/jpn/stfc/stt103j/0910_03_featurearticles/0910fa01/].

* cited by examiner

A          NI-204.10D12-VH  (variable heavy chain sequence VH)
```
FR1-------------------------CDR1-FR2----------CDR2-------------
EVQLVESGGDLVRPGGSLRLSCVASGFTFSNYWMHWVRQAPGQRPVWVSRTNTDGRNTAYADYAKG FR3----------------------------CDR3-------------JH---------
RFTISRDNAKSTLYLQLNSLRAEDTAVYFCARLRRNVADQITHNYYMDVWGKGTLVTVSS
```

NI-204.10D12-VK  (variable light chain sequence VK)
```
FR1-------------------CDR1----------FR2------------CDR2---FR3---
EIVLTQSPGSLAVSLGERATINCKSSQTVLYNNKNYLAWYQQKPGQPPKLLISWASSRESGVPDRF -------------------------CDR3-----JK--------
SGSGSGTDFTLTISSLQAEDVAVYYCQHYYGTPVTFGGGTKVEIK
```

B          NI-204.12G7-VH (variable heavy chain sequence VH)
```
FR1---------------------------CDR1-FR2----------CDR2-------------
QVQLVQSGAEVKKPGASVTLSCKASGYTFTAYYIHWVRQAREQGLEWMGVINPSTGTTFYAQNFPD
E    E
FR2-----------------------------CDR3----------JH---------
RVSVTRDTSTSTVFMELHNLKSEDTAVYYCARAISEHGSGSYSPYYWGQGTLVTVSS
```

NI-204.12G7-VL (variable light chain sequence VL)
```
FR1-------------------CDR1-------FR2------------CDR2---FR3-----
SYELTQPPSVSVSLGQMAAITCSGEALPKKYGYWYQQKPGQVPVLLIYRDVERPSGVPDRFSGSS
   V
----------------------CDR3------JK--------
SGTMVTLTISGVQAEDEADYYCLSADSSGTWVFGGGTKLTVL
```

C          NI-204.10A8-VH (variable heavy chain sequence VH)
```
FR1---------------------------CDR1-FR2----------CDR2-------------
QVQLVQSGAEVKEPGSSVRVSCKTSGGSFNRHVITWVRQAPGQGLEWMGEIIPFFGTPKYAPKFQG
E    E
-------------------------------CDR3--------JH---------
RVTIIADASTSTFFLDVKSLTSEDTALYFCWIVVVSVVQRREDFWGQGILVTVSS
```

NI-204.10A8-VK (variable light chain sequence VK)
```
FR1--------------------CDR1-------FR2------------CDR2---FR3-------
DIQMTQSPSSLSASVGDTVTITCRSSQNISNYLSWFQHKPGKAPRILVYAASTLQTGVPSRFSGRG
E VL
----------------------CDR3-----JK--------
SGTIFTLSITSLQSEDYATYYCQQNDKIPRTFGQGTKVEIK
```

Fig. 1

D  NI-204.9F6-VH (variable heavy chain sequence VH)
```
FR1---------------------------CDR1-FR2----------CDR2-------------
EVQLLESGGGLVQPGGSLRLSCAVSGFTFDTFAMSWVRQAPGKGLEWVSAITASSSKTYYADSVKG
    V
FR3-------------------------------CDR3------------JH---------
RFTISRDNSRNTVYLRLSSLRADDTAVYFCARPKGAHSGLYIESAFDLWGPGTMVTVSS
```

NI-204.9F6-VL (variable light chain sequence VL)
```
FR1-------------------CDR1-------FR2----------CDR2---FR3--------
SYELTQPPSVSVSAGQTASITCSADMLGDTYVSWYQKRPGQSPVLLIYQDSKRPSEIPERFSGSSS
    V
--------------------CDR3-------JK--------
EDTATLTITGTQALDEAAYYCQVWDRRTTTYVFGPGTEVTVL
```

E  NI-204.11F11-VH (variable heavy chain sequence VH)
```
FR1---------------------------CDR1-FR2----------CDR2-------------
EVQLVESGGGLVKPGGSLRLSCAASGLPFSKAWMSWVRQAPGKGLEWVGRIKSQADGGAIDYATSVNG FR3-------------------------------CDR3------------JH---------
RFTITRDDSKNTLYLQMTSLKTEDTAVYYCTPGIILRFLEGTLRGMDVWGQGTTVTVSS
```

NI-204.11F11-VL (variable light chain sequence VL)
```
FR1-------------------CDR1-------FR2------------CDR2---
EIVLTQSPPTLSLSPGERATLSCRASQTVSKYLAWYQQKPGQAPRLLVYDTSNRAI FR3-----------------------------CDR3-----JK--------
GIPPRFSGSGSGTDFTLTISTLEPEDFALYYCQQRSNWPPTFGQGTRLEIK
```

F  NI-204.67E12-VH (variable heavy chain sequence VH)
```
FR1---------------------------CDR1-FR2----------CDR2-------------
EVQLLESGGGLIRPGGSLRLSCAASGFTFSNYAMGWVRQAPGKGLEWVSAISGNGGSTYYGGSVKG FR3-------------------------------CDR3----------JH---------
RFTISRDKSKNTLYLQMNNLRADDTAVYFCAKLEAVAPTLTLRYFKHWGKGTLVTVSS
```

NI-204.67E12-VL (variable light chain sequence VL)
```
FR1-------------------CDR1-------FR2------------CDR2---
DIQMTQSPSTLSASVGDRVTITCRASQSISRWLAWYQQRPGRAPDLLIYDASNLES FR3-----------------------------CDR3-----JK--------
GVPSRFSGSGSGTEFTLTISSLQPGDFATYYCQQYYSYVYTFGQGTKLEIK
```

Fig. 1 (continued)

G      NI-204.6H1-VH (variable heavy chain sequence VH)
```
FR1-------------------------CDR1-FR2----------CDR2-------------
QVQLQQWGAGRLRPSETLSLTCAVYGGSFNGYARTWIRQPPGKGLEWIGEIDHRENTNYNPSLKS FR3-----------------------------CDR3----------JH---------
RVTMSVDTSKNQFSLRLNSVTAADTAVYFCARGQKNAKDQHEGFRYWGRGTLVTVSS
```

NI-204.6H1-VL (variable light chain sequence VL)
```
FR1-------------------CDR1-------FR2-----------CDR2---
SYELTQPPSVSVSPGQTARITCSGDALPKQFAYWYQQKSGQAPKLVIFKDTERPS FR3-----------------------------CDR3-------JK--------
GIPERFSASSSGTKATLTISGVQAEDEADYYCQSADRTATSWVFGGGTKLTVL
```

H      NI-204.12G3-VH (variable heavy chain sequence VH)
```
FR1--------------------------CDR1-FR2----------CDR2-------------
QVQLVESGGGVVQPGRSLRLSCAASGYIFSSFGMHWVRQTPGKGLEWVALIWYDGSRQSYADSVRG FR3-----------------------------CDR3--------JH---------
RFTISRDNSKNTVFLQMNSLRGEDTAVYHCARTGYDDKRGGFDTWGQGTMVTVSS
```

NI-204.12G3-VL (variable light chain sequence VL)
```
FR1-------------------CDR1-------FR2------------CDR2---
SYELTQPPSVSVSPGQTARITCSGDALAKQYSYWYQHKPGQAPVMVMYKDRERPS FR3-----------------------------CDR3------JK--------
GIPERFSGSSSGTTVTLTISAVQAEDEADYYCQSTGTDSPYIFGTGTKVTVL
```

I      NI-204.7G5-VH (variable heavy chain sequence VH)
```
FR1----------------------------CDR1-FR2----------CDR2-------------
QVQLVESGGGVVQAGGSLRLSCVASGLTFSSYGMHWVRQAPGKGLEWVAVISYDGRSKFYADSVKG
                                                                 E
FR3-----------------------------CDR3-----------------JH---------
RFTISRDNSKNTLYLQMNSLRAEDAAVYYCANARVRDACSGTRCDKFGFYMDVWGKGTTVTVSS
```

NI-204.7G5-VL (variable light chain sequence VL)
```
FR1-----------------CDR1-------FR2------------CDR2---
SYELTQPPSVSVSPGQTARITCSGDALPKKYAYWYQQKSGQAPVLVIYEDIKRPS
  E                                                    
  V
FR3-----------------------------CDR3-------JK--------
GIPERFSGSSSGTMATLTISGAQVEDEGDYYCYSADRSGNRWAFGGGTKLTVL
```

Fig. 1 (continued)

J    NI-204.7B3-VH (variable heavy chain sequence VH)
```
FR1---------------------------CDR1-FR2-----------CDR2-------------
EVQLVESGGDIVQSGGSLRLSCAASGFVFSSNWMHWVRQRPGKGLEWISLINVDGRTTKYADSVKG
     Q
FR3-----------------------------CDR3-JH---------
RFTISRDNAKKTVYLQMDSLRAEDTAVYYCVKVEGLNWGPGTLVTVSS
```

NI-204.7B3-VL (variable light chain sequence VL)
```
FR1-------------------CDR1-------FR2------------CDR2---
SEYLTQPPSVSVSPGQTARITCSGDELSKQYAYWYQKKSGQAPVMVVNEDTKRPP
LPV FR3-------------------------------CDR3------JK--------
GIPERFSGSSSGTTSTLTISGVQAEDEADYYCQSADITGSWVFGGGTKLTVL
```

K    NI-204.34A3-VH (variable heavy chain sequence VH)
```
FR1---------------------------CDR1-FR2-----------CDR2-------------
EVQLVESGGGLVKPGGSLRVSCDVSGQRLSKAWMNWVRQTPTRGLEWVGLIKRDADGGTTEFAAPVEG FR3-------------------------------CDR3-------JH---------
RFTISRDDIQNTMTLHMTRLRVDDTGVYYCVAGDIGCIKENCRWGEGTTVTVSS
```

NI-204.34A3-VL (variable light chain sequence VL)
```
FR1-------------------CDR1-------FR2------------CDR2---
SYELTQPPSVSVSPGQTARITCSGDALPTKFAFWYQQKSGQAPVLVIYEDDKRPS FR3-------------------------------CDR3-------JK--------
GIPQRFSGSSSGTTATLTISGAQEEDDADYYCYSKDSTNVERVFGTGTKLSVL
```

L    NI-204.25H3-VH (variable heavy chain sequence VH)
```
FR1---------------------------CDR1-FR2-----------CDR2-------------
QVQLQESGPGLVKPSETLSLTCTVSGGSISSSYWSWIRQPPGQGLEWIGYIYYSGNTYYNPSLKS FR3--------------------------CDR3------JH---------
RVTISIDTSKTQFSLNLTSVSAADTAVYYCARDGIPGAIGMDVWGQGTTVTVSS
```

NI-204.25H3-VL (variable light chain sequence VL)
```
FR1-------------------CDR1---------FR2------------CDR2---
QSVLTQPPSVSAAPGQKVNISCSGSSSNIGNNYVSWYQRLPGTAPKLLIYDNNKRPS FR3-------------------------------CDR3-------JK--------
GIPDRFSGSKSGTSATLGITGLQTGDGADYYCATWDKSLIAVVFGGGTKLTVL
```

Fig. 1 (continued)

HUMAN ANTI-SOD1 ANTIBODIES

CROSS REFERENCE TO RELATED APPLICATIONS

This application is a national stage application under 35 U.S.C. 371 and claims the benefit of PCT Application No. PCT/EP2011/073303 having an international filing date of 19 Dec. 2011, which designated the United States, and which PCT application claimed the benefit of European Patent Application No. 10015767.6 filed 17 Dec. 2010, and U.S. Provisional Application No. 61/424,451 filed 17 Dec. 2011, the disclosure of each of which is incorporated herein by reference.

REFERENCE TO SEQUENCE LISTING

This application contains a Sequence Listing submitted as an electronic text file named "NE30A30_P-WO_ST25.txt", having a size in bytes of 108 KB, and created on May 27, 2015. The information contained in this electronic file is hereby incorporated by reference in its entirety pursuant to 37 CFR §1.52(e)(5).

FIELD OF THE INVENTION

The present invention generally relates to novel molecules specifically binding to superoxide dismutase [Cu—Zn] also known as superoxide dismutase 1 or SOD1, particularly human antibodies as well as fragments, derivatives and variants thereof that recognize the SOD1 protein, and misfolded/aggregated forms of SOD1. In addition, the present invention relates to pharmaceutical and diagnostic compositions comprising such binding molecules, antibodies and mimics thereof valuable both as a diagnostic tool to identify SOD1 and misfolded/aggregated SOD1 species in plasma and CSF and also in passive vaccination strategies for treating disorders related to misfolded/aggregated SOD1 such as amyotrophic lateral sclerosis (ALS), also known as Lou Gehrig's disease, or Charcot's disease.

BACKGROUND OF THE INVENTION

Protein accumulation, modifications and aggregation are pathological aspects of numerous neurodegenerative diseases. A subgroup of the neurodegenerative diseases, known as motor neuron diseases is characterized by the gradual degeneration and death of motor neurons. One of the most common members of this group of disorders, amyotrophic lateral sclerosis (ALS) is a rapidly progressive, invariably fatal neurological disease that attacks the neurons responsible for controlling voluntary muscles, specifically motor neurons in the spinal cord, brain stem, and motor cortex (Bruijn et al., Annu. Rev. Neurosci. 27 (2004), 723-749). In 90 to 95 percent of all ALS cases, the disease's etiology is unknown with no clearly associated risk factors (sporadic ALS, sALS). Only 5 to 10 percent of all ALS cases are inherited (familiar ALS, fALS), with about 20 percent of them resulting from mutations in the gene producing the superoxide dismutase [Cu—Zn] enzyme also known as superoxide dismutase 1 or SOD1 (Bruijn et al., Annu. Rev. Neurosci. 27 (2004), 723-749; Valentine et al., Annu. Rev. Biochem. 74 (2005), 563-593; Andersen, Curr. Neurol. Neurosci. Rep. 6 (2006), 37-46).

Human SOD1 is a 32 kDa homodimeric metalloenzyme, with the gene locus on the chromosome 21, localized predominantly in the cytosol, nucleus and peroxisomes but also in the mitochondrial intermembrane space of eukaryotic cells. It contains an active site that binds a catalytic copper ion and a structural zinc ion. The functional role of SOD1 is to act as an antioxidant enzyme catalyzing the dismutation of superoxide radical to dioxygen and hydrogen peroxide lowering in that way the steady-state concentration of superoxide and the oxidative stress to the cell (Fridovich, Science 201 (1978), 875-879).

Over 100 different mutations, spread all over the SOD1 protein are known (http://alsod.iop.kcl.ac.uk/; Andersen, Amyotroph. Lateral Scler. Other Motor Neuron Disord. 1 Suppl. 1 (2000), S31-42; Andersen et al., Amyotroph. Lateral Scler. Other Motor Neuron Disord. 2 (2001), 63-69; Gaudette et al., Amyotroph. Lateral Scler. Other Motor Neuron Disord. 1 (2000), 83-89) and all but the D90A mutation cause dominantly inherited disease. It is not clarified completely, how mutant SOD1 leads to ALS. While some of the mutations differently affect the stability, metal ion affinity and enzymatic activity of the respective mutant SOD1-protein, others do not (Valentine et al., Annu. Rev. Biochem. 74 (2005), 563-593; Valentine and Hart, Proc. Natl. Acad. Sci. USA 100 (2003), 3617-3622; Lindberg et al., Proc. Natl. Acad. Sci. USA 102, 9754-9759; Taylor et al., Science 296 (2005), 1991-1995). However, the dominant inheritance of the disease in combination with the fact that SOD1 null mice do not develop ALS (Reaume et al., Nat. Genet. 13 (1996), 43-47) suggests that SOD1-mediated toxicity in ALS is not caused by a loss but rather by a gain of one or more toxic functions due to the mutations.

Three (G37R, G85R and G93A) of the known human mutations have been extensively characterized in transgenic mouse models (Bruijn and Cleveland, Neuropathol. Appl. Neurobiol. 22 (1996), 373-87; Gurney, N. Engl. J. Med. 331 (1994), 1721-1722; Ripps et al. Proc. Natl. Acad. Sci. USA 92 (1995), 689-93; Wong et al., Neuron 14 (1995), 1105-16). The human mutant proteins are expressed ubiquitously at levels equal or several fold higher than endogenous mouse SOD1. Contrary to the overexpression of wildtype human SOD1, the overexpression of the mutant forms leads to development of ALS in the animals with pathology similar to the human disease. For example, comparable to the tissues from ALS patients, proteinaceous inclusions rich in aggregates of mutant SOD1 have been found in the neurons and astrocytes (Stieber et al., Neurol. Sci. 173 (2000), 53-62) as perikaryal deposits and as macromolecular complexes associated with various mitochondrial compartments (Manfredi and Xu, Mitochondrion 5 (2005), 77-87), and inside the endoplasmic reticulum (Kikuchi et al., Proc. Natl. Acad. Sci. U.S.A. 103 (2006), 6025-6030).

The inclusions do not contain SOD1 solely. One of the additional, probably ALS causative as well, compounds of these is TAR DNA-binding protein 43 (TDP-43). Pathogenic mutations in the gene encoding TDP-43 (TARDBP) were recently reported in familial and sporadic ALS patients and seem to be responsible for at least 3.3% of the fALS cases (Neumann et al., Science 314 (2006), 130-133; Rutherford et al., PLoS Genet. 4 (2008), e1000193).

SOD1 has been further reported to be a major target of oxidative damage in brains of Alzheimer Disease (AD) and Parkinson Disease (PD) patients. The total level of SOD1 was increased and proteinaceous aggregates that are associated with amyloid senile plaques and neurofibrillary tangles were found in AD brains (Choi et al., J. Biol. Chem. 280 (2005), 11648-11655).

The exact mechanism leading to the aggregation of SOD1 is not known. Prevailing hypotheses however, suggest the aggregation of SOD1 as a consequence of the proteins misfolding due to mutation-induced conformational changes (Bruijn et al., Science 281 (1998), 1851-1854; Chattopadhyay and Valentine, Antioxid. Redox. Signal 11 (2009), 1603-1614; Furukawa et al., Proc. Natl. Acad. Sci. USA 103 (2006), 7148-7153; Prudencio et al., Hum. Mol. Genet. 18 (2009), 3217-3226; Wang et al., PLoS Biol. 6, e170 (2008)). Misfolded mutant or wtSOD1 is also secreted by glial cells to the extracellular environment, where it can trigger the selective death of motor neurons (Urushitani et al., Nature Neuroscience 9 (2006). 108-118). This offers a possible explanation for the non-cell-autonomous nature of mutant SOD1 toxicity and the rapid progression of disease once the first symptoms develop.

As already mentioned, the etiology of spontaneous forms of ALS accounting for 90-95 percent of all incidents, is not clarified. However, it is also believed that similar to the observations concerning the familial ALS forms, misfolding of wild type (wt) SOD1 is associated with the majority of the sporadic ALS cases (Bosco et al., Nature Neuroscience 13 (2010), 1396-1403). Wildtype SOD1 is a subject of massive post-translational modifications, such as subunit dimerization, building of the intrasubunit disulfide bond between residues Cys57 and Cys146, and the coordination of copper and zinc. Disruptions of these processes have all been shown to cause wild-type SOD1 to aggregate (Durazo et al., J. Biol. Chem. 277 (2009), 15923-15931; Estévez et al., Science 286 (1999), 2498-2500; Rakhit et al., J. Biol. Chem. 279 (2004), 15499-15504; Lindberg et al., Proc. Natl. Acad. Sci. USA 101 (2004), 15893-15898) providing therefore a possible pathogenic model for spontaneous ALS forms.

Immunotherapies targeting the mutant or misfolded SOD1 have produced encouraging results in animal models for familial ALS forms. Active immunization delayed disease's onset and mortality attenuated motor neuron loss and reduced SOD1 levels in SOD1 transgenic mice. The life-span extension correlated to antibody titers (Urushitani et al., Proc. Natl. Acad. Sci. USA 104 (2007), 2495-2500; Cashman, NDI conference Uppsala 2009, Takeuchi et al., J Neuropathol Exp Neurol. (2010), 1044-1056).

Passive immunization delayed bodyweight loss and hind limb reflex impairment and extended lifespan as well (Urushitani et al., Proc. Natl. Acad. Sci. USA 104 (2007), 2495-2500; Cashman, NDI conference Uppsala 2009; Gros-Louis Fetal., J. Neurochem 2010).

These findings highlight the potential benefit associated with active immunotherapy approaches targeting SOD1. Regardless of this high potential, approaches for active as well as passive immunotherapy can produce varying effects with respect to their efficacy towards specific therapeutic endpoints. As shown for Aβ directed approaches in preclinical mouse models of AD or in human, they can be also associated with adverse events such as autoimmune disease, meningoencephalitis, increased cerebral amyloid angiopathy and the induction of cerebral hemorrhages (Pfeifer et al., Science 298 (2002), 1379; Furlan et al., Brain 126 (2003), 285-291; Wilcock et al., J. Neuroinflammation 1:24 (2004); Lee at al., FEBS Lett. 579 (2005), 2564-8; Wilcock et al., Neuroscience 144 (2007), 950-960; Schenk, Nat. Rev. Neurosci. 3 (2002), 824-828; Orgogozo et al, Neurology 61 (2003), 46-54). This might be less of a problem in the context of ALS without the occurrence of massive extracellular protein deposits but should be taken into account nevertheless.

Summarizing the above, novel therapeutic strategies are urgently needed addressing misfolded/aggregated SOD1 proteins with efficacious and safe therapy.

Passive immunization with human antibodies which are evolutionarily optimized and affinity matured by the human immune system would provide a promising new therapeutic avenue with a high probability for excellent efficacy and safety.

SUMMARY OF THE INVENTION

The present invention makes use of the SOD1-specific immune response of healthy human subjects for the isolation of natural anti-SOD1 specific human monoclonal antibodies. In particular, experiments performed in accordance with the present invention were successful in the isolation of monoclonal SOD1-specific antibodies from a pool of healthy human subjects with no signs of ALS.

The present invention is thus directed to human antibodies, antigen-binding fragments and similar antigen-binding molecules which are capable of specifically recognizing SOD1. By "specifically recognizing SOD1", "antibody specific to/for SOD1" and "anti-SOD1 antibody" is meant specifically, generally, and collectively, antibodies to the native form of SOD1, or misfolded or aggregated SOD1 isoforms. Provided herein are human antibodies selective for full-length, misfolded and aggregated forms.

In a particularly preferred embodiment of the present invention, the human antibody or antigen-binding fragment thereof demonstrates the immunological binding characteristics of an antibody characterized by the variable regions $V_H$ and/or $V_L$ as set forth in FIG. 1.

The antigen-binding fragment of the antibody can be a single chain Fv fragment, an F(ab') fragment, an F(ab) fragment, and an F(ab')$_2$ fragment, or any other antigen-binding fragment. In a specific embodiment, infra, the antibody or fragment thereof is a human IgG isotype antibody. Alternatively, the antibody is a chimeric human-murine or murinized antibody, the latter being particularly useful for diagnostic methods and studies in animals.

Furthermore, the present invention relates to compositions comprising the antibody of the present invention or active fragments thereof, or agonists and cognate molecules, or alternately, antagonists of the same and to immunotherapeutic and immunodiagnostic methods using such compositions in the prevention, diagnosis or treatment of disorders related to misfolded/aggregated SOD1, such as ALS, wherein an effective amount of the composition is administered to a patient in need thereof.

Naturally, the present invention extends to the immortalized human B memory lymphocyte and B cell, respectively, that produces the antibody having the distinct and unique characteristics as defined below.

The present invention also relates to polynucleotides encoding at least a variable region of an immunoglobulin chain of the antibody of the invention. Preferably, said variable region comprises at least one complementarity determining region (CDR) of the $V_H$ and/or $V_L$ of the variable region as set forth in FIG. 1.

Accordingly, the present invention also encompasses vectors comprising said polynucleotides and host cells transformed therewith as well as their use for the production of an antibody and equivalent binding molecules which are specific for SOD1. Means and methods for the recombinant production of antibodies and mimics thereof as well as methods of screening for competing binding molecules, which may or may not be antibodies, are known in the art. However, as described herein, in particular with respect to therapeutic applications in human the antibody of the present invention is a human antibody in the sense that application of said antibody is substantially free of an immune response directed against such antibody otherwise observed for chimeric and even humanized antibodies.

Furthermore, disclosed herein are compositions and methods that can be used to identify SOD1 in samples. The disclosed anti-SOD1 antibodies can be used to screen human blood, CSF, and urine for the presence of SOD1 in samples, for example, by using ELISA-based or surface adapted assay. The methods and compositions disclosed herein can aid in disorders related to misfolded/aggregated SOD1 such as ALS diagnosis and can be used to monitor disease progression and therapeutic efficacy.

Hence, it is a particular object of the present invention to provide methods for treating, diagnosing or preventing a disease related to misfolded/aggregated SOD1 such as amyotrophic lateral sclerosis (ALS). The methods comprise administering an effective concentration of a human antibody or antibody derivative to the subject where the antibody targets SOD1.

In a further aspect the present invention provides a peptide having an epitope of SOD1 specifically recognized by an antibody of the present invention. Said peptide comprises or consists of an amino acid sequence as indicated below in the detailed description and in the examples or a modified sequence thereof in which one or more amino acids are substituted, deleted and/or added. Additionally, the present invention provides a method for diagnosing amyotrophic lateral sclerosis in a subject, comprising a step of determining the presence of an antibody that binds to said peptide in a biological sample of said subject.

Further embodiments of the present invention will be apparent from the description and Examples that follow.

BRIEF DESCRIPTION OF THE DRAWINGS

FIG. 1: Amino acid and nucleotide sequences of the variable region, i.e. heavy chain and kappa/lambda light chain of human antibodies NI-204.10D12 (A—SEQ ID NO: 60 and SEQ ID NO: 61, respectively), NI-204.12G7 (B—SEQ ID NO: 62 and SEQ ID NO: 63, respectively), NI-204.10A8 (C—SEQ ID NO: 64 and SEQ ID NO: 65, respectively), NI-204.9F6 (D—SEQ ID NO: 66 and SEQ ID NO: 67, respectively), NI-204.11F11 (E—SEQ ID NO: 68 and SEQ ID NO: 69, respectively), NI-204.67E12 (F—SEQ ID NO: 70 and SEQ ID NO: 71, respectively), NI-204.6H1 (G—SEQ ID NO: 72 and SEQ ID NO: 73, respectively), NI-204.12G3 (H—SEQ ID NO: 74 and SEQ ID NO: 75, respectively), NI-204.7G5 (I—SEQ ID NO: 76 and SEQ ID NO: 77, respectively), NI-204.7B3 (J—SEQ ID NO: 78 and SEQ ID NO: 79, respectively), NI-204.34A3 (K—SEQ ID NO: 80 and SEQ ID NO: 81, respectively) and NI-204.25H3 (L—SEQ ID NO: 82 and SEQ ID NO: 83, respectively). Framework (FR) and complementarity determining regions (CDRs) are indicated with the CDRs being underlined. The heavy chain joining region (JH) and light chain joining region (JK) are indicated as well. Due to the cloning strategy the amino acid sequence at the N-terminus of the heavy chain and light chain may potentially contain primer-induced alterations in FR1, which however do not substantially affect the biological activity of the antibody. In order to provide a consensus human antibody, the nucleotide and amino acid sequences of the original clone were aligned with and tuned in accordance with the pertinent human germ line variable region sequences in the database; see, e.g., Vbase (vbase.mrc-cpe.cam.ac.uk/) hosted by the MRC Centre for Protein Engineering (Cambridge, UK). Those amino acids, which are considered to potentially deviate from the consensus germ line sequence due to the PCR primer and thus have been replaced in the amino acid sequence, are indicated in bold.

(B) Attenuation of body weight loss in B6.Cg-Tg (SOD1*G93A)1Gur/J transgenic mice upon passive immunization with the NI-204.10D12 antibody. Body weight of B6.Cg-Tg(SOD1*G93A)1Gur/J transgenic mice treated intraventricularly with either PBS (dashed line) or NI-204.10D12 SOD1-specific antibody (plain line) expressed as percentage of baseline body weight determined after surgical pump implantation; * p<0.05.

Figure 11:
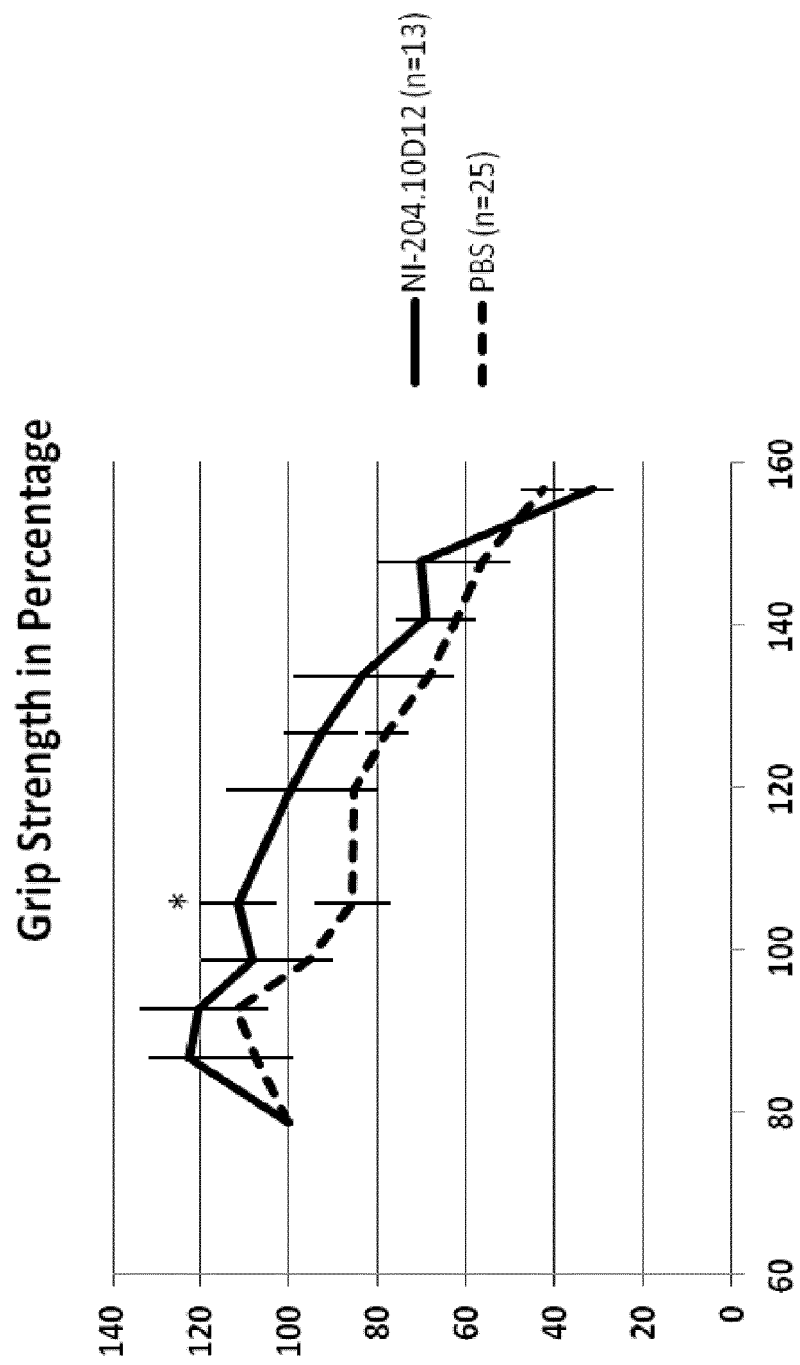

FIG. 11 Improvement of grip strength in B6.Cg-Tg (SOD1*G93A)1Gur/J transgenic mice by passive immunization with the NI-204.10D12 antibody. Grip strength of B6.Cg-Tg(SOD1*G93A)1Gur/J transgenic mice treated intraventricularly either with PBS (dash line) or NI-204.10D12 SOD1-specific antibody (plain line) expressed as percentage of grip strength at baseline after surgical pump implantation; * p<0.05.

Figure 12:
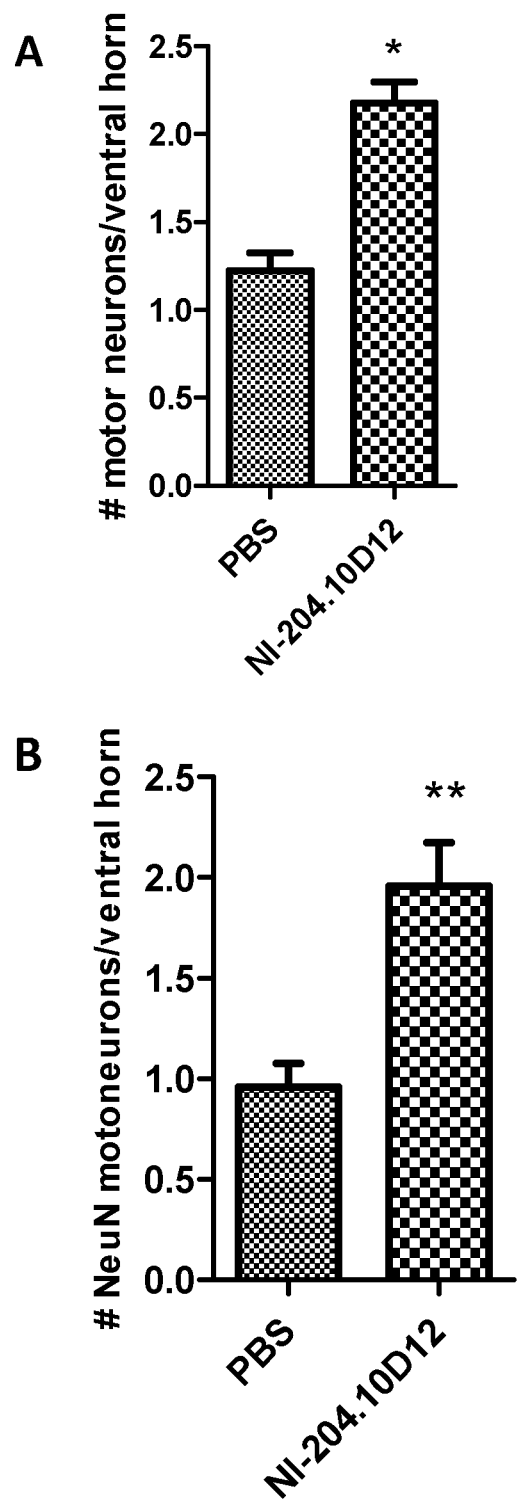

FIG. 12 Attenuation of motor neuron loss in the spinal cord of B6.Cg-Tg(SOD1*G93A)1Gur/J transgenic mice upon chronic NI-204.10D12 antibody treatment. Motor neuron counts in the ventral horns of the lumbar spinal cord in B6.Cg-Tg(SOD1*G93A)1Gur/J transgenic mice treated intraventricularly either with PBS or NI-204.10D12 SOD1-specific antibody. (A) Motor neurons count upon Nissl staining. Data represent the average ±SEM. (B) Motor neurons count upon NeuN staining. Data represent the average ±SEM; ** p<0.01.

DETAILED DESCRIPTION OF THE INVENTION

I. Definitions

Protein accumulation, modifications and aggregation are pathological aspects of numerous neurodegenerative diseases such as Huntington's, Alzheimer's (AD) and Parkinson's diseases (PD) (Taylor et al., Science 296 (2005), 1991-1995). Misfolding, aggregation and precipitation of proteins seem to be directly related to neurotoxicity in these diseases. The native homodimeric, copper-zinc superoxide dismutase (SOD1) protein (both wild-type and ALS1 variants) has a tendency to form fibrillar aggregates in the absence of the intramolecular disulfide bond or of bound zinc ions. Related to misfolded/aggregated SOD1 are disorders such as amyotrophic lateral sclerosis (ALS), also known as Lou Gehrig's disease, or Charcot's disease. Further, as mentioned before, oxidative modifications of SOD1 which may also induce the protein's misfolding have been found in AD and PD, and aggregates of SOD1 are associated with amyloid plaques and neurofibrillary tangles in AD patients (Choi et al., J. Biol. Chem. 280 (2005), 11648-11655) implicating a possible role of SOD1 in the pathology of these diseases.

Clinical features of ALS are gradual degeneration and death of motor neurons responsible for controlling voluntary muscles, specifically motor neurons in the spinal cord, brain stem, and motor cortex. The course of disease is rapidly progressive with gradual muscle weakening as a hallmark sign, wasting away (atrophy), and twitching (fasciculations), occurring in 60% of patients and invariably fatal, mostly by respiratory failure, with a mean survival time of three to five years.

Most cases of ALS (~90-95%) are sporadic (sALS), the remaining are familial inherited (fALS). Approximately 20% of fALS show a genetic association with mutations in the SOD1 gene. The molecular mechanism of ALS remains elusive in most cases, however some studies provide data showing that aberrant SOD1 species can be found in both sALS and fALS patients suggesting this as a possible common origin (Gruzman et al., Proc. Natl. Acad. Sci. USA 104 (2007), 12524-12529).

In transgenic ALS mouse models, comparable to the tissues from ALS patients, proteinaceous inclusions rich in aggregates of mutant SOD1 have been found in the neurons and astrocytes (Stieber et al., Neurol. Sci. 173 (2000), 53-62) as perikaryal deposits and as macromolecular complexes associated with various mitochondrial compartments (Manfredi and Xu, Mitochondrion 5 (2005), 77-87), and inside the endoplasmic reticulum (Kikuchi et al., Proc. Natl. Acad. Sci. U.S.A. 103 (2006), 6025-6030). Furthermore, misfolded mutant or wtSOD1 is also secreted by glial cells to the extracellular environment, where it can trigger the selective death of motor neurons (Urushitani et al., Nature Neuroscience 9 (2006). 108-118). This offers a possible explanation for the observed non-cell-autonomous nature of mutant SOD1 toxicity and the rapid progression of disease once the first symptoms develop.

The term "SOD1", is used interchangeable to specifically refer to the native monomer or dimeric form of SOD1. The term "SOD1" is also used to generally identify other conformers of SOD1, for example, oligomers or aggregates of SOD1. The term "SOD1" is also used to refer collectively to all types and forms of SOD1.

The protein sequence for human SOD1 is:

(SEQ ID NO: 1)
MATKAVCVLKGDGPVQGIINFEQKESNGPVKVWGSIKGLTEGLHGFHVHE

FGDNTAGCTSAGPHFNPLSRKHGGPKDEERHVGDLGNVTADKDGVADVSI

EDSVISLSGDHCIIGRTLVVHEKADDLGKGGNEESTKTGNAGSRLACGVI

GIAQ.

The amino acid sequence of SOD1 of 154 aa can be retrieved from the literature and pertinent databases; see, e.g., Sherman et al., Proc. Natl. Acad. Sci. USA. 80 (1983), 5465-9; Kajihara et al., J. Biochem. 104 (1988), 851-4; GenBank swissprot: locus SODC_HUMAN, accession number P00441. The "wild type" or recombinant human SOD1 amino acid sequence is represented by the above mentioned sequence according to SEQ ID NO: 1.

The human anti-SOD1 antibodies disclosed herein specifically bind SOD1 and epitopes thereof and to various conformations of SOD1 and epitopes thereof. For example, disclosed herein are antibodies that specifically bind SOD1, full-length SOD1 and pathologically misfolded/aggregated SOD1. As used herein, reference to an antibody that "specifically binds", "selectively binds", or "preferentially binds" SOD1 refers to an antibody that does not bind other unrelated proteins. In one example, an SOD1 antibody disclosed herein can bind SOD1 or an epitope thereof and show no binding above about 2 times background for other proteins. An antibody that "specifically binds" or "selectively binds" an SOD1 conformer refers to an antibody that does not bind all conformations of SOD1, i.e., does not bind at least one other SOD1 conformer. For example, disclosed herein are antibodies that can preferentially bind to aggregated forms of SOD1 both in vitro and in ALS tissues. Since the human anti-SOD1 antibodies of the present invention have been isolated from a pool of healthy human subjects exhibiting an SOD1-specific immune response the SOD1 antibodies of the present invention may also be called "human auto-antibodies" in order to emphasize that those antibodies were indeed expressed by the subjects and have not been isolated from, for example a human immunoglobulin expressing phage library, which hitherto represented one common method for trying to provide human-like antibodies.

It is to be noted that the term "a" or "an" entity refers to one or more of that entity; for example, "an antibody," is understood to represent one or more antibodies. As such, the terms "a" (or "an"), "one or more," and "at least one" can be used interchangeably herein.

As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, dipeptides, tripeptides, oligopeptides, "peptide," "protein," "amino acid chain," or any other term used to refer to a chain or chains of two or more amino acids, are included within the definition of "polypeptide," and the term "polypeptide" may be used instead of, or interchangeably with any of these terms.

The term "polypeptide" is also intended to refer to the products of post-expression modifications of the polypeptide, including without limitation glycosylation, acetylation, phosphorylation, amidation and derivatization by known protecting/blocking groups, proteolytic cleavage, or modification by non-naturally occurring amino acids. A polypeptide may be derived from a natural biological source or produced by recombinant technology, but is not necessarily translated from a designated nucleic acid sequence. It may be generated in any manner, including by chemical synthesis.

A polypeptide of the invention may be of a size of about 3 or more, 5 or more, 10 or more, 20 or more, 25 or more, 50 or more, 75 or more, 100 or more, 200 or more, 500 or more, 1,000 or more, or 2,000 or more amino acids. Polypeptides may have a defined three-dimensional structure, although they do not necessarily have such structure. Polypeptides with a defined three-dimensional structure are referred to as folded, and polypeptides which do not possess a defined three-dimensional structure, but rather can adopt a large number of different conformations, and are referred to as unfolded. As used herein, the term glycoprotein refers to a protein coupled to at least one carbohydrate moiety that is attached to the protein via an oxygen-containing or a nitrogen-containing side chain of an amino acid residue, e.g., a serine residue or an asparagine residue.

By an "isolated" polypeptide or a fragment, variant, or derivative thereof is intended a polypeptide that is not in its natural milieu. No particular level of purification is required. For example, an isolated polypeptide can be removed from its native or natural environment. Recombinantly produced polypeptides and proteins expressed in host cells are considered isolated for purposed of the invention, as are native or recombinant polypeptides which have been separated, fractionated, or partially or substantially purified by any suitable technique.

Also included as polypeptides of the present invention are fragments, derivatives, analogs or variants of the foregoing polypeptides and any combinations thereof. The terms "fragment," "variant," "derivative" and "analog" when referring to antibodies or antibody polypeptides of the present invention include any polypeptides which retain at least some of the antigen-binding properties of the corresponding native binding molecule, antibody, or polypeptide. Fragments of polypeptides of the present invention include proteolytic fragments, as well as deletion fragments, in addition to specific antibody fragments discussed elsewhere herein. Variants of antibodies and antibody polypeptides of the present invention include fragments as described above, and also polypeptides with altered amino acid sequences due to amino acid substitutions, deletions, or insertions. Variants may occur naturally or be non-naturally occurring. Non-naturally occurring variants may be produced using art-known mutagenesis techniques. Variant polypeptides may comprise conservative or non-conservative amino acid substitutions, deletions or additions. Derivatives of SOD1 specific binding molecules, e.g., antibodies and antibody polypeptides of the present invention, are polypeptides which have been altered so as to exhibit additional features not found on the native polypeptide. Examples include fusion proteins. Variant polypeptides may also be referred to herein as "polypeptide analogs". As used herein a "derivative" of a binding molecule or fragment thereof, an antibody, or an antibody polypeptide refers to a subject polypeptide having one or more residues chemically derivatized by reaction of a functional side group. Also included as "derivatives" are those peptides which contain one or more naturally occurring amino acid derivatives of the twenty standard amino acids. For example, 4-hydroxyproline may be substituted for proline; 5-hydroxylysine may be substituted for lysine; 3-methylhistidine may be substituted for histidine; homoserine may be substituted for serine; and ornithine may be substituted for lysine.

The term "polynucleotide" is intended to encompass a singular nucleic acid as well as plural nucleic acids, and refers to an isolated nucleic acid molecule or construct, e.g., messenger RNA (mRNA) or plasmid DNA (pDNA). A polynucleotide may comprise a conventional phosphodiester bond or a non-conventional bond (e.g., an amide bond, such as found in peptide nucleic acids (PNA)). The term "nucleic acid" refers to any one or more nucleic acid segments, e.g., DNA or RNA fragments, present in a polynucleotide. By "isolated" nucleic acid or polynucleotide is intended a nucleic acid molecule, DNA or RNA, which has been removed from its native environment. For example, a recombinant polynucleotide encoding an antibody contained in a vector is considered isolated for the purposes of the present invention. Further examples of an isolated polynucleotide include recombinant polynucleotides maintained in heterologous host cells or purified (partially or substantially) polynucleotides in solution. Isolated RNA molecules include in vivo or in vitro RNA transcripts of polynucleotides of the present invention. Isolated polynucleotides or nucleic acids according to the present invention further include such molecules produced synthetically. In addition, polynucleotide or a nucleic acid may be or may include a regulatory element such as a promoter, ribosome binding site, or a transcription terminator.

As used herein, a "coding region" is a portion of nucleic acid which consists of codons translated into amino acids. Although a "stop codon" (TAG, TGA, or TAA) is not translated into an amino acid, it may be considered to be part of a coding region, but any flanking sequences, for example promoters, ribosome binding sites, transcriptional terminators, introns, and the like, are not part of a coding region. Two or more coding regions of the present invention can be present in a single polynucleotide construct, e.g., on a single vector, or in separate polynucleotide constructs, e.g., on separate (different) vectors. Furthermore, any vector may contain a single coding region, or may comprise two or more coding regions, e.g., a single vector may separately encode an immunoglobulin heavy chain variable region and an immunoglobulin light chain variable region. In addition, a vector, polynucleotide, or nucleic acid of the invention may encode heterologous coding regions, either fused or unfused to a nucleic acid encoding a binding molecule, an antibody, or fragment, variant, or derivative thereof. Heterologous coding regions include without limitation specialized elements or motifs, such as a secretory signal peptide or a heterologous functional domain.

In certain embodiments, the polynucleotide or nucleic acid is DNA. In the case of DNA, a polynucleotide comprising a nucleic acid which encodes a polypeptide normally may include a promoter and/or other transcription or translation control elements operable associated with one or more coding regions. An operable association is when a coding region for a gene product, e.g., a polypeptide, is associated with one or more regulatory sequences in such a way as to place expression of the gene product under the influence or control of the regulatory sequence(s). Two DNA fragments (such as a polypeptide coding region and a promoter associated therewith) are "operable associated" or "operable linked" if induction of promoter function results in the transcription of mRNA encoding the desired gene product and if the nature of the linkage between the two DNA fragments does not interfere with the ability of the expression regulatory sequences to direct the expression of the gene product or interfere with the ability of the DNA template to be transcribed. Thus, a promoter region would be operable associated with a nucleic acid encoding a polypeptide if the promoter was capable of effecting transcription of that nucleic acid. The promoter may be a cell-specific promoter that directs substantial transcription of the DNA only in predetermined cells. Other transcription control elements, besides a promoter, for example enhancers, operators, repressors, and transcription termination signals, can be operable associated with the polynucleotide to direct cell-specific transcription. Suitable promoters and other transcription control regions are disclosed herein.

A variety of transcription control regions are known to those skilled in the art. These include, without limitation, transcription control regions which function in vertebrate cells, such as, but not limited to, promoter and enhancer segments from cytomegaloviruses (the immediate early promoter, in conjunction with intron-A), simian virus 40 (the early promoter), and retroviruses (such as Rous sarcoma virus). Other transcription control regions include those derived from vertebrate genes such as actin, heat shock protein, bovine growth hormone and rabbit β-globin, as well as other sequences capable of controlling gene expression in eukaryotic cells. Additional suitable transcription control regions include tissue-specific promoters and enhancers as well as lymphokine-inducible promoters (e.g., promoters inducible by interferons or interleukins).

Similarly, a variety of translation control elements are known to those of ordinary skill in the art. These include, but are not limited to ribosome binding sites, translation initiation and termination codons, and elements derived from picornaviruses (particularly an internal ribosome entry site, or IRES, also referred to as a CITE sequence).

In other embodiments, a polynucleotide of the present invention is RNA, for example, in the form of messenger RNA (mRNA).

Polynucleotide and nucleic acid coding regions of the present invention may be associated with additional coding regions which encode secretory or signal peptides, which direct the secretion of a polypeptide encoded by a polynucleotide of the present invention. According to the signal hypothesis, proteins secreted by mammalian cells have a signal peptide or secretory leader sequence which is cleaved from the mature protein once export of the growing protein chain across the rough endoplasmic reticulum has been initiated. Those of ordinary skill in the art are aware that polypeptides secreted by vertebrate cells generally have a signal peptide fused to the N-terminus of the polypeptide, which is cleaved from the complete or "full-length" polypeptide to produce a secreted or "mature" form of the polypeptide. In certain embodiments, the native signal peptide, e.g., an immunoglobulin heavy chain or light chain signal peptide is used, or a functional derivative of that sequence that retains the ability to direct the secretion of the polypeptide that is operable associated with it. Alternatively, a heterologous mammalian signal peptide, or a functional derivative thereof, may be used. For example, the wild-type leader sequence may be substituted with the leader sequence of human tissue plasminogen activator (TPA) or mouse β-glucuronidase.

Unless stated otherwise, the terms "disorder" and "disease" are used interchangeably herein.

A "binding molecule" as used in the context of the present invention relates primarily to antibodies, and fragments thereof, but may also refer to other non-antibody molecules that bind to SOD1 including but not limited to hormones, receptors, ligands, major histocompatibility complex (MHC) molecules, chaperones such as heat shock proteins (HSPs) as well as cell-cell adhesion molecules such as members of the cadherin, intergrin, C-type lectin and immunoglobulin (Ig) superfamilies. Thus, for the sake of clarity only and without restricting the scope of the present invention most of the following embodiments are discussed with respect to antibodies and antibody-like molecules which represent the preferred binding molecules for the development of therapeutic and diagnostic agents.

The terms "antibody" and "immunoglobulin" are used interchangeably herein. An antibody or immunoglobulin is an SOD1-binding molecule which comprises at least the variable domain of a heavy chain, and normally comprises at least the variable domains of a heavy chain and a light chain. Basic immunoglobulin structures in vertebrate systems are relatively well understood; see, e.g., Harlow et al., Antibodies: A Laboratory Manual, (Cold Spring Harbor Laboratory Press, 2nd ed. 1988).

As will be discussed in more detail below, the term "immunoglobulin" comprises various broad classes of polypeptides that can be distinguished biochemically. Those skilled in the art will appreciate that heavy chains are classified as gamma, mu, alpha, delta, or epsilon, ($\gamma$, $\mu$, $\alpha$, $\delta$, $\epsilon$) with some subclasses among them (e.g., $\gamma 1$-$\gamma 4$). It is the nature of this chain that determines the "class" of the antibody as IgG, IgM, IgA IgG, or IgE, respectively. The immunoglobulin subclasses (isotypes) e.g., IgG1, IgG2, IgG3, IgG4, IgA1, etc. are well characterized and are known to confer functional specialization. Modified versions of each of these classes and isotypes are readily discernable to the skilled artisan in view of the instant disclosure and, accordingly, are within the scope of the instant invention. All immunoglobulin classes are clearly within the scope of the present invention, the following discussion will generally be directed to the IgG class of immunoglobulin molecules. With regard to IgG, a standard immunoglobulin molecule comprises two identical light chain polypeptides of molecular weight approximately 23,000 Daltons, and two identical heavy chain polypeptides of molecular weight 53,000-70,000. The four chains are typically joined by disulfide bonds in a "Y" configuration wherein the light chains bracket the heavy chains starting at the mouth of the "Y" and continuing through the variable region.

Light chains are classified as either kappa or lambda (κ, λ). Each heavy chain class may be bound with either a kappa or lambda light chain. In general, the light and heavy chains are covalently bonded to each other, and the "tail" portions of the two heavy chains are bonded to each other by covalent disulfide linkages or non-covalent linkages when the immunoglobulins are generated either by hybridomas, B cells or genetically engineered host cells. In the heavy chain, the amino acid sequences run from an N-terminus at the forked ends of the Y configuration to the C-terminus at the bottom of each chain.

Both the light and heavy chains are divided into regions of structural and functional homology. The terms "constant" and "variable" are used functionally. In this regard, it will be appreciated that the variable domains of both the light ($V_L$) and heavy ($V_H$) chain portions determine antigen recognition and specificity. Conversely, the constant domains of the light chain (CL) and the heavy chain (CH1, CH2 or CH3) confer important biological properties such as secretion, transplacental mobility, Fc receptor binding, complement binding, and the like. By convention the numbering of the constant region domains increases as they become more distal from the antigen-binding site or amino-terminus of the antibody. The N-terminal portion is a variable region and at the C-terminal portion is a constant region; the CH3 and CL domains actually comprise the carboxy-terminus of the heavy and light chain, respectively.

As indicated above, the variable region allows the antibody to selectively recognize and specifically bind epitopes on antigens. That is, the $V_L$ domain and $V_H$ domain, or subset of the complementarity determining regions (CDRs), of an antibody combine to form the variable region that defines a three dimensional antigen-binding site. This quaternary antibody structure forms the antigen-binding site present at the end of each arm of the Y. More specifically, the antigen-binding site is defined by three CDRs on each of the $V_H$ and $V_L$ chains. Any antibody or immunoglobulin fragment which contains sufficient structure to specifically bind to SOD1 is denoted herein interchangeably as a "binding fragment" or an "immunospecific fragment."

In naturally occurring antibodies, an antibody comprises six hypervariable regions, sometimes called "complementarity determining regions" or "CDRs" present in each antigen-binding domain, which are short, non-contiguous sequences of amino acids that are specifically positioned to form the antigen-binding domain as the antibody assumes its three dimensional configuration in an aqueous environment. The "CDRs" are flanked by four relatively conserved "framework" regions or "FRs" which show less inter-molecular variability. The framework regions largely adopt a β-sheet conformation and the CDRs form loops which connect, and in some cases form part of, the β-sheet structure. Thus, framework regions act to form a scaffold that provides for positioning the CDRs in correct orientation by inter-chain, non-covalent interactions. The antigen-binding domain formed by the positioned CDRs defines a surface complementary to the epitope on the immunoreactive antigen. This complementary surface promotes the non-covalent binding of the antibody to its cognate epitope. The amino acids comprising the CDRs and the framework regions, respectively, can be readily identified for any given heavy or light chain variable region by one of ordinary skill in the art, since they have been precisely defined; see, "Sequences of Proteins of Immunological Interest," Kabat, E., et al., U.S. Department of Health and Human Services, (1983); and Chothia and Lesk, J. Mol. Biol., 196 (1987), 901-917, which are incorporated herein by reference in their entireties.

In the case where there are two or more definitions of a term which is used and/or accepted within the art, the definition of the term as used herein is intended to include all such meanings unless explicitly stated to the contrary. A specific example is the use of the term "complementarity determining region" ("CDR") to describe the non-contiguous antigen combining sites found within the variable region of both heavy and light chain polypeptides. This particular region has been described by Kabat et al., U.S. Dept. of Health and Human Services, "Sequences of Proteins of Immunological Interest" (1983) and by Chothia and Lesk, J. Mol. Biol., 196 (1987), 901-917, which are incorporated herein by reference, where the definitions include overlapping or subsets of amino acid residues when compared against each other. Nevertheless, application of either definition to refer to a CDR of an antibody or variants thereof is intended to be within the scope of the term as defined and used herein. The appropriate amino acid residues which encompass the CDRs as defined by each of the above cited references are set forth below in Table I as a comparison. The exact residue numbers which encompass a particular CDR will vary depending on the sequence and size of the CDR. Those skilled in the art can routinely determine which residues comprise a particular hypervariable region or CDR of the human IgG subtype of antibody given the variable region amino acid sequence of the antibody.

TABLE I

CDR Definitions[1]

|  | Kabat | Chothia |
|---|---|---|
| VH CDR1 | 31-35 | 26-32 |
| VH CDR2 | 50-65 | 52-58 |
| VH CDR3 | 95-102 | 95-102 |
| VL CDR1 | 24-34 | 26-32 |
| VL CDR2 | 50-56 | 50-52 |
| VL CDR3 | 89-97 | 91-96 |

[1]Numbering of all CDR definitions in Table I is according to the numbering conventions set forth by Kabat et al. (see below).

Kabat et al. also defined a numbering system for variable domain sequences that is applicable to any antibody. One of ordinary skill in the art can unambiguously assign this system of "Kabat numbering" to any variable domain sequence, without reliance on any experimental data beyond the sequence itself. As used herein, "Kabat numbering" refers to the numbering system set forth by Kabat et al., U.S. Dept. of Health and Human Services, "Sequence of Proteins of Immunological Interest" (1983). Unless otherwise specified, references to the numbering of specific amino acid residue positions in an antibody or antigen-binding fragment, variant, or derivative thereof of the present invention are according to the Kabat numbering system, which however is theoretical and may not equally apply to every antibody of the present invention. For example, depending on the position of the first CDR the following CDRs might be shifted in either direction.

Antibodies or antigen-binding fragments, immunospecific fragments, variants, or derivatives thereof of the invention include, but are not limited to, polyclonal, monoclonal, multispecific, human, humanized, primatized, murinized or chimeric antibodies, single chain antibodies, epitope-binding fragments, e.g., Fab, Fab' and F(ab')$_2$, Fd, Fvs, single-chain Fvs (scFv), single-chain antibodies, disulfide-linked Fvs (sdFv), fragments comprising either a $V_L$ or $V_H$ domain, fragments produced by a Fab expression library, and anti-idiotypic (anti-Id) antibodies (including, e.g., anti-Id antibodies to antibodies disclosed herein). ScFv molecules are known in the art and are described, e.g., in U.S. Pat. No. 5,892,019. Immunoglobulin or antibody molecules of the invention can be of any type (e.g., IgG, IgE, IgM, IgD, IgA, and IgY), class (e.g., IgG1, IgG2, IgG3, IgG4, IgA1 and IgA2) or subclass of immunoglobulin molecule.

In one embodiment, the antibody of the present invention is not IgM or a derivative thereof with a pentavalent structure. Particular, in specific applications of the present invention, especially therapeutic use, IgMs are less useful than IgG and other bivalent antibodies or corresponding binding molecules since IgMs due to their pentavalent structure and lack of affinity maturation often show unspecific cross-reactivities and very low affinity.

In a particularly preferred embodiment, the antibody of the present invention is not a polyclonal antibody, i.e. it substantially consists of one particular antibody species rather than being a mixture obtained from a plasma immunoglobulin sample.

Antibody fragments, including single-chain antibodies, may comprise the variable region(s) alone or in combination with the entirety or a portion of the following: hinge region, CH1, CH2, and CH3 domains. Also included in the invention are SOD1 binding fragments which comprise any combination of variable region(s) with a hinge region, CH1, CH2, and CH3 domains. Antibodies or immunospecific fragments thereof of the present invention may be from any animal origin including birds and mammals. Preferably, the antibodies are human, murine, donkey, rabbit, goat, guinea pig, camel, llama, horse, or chicken antibodies. In another embodiment, the variable region may be condricthoid in origin (e.g., from sharks).

In one aspect, the antibody of the present invention is a human monoclonal antibody isolated from a human. Optionally, the framework region of the human antibody is aligned and adopted in accordance with the pertinent human germ line variable region sequences in the database; see, e.g., Vbase (http://vbase.mrc-cpe.cam.ac.uk/) hosted by the MRC Centre for Protein Engineering (Cambridge, UK). For example, amino acids considered to potentially deviate from the true germ line sequence could be due to the PCR primer sequences incorporated during the cloning process. Compared to artificially generated human-like antibodies such as single chain antibody fragments (scFvs) from a phage displayed antibody library or xenogeneic mice the human monoclonal antibody of the present invention is characterized by (i) being obtained using the human immune response rather than that of animal surrogates, i.e. the antibody has been generated in response to natural SOD1 in its relevant conformation in the human body, (ii) having protected the individual or is at least significant for the presence of SOD1, and (iii) since the antibody is of human origin the risks of cross-reactivity against self-antigens is minimized. Thus, in accordance with the present invention the terms "human monoclonal antibody", "human monoclonal autoantibody", "human antibody" and the like are used to denote an SOD1 binding molecule which is of human origin, i.e. which has been isolated from a human cell such as a B cell or hybridoma thereof or the cDNA of which has been directly cloned from mRNA of a human cell, for example a human memory B cell. A human antibody is still "human" even if amino acid substitutions are made in the antibody, e.g., to improve binding characteristics.

Antibodies derived from human immunoglobulin libraries or from animals transgenic for one or more human immunoglobulins and that do not express endogenous immunoglobulins, as described infra and, for example in, U.S. Pat. No. 5,939,598 by Kucherlapati et al., are denoted human-like antibodies in order distinguish them from truly human antibodies of the present invention.

For example, the paring of heavy and light chains of human-like antibodies such as synthetic and semi-synthetic antibodies typically isolated from phage display do not necessarily reflect the original paring as it occurred in the original human B cell. Accordingly Fab and scFv fragments obtained from recombinant expression libraries as commonly used in the prior art can be considered as being artificial with all possible associated effects on immunogenicity and stability.

In contrast, the present invention provides isolated affinity-matured antibodies from selected human subjects, which are characterized by their therapeutic utility and their tolerance in man.

As used herein, the term "murinized antibody" or "murinized immunoglobulin" refers to an antibody comprising one or more CDRs from a human antibody of the present invention; and a human framework region that contains amino acid substitutions and/or deletions and/or insertions that are based on a mouse antibody sequence. The human immunoglobulin providing the CDRs is called the "parent" or "acceptor" and the mouse antibody providing the framework changes is called the "donor". Constant regions need not be present, but if they are, they are usually substantially identical to mouse antibody constant regions, i.e. at least about 85-90%, preferably about 95% or more identical. Hence, in some embodiments, a full-length murinized human heavy or light chain immunoglobulin contains a mouse constant region, human CDRs, and a substantially human framework that has a number of "murinizing" amino acid substitutions. Typically, a "murinized antibody" is an antibody comprising a murinized variable light chain and/or a murinized variable heavy chain. For example, a murinized antibody would not encompass a typical chimeric antibody, e.g., because the entire variable region of a chimeric antibody is non-mouse. A modified antibody that has been "murinized" by the process of "murinization" binds to the same antigen as the parent antibody that provides the CDRs and is usually less immunogenic in mice, as compared to the parent antibody.

As used herein, the term "heavy chain portion" includes amino acid sequences derived from an immunoglobulin heavy chain. A polypeptide comprising a heavy chain portion comprises at least one of: a CH1 domain, a hinge (e.g., upper, middle, and/or lower hinge region) domain, a CH2 domain, a CH3 domain, or a variant or fragment thereof. For example, a binding polypeptide for use in the invention may comprise a polypeptide chain comprising a CH1 domain; a polypeptide chain comprising a CH1 domain, at least a portion of a hinge domain, and a CH2 domain; a polypeptide chain comprising a CH1 domain and a CH3 domain; a polypeptide chain comprising a CH1 domain, at least a portion of a hinge domain, and a CH3 domain, or a polypeptide chain comprising a CH1 domain, at least a portion of a hinge domain, a CH2 domain, and a CH3 domain. In another embodiment, a polypeptide of the invention comprises a polypeptide chain comprising a CH3 domain. Further, a binding polypeptide for use in the invention may lack at least a portion of a CH2 domain (e.g., all or part of a CH2 domain). As set forth above, it will be understood by one of ordinary skill in the art that these domains (e.g., the heavy chain portions) may be modified such that they vary in amino acid sequence from the naturally occurring immunoglobulin molecule.

In certain antibodies, or antigen-binding fragments, variants, or derivatives thereof disclosed herein, the heavy chain portions of one polypeptide chain of a multimer are identical to those on a second polypeptide chain of the multimer. Alternatively, heavy chain portion-containing monomers of the invention are not identical. For example, each monomer may comprise a different target binding site, forming, for example, a bispecific antibody or diabody.

In another embodiment, the antibodies, or antigen-binding fragments, variants, or derivatives thereof disclosed herein are composed of a single polypeptide chain such as scFvs and are to be expressed intracellularly (intrabodies) for potential in vivo therapeutic and diagnostic applications.

The heavy chain portions of a binding polypeptide for use in the diagnostic and treatment methods disclosed herein may be derived from different immunoglobulin molecules. For example, a heavy chain portion of a polypeptide may comprise a CH1 domain derived from an IgG1 molecule and a hinge region derived from an IgG3 molecule. In another example, a heavy chain portion can comprise a hinge region derived, in part, from an IgG1 molecule and, in part, from an IgG3 molecule. In another example, a heavy chain portion can comprise a chimeric hinge derived, in part, from an IgG1 molecule and, in part, from an IgG4 molecule.

As used herein, the term "light chain portion" includes amino acid sequences derived from an immunoglobulin light chain. Preferably, the light chain portion comprises at least one of a $V_L$ or CL domain.

The minimum size of a peptide or polypeptide epitope for an antibody is thought to be about four to five amino acids. Peptide or polypeptide epitopes preferably contain at least seven, more preferably at least nine and most preferably between at least about 15 to about 30 amino acids. Since a CDR can recognize an antigenic peptide or polypeptide in its tertiary form, the amino acids comprising an epitope need not be contiguous, and in some cases, may not even be on the same peptide chain. In the present invention, a peptide or polypeptide epitope recognized by antibodies of the present invention contains a sequence of at least 4, at least 5, at least 6, at least 7, more preferably at least 8, at least 9, at least 10, at least 15, at least 20, at least 25, or between about 15 to about 30 contiguous or non-contiguous amino acids of SOD1.

By "specifically binding", or "specifically recognizing", used interchangeably herein, it is generally meant that a binding molecule, e.g., an antibody binds to an epitope via its antigen-binding domain, and that the binding entails some complementarity between the antigen-binding domain and the epitope. According to this definition, an antibody is said to "specifically bind" to an epitope when it binds to that epitope, via its antigen-binding domain more readily than it would bind to a random, unrelated epitope. The term "specificity" is used herein to qualify the relative affinity by which a certain antibody binds to a certain epitope.

For example, antibody "A" may be deemed to have a higher specificity for a given epitope than antibody "B," or antibody "A" may be said to bind to epitope "C" with a higher specificity than it has for related epitope "D".

Where present, the term "immunological binding characteristics," or other binding characteristics of an antibody with an antigen, in all of its grammatical forms, refers to the specificity, affinity, cross-reactivity, and other binding characteristics of an antibody.

By "preferentially binding", it is meant that the binding molecule, e.g., antibody specifically binds to an epitope more readily than it would bind to a related, similar, homologous, or analogous epitope. Thus, an antibody which "preferentially binds" to a given epitope would more likely bind to that epitope than to a related epitope, even though such an antibody may cross-react with the related epitope.

By way of non-limiting example, a binding molecule, e.g., an antibody may be considered to bind a first epitope preferentially if it binds said first epitope with a dissociation constant ($K_D$) that is less than the antibody's $K_D$ for the second epitope. In another non-limiting example, an antibody may be considered to bind a first antigen preferentially if it binds the first epitope with an affinity that is at least one order of magnitude less than the antibody's $K_D$ for the second epitope. In another non-limiting example, an antibody may be considered to bind a first epitope preferentially if it binds the first epitope with an affinity that is at least two orders of magnitude less than the antibody's $K_D$ for the second epitope.

In another non-limiting example, a binding molecule, e.g., an antibody may be considered to bind a first epitope preferentially if it binds the first epitope with an off rate (k(off)) that is less than the antibody's k(off) for the second epitope. In another non-limiting example, an antibody may be considered to bind a first epitope preferentially if it binds the first epitope with an affinity that is at least one order of magnitude less than the antibody's k(off) for the second epitope. In another non-limiting example, an antibody may be considered to bind a first epitope preferentially if it binds the first epitope with an affinity that is at least two orders of magnitude less than the antibody's k(off) for the second epitope.

A binding molecule, e.g., an antibody or antigen-binding fragment, variant, or derivative disclosed herein may be said to bind SOD1 or a fragment or variant thereof with an off rate (k(off)) of less than or equal to $5 \times 10^{-2}$ sec$^{-1}$, $10^{-2}$ sec$^{-1}$, $5 \times 10^{-3}$ sec$^{-1}$ or $10^{-3}$ sec$^{-1}$. More preferably, an antibody of the invention may be said to bind SOD1 or a fragment or variant thereof with an off rate (k(off)) less than or equal to $5 \times 10^{-4}$ sec$^{-1}$, $10^{-4}$ sec$^{-1}$, $5 \times 10^{-5}$ sec$^{-1}$, or $10^{-5}$ sec$^{-1}$ $5 \times 10^{-6}$ sec$^{-1}$, $10^{-6}$ sec$^{-1}$, $5 \times 10^{-7}$ sec$^{-1}$ or $10^{-7}$ sec$^{-1}$.

A binding molecule, e.g., an antibody or antigen-binding fragment, variant, or derivative disclosed herein may be said to bind SOD1 or a fragment or variant thereof with an on rate (k(on)) of greater than or equal to $10^3$ M$^{-1}$ sec$^{-1}$, $5 \times 10^3$ M$^{-1}$ sec$^{-1}$, $10^4$ M$^{-1}$ sec$^{-1}$ or $5 \times 10^4$ M$^{-1}$ sec$^{-1}$. More preferably, an antibody of the invention may be said to bind SOD1 or a fragment or variant thereof with an on rate (k(on)) greater than or equal to $10^5$ M$^{-1}$ sec$^{-1}$, $5 \times 10^5$ M$^{-1}$ sec$^{-1}$, $10^6$ M$^{-1}$ sec$^{-1}$, or $5 \times 10^6$ M$^{-1}$ sec$^{-1}$ or $10^7$ M$^{-1}$ sec$^{-1}$.

A binding molecule, e.g., an antibody is said to competitively inhibit binding of a reference antibody to a given epitope if it preferentially binds to that epitope to the extent that it blocks, to some degree, binding of the reference antibody to the epitope. Competitive inhibition may be determined by any method known in the art, for example, competition ELISA assays. An antibody may be said to competitively inhibit binding of the reference antibody to a given epitope by at least 90%, at least 80%, at least 70%, at least 60%, or at least 50%.

As used herein, the term "affinity" refers to a measure of the strength of the binding of an individual epitope with the CDR of a binding molecule, e.g., an immunoglobulin molecule; see, e.g., Harlow et al., Antibodies: A Laboratory Manual, Cold Spring Harbor Laboratory Press, 2nd ed. (1988) at pages 27-28. As used herein, the term "avidity" refers to the overall stability of the complex between a population of immunoglobulins and an antigen, that is, the functional combining strength of an immunoglobulin mixture with the antigen; see, e.g., Harlow at pages 29-34. Avidity is related to both the affinity of individual immunoglobulin molecules in the population with specific epitopes, and also the valencies of the immunoglobulins and the antigen. For example, the interaction between a bivalent monoclonal antibody and an antigen with a highly repeating epitope structure, such as a polymer, would be one of high avidity. The affinity or avidity of an antibody for an antigen can be determined experimentally using any suitable method; see, for example, Berzofsky et al., "Antibody-Antigen Interactions" In *Fundamental Immunology*, Paul, W. E., Ed., Raven Press New York, N Y (1984), Kuby, Janis Immunology, W. H. Freeman and Company New York, N Y (1992), and methods described herein. General techniques for measuring the affinity of an antibody for an antigen include ELISA, RIA, and surface plasmon resonance. The measured affinity of a particular antibody-antigen interaction can vary if measured under different conditions, e.g., salt concentration, pH. Thus, measurements of affinity and other antigen-binding parameters, e.g., $K_D$, $IC_{50}$, are preferably made with standardized solutions of antibody and antigen, and a standardized buffer.

Binding molecules, e.g., antibodies or antigen-binding fragments, variants or derivatives thereof of the invention may also be described or specified in terms of their cross-reactivity. As used herein, the term "cross-reactivity" refers to the ability of an antibody, specific for one antigen, to react with a second antigen; a measure of relatedness between two different antigenic substances. Thus, an antibody is cross reactive if it binds to an epitope other than the one that induced its formation. The cross reactive epitope generally contains many of the same complementary structural features as the inducing epitope, and in some cases, may actually fit better than the original.

For example, certain antibodies have some degree of cross-reactivity, in that they bind related, but non-identical epitopes, e.g., epitopes with at least 95%, at least 90%, at least 85%, at least 80%, at least 75%, at least 70%, at least 65%, at least 60%, at least 55%, and at least 50% identity (as calculated using methods known in the art and described herein) to a reference epitope. An antibody may be said to have little or no cross-reactivity if it does not bind epitopes with less than 95%, less than 90%, less than 85%, less than 80%, less than 75%, less than 70%, less than 65%, less than 60%, less than 55%, and less than 50% identity (as calculated using methods known in the art and described herein) to a reference epitope. An antibody may be deemed "highly specific" for a certain epitope, if it does not bind any other analog, ortholog, or homolog of that epitope.

Binding molecules, e.g., antibodies or antigen-binding fragments, variants or derivatives thereof of the invention may also be described or specified in terms of their binding affinity to SOD1. Preferred binding affinities include those with a dissociation constant or Kd less than $5\times10^{-2}$M, $10^{-2}$M, $5\times10^{-3}$M, $10^{-3}$M, $5\times10^{-4}$M, $10^{-4}$M, $5\times10^{-5}$M, $10^{-5}$M, $5\times10^{-6}$M, $10^{-6}$M, $5\times10^{-7}$M, $10^{-7}$M, $5\times10^{-8}$M, $10^{-8}$M, $5\times10^{-9}$M, $10^{-9}$M, $5\times10^{-10}$M, $10^{-10}$M, $5\times10^{-11}$M, $10^{-11}$M, $5\times10^{-12}$M, $10^{-12}$M, $5\times10^{-13}$M, $10^{-13}$M, $5\times10^{-14}$M, $10^{-14}$M, $5\times10^{-15}$M, or $10^{-15}$M.

As previously indicated, the subunit structures and three dimensional configuration of the constant regions of the various immunoglobulin classes are well known. As used herein, the term "$V_H$ domain" includes the amino terminal variable domain of an immunoglobulin heavy chain and the term "CH1 domain" includes the first (most amino terminal) constant region domain of an immunoglobulin heavy chain. The CH1 domain is adjacent to the $V_H$ domain and is amino terminal to the hinge region of an immunoglobulin heavy chain molecule.

As used herein the term "CH2 domain" includes the portion of a heavy chain molecule that extends, e.g., from about residue 244 to residue 360 of an antibody using conventional numbering schemes (residues 244 to 360, Kabat numbering system; and residues 231-340, EU numbering system; see Kabat E A et al. op. cit). The CH2 domain is unique in that it is not closely paired with another domain. Rather, two N-linked branched carbohydrate chains are interposed between the two CH2 domains of an intact native IgG molecule. It is also well documented that the CH3 domain extends from the CH2 domain to the C-terminal of the IgG molecule and comprises approximately 108 residues.

As used herein, the term "hinge region" includes the portion of a heavy chain molecule that joins the CH1 domain to the CH2 domain. This hinge region comprises approximately 25 residues and is flexible, thus allowing the two N-terminal antigen-binding regions to move independently. Hinge regions can be subdivided into three distinct domains: upper, middle, and lower hinge domains; see Roux et al., J. Immunol. 161 (1998), 4083-4090.

As used herein the term "disulfide bond" includes the covalent bond formed between two sulfur atoms. The amino acid cysteine comprises a thiol group that can form a disulfide bond or bridge with a second thiol group. In most naturally occurring IgG molecules, the CH1 and CL regions are linked by a disulfide bond and the two heavy chains are linked by two disulfide bonds at positions corresponding to 239 and 242 using the Kabat numbering system (position 226 or 229, EU numbering system).

As used herein, the terms "linked", "fused" or "fusion" are used interchangeably. These terms refer to the joining together of two more elements or components, by whatever means including chemical conjugation or recombinant means. An "in-frame fusion" refers to the joining of two or more polynucleotide open reading frames (ORFs) to form a continuous longer ORF, in a manner that maintains the correct translational reading frame of the original ORFs. Thus, a recombinant fusion protein is a single protein containing two or more segments that correspond to polypeptides encoded by the original ORFs (which segments are not normally so joined in nature). Although the reading frame is thus made continuous throughout the fused segments, the segments may be physically or spatially separated by, for example, in-frame linker sequence. For example, polynucleotides encoding the CDRs of an immunoglobulin variable region may be fused, in-frame, but be separated by a polynucleotide encoding at least one immunoglobulin framework region or additional CDR regions, as long as the "fused" CDRs are co-translated as part of a continuous polypeptide.

The term "expression" as used herein refers to a process by which a gene produces a biochemical, for example, an RNA or polypeptide. The process includes any manifestation of the functional presence of the gene within the cell including, without limitation, gene knockdown as well as both transient expression and stable expression. It includes without limitation transcription of the gene into messenger RNA (mRNA), transfer RNA (tRNA), small hairpin RNA (shRNA), small interfering RNA (siRNA) or any other RNA product, and the translation of such mRNA into polypeptide(s). If the final desired product is a biochemical, expression includes the creation of that biochemical and any precursors. Expression of a gene produces a "gene product." As used herein, a gene product can be either a nucleic acid, e.g., a messenger RNA produced by transcription of a gene, or a polypeptide which is translated from a transcript. Gene products described herein further include nucleic acids with post transcriptional modifications, e.g., polyadenylation, or polypeptides with post translational modifications, e.g., methylation, glycosylation, the addition of lipids, association with other protein subunits, proteolytic cleavage, and the like.

As used herein, the term "sample" refers to any biological material obtained from a subject or patient. In one aspect, a sample can comprise blood, cerebrospinal fluid ("CSF"), or urine. In other aspects, a sample can comprise whole blood, plasma, B cells enriched from blood samples, and cultured cells (e.g., B cells from a subject). A sample can also include a biopsy or tissue sample including neural tissue. In still other aspects, a sample can comprise whole cells and/or a lysate of the cells. Blood samples can be collected by methods known in the art. In one aspect, the pellet can be resuspended by vortexing at 4° C. in 200 μl buffer (20 mM Tris, pH. 7.5, 0.5% Nonidet, 1 mM EDTA, 1 mM PMSF, 0.1M NaCl, IX Sigma Protease Inhibitor, and IX Sigma Phosphatase Inhibitors 1 and 2). The suspension can be kept on ice for 20 minutes with intermittent vortexing. After spinning at 15,000×g for 5 minutes at about 4° C., aliquots of supernatant can be stored at about −70° C.

As used herein, the terms "treat" or "treatment" refer to both therapeutic treatment and prophylactic or preventative measures, wherein the object is to prevent or slow down (lessen) an undesired physiological change or disorder, such as the development of amyotrophic lateral sclerosis (ALS). Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable.

"Treatment" can also mean prolonging survival as compared to expected survival if not receiving treatment. Those in need of treatment include those already with the condition or disorder as well as those prone to have the condition or disorder or those in which the manifestation of the condition or disorder is to be prevented.

By "subject" or "individual" or "animal" or "patient" or "mammal," is meant any subject, particularly a mammalian subject, e.g., a human patient, for whom diagnosis, prognosis, prevention, or therapy is desired.

II. Antibodies

The present invention generally relates to human anti-SOD1 antibodies and antigen-binding fragments thereof, which preferably demonstrate the immunological binding characteristics and/or biological properties as outlined for the antibodies illustrated in the Examples. In accordance with the present invention human monoclonal antibodies specific for SOD1 were cloned from a pool of healthy human subjects.

In the course of the experiments performed in accordance with the present invention antibodies in conditioned media of human memory B cell cultures were screened in parallel for binding to recombinant or misfolded/aggregated SOD1 protein—and bovine serum albumin (BSA). Only B-cell cultures that were positive for recombinant or misfolded/aggregated SOD1 but not for BSA were subjected to antibody cloning. In a second round of screening also B-cell cultures that were positive for aggregated SOD1 were subjected to antibody cloning.

Initial attempts to isolating to specific antibodies were focused at pools of healthy human subjects with high plasma binding activity to SOD1, suggestive of elevated levels of circulating SOD1 antibodies in plasma. Unexpectedly, these attempts failed to produce SOD1 specific human memory B cells and the antibodies described in the current invention were isolated from pools of healthy human subjects that were not preselected for high SOD1 plasma reactivity or had low plasma reactivity to SOD1.

Figure 2:
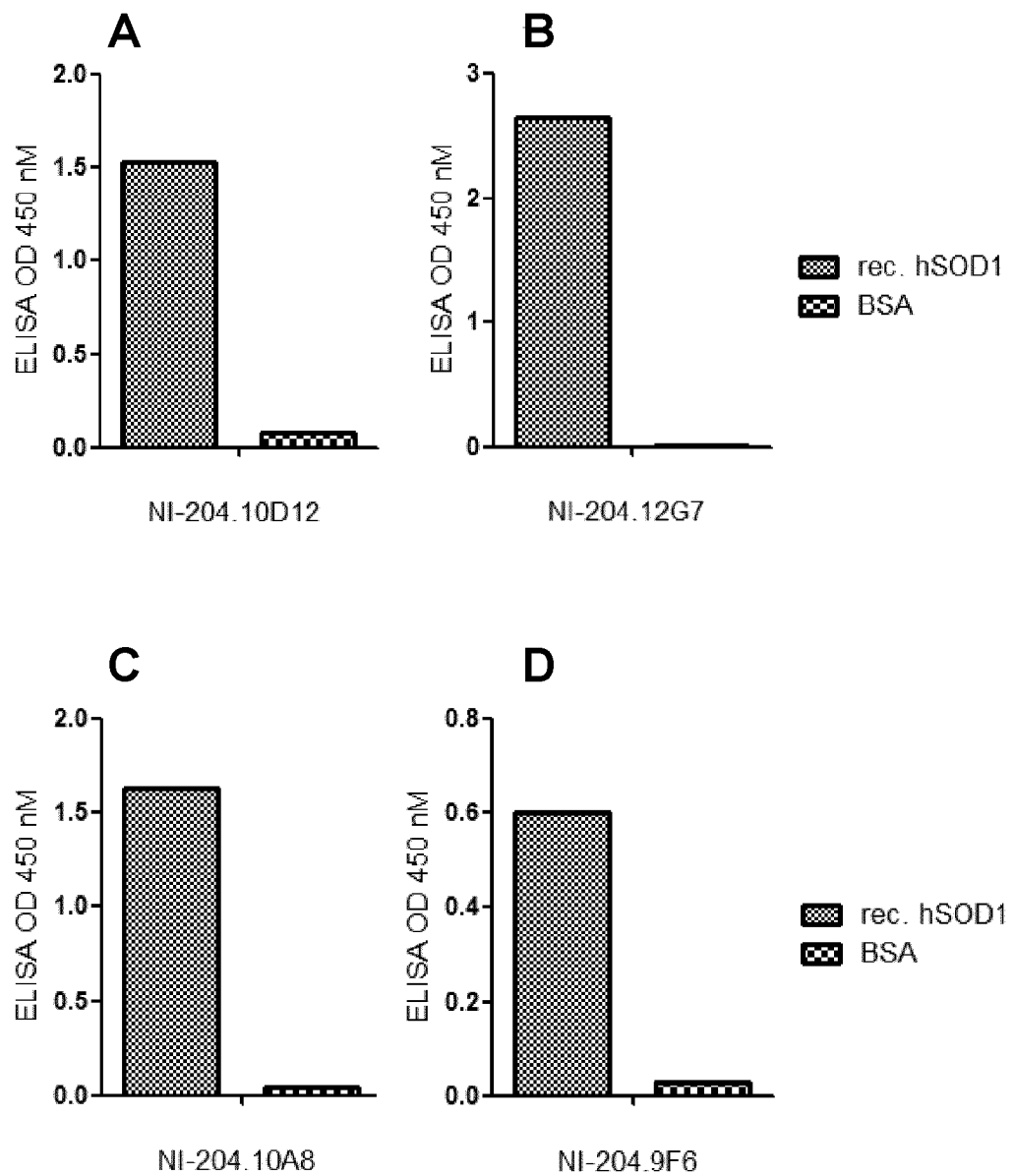
FIG. 2: Superoxide dismutase 1-binding specificity of human recombinant antibodies. (A) Specific binding of recombinant NI-204.10D12 to human SOD1 in direct ELISA. (B) Specific binding of recombinant NI-204.12G7 to human SOD1 in direct ELISA. (C) Specific binding of recombinant NI-204.10A8 to human SOD1 in direct ELISA. (D) Specific binding of recombinant NI-204.9F6 to human SOD1 in direct ELISA.
Figure 3:
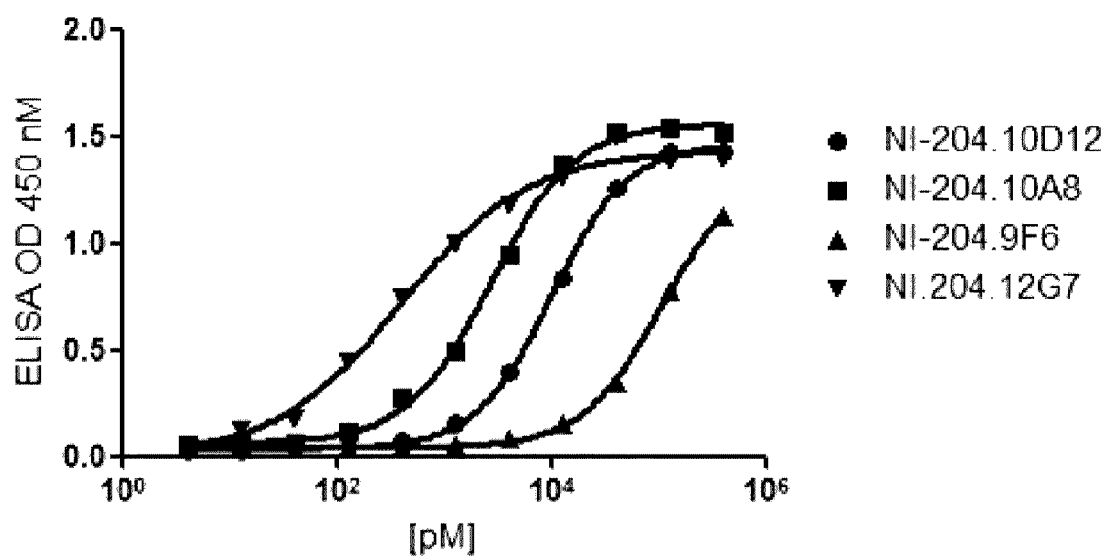
FIG. 3: $EC_{50}$ determination of the recombinant human-derived anti-SOD1 antibodies. (A) ELISA plates were coated with recombinant human SOD1 and incubated with the indicated concentrations of recombinant human-derived antibodies NI-204.10D12 (●), NI-204.10A8 (■), NI-204.9F6 (▲) or NI-204.12G7 (▼). The antibodies NI-204.10D12, NI-204.10A8 and NI-204.12G7 bind with high affinity to recombinant human SOD1 with an $EC_{50}$ of 10.0 nM, 2.7 nM and 0.4 nM, respectively. NI-204.9F6 binds to recombinant SOD1 with an $EC_{50}$ in the nanomolar range of 104.8 nM.
Figure 4:
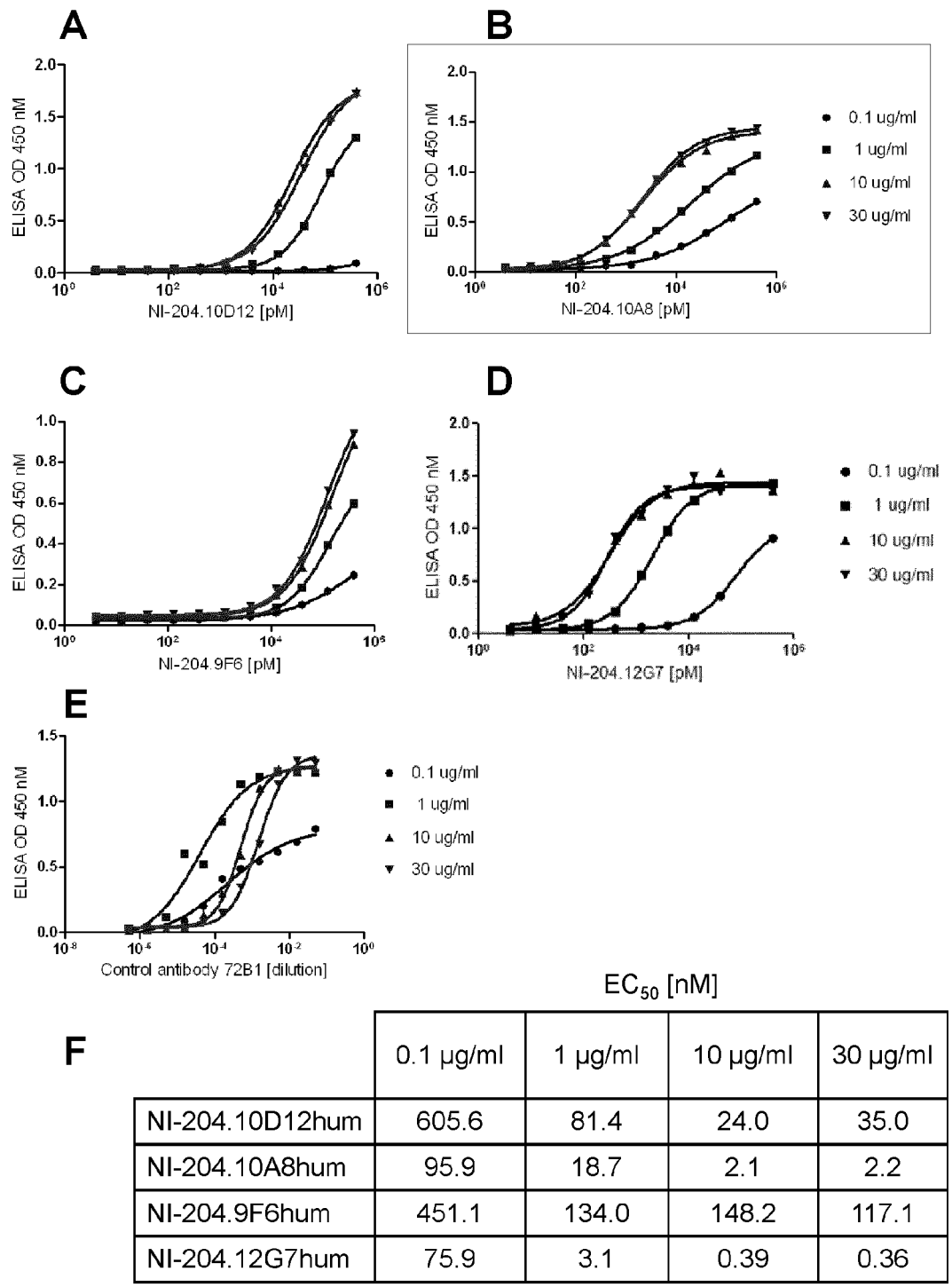
FIG. 4: $EC_{50}$ analysis at increasing coating concentrations of human SOD1 that favors the formation of conformational epitopes. Human antibodies NI-204.10D12 (A), NI-204.10A8 (B), NI-204.9F6 (C) and NI-204.12G7 (D) $EC_{50}$ determination and murine monoclonal antibody SOD-1 72B1 binding affinity (E) for recombinant human SOD1 at increasing coating concentration (▼30 µg/ml; ▲10 µg/ml; ■1 µg/ml; ●0.1 µg/ml; coating concentration of recombinant human SOD1) using direct ELISA. Determined $EC_{50}$ values are indicated in Table (F) below. NI-204.10D12 antibody (A) and NI-204.12G7 antibody (D) preferentially target an epitope of human SOD1 that is most probably exposed or formed at high coating concentrations and concomitant misfolding or aggregation of recombinant human SOD1. Both NI-204.10A8 (B) and the NI-204.9F6 antibody (C) recognize an epitope of human SOD1 that is present both in the physiological protein conformation as well as in the misfolded/aggregated SOD1.
Figure 5:
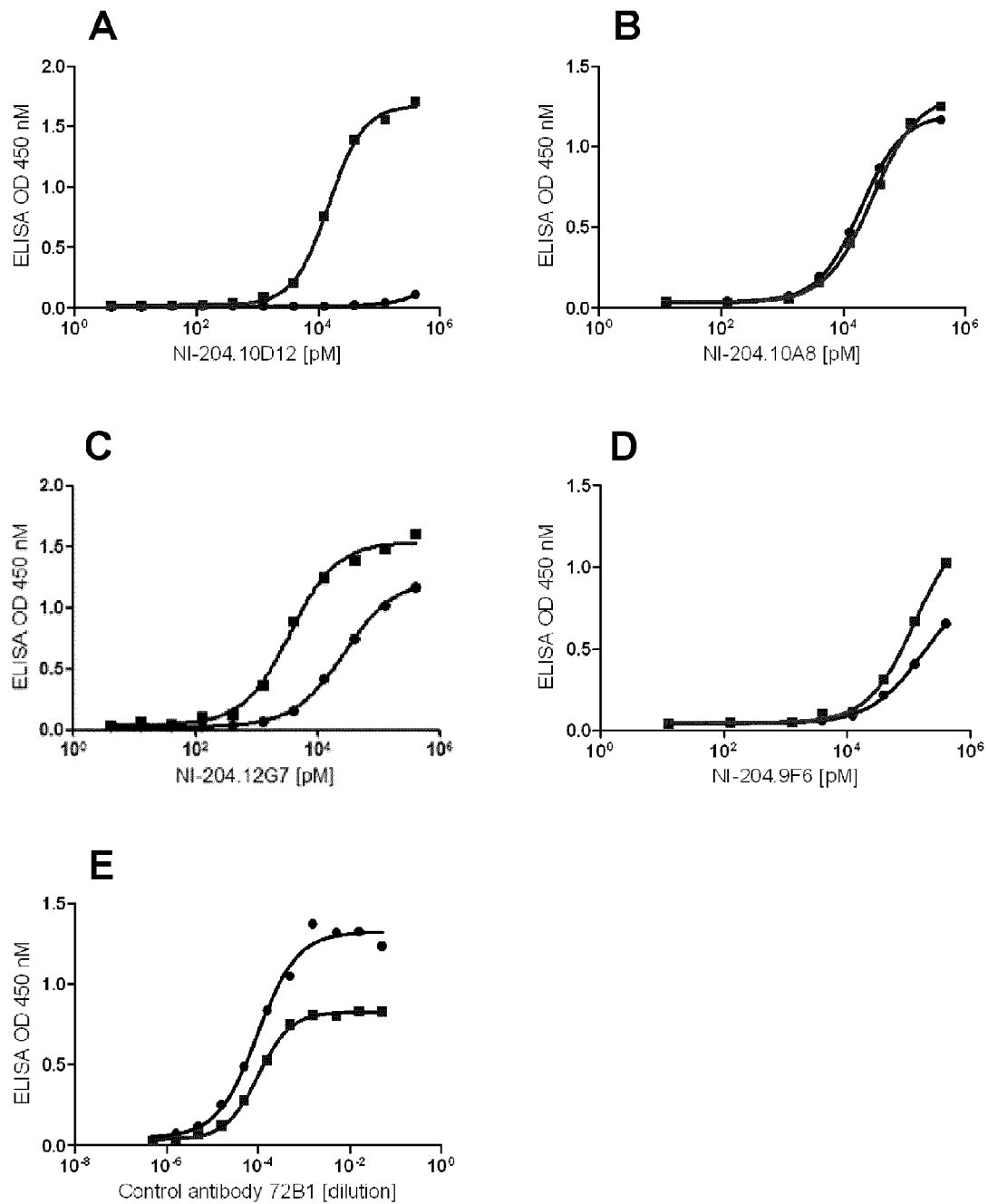
FIG. 5: NI-204.10D12, NI-204.10A8, NI-204.12G7 and NI-204.9F6 $EC_{50}$ determination and SOD-1 72B1 binding affinity for superoxide dismutase 1 aggregates (■) and physiological dimers (●) using direct ELISA. (A) High affinity binding of recombinant NI-204.10D12 to misfolded/aggregated human SOD1 but not to physiological human SOD1 dimers. (B) High affinity binding of NI-204.10A8 to both human physiological SOD1 dimers and misfolded/aggregated human SOD1. (C) High affinity binding of recombinant NI-204.12G7 to misfolded/aggregated human SOD1 but not to physiological human SOD1 dimers. (D) Slightly preferential binding of recombinant NI-204.9F6 to misfolded/aggregated human SOD1. (E) No preferential binding to misfolded/aggregated human SOD1 of the commercially available SOD-1 72B1 antibody.
Figure 9:
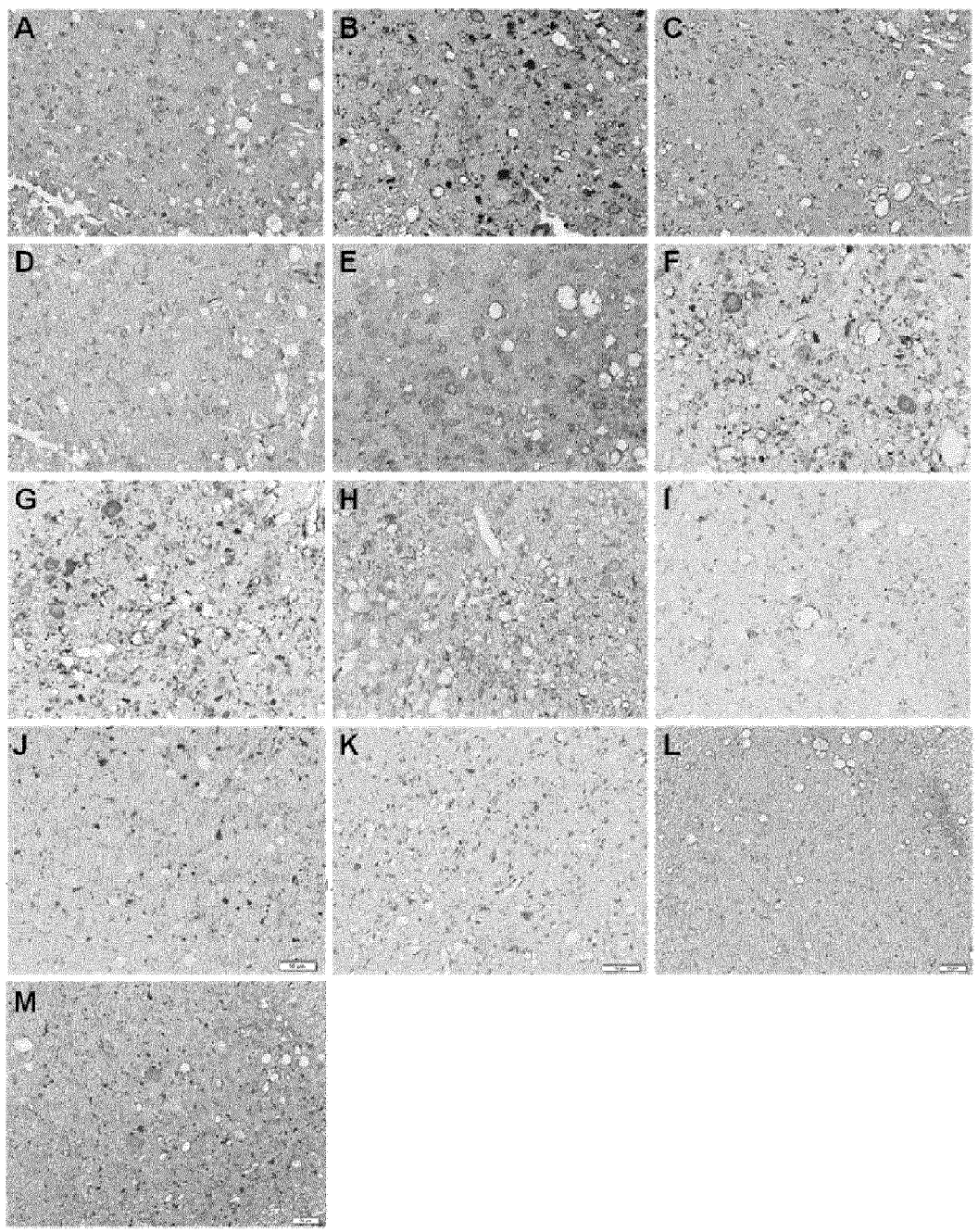
FIG. 9: Immunohistochemical analysis of B6.Cg-Tg (SOD1*G93A)1Gur/J transgenic spinal cords at terminal stage of disease. Detection of SOD1 pathology and/or physiological SOD1 in the spinal cord of B6.Cg-Tg(SOD1*G93A) 1Gur/J transgenic animal at terminal stage of disease with NI-204.10D12, 50 nM (A); NI-204-12G7, 5 nM (B); NI-204.11F11, 5 nM (C); NI-204.10A8, 50 nM (D); NI-204.67E12, 5 nM (E); NI.204.6H1, 5 nM (F); NI.204.12G3, 50 nM (G); NI.204.7G5, 50 nM (H); NI.204.25H3, 50 nM (I); NI.204.34A3, 50 nM (J); NI.204.7B3, 50 nM (K) and the control antibodies C4F6 (L) and B8H10 (M).

Due to this measure, several antibodies could be isolated. Selected antibodies were further analyzed for class and light chain subclass determination. Selected relevant antibody messages from memory B cell cultures are then transcribed by RT-PCR, cloned and combined into expression vectors for recombinant production; see the appended Examples. Recombinant expression of the human antibodies in HEK293 or CHO cells and the subsequent characterization of their binding specificities towards human recombinant SOD1 (FIG. 2 and FIG. 3), and their distinctive binding to pathologically misfolded/aggregated forms thereof (FIG. 4 to FIG. 6) confirmed that for the first time human antibodies have been cloned that are highly specific for SOD1 and recognize distinctive the pathologically misfolded/aggregated forms of SOD1 protein. A second round of experiments confirmed the above findings as shown in FIG. 9. See as well Table III summarizing the information concerning the binding affinities of the antibodies of the present invention.

Thus, the present invention generally relates to an isolated naturally occurring human monoclonal anti-SOD1 antibody and binding fragments, derivatives and variants thereof. In one embodiment of the invention, the antibody is capable of specifically binding full-length recombinant SOD1 and/or the pathologically misfolded/aggregated forms of recombinant SOD1 (see FIG. 4 and Example 2), aggregates of physiological SOD1-dimers (see FIG. 5 and Example 3) and SOD1 aggregates in vivo (see FIG. 6 and Example 4). In one embodiment the antibody of the present invention binds specifically the C-terminus of SOD1. In another embodiment the antibody of the present invention binds specifically the N-terminus of SOD1. In a further embodiment the antibody of the present invention binds specifically the central domain of SOD1 (see Example 5 and Table IV for a summary).

In one embodiment, the present invention is directed to an anti-SOD1 antibody, or antigen-binding fragment, variant or derivatives thereof, where the antibody specifically binds to the same epitope of SOD1 as a reference antibody selected from the group consisting of NI-204.10D12, NI-204.10A8, NI-204.12G7, NI-204.9F6, NI-204.11F11, NI-204.67E12, NI-204.6H1, NI-204.12G3, NI-204.7G5, NI-204.7B3, NI-204.34A3 and NI-204.25H3. Epitope mapping identified a sequence within the microtubule binding domain of human SOD1 including aa 93-99 DGVADVS (SEQ ID NO: 2) as the unique linear epitope recognized by antibody NI-204.10D12 of this invention. Epitope mapping identified a sequence within the SOD1 N-terminal domain including aa 10-60 in which the epitope recognized by antibody NI-204.10A8 of this invention is localized. Further mapping confined the epitope recognized by antibody NI-204.10A8 of this invention to the sequence including aa 9-55 LKGDGPVQGIIN-FEQKESNGPVKVWGSIKGLTEGLHGFHVHEFGDNT (SEQ ID NO: 52). As described in detail in Example 5 and Table IV therein, the epitopes of the following antibodies of the present invention have been mapped as well and are localized within the SOD-1 sequence including: for antibody NI-204.12G7 aa 73-83 GGPKDEERHVG (SEQ ID NO: 51); for antibody NI-204.11F11 aa 113-119 IIGRTLV (SEQ ID NO: 53); for antibody NI-204.6H1 aa 85-95 LGNVTAD-KDGV (SEQ ID NO: 54); for antibody NI-204.12G3 aa 121-135 HEKADDLGKGGNEES (SEQ ID NO: 55); for antibody NI-204.7G5 aa 101-107 EDSVISL (SEQ ID NO: 56); for antibody NI-204.7B3 aa 137-143 KTGNAGS (SEQ ID NO: 57); for antibody NI-204.34A3 aa 85-95 LGNVTAD-KDGV (SEQ ID NO: 58); and for antibody NI-204.25H3 aa 73-79 GGPKDEE (SEQ ID NO: 59).

Most advantageously, the epitope recognized by the antibody NI-204.10D12 of this invention is highly conserved in other species, such as mouse and rat as well providing an additional research tool in respective animal models with the antibodies of the present invention.

Figure 6:
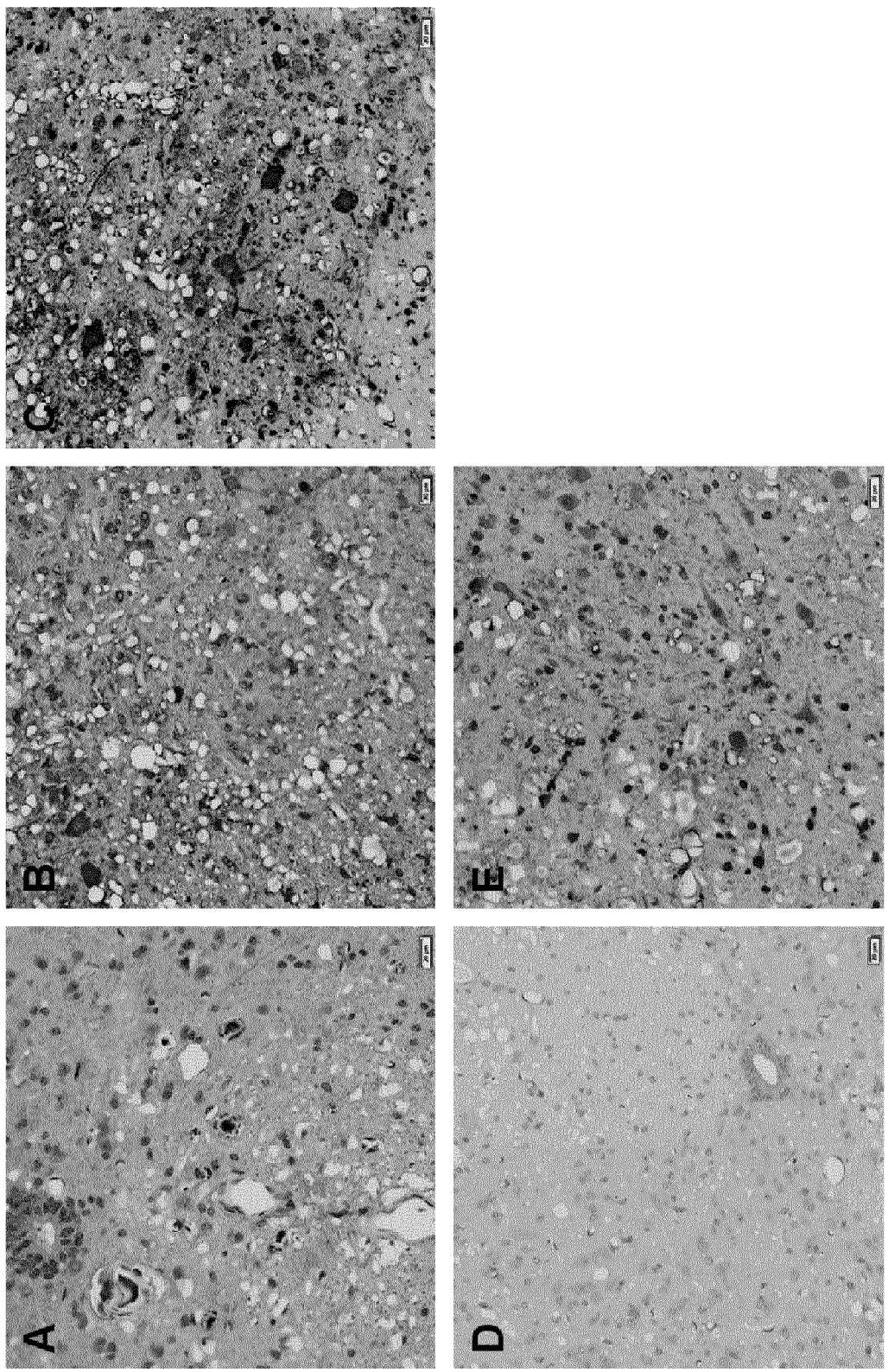
FIG. 6: NI-204.10D12, NI-204.10A8, NI-204.12G7 and NI-209.9F6 recognize pathological superoxide dismutase 1 aggregates in SOD1G93A transgenic mouse models. Immunohistochemical analysis shows a detection of SOD1 pathology and/or physiological SOD1 in the spinal cord of B6.Cg-Tg(SOD1*G93A)1Gur/J transgenic animals at terminal stage of disease with chimeric NI-204.10D12 (A); with human NI-204-10A8 (B), with human NI-204.12G7 (C), with human NI-204.9F6 (D) and with EPR1726 anti-SOD1 (E) antibodies.

Furthermore, without intending to be bound by initial experimental observations as demonstrated in the Example 4 and shown in FIG. 6, the human monoclonal NI-204.10D12 and NI-204.12G7 anti-SOD1 antibodies of the present invention are preferably characterized in specifically binding pathologically misfolded/aggregated SOD1 and not substantially recognizing SOD1 in the physiological form in spinal cord tissue. Hence, the present invention provides a set of human SOD1 antibodies with binding specificities, which are thus particularly useful for diagnostic and therapeutic purposes. For further details and a summarizing overview in respect of binding specificities of the present invention see also FIG. 9 and Table III.

In one embodiment, the antibody of the present invention exhibits the binding properties of the exemplary NI-204.10D12 antibody as described in the Examples. In addition, or alternatively, the SOD1 antibody of the present invention preferentially recognizes pathologically misfolded/aggregated SOD1 rather than physiological SOD1 dimers, in particular when analyzed according to Examples 3 and 4. In addition, or alternatively, the anti-SOD1 antibody of the present invention binds to disease causing mutants of human SOD1, in particular those described in Example 4. In this context, the binding specificities may be in the range as shown for the exemplary NI-204.10D12, NI-204.10A8, NI-204.12G7 and NI-204.9F6 antibodies in FIG. 3, respective FIG. 4, i.e. having half maximal effective concentrations (EC50) of about 10 pM to 100 nM, most preferably an EC50 of about 100 pM to 10 nM for wild-type SOD1 as shown for NI-204.10D12 and NI-204.10A8, or an EC50 of about 10 pM to 1 nM for wild-type SOD1 as shown for NI-204.12G7. In addition or alternatively the binding specificities may be in the range as shown for the exemplary antibodies of the present invention in Example 8 and Table III therein, i.e. having half maximal effective concentrations (EC50) for wild-type (recombinant) SOD1 of about 10 pM to 100 nM, most preferably an EC50 of about 100 pM to 75 nM as shown for NI-204.7G5 and NI-204.7B3; of about 10 pM to 100 nM, most preferably an EC50 of about 100 pM to 10 nM as shown for NI-204.6H1 and NI-204.34A3; or of about 100 pM to 10 nM, most preferably an EC50 of about 10 pM to 1 nM as shown for NI-204.11F11, NI-204.67E12, NI-204.12G3 and NI-204.25H3.

Some purified antibodies bind to a wide array of biomolecules, e.g., proteins. As the skilled artisan will appreciate, the term specific is used herein to indicate that other biomolecules than SOD-1 proteins or fragments thereof do not significantly bind to the antigen-binding molecule, e.g., one of the antibodies of the present invention. Preferably, the level of binding to a biomolecule other than SOD-1 results in a binding affinity which is at most only 20% or less, 10% or less, only 5% or less, only 2% or less or only 1% or less (i.e. at least 5, 10, 20, 50 or 100 fold lower) of the affinity to SOD-1, respectively.

Hence, the anti-SOD1 antibody of the present invention preferably binds preferentially to pathological forms of SOD1, e.g., pathological misfolded/aggregated SOD1 as exemplified by direct ELISA in Example 3 and in spinal cord by immunohistochemical staining described in Example 4. In another embodiment the anti-SOD1 antibody of the present invention preferentially binds to both recombinant SOD1 and pathologically misfolded/aggregated forms of SOD1 as exemplified in Example 2 and Example 3 by direct ELISA.

As mentioned before, SOD1 aggregates can also be found associated with amyloid senile plaques and neurofibrillary tangles of AD patients. Therefore, in one embodiment the antibody of the present invention may be useful in treatment of the Alzheimer's Disease.

The present invention is also drawn to an antibody, or antigen-binding fragment, variant or derivatives thereof, where the antibody comprises an antigen-binding domain identical to that of an antibody selected from the group consisting of NI-204.10D12, NI-204.10A8, NI-204.12G7, NI-204.9F6, NI-204.11F11, NI-204.67E12, NI-204.6H1, NI-204.12G3, NI-204.7G5, NI-204.7B3, NI-204.34A3 and NI-204.25H3.

The present invention further exemplifies several such binding molecules, e.g. antibodies and binding fragments thereof, which may be characterized by comprising in their variable region, e.g. binding domain at least one complementarity determining region (CDR) of the $V_H$ and/or $V_L$ variable region comprising any one of the amino acid sequences depicted in FIG. 1. The corresponding nucleotide sequences encoding the above-identified variable regions are set forth in Table II below. An exemplary set of CDRs of the above amino acid sequences of the $V_H$ and/or $V_L$ region as depicted in FIG. 1. However, as discussed in the following the person skilled in the art is well aware of the fact that in addition or alternatively CDRs may be used, which differ in their amino acid sequence from those set forth in FIG. 1 by one, two, three or even more amino acids in case of CDR2 and CDR3.

In one embodiment, the antibody of the present invention is any one of the antibodies comprising an amino acid sequence of the $V_H$ and/or $V_L$ region as depicted in FIG. 1. Preferably, the antibody of the present invention is characterized by the preservation of the cognate pairing of the heavy and light chain as was present in the human B-cell.

Alternatively, the antibody of the present invention is an antibody or antigen-binding fragment, derivative or variant thereof, which competes for binding to SOD1 with at least one of the antibodies having the $V_H$ and/or $V_L$ region as depicted in FIG. 1. Those antibodies may be human as well, in particular for therapeutic applications. Alternatively, the antibody is a murine, murinized and chimeric murine-human antibody, which are particularly useful for diagnostic methods and studies in animals.

In one embodiment the antibody of the present invention is provided by cultures of single or oligoclonal B-cells that are cultured and the supernatant of the culture, which contains antibodies produced by said B-cells, is screened for presence and affinity of anti-SOD1 antibodies therein. The screening process comprises the steps of a sensitive tissue amyloid plaque immunoreactivity (TAPIR) assay such as described in international application WO2004/095031, the disclosure content of which is incorporated herein by reference; screen on brain and spinal cord sections for binding to aggregated SOD1 such as described in international application WO2008/081008; screening for binding of a peptide derived from SOD1 of the amino acid sequence represented by SEQ ID NO: 1; a screen for binding of recombinant human SOD1 of the amino acid sequence represented by SEQ ID NO: 1; a screen for binding of aggregates of physiological SOD1-dimers of the amino acid sequence represented SEQ ID NO: 1 and isolating the antibody for which binding is detected or the cell producing said antibody.

Figure 7:
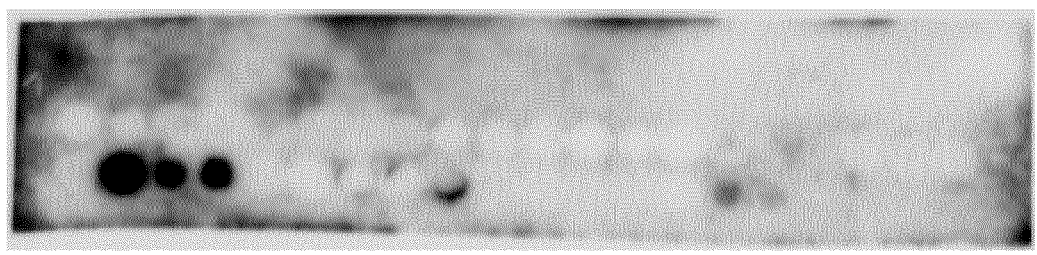
FIG. 7: NI.204.10D12 binds to the central domain of human SOD1 as assessed by pepscan analysis. Antibody binding occurs at peptides covering amino acids 85-107. The NI.204.10D12 binding epitope comprises accordingly amino acids 93-99 with the sequence DGVADVS (SEQ ID NO: 2).

As mentioned above, due to its generation upon a human immune response the human monoclonal antibody of the present invention will recognize epitopes which are of particular pathological relevance and which might not be accessible or less immunogenic in case of immunization processes for the generation of, for example, mouse monoclonal antibodies and in vitro screening of phage display libraries, respectively. Accordingly, it is prudent to stipulate that the epitope of the human anti-SOD1 antibody of the present invention is unique and no other antibody which is capable of binding to the epitope recognized by the human monoclonal antibody of the present invention exists; see also FIG. 7 which shows the unique epitope of antibody NI-204.10D12 and Table IV showing the unique epitopes of the antibodies NI-204.10A8, NI-204.12G7, NI-204.11F11, NI-204.6H1, NI-204.12G3, NI-204.7G5, NI-204.7B3, NI-204.34A3 and NI-204.25H3.

Therefore, the present invention also extends generally to anti-SOD1 antibodies and SOD1 binding molecules which compete with the human monoclonal antibody of the present invention for specific binding to SOD1. The present invention is more specifically directed to an antibody, or antigen-binding fragment, variant or derivatives thereof, where the antibody specifically binds to the same epitope of SOD1 as a reference antibody selected from the group consisting of NI-204.10D12, NI-204.12G7, NI-204.10A8, NI-204.9F6, NI-204.11F11, NI-204.67E12, NI-204.6H1, NI-204.12G3, NI-204.7G5, NI-204.7B3, NI-204.34A3 and NI-204.25H3.

Competition between antibodies is determined by an assay in which the immunoglobulin under test inhibits specific binding of a reference antibody to a common antigen, such as SOD1. Numerous types of competitive binding assays are known, for example: solid phase direct or indirect radioimmunoassay (MA), solid phase direct or indirect enzyme immunoassay (EIA), sandwich competition assay; see Stahli et al., Methods in Enzymology 9 (1983), 242-253; solid phase direct biotin-avidin EIA; see Kirkland et al., J. Immunol. 137 (1986), 3614-3619 and Cheung et al., Virology 176 (1990), 546-552; solid phase direct labeled assay, solid phase direct labeled sandwich assay; see Harlow and Lane, Antibodies, A Laboratory Manual, Cold Spring Harbor Press (1988); solid phase direct label RIA using $I^{125}$ label; see Morel et al, Molec. Immunol. 25 (1988), 7-15 and Moldenhauer et al., Scand. J. Immunol. 32 (1990), 77-82. Typically, such an assay involves the use of purified SOD1 or aggregates thereof bound to a solid surface or cells bearing either of these, an unlabelled test immunoglobulin and a labeled reference immunoglobulin, i.e. the human monoclonal antibody of the present invention. Competitive inhibition is measured by determining the amount of label bound to the solid surface or cells in the presence of the test immunoglobulin. Usually the test immunoglobulin is present in excess. Preferably, the competitive binding assay is performed under conditions as described for the ELISA assay in the appended Examples. Antibodies identified by competition assay (competing antibodies) include antibodies binding to the same epitope as the reference antibody and antibodies binding to an adjacent epitope sufficiently proximal to the epitope bound by the reference antibody for steric hindrance to occur. Usually, when a competing antibody is present in excess, it will inhibit specific binding of a reference antibody to a common antigen by at least 50% or 75%. Hence, the present invention is further drawn to an antibody, or antigen-binding fragment, variant or derivatives thereof, where the antibody competitively inhibits a reference antibody selected from the group consisting of NI-204.10D12, NI-204.12G7, NI-204.10A8, NI-204.9F6, NI-204.11F11, NI-204.67E12, NI-204.6H1, NI-204.12G3, NI-204.7G5, NI-204.7B3, NI-204.34A3 and NI-204.25H3 from binding to SOD1.

In another embodiment, the present invention provides an isolated polypeptide comprising, consisting essentially of, or consisting of an immunoglobulin heavy chain variable region ($V_H$), where at least one of $V_H$-CDRs of the heavy chain variable region or at least two of the $V_H$-CDRs of the heavy chain variable region are at least 80%, 85%, 90% or 95% identical to reference heavy chain $V_H$-CDR1, $V_H$-CDR2 or $V_H$-CDR3 amino acid sequences from the antibodies disclosed herein. Alternatively, the $V_H$-CDR1, $V_H$-CDR2 and $V_H$-CDR3 regions of the $V_H$ are at least 80%, 85%, 90% or 95% identical to reference heavy chain $V_H$-CDR1, $V_H$-CDR2 and $V_H$-CDR3 amino acid sequences from the antibodies disclosed herein. Thus, according to this embodiment a heavy chain variable region of the invention has $V_H$-CDR1, $V_H$-CDR2 and $V_H$-CDR3 polypeptide sequences related to the groups shown in FIG. 1. While FIG. 1 shows $V_H$-CDRs defined by the Kabat system, other CDR definitions, e.g., $V_H$-CDRs defined by the Chothia system, are also included in the present invention, and can be easily identified by a person of ordinary skill in the art using the data presented in FIG. 1.

In another embodiment, the present invention provides an isolated polypeptide comprising, consisting essentially of, or consisting of an immunoglobulin heavy chain variable region ($V_H$) in which the $V_H$-CDR1, $V_H$-CDR2 and $V_H$-CDR3 regions have polypeptide sequences which are identical to the $V_H$-CDR1, $V_H$-CDR2 and $V_H$-CDR3 groups shown in FIG. 1.

In another embodiment, the present invention provides an isolated polypeptide comprising, consisting essentially of, or consisting of an immunoglobulin heavy chain variable region ($V_H$) in which the $V_H$-CDR1, $V_H$-CDR2 and $V_H$-CDR3 regions have polypeptide sequences which are identical to the $V_H$-CDR1, $V_H$-CDR2 and $V_H$-CDR3 groups shown in FIG. 1, except for one, two, three, four, five, or six amino acid substitutions in any one $V_H$-CDR. In certain embodiments the amino acid substitutions are conservative.

In another embodiment, the present invention provides an isolated polypeptide comprising, consisting essentially of, or consisting of an immunoglobulin light chain variable region ($V_L$), where at least one of the $V_L$-CDRs of the light chain variable region or at least two of the $V_L$-CDRs of the light chain variable region are at least 80%, 85%, 90% or 95% identical to reference light chain $V_L$-CDR1, $V_L$-CDR2 or $V_L$-CDR3 amino acid sequences from antibodies disclosed herein. Alternatively, the $V_L$-CDR1, $V_L$-CDR2 and $V_L$-CDR3 regions of the $V_L$ are at least 80%, 85%, 90% or 95% identical to reference light chain $V_L$-CDR1, $V_L$-CDR2 and $V_L$-CDR3 amino acid sequences from antibodies disclosed herein. Thus, according to this embodiment a light chain variable region of the invention has $V_L$-CDR1, $V_L$-CDR2 and $V_L$-CDR3 polypeptide sequences related to the polypeptides shown in FIG. 1. While FIG. 1 shows $V_L$-CDRs defined by the Kabat system, other CDR definitions, e.g., $V_L$-CDRs defined by the Chothia system, are also included in the present invention.

In another embodiment, the present invention provides an isolated polypeptide comprising, consisting essentially of, or consisting of an immunoglobulin light chain variable region ($V_L$) in which the $V_L$-CDR1, $V_L$-CDR2 and $V_L$-CDR3 regions have polypeptide sequences which are identical to the $V_L$-CDR1, $V_L$-CDR2 and $V_L$-CDR3 groups shown in FIG. 1.

In another embodiment, the present invention provides an isolated polypeptide comprising, consisting essentially of, or consisting of an immunoglobulin heavy chain variable region ($V_L$) in which the $V_L$-CDR1, $V_L$-CDR2 and $V_L$-CDR3 regions have polypeptide sequences which are identical to the $V_L$-CDR1, $V_L$-CDR2 and $V_L$-CDR3 groups shown in FIG. 1, except for one, two, three, four, five, or six amino acid substitutions in any one $V_L$-CDR. In certain embodiments the amino acid substitutions are conservative.

An immunoglobulin or its encoding cDNA may be further modified. Thus, in a further embodiment the method of the present invention comprises any one of the step(s) of producing a chimeric antibody, murinized antibody, single-chain antibody, Fab-fragment, bispecific antibody, fusion antibody, labeled antibody or an analog of any one of those. Corresponding methods are known to the person skilled in the art and are described, e.g., in Harlow and Lane "Antibodies, A Laboratory Manual", CSH Press, Cold Spring Harbor (1988). When derivatives of said antibodies are obtained by the phage display technique, surface plasmon resonance as employed in the BIAcore system can be used to increase the efficiency of phage antibodies which bind to the same epitope as that of any one of the antibodies described herein (Schier, Human Antibodies Hybridomas 7 (1996), 97-105; Malmborg, J. Immunol. Methods 183 (1995), 7-13). The production of chimeric antibodies is described, for example, in international application WO89/09622. Methods for the production of humanized antibodies are described in, e.g., European application EP-A1 0 239 400 and international application WO90/07861. Further sources of antibodies to be utilized in accordance with the present invention are so-called xenogeneic antibodies. The general principle for the production of xenogeneic antibodies such as human-like antibodies in mice is described in, e.g., international applications WO91/10741, WO94/02602, WO96/34096 and WO 96/33735. As discussed above, the antibody of the invention may exist in a variety of forms besides complete antibodies; including, for example, Fv, Fab and F(ab)$_2$, as well as in single chains; see e.g. international application WO88/09344.

The antibodies of the present invention or their corresponding immunoglobulin chain(s) can be further modified using conventional techniques known in the art, for example, by using amino acid deletion(s), insertion(s), substitution(s), addition(s), and/or recombination(s) and/or any other modification(s) known in the art either alone or in combination. Methods for introducing such modifications in the DNA sequence underlying the amino acid sequence of an immunoglobulin chain are well known to the person skilled in the art; see, e.g., Sambrook, *Molecular Cloning A Laboratory Manual*, Cold Spring Harbor Laboratory (1989) N.Y. and Ausubel, *Current Protocols in Molecular Biology*, Green Publishing Associates and Wiley Interscience, N.Y. (1994). Modifications of the antibody of the invention include chemical and/or enzymatic derivatizations at one or more constituent amino acids, including side chain modifications, backbone modifications, and N- and C-terminal modifications including acetylation, hydroxylation, methylation, amidation, and the attachment of carbohydrate or lipid moieties, cofactors, and the like. Likewise, the present invention encompasses the production of chimeric proteins which comprise the described antibody or some fragment thereof at the amino terminus fused to heterologous molecule such as an immunostimulatory ligand at the carboxyl terminus; see, e.g., international application WO00/30680 for corresponding technical details.

Additionally, the present invention encompasses peptides including those containing a binding molecule as described above, for example containing the CDR3 region of the variable region of any one of the mentioned antibodies, in particular CDR3 of the heavy chain since it has frequently been observed that heavy chain CDR3 (HCDR3) is the region having a greater degree of variability and a predominant participation in antigen-antibody interaction. Such peptides may easily be synthesized or produced by recombinant means to produce a binding agent useful according to the invention. Such methods are well known to those of ordinary skill in the art. Peptides can be synthesized for example, using automated peptide synthesizers which are commercially available. The peptides can also be produced by recombinant techniques by incorporating the DNA expressing the peptide into an expression vector and transforming cells with the expression vector to produce the peptide.

Hence, the present invention relates to any binding molecule, e.g., an antibody or binding fragment thereof which is oriented towards the human anti-SOD1 antibodies of the present invention and display the mentioned properties, i.e. which specifically recognize SOD1. Such antibodies and binding molecules can be tested for their binding specificity and affinity by ELISA and immunohistochemistry as described herein, see, e.g., the Examples. These characteristics of the antibodies and binding molecules can be tested by Western Blot as well. Preliminary results of subsequent experiments performed in accordance with the present invention revealed that the human anti-SOD1 antibody of the present invention, in particular antibody NI-204.10D12 and NI-204.12G7 were able to differentially bind to SOD1 pathologies in transgenic mouse overexpressing human G93A SOD1. NI-204.10D12 and NI-204.12G7 show strong binding preference to pathologically misfolded/aggregated SOD1 in neurofilament-rich spheroids, similar to those seen in human amyotrophic lateral sclerosis, that are more frequently found in the anterior horn and in the anterior and lateral columns of the white matter than in the posterior horn, and neurofilament-rich inclusions filling thickened dystrophic neurites. Preferential binding of the antibodies can also be observed within intracellular dispersed inclusions, Lewy body-like inclusions and extracellular aggregates, which mainly consist of abnormal aggregates of the superoxide dismutase 1; see Example 4 and FIG. 6. A repetition of these experiments (see Example 4 and FIG. 9) supports the above assessment and extends the preliminary results in respect of the binding specificities of further antibodies of the present invention. In accordance with the above observations antibodies of the present invention are capable of revealing distinct patterns of SOD1 pathology in the lumbar spinal cord of ALS model mice. Particularly antibody NI-204.12G7 and further antibodies NI-204.11F11, NI.204.6H1, NI.204.12G3, NI.204.25H3, NI.204.34A3 and NI.204.7B3 can be used according to the present invention for visualization of SOD1 pathology including cytoplasmic SOD1 inclusions, mainly in motor neurons, and extracellular SOD1 aggregates. This binding specificity towards pathological forms of SOD1 in animal tissue emphasizes besides the biochemical experiments showed herein (see Examples 3 and 8) the usability of the antibodies of the present invention in treatment and diagnosis of diseases associated with occurrence of misfolded/aggregated SOD1 in the brain.

Antibody NI-204.10A8 has shown equal binding affinity to human physiological SOD1 dimers and misfolded/aggregated human SOD1 in the experiments described above. However, as indicated in detail in the examples section (Example 8), repeated experiments with antibody NI-204.10A8 showed a significant loss of binding affinity for physiological and for aggregated SOD1 as well. These findings seem to indicate a storage sensitivity of said antibody, which might be at least partially responsible for the observed affinity change for both physiological and misfolded/aggregated SOD1 conformations, from 20 nM, respective 30 nM as calculated in Example 3 to over 100 nM for both forms of SOD1 as indicated in Table III.

In this respect, in one embodiment the present invention provides temperature and/or storage insensitive antibodies, retaining at least to a large extend their binding capabilities over prolonged storage periods and/or after exposure to non-physiological temperatures, i.e. below 4° C., in particular storage at about −80° C. to −20° C. Furthermore, in one embodiment, the present invention further provides antibodies which are temperature and/or storage sensitive showing an amended binding affinity and/or affinity after prolonged storage. This change of affinity, as referred herein to, is defined as a change from discriminative to non-discriminative binding of physiological respective misfolded/aggregated SOD-1 proteins.

In respect of the preliminary staining results, all antibodies shown in FIG. 9 show staining of intracellular dispersed inclusions, diffuse cytoplasmic structures and vacuolar structures if the appropriate concentration of antibody is used. Staining of the larger aggregates comparable to reference antibody B8H10 (FIG. 9M) divides the antibodies of the present invention into two groups: antibodies NI204-12G7, NI204-11F11, NI204-6H1, NI204-12G3, NI204-7G5, NI204-25H3, NI204-34A3 and NI204-7B3 (FIGS. 9 B, C, F, G, H, I, J and K) stain these aggregates in the ventral horn of the spinal cord whereas NI204-10D12, NI204-10A8 and NI204-67E12 (FIGS. 9A, D and E) do not stain these structures, similar to reference antibody C4F6 ((FIG. 9L) which is specific for soluble, misfolded forms of mutant human SOD1 (Bosco et al, 2010, Nat Neuroscience 13(11); 1396-1403). In addition, antibodies NI204-10D12, NI204-6H1 and NI204-7G5 show diffuse staining in the substantia gelatinosa in the dorsal horn of the spinal cord sections.

As an alternative to obtaining immunoglobulins directly from the culture of B cells or B memory cells, the cells can be used as a source of rearranged heavy chain and light chain loci for subsequent expression and/or genetic manipulation. Rearranged antibody genes can be reverse transcribed from appropriate mRNAs to produce cDNA. If desired, the heavy chain constant region can be exchanged for that of a different isotype or eliminated altogether. The variable regions can be linked to encode single chain Fv regions. Multiple Fv regions can be linked to confer binding ability to more than one target or chimeric heavy and light chain combinations can be employed. Once the genetic material is available, design of analogs as described above which retain both their ability to bind the desired target is straightforward. Methods for the cloning of antibody variable regions and generation of recombinant antibodies are known to the person skilled in the art and are described, for example, Gilliland et al., Tissue Antigens 47 (1996), 1-20; Doenecke et al., Leukemia 11 (1997), 1787-1792.

Once the appropriate genetic material is obtained and, if desired, modified to encode an analog, the coding sequences, including those that encode, at a minimum, the variable regions of the heavy and light chain, can be inserted into expression systems contained on vectors which can be transfected into standard recombinant host cells. A variety of such host cells may be used; for efficient processing, however, mammalian cells are preferred. Typical mammalian cell lines useful for this purpose include, but are not limited to, CHO cells, HEK 293 cells, or NSO cells.

The production of the antibody or analog is then undertaken by culturing the modified recombinant host under culture conditions appropriate for the growth of the host cells and the expression of the coding sequences. The antibodies are then recovered by isolating them from the culture. The expression systems are preferably designed to include signal peptides so that the resulting antibodies are secreted into the medium; however, intracellular production is also possible.

In accordance with the above, the present invention also relates to a polynucleotide encoding the antibody or equivalent binding molecule of the present invention, in case of the antibody preferably at least a variable region of an immunoglobulin chain of the antibody described above. Typically, said variable region encoded by the polynucleotide comprises at least one complementarity determining region (CDR) of the $V_H$ and/or $V_L$ of the variable region of the said antibody.

The person skilled in the art will readily appreciate that the variable domain of the antibody having the above-described variable domain can be used for the construction of other polypeptides or antibodies of desired specificity and biological function. Thus, the present invention also encompasses polypeptides and antibodies comprising at least one CDR of the above-described variable domain and which advantageously have substantially the same or similar binding properties as the antibody described in the appended examples. The person skilled in the art knows that binding affinity may be enhanced by making amino acid substitutions within the CDRs or within the hypervariable loops (Chothia and Lesk, J. Mol. Biol. 196 (1987), 901-917) which partially overlap with the CDRs as defined by Kabat; see, e.g., Riechmann, et al, Nature 332 (1988), 323-327. Thus, the present invention also relates to antibodies wherein one or more of the mentioned CDRs comprise one or more, preferably not more than two amino acid substitutions. Preferably, the antibody of the invention comprises in one or both of its immunoglobulin chains two or all three CDRs of the variable regions as set forth in FIG. 1.

Binding molecules, e.g., antibodies, or antigen-binding fragments, variants, or derivatives thereof of the invention, as known by those of ordinary skill in the art, can comprise a constant region which mediates one or more effector functions. For example, binding of the C1 component of complement to an antibody constant region may activate the complement system. Activation of complement is important in the opsonization and lysis of cell pathogens. The activation of complement also stimulates the inflammatory response and may also be involved in autoimmune hypersensitivity. Further, antibodies bind to receptors on various cells via the Fc region, with a Fc receptor binding site on the antibody Fc region binding to a Fc receptor (FcR) on a cell. There are a number of Fc receptors which are specific for different classes of antibody, including IgG (gamma receptors), IgE (epsilon receptors), IgA (alpha receptors) and IgM (mu receptors). Binding of antibody to Fc receptors on cell surfaces triggers a number of important and diverse biological responses including engulfment and destruction of antibody-coated particles, clearance of immune complexes, lysis of antibody-coated target cells by killer cells (called antibody-dependent cell-mediated cytotoxicity, or ADCC), release of inflammatory mediators, placental transfer and control of immunoglobulin production.

Accordingly, certain embodiments of the present invention include an antibody, or antigen-binding fragment, variant, or derivative thereof, in which at least a fraction of one or more of the constant region domains has been deleted or otherwise altered so as to provide desired biochemical characteristics such as reduced effector functions, the ability to non-covalently dimerize, increased ability to localize at the site of SOD1 aggregation and deposition, reduced serum half-life, or increased serum half-life when compared with a whole, unaltered antibody of approximately the same immunogenicity. For example, certain antibodies for use in the diagnostic and treatment methods described herein are domain deleted antibodies which comprise a polypeptide chain similar to an immunoglobulin heavy chain, but which lack at least a portion of one or more heavy chain domains. For instance, in certain antibodies, one entire domain of the constant region of the modified antibody will be deleted, for example, all or part of the CH2 domain will be deleted. In other embodiments, certain antibodies for use in the diagnostic and treatment methods described herein have a constant region, e.g., an IgG heavy chain constant region, which is altered to eliminate glycosylation, referred to elsewhere herein as aglycosylated or "agly" antibodies. Such "agly" antibodies may be prepared enzymatically as well as by engineering the consensus glycosylation site(s) in the constant region. While not being bound by theory, it is believed that "agly" antibodies may have an improved safety and stability profile in vivo. Methods of producing aglycosylated antibodies, having desired effector function are found for example in international application WO2005/018572, which is incorporated by reference in its entirety.

In certain antibodies, or antigen-binding fragments, variants, or derivatives thereof described herein, the Fc portion may be mutated to decrease effector function using techniques known in the art. For example, the deletion or inactivation (through point mutations or other means) of a constant region domain may reduce Fc receptor binding of the circulating modified antibody thereby increasing SOD1 localization. In other cases it may be that constant region modifications consistent with the instant invention moderate complement binding and thus reduce the serum half-life and nonspecific association of a conjugated cytotoxin. Yet other modifications of the constant region may be used to modify disulfide linkages or oligosaccharide moieties that allow for enhanced localization due to increased antigen specificity or antibody flexibility. The resulting physiological profile, bioavailability and other biochemical effects of the modifications, such as SOD1 localization, biodistribution and serum half-life, may easily be measured and quantified using well know immunological techniques without undue experimentation.

In certain antibodies, or antigen-binding fragments, variants, or derivatives thereof described herein, the Fc portion may be mutated or exchanged for alternative protein sequences to increase the cellular uptake of antibodies by way of example by enhancing receptor-mediated endocytosis of antibodies via Fcγ receptors, LRP, or Thy1 receptors or by 'SuperAntibody Technology', which is said to enable antibodies to be shuttled into living cells without harming them (Expert Opin. Biol. Ther. (2005), 237-241). For example, the generation of fusion proteins of the antibody binding region and the cognate protein ligands of cell surface receptors or bi- or multi-specific antibodies with a specific sequences biding to SOD1 as well as a cell surface receptor may be engineered using techniques known in the art.

In certain antibodies, or antigen-binding fragments, variants, or derivatives thereof described herein, the Fc portion may be mutated or exchanged for alternative protein sequences or the antibody may be chemically modified to increase its blood brain barrier penetration.

Modified forms of antibodies, or antigen-binding fragments, variants, or derivatives thereof of the invention can be made from whole precursor or parent antibodies using techniques known in the art. Exemplary techniques are discussed in more detail herein. Antibodies, or antigen-binding fragments, variants, or derivatives thereof of the invention can be made or manufactured using techniques that are known in the art. In certain embodiments, antibody molecules or fragments thereof are "recombinantly produced," i.e., are produced using recombinant DNA technology. Exemplary techniques for making antibody molecules or fragments thereof are discussed in more detail elsewhere herein.

Antibodies, or antigen-binding fragments, variants, or derivatives thereof of the invention also include derivatives that are modified, e.g., by the covalent attachment of any type of molecule to the antibody such that covalent attachment does not prevent the antibody from specifically binding to its cognate epitope. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

In particular preferred embodiments, antibodies, or antigen-binding fragments, variants, or derivatives thereof of the invention will not elicit a deleterious immune response in the animal to be treated, e.g., in a human. In certain embodiments, binding molecules, e.g., antibodies, or antigen-binding fragments thereof of the invention are derived from a patient, e.g., a human patient, and are subsequently used in the same species from which they are derived, e.g., human, alleviating or minimizing the occurrence of deleterious immune responses.

De-immunization can also be used to decrease the immunogenicity of an antibody. As used herein, the term "de-immunization" includes alteration of an antibody to modify T cell epitopes; see, e.g., international applications WO98/52976 and WO00/34317. For example, $V_H$ and $V_L$ sequences from the starting antibody are analyzed and a human T cell epitope "map" from each V region showing the location of epitopes in relation to complementarity determining regions (CDRs) and other key residues within the sequence. Individual T cell epitopes from the T cell epitope map are analyzed in order to identify alternative amino acid substitutions with a low risk of altering activity of the final antibody. A range of alternative $V_H$ and $V_L$ sequences are designed comprising combinations of amino acid substitutions and these sequences are subsequently incorporated into a range of binding polypeptides, e.g., SOD1-specific antibodies or immunospecific fragments thereof for use in the diagnostic and treatment methods disclosed herein, which are then tested for function. Typically, between 12 and 24 variant antibodies are generated and tested. Complete heavy and light chain genes comprising modified V and human C regions are then cloned into expression vectors and the subsequent plasmids introduced into cell lines for the production of whole antibody. The antibodies are then compared in appropriate biochemical and biological assays, and the optimal variant is identified.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, Cold Spring Harbor Laboratory Press, 2nd ed. (1988); Hammerling et al., in: *Monoclonal Antibodies and T-Cell Hybridomas* Elsevier, N.Y., 563-681 (1981), said references incorporated by reference in their entireties. The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced. Thus, the term "monoclonal antibody" is not limited to antibodies produced through hybridoma technology. In certain embodiments, antibodies of the present invention are derived from human B cells which have been immortalized via transformation with Epstein-Barr virus, as described herein.

In the well-known hybridoma process (Kohler et al., Nature 256 (1975), 495) the relatively short-lived, or mortal, lymphocytes from a mammal, e.g., B cells derived from a human subject as described herein, are fused with an immortal tumor cell line (e.g., a myeloma cell line), thus, producing hybrid cells or "hybridomas" which are both immortal and capable of producing the genetically coded antibody of the B cell. The resulting hybrids are segregated into single genetic strains by selection, dilution, and re-growth with each individual strain comprising specific genes for the formation of a single antibody. They produce antibodies, which are homogeneous against a desired antigen and, in reference to their pure genetic parentage, are termed "monoclonal".

Hybridoma cells thus prepared are seeded and grown in a suitable culture medium that preferably contains one or more substances that inhibit the growth or survival of the unfused, parental myeloma cells. Those skilled in the art will appreciate that reagents, cell lines and media for the formation, selection and growth of hybridomas are commercially available from a number of sources and standardized protocols are well established. Generally, culture medium in which the hybridoma cells are growing is assayed for production of monoclonal antibodies against the desired antigen. The binding specificity of the monoclonal antibodies produced by hybridoma cells is determined by in vitro assays such as immunoprecipitation, radioimmunoassay (MA) or enzyme-linked immunoabsorbent assay (ELISA) as described herein. After hybridoma cells are identified that produce antibodies of the desired specificity, affinity and/or activity, the clones may be subcloned by limiting dilution procedures and grown by standard methods; see, e.g., Goding, *Monoclonal Antibodies: Principles and Practice*, Academic Press, pp. 59-103 (1986). It will further be appreciated that the monoclonal antibodies secreted by the subclones may be separated from culture medium, ascites fluid or serum by conventional purification procedures such as, for example, protein-A, hydroxylapatite chromatography, gel electrophoresis, dialysis or affinity chromatography.

In another embodiment, lymphocytes can be selected by micromanipulation and the variable genes isolated. For example, peripheral blood mononuclear cells can be isolated from an immunized or naturally immune mammal, e.g., a human, and cultured for about 7 days in vitro. The cultures can be screened for specific IgGs that meet the screening criteria. Cells from positive wells can be isolated. Individual Ig-producing B cells can be isolated by FACS or by identifying them in a complement-mediated hemolytic plaque assay. Ig-producing B cells can be micromanipulated into a tube and the $V_H$ and $V_L$ genes can be amplified using, e.g., RT-PCR. The $V_H$ and $V_L$ genes can be cloned into an antibody expression vector and transfected into cells (e.g., eukaryotic or prokaryotic cells) for expression.

Alternatively, antibody-producing cell lines may be selected and cultured using techniques well known to the skilled artisan. Such techniques are described in a variety of laboratory manuals and primary publications. In this respect, techniques suitable for use in the invention as described below are described in *Current Protocols in Immunology*, Coligan et al., Eds., Green Publishing Associates and Wiley-Interscience, John Wiley and Sons, New York (1991) which is herein incorporated by reference in its entirety, including supplements.

Antibody fragments that recognize specific epitopes may be generated by known techniques. For example, Fab and F(ab')$_2$ fragments may be produced recombinantly or by proteolytic cleavage of immunoglobulin molecules, using enzymes such as papain (to produce Fab fragments) or pepsin (to produce F(ab')$_2$ fragments). F(ab')$_2$ fragments contain the variable region, the light chain constant region and the CH1 domain of the heavy chain. Such fragments are sufficient for use, for example, in immunodiagnostic procedures involving coupling the immunospecific portions of immunoglobulins to detecting reagents such as radioisotopes.

Human antibodies, such as described herein, are particularly desirable for therapeutic use in human patients. Human antibodies of the present invention are isolated, e.g., from healthy human subjects who because of their age may be suspected to be at risk of developing a neurodegenerative disorder, e.g., ALS, or a patient with the disorder but with an unusually stable disease course or unusually mild form of the disease. However, though it is prudent to expect that elderly healthy and symptom-free subjects, respectively, more regularly will have developed protective anti-SOD1 antibodies than younger subjects, the latter may be used as well as source for obtaining a human antibody of the present invention. This is particularly true for younger patients who are predisposed to develop a familial form of ALS but remain symptom-free since their immune system functions more efficiently than that in older adults.

In one embodiment, an antibody of the invention comprises at least one heavy or light chain CDR of an antibody molecule. In another embodiment, an antibody of the invention comprises at least two CDRs from one or more antibody molecules. In another embodiment, an antibody of the invention comprises at least three CDRs from one or more antibody molecules. In another embodiment, an antibody of the invention comprises at least four CDRs from one or more antibody molecules. In another embodiment, an antibody of the invention comprises at least five CDRs from one or more antibody molecules. In another embodiment, an antibody of the invention comprises at least six CDRs from one or more antibody molecules. Exemplary antibody molecules comprising at least one CDR that can be included in the subject antibodies are described herein.

Antibodies of the present invention can be produced by any method known in the art for the synthesis of antibodies, in particular, by chemical synthesis or preferably by recombinant expression techniques as described herein.

In one embodiment, an antibody, or antigen-binding fragment, variant, or derivative thereof of the invention comprises a synthetic constant region wherein one or more domains are partially or entirely deleted ("domain-deleted antibodies"). In certain embodiments compatible modified antibodies will comprise domain deleted constructs or variants wherein the entire CH2 domain has been removed (ΔCH2 constructs). For other embodiments a short connecting peptide may be substituted for the deleted domain to provide flexibility and freedom of movement for the variable region. Those skilled in the art will appreciate that such constructs are particularly preferred due to the regulatory properties of the CH2 domain on the catabolic rate of the antibody. Domain deleted constructs can be derived using a vector encoding an IgG$_1$ human constant domain, see, e.g., international applications WO02/060955 and WO02/096948A2. This vector is engineered to delete the CH2 domain and provide a synthetic vector expressing a domain deleted IgG$_1$ constant region.

In certain embodiments, antibodies, or antigen-binding fragments, variants, or derivatives thereof of the present invention are minibodies. Minibodies can be made using methods described in the art, see, e.g., U.S. Pat. No. 5,837,821 or international application WO 94/09817.

In one embodiment, an antibody, or antigen-binding fragment, variant, or derivative thereof of the invention comprises an immunoglobulin heavy chain having deletion or substitution of a few or even a single amino acid as long as it permits association between the monomeric subunits. For example, the mutation of a single amino acid in selected areas of the CH2 domain may be enough to substantially reduce Fc binding and thereby increase SOD1 localization. Similarly, it may be desirable to simply delete that part of one or more constant region domains that control the effector function (e.g. complement binding) to be modulated. Such partial deletions of the constant regions may improve selected characteristics of the antibody (serum half-life) while leaving other desirable functions associated with the subject constant region domain intact. Moreover, as alluded to above, the constant regions of the disclosed antibodies may be synthetic through the mutation or substitution of one or more amino acids that enhances the profile of the resulting construct. In this respect it may be possible to disrupt the activity provided by a conserved binding site (e.g. Fc binding) while substantially maintaining the configuration and immunogenic profile of the modified antibody. Yet other embodiments comprise the addition of one or more amino acids to the constant region to enhance desirable characteristics such as an effector function or provide for more cytotoxin or carbohydrate attachment. In such embodiments it may be desirable to insert or replicate specific sequences derived from selected constant region domains.

The present invention also provides antibodies that comprise, consist essentially of, or consist of, variants (including derivatives) of antibody molecules (e.g., the $V_H$ regions and/or $V_L$ regions) described herein, which antibodies or fragments thereof immunospecifically bind to SOD1. Standard techniques known to those of skill in the art can be used to introduce mutations in the nucleotide sequence encoding an antibody, including, but not limited to, site-directed mutagenesis and PCR-mediated mutagenesis which result in amino acid substitutions. Preferably, the variants (including derivatives) encode less than 50 amino acid substitutions, less than 40 amino acid substitutions, less than 30 amino acid substitutions, less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to the reference $V_H$ region, $V_H$-CDR1, $V_H$-CDR2, $V_H$-CDR3, $V_L$ region, $V_L$-CDR1, $V_L$-CDR2, or $V_L$-CDR3. A "conservative amino acid substitution" is one in which the amino acid residue is replaced with an amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity (e.g., the ability to bind SOD1).

For example, it is possible to introduce mutations only in framework regions or only in CDR regions of an antibody molecule. Introduced mutations may be silent or neutral missense mutations, e.g., have no, or little, effect on an antibody's ability to bind antigen, indeed some such mutations do not alter the amino acid sequence whatsoever. These types of mutations may be useful to optimize codon usage, or improve a hybridoma's antibody production. Codon-optimized coding regions encoding antibodies of the present invention are disclosed elsewhere herein. Alternatively, non-neutral missense mutations may alter an antibody's ability to bind antigen. The location of most silent and neutral missense mutations is likely to be in the framework regions, while the location of most non-neutral missense mutations is likely to be in CDR, though this is not an absolute requirement. One of skill in the art would be able to design and test mutant molecules with desired properties such as no alteration in antigen-binding activity or alteration in binding activity (e.g., improvements in antigen-binding activity or change in antibody specificity). Following mutagenesis, the encoded protein may routinely be expressed and the functional and/or biological activity of the encoded protein, (e.g., ability to immunospecifically bind at least one epitope of SOD1) can be determined using techniques described herein or by routinely modifying techniques known in the art.

III. Polynucleotides Encoding Antibodies

A polynucleotide encoding an antibody, or antigen-binding fragment, variant, or derivative thereof can be composed of any polyribonucleotide or polydeoxribonucleotide, which may be unmodified RNA or DNA or modified RNA or DNA. For example, a polynucleotide encoding an antibody, or antigen-binding fragment, variant, or derivative thereof can be composed of single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, a polynucleotide encoding an antibody, or antigen-binding fragment, variant, or derivative thereof can be composed of triple-stranded regions comprising RNA or DNA or both RNA and DNA. A polynucleotide encoding an antibody, or antigen-binding fragment, variant, or derivative thereof may also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms.

An isolated polynucleotide encoding a non-natural variant of a polypeptide derived from an immunoglobulin (e.g., an immunoglobulin heavy chain portion or light chain portion)

can be created by introducing one or more nucleotide substitutions, additions or deletions into the nucleotide sequence of the immunoglobulin such that one or more amino acid substitutions, additions or deletions are introduced into the encoded protein. Mutations may be introduced by standard techniques, such as site-directed mutagenesis and PCR-mediated mutagenesis. Preferably, conservative amino acid substitutions are made at one or more non-essential amino acid residues.

As is well known, RNA may be isolated from the original B cells, hybridoma cells or from other transformed cells by standard techniques, such as a guanidinium isothiocyanate extraction and precipitation followed by centrifugation or chromatography. Where desirable, mRNA may be isolated from total RNA by standard techniques such as chromatography on oligo dT cellulose. Suitable techniques are familiar in the art. In one embodiment, cDNAs that encode the light and the heavy chains of the antibody may be made, either simultaneously or separately, using reverse transcriptase and DNA polymerase in accordance with well-known methods. PCR may be initiated by consensus constant region primers or by more specific primers based on the published heavy and light chain DNA and amino acid sequences. As discussed above, PCR also may be used to isolate DNA clones encoding the antibody light and heavy chains. In this case the libraries may be screened by consensus primers or larger homologous probes, such as human constant region probes.

DNA, typically plasmid DNA, may be isolated from the cells using techniques known in the art, restriction mapped and sequenced in accordance with standard, well known techniques set forth in detail, e.g., in the foregoing references relating to recombinant DNA techniques. Of course, the DNA may be synthetic according to the present invention at any point during the isolation process or subsequent analysis.

In one embodiment, the present invention provides an isolated polynucleotide comprising, consisting essentially of, or consisting of a nucleic acid encoding an immunoglobulin heavy chain variable region ($V_H$), where at least one of the CDRs of the heavy chain variable region or at least two of the $V_H$-CDRs of the heavy chain variable region are at least 80%, 85%, 90% or 95% identical to reference heavy chain $V_H$-CDR1, $V_H$-CDR2, or $V_H$-CDR3 amino acid sequences from the antibodies disclosed herein. Alternatively, the $V_H$-CDR1, $V_H$-CDR2, or $V_H$-CDR3 regions of the $V_H$ are at least 80%, 85%, 90% or 95% identical to reference heavy chain $V_H$-CDR1, $V_H$-CDR2, and $V_H$-CDR3 amino acid sequences from the antibodies disclosed herein. Thus, according to this embodiment a heavy chain variable region of the invention has $V_H$-CDR1, $V_H$-CDR2, or $V_H$-CDR3 polypeptide sequences related to the polypeptide sequences shown in FIG. 1.

In another embodiment, the present invention provides an isolated polynucleotide comprising, consisting essentially of, or consisting of a nucleic acid encoding an immunoglobulin light chain variable region ($V_L$), where at least one of the $V_L$-CDRs of the light chain variable region or at least two of the $V_L$-CDRs of the light chain variable region are at least 80%, 85%, 90% or 95% identical to reference light chain $V_L$-CDR1, $V_L$-CDR2, or $V_L$-CDR3 amino acid sequences from the antibodies disclosed herein. Alternatively, the $V_L$-CDR1, $V_L$-CDR2, or $V_L$-CDR3 regions of the $V_L$ are at least 80%, 85%, 90% or 95% identical to reference light chain $V_L$-CDR1, $V_L$-CDR2, and $V_L$-CDR3 amino acid sequences from the antibodies disclosed herein. Thus, according to this embodiment a light chain variable region of the invention has $V_L$-CDR1, $V_L$-CDR2, or $V_L$-CDR3 polypeptide sequences related to the polypeptide sequences shown in FIG. 1.

In another embodiment, the present invention provides an isolated polynucleotide comprising, consisting essentially of, or consisting of a nucleic acid encoding an immunoglobulin heavy chain variable region ($V_H$) in which the $V_H$-CDR1, $V_H$-CDR2, and $V_H$-CDR3 regions have polypeptide sequences which are identical to the $V_H$-CDR1, $V_H$-CDR2, and $V_H$-CDR3 groups shown in FIG. 1.

As known in the art, "sequence identity" between two polypeptides or two polynucleotides is determined by comparing the amino acid or nucleic acid sequence of one polypeptide or polynucleotide to the sequence of a second polypeptide or polynucleotide. When discussed herein, whether any particular polypeptide is at least about 40%, 45%, 50%, 55%, 60%, 65%, 70%, 75%, 80%, 85%, 90% or 95% identical to another polypeptide can be determined using methods and computer programs/software known in the art such as, but not limited to, the BESTFIT program (Wisconsin Sequence Analysis Package, Version 8 for Unix, Genetics Computer Group, University Research Park, 575 Science Drive, Madison, Wis. 53711). BESTFIT uses the local homology algorithm of Smith and Waterman, Advances in Applied Mathematics 2 (1981), 482-489, to find the best segment of homology between two sequences. When using BESTFIT or any other sequence alignment program to determine whether a particular sequence is, for example, 95% identical to a reference sequence according to the present invention, the parameters are set, of course, such that the percentage of identity is calculated over the full length of the reference polypeptide sequence and that gaps in homology of up to 5% of the total number of amino acids in the reference sequence are allowed.

In a preferred embodiment of the present invention, the polynucleotide comprises, consists essentially of, or consists of a nucleic acid having a polynucleotide sequence of the $V_H$ or $V_L$ region of an anti-SOD1 antibody as depicted in Table II. In this respect, the person skilled in the art will readily appreciate that the polynucleotides encoding at least the variable domain of the light and/or heavy chain may encode the variable domain of both immunoglobulin chains or only one.

TABLE II

Nucleotide sequences of the $V_H$ and $V_L$ region of SOD1 specific antibodies.

| Antibody | Nucleotide sequences of variable heavy (VH) and variable light (VL) chains |
| --- | --- |
| NI-204.10D12-$V_H$ | GAGGTGCAGCTGGTGGAGTCTGGGGGGGACTTAG TTCGCCCTGGGGGGTCCCTGAGACTCTCCTGTGT CGCCTCTGGATTCACCTTCAGCAACTACTGGATG CACTGGGTCCGCCAAGCTCCAGGGCAGCGGCCGG TGTGGGTCTCACGTACTAATACTGATGGCCGTAA CACAGCCTACGCGGACTACGCGAAGGGCCGATTC ACCATCTCCAGAGACAATGCCAAGAGCACGCTGT ATCTGCAACTGAACAGTCTGAGAGCCGAAGACAC GGCTGTGTACTTCTGTGCAAGGCTGCGAAGAAAC GTCGCCGACCAAATCACTCACAACTACTACATGG ACGTCTGGGGCAAAGGCACCCTGGTCACCGTCTC CTCG SEQ ID NO: 3 |
| NI-204.10D12-$V_L$ | GAAATTGTGCTGACTCAGTCTCCAGGCTCCCTGG CTGTGTCTCTGGGCGAGAGGGCCACCATCAACTG CAAGTCCAGCCAGACTGTTTTATACAATAATAAG AACTATTTAGCTTGGTACCAGCAGAAACCAGGAC AGCCTCCGAAGTTGCTCATTTCCTGGGCATCTTC CCGAGAATCCGGGGTCCCTGACCGGTTCAGTGGC AGCGGGTCTGGGACAGATTTCACTCTCACCATCA |

TABLE II-continued

Nucleotide sequences of the $V_H$ and $V_L$ region of SOD1 specific antibodies.

| Antibody | Nucleotide sequences of variable heavy (VH) and variable light (VL) chains |
|---|---|
|  | GCAGCCTGCAGGCTGAAGATGTGGCAGTTTATTA CTGTCAGCACTATTATGGTACTCCTGTCACTTTC GGCGGAGGGACCAAGGTGGAAATCAAA SEQ ID NO: 5 |
| NI-204.12G7-$V_H$ | GAGGTGCAGCTGGTGGAGTCTGGGGCTGAGGTGA AGAAGCCTGGGGCCTCAGTGACACTGTCCTGCAA GGCATCTGGATACACCTTCACCGCTACTATATA CACTGGGTGCGACAGGCCCCGAGAACAAGGGCTTG AGTGGATGGGCGTAATCAACCCTAGTACTGGAAC CACATTTTACGCACAGAACTTCCCGGACAGAGTC TCCGTGACCAGGGACACGTCCACGAGTACAGTCT TCATGGAGCTGCACAACCTGAAATCTGAGGACAC GGCCGTATATTACTGTGCGAGAGCAATCAGTGAG CATGGTTCAGGGAGTTATTCACCTTATTACTGGG GCCAGGGCACCCTGGTCACCGTCTCCTCG SEQ ID NO: 7 |
| NI-204.12G7-$V_L$ | TCCTATGTGCTGACTCAGCCACCCTCGGTGTCAG TGTCCCTAGGACAGATGGCCGCGATCACCTGCTC TGGAGAGGCATTGCCAAAAAGTATGGTTATTGG TACCAGCAGAAGCCAGGCCAGGTCCCTGTTCTGC TAATTTATAGAGACGTCGAGAGGCCCTCAGGGGT CCCTGACCGATTCTCTGGCTCCAGCTCAGGGACA ATGGTCACATTGACCATCAGTGGAGTCCAGGCAG AGGACGAGGCTGACTATTACTGTCTCTCAGCAGA CAGCAGTGGTACTTGGGTGTTCGGCGGAGGGACC AAGCTGACCGTCCTA SEQ ID NO: 9 |
| NI-204.10A8-$V_H$ | GAGGTGCAGCTGGTGGAGTCTGGGGCTGAGGTGA AGGAGCCTGGGTCGTCGGTGAGGGTCTCCTGCAA GACTTCTGGAGGCTCCTTCAACAGACATGTTATC ACCTGGGTGCGACAGGCCCCTGGACAAGGGCTTG AGTGGATGGGCGAGATCATCCCTTTCTTTGGTAC ACCAAAGTATGCACCAGAAGTTCCAGACAGAGTC ACCATTATCGCCGACGCGTCCACGAGCACATTCT TCTTGGACGTGAAGAGCCTGACATCTGAGGACAC GGCCCTGTATTTCTGTTGGATTGTTGTGGTGTCT GTTGTTCAGCGAAGGGAGGACTTCTGGGGCCAGG GAATCCTGGTCACCGTCTCCTCG SEQ ID NO: 11 |
| NI-204.10A8-$V_L$ | GAAATTGTGTTGACGCAGTCTCCATCGTCCCTGT CTGCATCTGTTGGAGACACAGTCACCATCACTTG CCGGTCAAGTCAGAACATCAGCAACTATCTGAGT TGGTTTCAGCATAAGCCAGGCAAGGCCCCTAGAA TCTGGTCTATGCTGCATCCACTTTGCAGACTGG GGTCCCGTCAAGGTTCAGTGGCAGAGGATCTGGG ACAATTTTCACTCTTTCCATCACCAGTCTACAAT CCGAGGATTATGCAACTTACTACTGTCAACAGAA TGACAAAATTCCCGAACGTTCGGCCAAGGGACC AAGGTGGAAATCAAA SEQ ID NO: 13 |
| NI-204.9F6-$V_H$ | GAGGTGCAGCTGGTGGAGTCTGGGGGAGGCCTGG TCCAGCCGGGGGGGTCCCTAAGACTCTCCTGTGC GGTCTCTGGATTCACCTTTGACACCCTTTGCCATG AGTTGGGTCCGCCAGGCTCCAGGGAAGGGTCTGG AGTGGGTCTCGGCAATTACTGCCAGTTCTTCTAA GACGTACTACGCCGACTCCGTGAAGGGCCGCTTC ACCATCTCCAGAGACAATTCCAAGAATACGGTGT ATCTGCGCCTGAGCAGTCTGAGAGCCGACGACAC GGCCGTTTATTTCTGTGCGAGGCCGAAAGGGGCA CACAGTGGCCTCTACATAGAAAGCGCTTTTGATC TGTGGGGCCCAGGGACAATGGTCACCGTCTCTTC G SEQ ID NO: 15 |
| NI-204.9F6-$V_L$ | TCCTATGTGCTGACTCAGCCACCCTCAGTGTCCG TGTCCGCAGGACAGACAGCCTCCATCACCTGCTC TGCAGATATGTTGGGGGACACATATGTTTCCTGG TATCAGAAGAGGCCAGGCCAGTCCCCTGTCCTGC TCATCTATCAGGATTCCAAGAGGCCCTCAGAGAT CCCTGAGCGATTCTCTGGCTCCAGCTCTGAGGAC ACAGCTACTCTGACCATTACCGGGACCCAGGCTC |
| | TCGATGAGGCTGCCTATTACTGTCAAGTGTGGGA CAGGCGCACTACAACATATGTCTTCGGACCTGGG ACCGAGGTCACCGTCCTG SEQ ID NO: 17 |
| NI-204.11F11-$V_H$ | GAGGTGCAGCTGGTGGAGTCTGGGGGAGGCTTGG TTAAGCCGGGGGGGTCCCTTAGACTCTCCTGTGC AGCCTCTGGATTGCCTTTCAGCAAGGCCTGGATG AGCTGGGTCCGCCAGGCTCAGGGAAGGGGCTGG AGTGGGTCGGCCGTATCAAAAGTCAAGCTGATGG TGGGGCAATAGATACGCTACATCCGTGAATGGC AGATTCACCATCACAAGAGATGATTCAAAAAATA CGCTGTATCTGCAAATGACCAGCCTGAAAACCGA GGACACAGCCGTGTATTACTGTACCCCGGGGATA ATATTACGATTTTTGGAGGGCACCCTTCGGGGAA TGGACGTCTGGGGCCAAGGGACCACGGTCACCGT CTCCTCG SEQ ID NO: 19 |
| NI-204.11F11-$V_L$ | GAAATTGTGCTGACTCAGTCTCCACCCACCCTGT CTTTGTCTCCAGGGGAAAGAGCCACCCTCTCCTG CAGGGCCAGTCAGACTGTTAGTAAGTACTTAGCC TGGTACCAACAGAAGCCTGGCCAGGCTCCCAGGC TCCTCGTCTATGATACATCCAACAGGGCCATTGG CATCCCACCCAGGTTCAGTGGCAGTGGGTCTGGG ACAGACTTCACTCTCACCATCAGCACCCTAGAGC CTGAGGATTTCGCACTTTATTATTGTCAGCAGCG TAGCAACTGGCCTCCGACCTTCGGCCAAGGGACA CGACTGGAGATTAAA SEQ ID NO: 21 |
| NI-204.67E12-$V_H$ | GAGGTGCAGCTGTTGGAGTCTGGGGGAGGCTTAA TCCGGCCTGGGGGGTCCCTGAGACTCTCCTGTGC AGCCTCTGGATTCACCTTCAGTAACTATGCCATG GGCTGGGTCCGCCAGGCTCCAGGGAAGGGGCTGG AGTGGGTCTCAGCCATCAGTGGCAATGGTGGAAG CACCTATATGGAGGCTCCGTGAAGGGCCGGTTC ACCATCTCCAGAGACAATTCCAAGAATACCCTGT ATCTACAAATGAACAACTTGAGAGCCGACGACAC GGCCGTTTACTTTTGTGCGAAATTAGAGGCCGTA GCCCCCACTTTGACATTGCGATACTTCAAGCACT GGGGCAAGGGCACCCTGGTCACCGTCTCCTCG SEQ ID NO: 23 |
| NI-204.67E12-$V_L$ | GACATCCAGATGACCCAGTCTCCATCCACCCTGT CTGCATCTGTAGGAGACAGAGTCACCATCACTTG TCGGGCCAGTCAGAGTATTAGCAGGTGGTTGGCC TGGTATCAACAGAGACCAGGTAGAGCCCCTGACC TCCTGATCTATGATGCCTCCAACTTGGAAAGTGG GGTCCCATCAAGGTTCAGCGGCAGTGGATCTGGG ACAGAGTTCACTCTCACCATCAGTAGCCTGCAGC CTGGTGATTTCGCAACTTATTACTGTCAACAATA TTATAGTTATGTTTACACTTTTGGCCAGGGGACC AAGCTGGAGATCAAA SEQ ID NO: 25 |
| NI-204.6H1-$V_H$ | CAGGTGCAGCTACAGCAGTGGGGCGCAGGACTGGC TGAGGCCTTCGGAGACCCTGTCCCTCACCTGCGC TGTCTATGGTGGGTCCTTCAATGGTTACGCCAGG ACCTGGATCCGCCAGCCCCCGGGGAAGGGGCTGG AGTGGATTGGGGAAATCGATCATAGGGAAAACAC CAACTACAACCCGTCCCTCAAGAGTCGAGTCACC ATGTCAGTAGACACGTCCAAGAATCAGTTCTCCC TGAGGCTGAACTCTGTGACCGCCGCGGACACGG TGTTTATTTCTGTGCGAGAGGCCAAAAGAACGCG AAGGATCAACACGAGGGTTTTCGCTACTGGGGCC GGGGAACCCTGGTCACCGTCTCCTCG SEQ ID NO: 27 |
| NI-204.6H1-$V_L$ | TCCTATGAGCTGACTCAGCCACCCTCGGTGTCAG TGTCCCCAGGACAGACGGCCAGGATCACCTGTTC TGGAGATGCATTGCCAAAGCAATTTGTTTATTGG TACCAGCAGAAGTCAGGCCAGGCCCCTAAATTGG TGATCTTTAAAGACACTGAGAGGCCCTCAGGGAT CCCTGAGCGATTCTCTGCCTCCAGCTCAGGTACA AAAGCCACGTTGACCATCAGTGGAGTCCAGGCAG AGGATGAGGCTGACTATTACTGTCAATCAGCGGA |

TABLE II-continued

Nucleotide sequences of the $V_H$ and $V_L$ region of SOD1 specific antibodies.

| Antibody | Nucleotide sequences of variable heavy (VH) and variable light (VL) chains |
|---|---|
| | CAGAACTGCTACTTCTTGGGTGTTCGGCGGAGGG ACCAAGCTGACCGTCCTA SEQ ID NO: 29 |
| NI-204.12G3-$V_H$ | CAGGTGCAGCTGGTGGAGTCTGGGGGAGGCGTGG TCCAGCCTGGGAGGTCCCTCAGACTCTCCTGTGC AGCCTCTGGATACATCTTCAGTAGCTTTGGCATG CACTGGGTCCGCCAGACTCCAGGCAAGGGGCTGG AGTGGGTGGCACTCATTTGGTATGATGGAAGTCG TCAGTCCTATGCGGACTCTGTGAGGGGCCGGTTC ACCATCTCCAGAGACAATTCTAAGAACACGGTGT TTTTGCAAATGAACAGCCTGAGAGGCGAGGACAC GGCTGTATATCACTGTGCGAGAACGGGCTACGAT GACAAACGCGGTGGTTTTGATACTTGGGGCCAAG GGACAATGGTCACCGTCTCTTCG SEQ ID NO: 31 |
| NI-204.12G3-$V_L$ | TCCTATGAGCTGACTCAGCCACCCTCGGTGTCAG TGTCCCCAGGACAGACGGCTAGGATCACCTGCTC TGGAGATGCATTGGCAAAGCAATATTCTTATTGG TACCAGCATAAGCCAGGCCAGGCCCCTGTGATGG TGATGTATAAAGACAGAGAGAGGCCCTCAGGGAT CCCTGAGCGATTCTCTGGCTCCAGTTCAGGGACA ACAGTCACGTTGACCATCAGTGCAGTCCAGGCCG AAGACGAGGCTGACTATTACTGTCAATCAACAGG CACCGATAGTCCTTATATCTTCGGAACTGGGACC AAGGTCACCGTCTTA SEQ ID NO: 33 |
| NI-204.7G5-$V_H$ | GAGGTGCAGCTGGTGGAGTCTGGGGGAGGCGTGG TCCAGGCTGGGGGGTCCCTGAGACTCTCCTGTGT AGCCTCTGGACTCACCTTCAGTTCCTATGGCATG CACTGGGTCCGCCAGGCTCCAGGCAAGGGGCTGG AGTGGGTGGCAGTCATTTCATATGATGGAAGAAG TAAATTCTATGCAGACTCCGTGAAGGGCCGATTC ACCATCTCCAGAGACAATTCCAAGAACACGTTGT ATCTCCAAATGAACAGCCTGAGAGCTGAGGACGC GGCTGTGTATTACTGTGCGAACGCACGCGTCCGT GACGCTTGTTCTGGTACCAGATGCGATAAATTTG GCTTCTACATGGACGTCTGGGGCAAAGGGACCAC GGTCACCGTCTCCTG SEQ ID NO: 35 |
| NI-204.7G5-$V_L$ | TCCTATGCTGACTCAGCCACCCTCGGTGTCAG TGTCCCCAGGACAAACGGCCAGGATCACCTGCTC TGGAGATGCATTGCCAAAGAAATATGCTTATTGG TACCAGCAGAAGTCAGGCCAGGCCCCTGTGCTGG TCATCTATGAGGACATCAAGCGACCCTCCGGGAT CCCTGAGAGATTCTCTGGCTCCAGCTCAGGGACA ATGGCCACCTTGACTATCAGTGGGGCCCAGGTGG AGGATGAAGGTGACTATTATTGTTACTCAGCAGA CAGAAGTGGAAATCGCTGGGCGTTCGGCGGAGGG ACCAAGCTGACCGTCCTA SEQ ID NO: 37 |
| NI-204.7B3-$V_H$ | GAGGTGCAGCTGGTGCAGTCTGGGGGAGACATCG TTCAGTCGGGAGGGTCCCTGAGACTCTCCTGTGC AGCCTCTGGATTCGTCTTCAGTAGCAACTGGATG CACTGGGTCCGCCAACGTCCAGGGAAGGGACTGG AGTGGATCTCACTTATTAATGTCGATGGGCGAAC CACAAAGTATGCGGACTCCGTGAAGGGCCGATTC ACCATTTCCAGAGACAACGCCAAGAAAACAGTGT ATCTGCAGATGGACAGTCTGAGAGCCGAAGACAC GGCCGTGTATTACTGTGTGAAAGTGGAGGGATTG AACTGGGGCCCGGGAACCCTGGTCACCGTCTCCT CG SEQ ID NO: 39 |
| NI-204.7B3-$V_L$ | CTGCCTGTGCTGACTCAGCCACCCTCGGTGTCAG TGTCCCCAGGACAGACGGCCAGGATCACCTGCTC TGGAGACGAGTTGTCAAAACAATATGCTTATTGG TACCAGAAGAAGTCAGGCCAGGCCCCTGTGATGG TGGTGAATGAAGACACTAAGAGGCCCCCGGGGAT TCCTGAACGGTTTTCTGGTTCCAGTTCAGGGACA ACAAGCACATTGACCATCAGTGGAGTCCAGGCGG AAGATGAGGCTGACTATTATTGTCAATCAGCAGA CATAACCGGTTCTTGGGTGTTTGGCGGAGGGACC AAATTGACCGTCCTA SEQ ID NO: 41 |
| NI-204.34A3-$V_H$ | GAGGTGCAGCTGGTGGAGTCTGGGGGAGGCCTGG TGAAGCCGGGGGGGTCCCTAAGAGTCTCCTGTGA CGTCTCTGGGCAGAGACTTTCTAAGGCTTGGATG AACTGGGTCCGCCAAACTCCAACGAGGGGACTGG AGTGGGTCGGCCTAATTAAGAGAGATGCAGATGG AGGGACCACAGAATTCGCTGCACCCGTGGAGGGA CGGTTCACTATTTCAAGGGATGACATACAAACA CCATGACTCTGCATATGACCAGGCTGAGAGTCGA CGACACGGCGTGTATTACTGTGTCGCAGGAGAT ATCGGCTGCATTAAAGAGAATTGCCGTTGGGGCG AGGGGACCACGGTCACCGTCTCCTCG SEQ ID NO: 43 |
| NI-204.34A3-$V_L$ | TCCTATGAGCTGACTCAGCCACCCTCGGTGTCAG TGTCCCCAGGACAAACGGCCAGGATCACCTGCTC TGGAGACGCGTTGCCAACAAATTTGCTTTTTGG TATCAACAAAAATCAGGCCAGGCCCCTGTCTTGG TCATCTATGAGGACGACAAACGACCTTCCGGGAT TCCTCAGAGATTCTCTGGCTCCAGTTCTGGGACA ACGGCCACCCTGACTATCAGTGGGGCCCAGGAGG AAGATGACGCTGATTACTATTGTTATTCAAAAGA CAGCACTAATGTTGAACGAGTCTTCGGAACAGGG ACCAAGCTCTCCGTCCTG SEQ ID NO: 45 |
| NI-204.25H3-$V_H$ | CAGGTGCAGCTGCAGGAGTCGGGCCCAGGACTGG TGAAGCCCTCGGAGACCCTGTCCCTCACCTGCAC TGTCTCTGGTGGCTCCATCAGTAGTTCTTACTGG AGTTGGATCCGGCAGCCCCCAGGGCAGGGACTGG AGTGGATTGGGTATATCTATTACAGCGGAAACAC CTACTACAACCCCTCCCTCAAGAGTCGAGTCACC ATATCAATAGACACGTCCAAGACCCAGTTCTCCC TGAACCTGACCTCTGTGAGCGCTGCGGACACGGC CGTGTATTACTGTGCGAGAGATGGCATACCAGGA GCCATAGGTATGGACGTCTGGGGCCAAGGGACCA CGGTCACCGTCTCCTCG SEQ ID NO: 47 |
| NI-204.25H3-$V_L$ | CAGTCTGTGTTGACGCAGCCGCCCTCAGTGTCTG CGGCCCCAGGACAGAAGGTCAACATCTCCTGCTC TGGAAGCAGCTCCAACATTGGGAATAATTATGTA TCCTGGTACCAGCGACTCCCAGGAACAGCCCCCA AACTCCTCATTTATGACAATAATAAACGACCCTC AGGGATTCCTGACCGATTCTCTGGCTCCAAGTCT GGCACGTCAGCCACCCTGGGCATCACCGGACTCC AGACTGGGGACGGGGCCGATTATTACTGCGCAAC TTGGGATAAAAGCCTGATTGCTGTGGTGTTCGGC GGAGGGACCAAGCTGACCGTCTTA SEQ ID NO: 49 |

The present invention also includes fragments of the polynucleotides of the invention, as described elsewhere. Additionally polynucleotides which encode fusion polynucleotides, Fab fragments, and other derivatives, as described herein, are also contemplated by the invention.

The polynucleotides may be produced or manufactured by any method known in the art. For example, if the nucleotide sequence of the antibody is known, a polynucleotide encoding the antibody may be assembled from chemically synthesized oligonucleotides, e.g., as described in Kutmeier et al., BioTechniques 17 (1994), 242, which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an antibody, or antigen-binding fragment, variant, or derivative thereof may be generated from nucleic acid from a suitable source. If a clone containing a nucleic acid encoding a particular antibody is not available, but the sequence of the antibody molecule is known, a nucleic acid encoding the antibody may be chemically synthesized or obtained from a suitable source (e.g., an antibody cDNA library, or a cDNA library generated from, or nucleic acid, preferably polyA+ RNA, isolated from, any tissue or cells expressing the SOD1-specific antibody, such as hybridoma cells selected to express an antibody) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

Once the nucleotide sequence and corresponding amino acid sequence of the antibody, or antigen-binding fragment, variant, or derivative thereof is determined, its nucleotide sequence may be manipulated using methods well known in the art for the manipulation of nucleotide sequences, e.g., recombinant DNA techniques, site directed mutagenesis, PCR, etc. (see, for example, the techniques described in Sambrook et al., *Molecular Cloning*, A Laboratory Manual, 2d Ed., Cold Spring Harbor Laboratory, Cold Spring Harbor, N.Y. (1990) and Ausubel et al., eds., *Current Protocols in Molecular Biology*, John Wiley & Sons, NY (1998), which are both incorporated by reference herein in their entireties), to generate antibodies having a different amino acid sequence, for example to create amino acid substitutions, deletions, and/or insertions.

IV. Expression of Antibody Polypeptides

Following manipulation of the isolated genetic material to provide antibodies, or antigen-binding fragments, variants, or derivatives thereof of the invention, the polynucleotides encoding the antibodies are typically inserted in an expression vector for introduction into host cells that may be used to produce the desired quantity of antibody. Recombinant expression of an antibody, or fragment, derivative or analog thereof, e.g., a heavy or light chain of an antibody which binds to a target molecule is described herein. Once a polynucleotide encoding an antibody molecule or a heavy or light chain of an antibody, or portion thereof (preferably containing the heavy or light chain variable domain), of the invention has been obtained, the vector for the production of the antibody molecule may be produced by recombinant DNA technology using techniques well known in the art. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody molecule of the invention, or a heavy or light chain thereof, or a heavy or light chain variable domain, operable linked to a promoter. Such vectors may include the nucleotide sequence encoding the constant region of the antibody molecule (see, e.g., international applications WO 86/05807 and WO 89/01036; and U.S. Pat. No. 5,122,464) and the variable domain of the antibody may be cloned into such a vector for expression of the entire heavy or light chain.

The term "vector" or "expression vector" is used herein to mean vectors used in accordance with the present invention as a vehicle for introducing into and expressing a desired gene in a host cell. As known to those skilled in the art, such vectors may easily be selected from the group consisting of plasmids, phages, viruses and retroviruses. In general, vectors compatible with the instant invention will comprise a selection marker, appropriate restriction sites to facilitate cloning of the desired gene and the ability to enter and/or replicate in eukaryotic or prokaryotic cells. For the purposes of this invention, numerous expression vector systems may be employed. For example, one class of vector utilizes DNA elements which are derived from animal viruses such as bovine papilloma virus, polyoma virus, adenovirus, vaccinia virus, baculovirus, retroviruses (RSV, MMTV or MOMLV) or SV40 virus. Others involve the use of polycistronic systems with internal ribosome binding sites. Additionally, cells which have integrated the DNA into their chromosomes may be selected by introducing one or more markers which allow selection of transfected host cells. The marker may provide for prototrophy to an auxotrophic host, biocide resistance (e.g., antibiotics) or resistance to heavy metals such as copper. The selectable marker gene can either be directly linked to the DNA sequences to be expressed, or introduced into the same cell by co-transformation. Additional elements may also be needed for optimal synthesis of mRNA. These elements may include signal sequences, splice signals, as well as transcriptional promoters, enhancers, and termination signals.

In particularly preferred embodiments the cloned variable region genes are inserted into an expression vector along with the heavy and light chain constant region genes (preferably human) as discussed above. In one embodiment, this is effected using a proprietary expression vector of Biogen IDEC, Inc., referred to as NEOSPLA, disclosed in U.S. Pat. No. 6,159,730. This vector contains the cytomegalovirus promoter/enhancer, the mouse beta globin major promoter, the SV40 origin of replication, the bovine growth hormone polyadenylation sequence, neomycin phosphotransferase exon 1 and exon 2, the dihydrofolate reductase gene and leader sequence. This vector has been found to result in very high level expression of antibodies upon incorporation of variable and constant region genes, transfection in CHO cells, followed by selection in G418 containing medium and methotrexate amplification. Of course, any expression vector which is capable of eliciting expression in eukaryotic cells may be used in the present invention. Examples of suitable vectors include, but are not limited to plasmids pcDNA3, pHCMV/Zeo, pCR3.1, pEF1/His, pIND/GS, pRc/HCMV2, pSV40/Zeo2, pTRACER-HCMV, pUB6/V5-His, pVAX1, and pZeoSV2 (available from Invitrogen, San Diego, Calif.), and plasmid pCI (available from Promega, Madison, Wis.). In general, screening large numbers of transformed cells for those which express suitably high levels if immunoglobulin heavy and light chains is routine experimentation which can be carried out, for example, by robotic systems. Vector systems are also taught in U.S. Pat. Nos. 5,736,137 and 5,658,570, each of which is incorporated by reference in its entirety herein. This system provides for high expression levels, e.g., >30 pg/cell/day. Other exemplary vector systems are disclosed e.g., in U.S. Pat. No. 6,413,777.

In other preferred embodiments the antibodies, or antigen-binding fragments, variants, or derivatives thereof of the invention may be expressed using polycistronic constructs such as those disclosed in US patent application publication no. 2003-0157641 A1 and incorporated herein in its entirety. In these expression systems, multiple gene products of interest such as heavy and light chains of antibodies may be produced from a single polycistronic construct. These systems advantageously use an internal ribosome entry site (IRES) to provide relatively high levels of antibodies. Compatible IRES sequences are disclosed in U.S. Pat. No. 6,193, 980 which is also incorporated herein. Those skilled in the art will appreciate that such expression systems may be used to effectively produce the full range of antibodies disclosed in the instant application.

More generally, once the vector or DNA sequence encoding a monomeric subunit of the antibody has been prepared, the expression vector may be introduced into an appropriate host cell. Introduction of the plasmid into the host cell can be accomplished by various techniques well known to those of skill in the art. These include, but are not limited to, transfection including lipotransfection using, e.g., Fugene® or lipofectamine, protoplast fusion, calcium phosphate precipitation, cell fusion with enveloped DNA, microinjection, and infection with intact virus. Typically, plasmid introduction into the host is via standard calcium phosphate co-precipitation method. The host cells harboring the expression construct are grown under conditions appropriate to the production of the light chains and heavy chains, and assayed for heavy and/or light chain protein synthesis. Exemplary assay techniques include enzyme-linked immunosorbent assay (ELISA), radioimmunoassay (MA), or fluorescence-activated cell sorter analysis (FACS), immunohistochemistry and the like.

The expression vector is transferred to a host cell by conventional techniques and the transfected cells are then cultured by conventional techniques to produce an antibody for use in the methods described herein. Thus, the invention includes host cells containing a polynucleotide encoding an antibody of the invention, or a heavy or light chain thereof, operable linked to a heterologous promoter. In preferred embodiments for the expression of double-chained antibodies, vectors encoding both the heavy and light chains may be co-expressed in the host cell for expression of the entire immunoglobulin molecule, as detailed below.

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes both heavy and light chain polypeptides. In such situations, the light chain is advantageously placed before the heavy chain to avoid an excess of toxic free heavy chain; see Proudfoot, Nature 322 (1986), 52; Kohler, Proc. Natl. Acad. Sci. USA 77 (1980), 2197. The coding sequences for the heavy and light chains may comprise cDNA or genomic DNA.

As used herein, "host cells" refers to cells which harbor vectors constructed using recombinant DNA techniques and encoding at least one heterologous gene. In descriptions of processes for isolation of antibodies from recombinant hosts, the terms "cell" and "cell culture" are used interchangeably to denote the source of antibody unless it is clearly specified otherwise. In other words, recovery of polypeptide from the "cells" may mean either from spun down whole cells, or from the cell culture containing both the medium and the suspended cells.

A variety of host-expression vector systems may be utilized to express antibody molecules for use in the methods described herein. Such host-expression systems represent vehicles by which the coding sequences of interest may be produced and subsequently purified, but also represent cells which may, when transformed or transfected with the appropriate nucleotide coding sequences, express an antibody molecule of the invention in situ. These include but are not limited to microorganisms such as bacteria (e.g., *E. coli*, *B. subtilis*) transformed with recombinant bacteriophage DNA, plasmid DNA or cosmid DNA expression vectors containing antibody coding sequences; yeast (e.g., *Saccharomyces*, *Pichia*) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, NSO, BLK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as *Escherichia coli*, and more preferably, eukaryotic cells, especially for the expression of whole recombinant antibody molecule, are used for the expression of a recombinant antibody molecule. For example, mammalian cells such as Chinese Hamster Ovary (CHO) cells, in conjunction with a vector such as the major intermediate early gene promoter element from human cytomegalovirus is an effective expression system for antibodies; see, e.g., Foecking et al., Gene 45 (1986), 101; Cockett et al., Bio/Technology 8 (1990), 2.

The host cell line used for protein expression is often of mammalian origin; those skilled in the art are credited with ability to preferentially determine particular host cell lines which are best suited for the desired gene product to be expressed therein. Exemplary host cell lines include, but are not limited to, CHO (Chinese Hamster Ovary), DG44 and DUXB11 (Chinese Hamster Ovary lines, DHFR minus), HELA (human cervical carcinoma), CVI (monkey kidney line), COS (a derivative of CVI with SV40 T antigen), VERY, BHK (baby hamster kidney), MDCK, WI38, R1610 (Chinese hamster fibroblast) BALBC/3T3 (mouse fibroblast), HAK (hamster kidney line), SP2/0 (mouse myeloma), P3x63-Ag3.653 (mouse myeloma), BFA-1c1BPT (bovine endothelial cells), RAJI (human lymphocyte) and 293 (human kidney). CHO and 293 cells are particularly preferred. Host cell lines are typically available from commercial services, the American Tissue Culture Collection or from published literature.

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used.

For long-term, high-yield production of recombinant proteins, stable expression is preferred. For example, cell lines which stably express the antibody molecule may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker.

Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which stably express the antibody molecule.

A number of selection systems may be used, including but not limited to the herpes simplex virus thymidine kinase (Wigler et al., Cell 11 (1977), 223), hypoxanthine-guanine phosphoribosyltransferase (Szybalska & Szybalski, Proc. Natl. Acad. Sci. USA 48 (1992), 202), and adenine phosphoribosyltransferase (Lowy et al., Cell 22 (1980), 817) genes can be employed in tk-, hgprt- or aprt-cells, respectively. Also, anti-metabolite resistance can be used as the basis of selection for the following genes: dhfr, which confers resistance to methotrexate (Wigler et al., Natl. Acad. Sci. USA 77 (1980), 357; O'Hare et al., Proc. Natl. Acad. Sci. USA 78 (1981), 1527); gpt, which confers resistance to mycophenolic acid (Mulligan & Berg, Proc. Natl. Acad. Sci. USA 78 (1981), 2072); neo, which confers resistance to the aminoglycoside G-418 Goldspiel et al., Clinical Pharmacy 12 (1993), 488-505; Wu and Wu, Biotherapy 3 (1991), 87-95; Tolstoshev, Ann. Rev. Pharmacol. Toxicol. 32 (1993), 573-596; Mulligan, Science 260 (1993), 926-932; and Morgan and Anderson, Ann. Rev. Biochem. 62 (1993), 191-217; TIB TECH 11 (1993), 155-215; and hygro, which confers resistance to hygromycin (Santerre et al., Gene 30 (1984), 147. Methods commonly known in the art of recombinant DNA technology which can be used are described in Ausubel et al. (eds.), *Current Protocols in Molecular Biology*, John Wiley & Sons, NY (1993); Kriegler, Gene Transfer and Expression, A Laboratory Manual, Stockton Press, NY (1990); and in Chapters 12 and 13, Dracopoli et al. (eds), *Current Protocols in Human Genetics*, John Wiley & Sons, NY (1994); Colberre-Garapin et al., J. Mol. Biol. 150:1 (1981), which are incorporated by reference herein in their entireties.

The expression levels of an antibody molecule can be increased by vector amplification, for a review, see Bebbington and Hentschel, *The use of vectors based on gene amplification for the expression of cloned genes in mammalian cells in DNA cloning*, Academic Press, New York, Vol. 3. (1987). When a marker in the vector system expressing antibody is amplifiable, increase in the level of inhibitor present in culture of host cell will increase the number of copies of the marker gene. Since the amplified region is associated with the antibody gene, production of the antibody will also increase; see Crouse et al., Mol. Cell. Biol. 3 (1983), 257. In vitro production allows scale-up to give large amounts of the desired polypeptides. Techniques for mammalian cell cultivation under tissue culture conditions are known in the art and include homogeneous suspension culture, e.g. in an airlift reactor or in a continuous stirrer reactor, or immobilized or entrapped cell culture, e.g. in hollow fibers, microcapsules, on agarose microbeads or ceramic cartridges. If necessary and/or desired, the solutions of polypeptides can be purified by the customary chromatography methods, for example gel filtration, ion-exchange chromatography, chromatography over DEAE-cellulose or (immuno-) affinity chromatography, e.g., after preferential biosynthesis of a synthetic hinge region polypeptide or prior to or subsequent to the HIC chromatography step described herein.

Genes encoding antibodies, or antigen-binding fragments, variants or derivatives thereof of the invention can also be expressed in non-mammalian cells such as bacteria or insect or yeast or plant cells. Bacteria which readily take up nucleic acids include members of the enterobacteriaceae, such as strains of *Escherichia coli* or *Salmonella*; Bacillaceae, such as *Bacillus subtilis; Pneumococcus; Streptococcus*, and *Haemophilus influenzae*. It will further be appreciated that, when expressed in bacteria, the heterologous polypeptides typically become part of inclusion bodies. The heterologous polypeptides must be isolated, purified and then assembled into functional molecules. Where tetravalent forms of antibodies are desired, the subunits will then self-assemble into tetravalent antibodies; see, e.g., international application WO02/096948.

In bacterial systems, a number of expression vectors may be advantageously selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified may be desirable. Such vectors include, but are not limited, to the *E. coli* expression vector pUR278 (Ruther et al., EMBO J. 2 (1983), 1791), in which the antibody coding sequence may be ligated individually into the vector in frame with the lacZ coding region so that a fusion protein is produced; pIN vectors (Inouye & Inouye, Nucleic Acids Res. 13 (1985), 3101-3109; Van Heeke & Schuster, J. Biol. Chem. 24 (1989), 5503-5509); and the like. pGEX vectors may also be used to express foreign polypeptides as fusion proteins with glutathione S-transferase (GST). In general, such fusion proteins are soluble and can easily be purified from lysed cells by adsorption and binding to a matrix of glutathione-agarose beads followed by elution in the presence of free glutathione. The pGEX vectors are designed to include thrombin or factor Xa protease cleavage sites so that the cloned target gene product can be released from the GST moiety.

In addition to prokaryotes, eukaryotic microbes may also be used. *Saccharomyces cerevisiae*, or common baker's yeast, is the most commonly used among eukaryotic microorganisms although a number of other strains are commonly available, e.g., *Pichia pastoris*. For expression in *Saccharomyces*, the plasmid YRp7, for example, (Stinchcomb et al., Nature 282 (1979), 39; Kingsman et al., Gene 7 (1979), 141; Tschemper et al., Gene 10 (1980), 157) is commonly used. This plasmid already contains the TRP1 gene which provides a selection marker for a mutant strain of yeast lacking the ability to grow in tryptophan, for example ATCC No. 44076 or PEP4-1 (Jones, Genetics 85 (1977), 12). The presence of the trpl lesion as a characteristic of the yeast host cell genome then provides an effective environment for detecting transformation by growth in the absence of tryptophan.

In an insect system, *Autographa californica* nuclear polyhedrosis virus (AcNPV) is typically used as a vector to express foreign genes. The virus grows in *Spodoptera frugiperda* cells. The antibody coding sequence may be cloned individually into non-essential regions (for example the polyhedrin gene) of the virus and placed under control of an AcNPV promoter (for example the polyhedrin promoter).

Once an antibody molecule of the invention has been recombinantly expressed, the whole antibodies, their dimers, individual light and heavy chains, or other immunoglobulin forms of the present invention, can be purified according to standard procedures of the art, including for example, by chromatography (e.g., ion exchange, affinity, particularly by affinity for the specific antigen after Protein A, and sizing column chromatography), centrifugation, differential solubility, e.g. ammonium sulfate precipitation, or by any other standard technique for the purification of proteins; see, e.g., Scopes, "Protein Purification", Springer Verlag, N.Y. (1982). Alternatively, a preferred method for increasing the affinity of antibodies of the invention is disclosed in US patent publication 2002-0123057 A1.

V. Fusion Proteins and Conjugates

In certain embodiments, the antibody polypeptide comprises an amino acid sequence or one or more moieties not normally associated with an antibody. Exemplary modifications are described in more detail below. For example, a single-chain fv antibody fragment of the invention may comprise a flexible linker sequence, or may be modified to add a functional moiety (e.g., PEG, a drug, a toxin, or a label such as a fluorescent, radioactive, enzyme, nuclear magnetic, heavy metal and the like)

An antibody polypeptide of the invention may comprise, consist essentially of, or consist of a fusion protein. Fusion proteins are chimeric molecules which comprise, for example, an immunoglobulin SOD1-binding domain with at least one target binding site, and at least one heterologous portion, i.e., a portion with which it is not naturally linked in nature. The amino acid sequences may normally exist in separate proteins that are brought together in the fusion polypeptide or they may normally exist in the same protein but are placed in a new arrangement in the fusion polypeptide. Fusion proteins may be created, for example, by chemical synthesis, or by creating and translating a polynucleotide in which the peptide regions are encoded in the desired relationship.

The term "heterologous" as applied to a polynucleotide or a polypeptide, means that the polynucleotide or polypeptide is derived from a distinct entity from that of the rest of the entity to which it is being compared. For instance, as used herein, a "heterologous polypeptide" to be fused to an antibody, or an antigen-binding fragment, variant, or analog thereof is derived from a non-immunoglobulin polypeptide of the same species, or an immunoglobulin or non-immunoglobulin polypeptide of a different species.

As discussed in more detail elsewhere herein, antibodies, or antigen-binding fragments, variants, or derivatives thereof of the invention may further be recombinantly fused to a heterologous polypeptide at the N- or C-terminus or chemically conjugated (including covalent and non-covalent conjugations) to polypeptides or other compositions. For example, antibodies may be recombinantly fused or conjugated to molecules useful as labels in detection assays and effector molecules such as heterologous polypeptides, drugs, radionuclides, or toxins; see, e.g., international applications WO92/08495; WO91/14438; WO89/12624; U.S. Pat. No. 5,314,995; and European patent application EP 0 396 387.

Antibodies, or antigen-binding fragments, variants, or derivatives thereof of the invention can be composed of amino acids joined to each other by peptide bonds or modified peptide bonds, i.e., peptide isosteres, and may contain amino acids other than the 20 gene-encoded amino acids. Antibodies may be modified by natural processes, such as posttranslational processing, or by chemical modification techniques which are well known in the art. Such modifications are well described in basic texts and in more detailed monographs, as well as in a voluminous research literature. Modifications can occur anywhere in the antibody, including the peptide backbone, the amino acid side-chains and the amino or carboxyl termini, or on moieties such as carbohydrates. It will be appreciated that the same type of modification may be present in the same or varying degrees at several sites in a given antibody. Also, a given antibody may contain many types of modifications. Antibodies may be branched, for example, as a result of ubiquitination, and they may be cyclic, with or without branching. Cyclic, branched, and branched cyclic antibodies may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination; see, e.g., *Proteins—Structure And Molecular Properties*, T. E. Creighton, W. H. Freeman and Company, New York 2nd Ed., (1993); *Posttranslational Covalent Modification Of Proteins*, B. C. Johnson, Ed., Academic Press, New York, pgs. 1-12 (1983); Seifter et al., Meth. Enzymol. 182 (1990), 626-646; Rattan et al., Ann. NY Acad. Sci. 663 (1992), 48-62).

The present invention also provides for fusion proteins comprising an antibody, or antigen-binding fragment, variant, or derivative thereof, and a heterologous polypeptide. In one embodiment, a fusion protein of the invention comprises, consists essentially of, or consists of, a polypeptide having the amino acid sequence of any one or more of the $V_H$ regions of an antibody of the invention or the amino acid sequence of any one or more of the $V_L$ regions of an antibody of the invention or fragments or variants thereof, and a heterologous polypeptide sequence. In another embodiment, a fusion protein for use in the diagnostic and treatment methods disclosed herein comprises, consists essentially of, or consists of a polypeptide having the amino acid sequence of any one, two, three of the $V_H$-CDRs of an antibody, or fragments, variants, or derivatives thereof, or the amino acid sequence of any one, two, three of the $V_L$-CDRs of an antibody, or fragments, variants, or derivatives thereof, and a heterologous polypeptide sequence. In one embodiment, the fusion protein comprises a polypeptide having the amino acid sequence of a $V_H$-CDR3 of an antibody of the present invention, or fragment, derivative, or variant thereof, and a heterologous polypeptide sequence, which fusion protein specifically binds to SOD1. In another embodiment, a fusion protein comprises a polypeptide having the amino acid sequence of at least one $V_H$ region of an antibody of the invention and the amino acid sequence of at least one $V_L$ region of an antibody of the invention or fragments, derivatives or variants thereof, and a heterologous polypeptide sequence. Preferably, the $V_H$ and $V_L$ regions of the fusion protein correspond to a single source antibody (or scFv or Fab fragment) which specifically binds SOD1. In yet another embodiment, a fusion protein for use in the diagnostic and treatment methods disclosed herein comprises a polypeptide having the amino acid sequence of any one, two, three or more of the $V_H$ CDRs of an antibody and the amino acid sequence of any one, two, three or more of the $V_L$ CDRs of an antibody, or fragments or variants thereof, and a heterologous polypeptide sequence. Preferably, two, three, four, five, six, or more of the $V_H$-CDR(s) or $V_L$-CDR(s) correspond to single source antibody (or scFv or Fab fragment) of the invention. Nucleic acid molecules encoding these fusion proteins are also encompassed by the invention.

Exemplary fusion proteins reported in the literature include fusions of the T cell receptor (Gascoigne et al., Proc. Natl. Acad. Sci. USA 84 (1987), 2936-2940; CD4 (Capon et al., Nature 337 (1989), 525-531; Traunecker et al., Nature 339 (1989), 68-70; Zettmeissl et al., DNA Cell Biol. USA 9 (1990), 347-353; and Byrn et al., Nature 344 (1990), 667-670); L-selectin (homing receptor) (Watson et al., J. Cell. Biol. 110 (1990), 2221-2229; and Watson et al., Nature 349 (1991), 164-167); CD44 (Aruffo et al., Cell 61 (1990), 1303-1313); CD28 and B7 (Linsley et al., J. Exp. Med. 173 (1991), 721-730); CTLA-4 (Lisley et al., J. Exp. Med. 174 (1991), 561-569); CD22 (Stamenkovic et al., Cell 66 (1991), 1133-1144); TNF receptor (Ashkenazi et al., Proc. Natl. Acad. Sci. USA 88 (1991), 10535-10539; Lesslauer et al., Eur. J. Immunol. 27 (1991), 2883-2886; and Peppel et al., J. Exp. Med. 174 (1991), 1483-1489 (1991); and IgE receptor a (Ridgway and Gorman, J. Cell. Biol. 115 (1991), Abstract No. 1448).

As discussed elsewhere herein, antibodies, or antigen-binding fragments, variants, or derivatives thereof of the invention may be fused to heterologous polypeptides to increase the in vivo half-life of the polypeptides or for use in immunoassays using methods known in the art. For example, in one embodiment, PEG can be conjugated to the antibodies of the invention to increase their half-life in vivo; see, e.g., Leong et al., Cytokine 16 (2001), 106-119; Adv. in Drug Deliv. Rev. 54 (2002), 531; or Weir et al., Biochem. Soc. Transactions 30 (2002), 512.

Moreover, antibodies, or antigen-binding fragments, variants, or derivatives thereof of the invention can be fused to marker sequences, such as a peptide to facilitate their purification or detection. In preferred embodiments, the marker amino acid sequence is a hexa-histidine peptide (HIS), such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86 (1989), 821-824, for instance, hexa-histidine provides for convenient purification of the fusion protein. Other peptide tags useful for purification include, but are not limited to, the "HA" tag, which corresponds to an epitope derived from the influenza hemagglutinin protein (Wilson et al., Cell 37 (1984), 767) and the "flag" tag.

Fusion proteins can be prepared using methods that are well known in the art; see for example U.S. Pat. Nos. 5,116,964 and 5,225,538. The precise site at which the fusion is made may be selected empirically to optimize the secretion or binding characteristics of the fusion protein. DNA encoding the fusion protein is then transfected into a host cell for expression.

Antibodies of the present invention may be used in non-conjugated form or may be conjugated to at least one of a variety of molecules, e.g., to improve the therapeutic properties of the molecule, to facilitate target detection, or for imaging or therapy of the patient. Antibodies, or antigen-binding fragments, variants, or derivatives thereof of the invention can be labeled or conjugated either before or after purification, when purification is performed. In particular, antibodies, or antigen-binding fragments, variants, or derivatives thereof of the invention may be conjugated to therapeutic agents, prodrugs, peptides, proteins, enzymes, viruses, lipids, biological response modifiers, pharmaceutical agents, or PEG.

Conjugates that are immunotoxins including conventional antibodies have been widely described in the art. The toxins may be coupled to the antibodies by conventional coupling techniques or immunotoxins containing protein toxin portions can be produced as fusion proteins. The antibodies of the present invention can be used in a corresponding way to obtain such immunotoxins. Illustrative of such immunotoxins are those described by Byers, Seminars Cell. Biol. 2 (1991), 59-70 and by Fanger, Immunol. Today 12 (1991), 51-54.

Those skilled in the art will appreciate that conjugates may also be assembled using a variety of techniques depending on the selected agent to be conjugated. For example, conjugates with biotin are prepared, e.g., by reacting an SOD1 binding polypeptide with an activated ester of biotin such as the biotin N-hydroxysuccinimide ester. Similarly, conjugates with a fluorescent marker may be prepared in the presence of a coupling agent, e.g. those listed herein, or by reaction with an isothiocyanate, preferably fluorescein-isothiocyanate. Conjugates of the antibodies, or antigen-binding fragments, variants or derivatives thereof of the invention are prepared in an analogous manner.

The present invention further encompasses antibodies, or antigen-binding fragments, variants, or derivatives thereof of the invention conjugated to a diagnostic or therapeutic agent. The antibodies can be used diagnostically to, for example, demonstrate presence of a neurodegenerative disease, to indicate the risk of getting a neurodegenerative disease, to monitor the development or progression of a neurodegenerative disease, i.e. a disease showing the occurrence of, or related to misfolded/aggregated SOD1 as part of a clinical testing procedure to, e.g., determine the efficacy of a given treatment and/or prevention regimen. Detection can be facilitated by coupling the antibody, or antigen-binding fragment, variant, or derivative thereof to a detectable substance. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions; see, e.g., U.S. Pat. No. 4,741,900 for metal ions which can be conjugated to antibodies for use as diagnostics according to the present invention. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}$I, $^{131}$I, $^{111}$In or $^{99}$Tc.

An antibody, or antigen-binding fragment, variant, or derivative thereof also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

One of the ways in which an antibody, or antigen-binding fragment, variant, or derivative thereof can be detectably labeled is by linking the same to an enzyme and using the linked product in an enzyme immunoassay (EIA) (Voller, A., "The Enzyme Linked Immunosorbent Assay (ELISA)" Microbiological Associates Quarterly Publication, Walkersville, Md., Diagnostic Horizons 2 (1978), 1-7); Voller et al., J. Clin. Pathol. 31 (1978), 507-520; Butler, *Meth. Enzymol.* 73 (1981), 482-523; Maggio, E. (ed.), *Enzyme Immunoassay*, CRC Press, Boca Raton, Fla., (1980); Ishikawa, E. et al., (eds.), *Enzyme Immunoassay*, Kgaku Shoin, Tokyo (1981). The enzyme, which is bound to the antibody, will react with an appropriate substrate, preferably a chromogenic substrate, in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. Additionally, the detection can be accomplished by colorimetric methods which employ a chromogenic substrate for the enzyme. Detection may also be accomplished by visual comparison of the extent of enzymatic reaction of a substrate in comparison with similarly prepared standards.

Detection may also be accomplished using any of a variety of other immunoassays. For example, by radioactively labeling the antibody, or antigen-binding fragment, variant, or derivative thereof, it is possible to detect the antibody through the use of a radioimmunoassay (MA) (see, for example, Weintraub, B., *Principles of Radioimmunoassays, Seventh Training Course on Radioligand Assay Techniques*, The Endocrine Society, (March, 1986)), which is incorporated by reference herein). The radioactive isotope can be detected by means including, but not limited to, a gamma counter, a scintillation counter, or autoradiography.

An antibody, or antigen-binding fragment, variant, or derivative thereof can also be detectably labeled using fluorescence emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA).

Techniques for conjugating various moieties to an antibody, or antigen-binding fragment, variant, or derivative thereof are well known, see, e.g., Amon et al., "Monoclonal Antibodies For Immunotargeting Of Drugs In Cancer Therapy", in *Monoclonal Antibodies And Cancer Therapy*, Reisfeld et al. (eds.), pp. 243-56 (Alan R. Liss, Inc. (1985); Hellstrom et al., "Antibodies For Drug Delivery", in *Controlled Drug Delivery* (2nd Ed.), Robinson et al. (eds.), Marcel Dekker, Inc., pp. 623-53 (1987); Thorpe, "Antibody Carriers Of Cytotoxic Agents In Cancer Therapy: A Review", in *Monoclonal Antibodies '84: Biological And Clinical Applications*, Pinchera et al. (eds.), pp. 475-506 (1985); "Analysis, Results, And Future Prospective Of The Therapeutic Use Of Radiolabeled Antibody In Cancer Therapy", in *Monoclonal Antibodies For Cancer Detection And Therapy*, Baldwin et al. (eds.), Academic Press pp. 303-16 (1985), and Thorpe et al., "The Preparation And Cytotoxic Properties Of Antibody-Toxin Conjugates", Immunol. Rev. 62 (1982), 119-158.

As mentioned, in certain embodiments, a moiety that enhances the stability or efficacy of a binding molecule, e.g., a binding polypeptide, e.g., an antibody or immunospecific fragment thereof can be conjugated. For example, in one embodiment, PEG can be conjugated to the binding molecules of the invention to increase their half-life in vivo. Leong et al., Cytokine 16 (2001), 106; Adv. in Drug Deliv. Rev. 54 (2002), 531; or Weir et al., Biochem. Soc. Transactions 30 (2002), 512.

VI. Compositions and Methods of Use

The present invention relates to compositions comprising the aforementioned SOD1 binding molecule, e.g., antibody or antigen-binding fragment thereof of the present invention or derivative or variant thereof, or the polynucleotide, vector or cell of the invention. The composition of the present invention may further comprise a pharmaceutically acceptable carrier. Furthermore, the pharmaceutical composition of the present invention may comprise further agents such as interleukins or interferons depending on the intended use of the pharmaceutical composition. For use in the treatment of a neurodegenerative disease showing the occurrence of, or related to misfolded/aggregated SOD1, e.g., of amyotrophic lateral sclerosis, Alzheimer's or Parkinson's disease the additional agent may be selected from the group consisting of small organic molecules, anti-SOD1 antibodies, and combinations thereof. Hence, in a particular preferred embodiment the present invention relates to the use of the SOD1 binding molecule, e.g., antibody or antigen-binding fragment thereof of the present invention or of a binding molecule having substantially the same binding specificities of any one thereof, the polynucleotide, the vector or the cell of the present invention for the preparation of a pharmaceutical or diagnostic composition for prophylactic and therapeutic treatment of a neurodegenerative disease, monitoring the progression of a neurodegenerative disease or a response to a neurodegenerative disease treatment in a subject or for determining a subject's risk for developing a neurodegenerative disease.

Hence, in one embodiment the present invention relates to a method of treating a neurodegenerative disorder characterized by abnormal accumulation and/or deposition of SOD1 in the brain and the central nervous system, respectively, which method comprises administering to a subject in need thereof a therapeutically effective amount of any one of the aforedescribed SOD1 binding molecules, antibodies, polynucleotides, vectors or cells of the instant invention. The terms "neurodegenerative disorder" includes but is not limited to diseases such as amyotrophic lateral sclerosis, Alzheimer's disease (AD), amyotrophic lateral sclerosis/parkinsonism-dementia complex (ALS-PDC), Down's syndrome and Parkinson's disease (PD). The term "neuro-muscular disorder" includes but is not limited to diseases such as amyotrophic lateral sclerosis (ALS). Unless stated otherwise, the terms neurodegenerative, neurological are used interchangeably. Limited to the description of amyotrophic lateral sclerosis, the terms neurodegenerative, neurological and neuro-muscular are used interchangeably as well.

A particular advantage of the therapeutic approach of the present invention lies in the fact that the antibodies of the present invention are derived from B cells or B memory cells from healthy human subjects with no signs of a disease showing the occurrence of, or related to misfolded/aggregated SOD1 such as ALS and thus are, with a certain probability, capable of preventing a clinically manifest disease related to misfolded/aggregated SOD1, or of diminishing the risk of the occurrence of the clinically manifest disease, or of delaying the onset or progression of the clinically manifest disease. Typically, the antibodies of the present invention also have already successfully gone through somatic maturation, i.e. the optimization with respect to selectivity and effectiveness in the high affinity binding to the target SOD1 molecule by means of somatic variation of the variable regions of the antibody.

The knowledge that such cells in vivo, e.g. in a human, have not been activated by means of related or other physiological proteins or cell structures in the sense of an autoimmunological or allergic reaction is also of great medical importance since this signifies a considerably increased chance of successfully living through the clinical test phases. So to speak, efficiency, acceptability and tolerability have already been demonstrated before the preclinical and clinical development of the prophylactic or therapeutic antibody in at least one human subject. It can thus be expected that the human anti-SOD1 antibodies of the present invention, both its target structure-specific efficiency as therapeutic agent and its decreased probability of side effects significantly increase its clinical probability of success.

The present invention also provides a pharmaceutical and diagnostic, respectively, pack or kit comprising one or more containers filled with one or more of the above described ingredients, e.g. anti-SOD1 antibody, binding fragment, derivative or variant thereof, polynucleotide, vector or cell of the present invention. Associated with such container(s) can be a notice in the form prescribed by a governmental agency regulating the manufacture, use or sale of pharmaceuticals or biological products, which notice reflects approval by the agency of manufacture, use or sale for human administration. In addition or alternatively the kit comprises reagents and/or instructions for use in appropriate diagnostic assays. The composition, e.g. kit of the present invention is of course particularly suitable for the risk assessment, diagnosis, prevention and treatment of a disorder which is accompanied with the presence of misfolded/aggregated SOD1, and in particular applicable for the treatment of amyotrophic lateral sclerosis, Alzheimer's disease (AD), amyotrophic lateral sclerosis/parkinsonism-dementia complex (ALS-PDC), Down's syndrome or Parkinson's disease, for example.

The pharmaceutical compositions of the present invention can be formulated according to methods well known in the art; see for example Remington: The Science and Practice of Pharmacy (2000) by the University of Sciences in Philadelphia, ISBN 0-683-306472. Examples of suitable pharmaceutical carriers are well known in the art and include phosphate buffered saline solutions, water, emulsions, such as oil/water emulsions, various types of wetting agents, sterile solutions etc. Compositions comprising such carriers can be formulated by well-known conventional methods. These pharmaceutical compositions can be administered to the subject at a suitable dose. Administration of the suitable compositions may be effected by different ways, e.g., by intravenous, intraperitoneal, subcutaneous, intramuscular, intranasal, topical or intradermal administration or spinal or brain delivery. Aerosol formulations such as nasal spray formulations include purified aqueous or other solutions of the active agent with preservative agents and isotonic agents. Such formulations are preferably adjusted to a pH and isotonic state compatible with the nasal mucous membranes. Formulations for rectal or vaginal administration may be presented as a suppository with a suitable carrier.

Furthermore, whereas the present invention includes the now standard (though fortunately infrequent) procedure of drilling a small hole in the skull to administer a drug of the present invention, in a preferred aspect, the binding molecule, especially antibody or antibody based drug of the present invention can cross the blood-brain barrier, which allows for intravenous or oral administration.

The dosage regimen will be determined by the attending physician and clinical factors. As is well known in the medical arts, dosages for any one patient depends upon many factors, including the patient's size, body surface area, age, the particular compound to be administered, sex, time and route of administration, general health, and other drugs being administered concurrently. A typical dose can be, for example, in the range of 0.001 to 1000 µg (or of nucleic acid for expression or for inhibition of expression in this range); however, doses below or above this exemplary range are envisioned, especially considering the aforementioned factors. Generally, the dosage can range, e.g., from about 0.0001 to 100 mg/kg, and more usually 0.01 to 5 mg/kg (e.g., 0.02 mg/kg, 0.25 mg/kg, 0.5 mg/kg, 0.75 mg/kg, 1 mg/kg, 2 mg/kg, etc.), of the host body weight. For example dosages can be 1 mg/kg body weight or 10 mg/kg body weight or within the range of 1-10 mg/kg, preferably at least 1 mg/kg. Doses intermediate in the above ranges are also intended to be within the scope of the invention. Subjects can be administered such doses daily, on alternative days, weekly or according to any other schedule determined by empirical analysis. An exemplary treatment entails administration in multiple dosages over a prolonged period, for example, of at least six months. Additional exemplary treatment regimes entail administration once per every two weeks or once a month or once every 3 to 6 months. Exemplary dosage schedules include 1-10 mg/kg or 15 mg/kg on consecutive days, 30 mg/kg on alternate days or 60 mg/kg weekly. In some methods, two or more monoclonal antibodies with different binding specificities are administered simultaneously, in which case the dosage of each antibody administered falls within the ranges indicated. Progress can be monitored by periodic assessment. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Furthermore, the pharmaceutical composition of the invention may comprise further agents such as dopamine or psychopharmacologic drugs, depending on the intended use of the pharmaceutical composition.

Furthermore, in a preferred embodiment of the present invention the pharmaceutical composition may be formulated as a vaccine, for example, if the pharmaceutical composition of the invention comprises an anti-SOD1 antibody or binding fragment, derivative or variant thereof for passive immunization. As mentioned in the background section, aggregated SOD1 species have been reported extracellularly in plasma and CSF (Gruzman et al., Proc. Natl. Acad. Sci. USA 104 (2007), 12524-12529) and studies in transgenic mouse lines using active and passive vaccination with humanized murine antibodies revealed reduced brain levels of SOD1 aggregates in the brain, slowed progression of behavior impairments and delayed death (Urushitani et al., Proc. Natl. Acad. Sci. USA 104 (2007), 2495-2500). Accordingly, it is prudent to expect that passive immunization with human anti-SOD1 antibodies and equivalent SOD1 binding molecules of the present invention will help to circumvent several adverse effects of active immunization therapy concepts as already discussed in the background section. Therefore, the present anti-SOD1 antibodies and their equivalents of the present invention will be particularly useful as a vaccine for the prevention or amelioration of diseases showing the presence of, or caused by misfolded/aggregated SOD1 such as amyotrophic lateral sclerosis, Alzheimer's disease (AD), amyotrophic lateral sclerosis/parkinsonism-dementia complex (ALS-PDC), Down's syndrome or Parkinson's disease, for example.

In one embodiment, it may be beneficial to use recombinant bispecific or multispecific constructs of the antibody of the present invention. For a reference see Fischer and Léger, Pathobiology 74 (2007), 3-14. Such bispecific molecule might be designed to target SOD1 with one binding arm and another pathologic entity such as Aβ or alpha-synuclein or a pathological conformation of SOD1 with a second binding arm. Alternatively the second binding arm may be designed to target a protein present at the blood-brain-barrier to facilitate antibody penetration into the brain.

In one embodiment, it may be beneficial to use recombinant Fab (rFab) and single chain fragments (scFvs) of the antibody of the present invention, which might more readily penetrate a cell membrane. For example, Robert et al., Protein Eng. Des. Sel. (2008) Oct. 16; S1741-0134, published online ahead, describe the use of chimeric recombinant Fab (rFab) and single chain fragments (scFvs) of monoclonal antibody WO-2 which recognizes an epitope in the N-terminal region of Aβ. The engineered fragments were able to (i) prevent amyloid fibrillization, (ii) disaggregate preformed A131-42 fibrils and (iii) inhibit A131-42 oligomer-mediated neurotoxicity in vitro as efficiently as the whole IgG molecule. The perceived advantages of using small Fab and scFv engineered antibody formats which lack the effector function include more efficient passage across the blood-brain barrier and minimizing the risk of triggering inflammatory side reactions. Furthermore, besides scFv and single-domain antibodies retain the binding specificity of full-length antibodies, they can be expressed as single genes and intracellularly in mammalian cells as intrabodies, with the potential for alteration of the folding, interactions, modifications, or subcellular localization of their targets; see for review, e.g., Miller and Messer, Molecular Therapy 12 (2005), 394-401.

In a different approach Muller et al., Expert Opin. Biol. Ther. (2005), 237-241, describe a technology platform, so-called 'SuperAntibody Technology', which is said to enable antibodies to be shuttled into living cells without harming them. Such cell-penetrating antibodies open new diagnostic and therapeutic windows. The term 'TransMabs' has been coined for these antibodies.

In a further embodiment, co-administration or sequential administration of other antibodies useful for treating a disease related to the occurrence of misfolded/aggregated SOD1 may be desirable. In one embodiment, the additional antibody is comprised in the pharmaceutical composition of the present invention. Examples of antibodies which can be used to treat a subject include, but are not limited to, antibodies targeting beta-amyloid, alpha-synuclein, TDP-43 and tau.

In a further embodiment, co-administration or sequential administration of other neuroprotective agents useful for treating a disease related to misfolded/aggregated SOD1 may be desirable. In one embodiment, the additional agent is comprised in the pharmaceutical composition of the present invention. Examples of neuroprotective agents which can be used to treat a subject include, but are not limited to, an acetylcholinesterase inhibitor, a glutamatergic receptor antagonist, kinase inhibitors, HDAC inhibitors, anti-inflammatory agents, divalproex sodium, or any combination thereof. Examples of other neuroprotective agents that may be used concomitant with pharmaceutical composition of the present invention are described in the art; see, e.g. international application WO2007/011907. In one embodiment, the additional agent is dopamine or a dopamine receptor agonist.

A therapeutically effective dose or amount refers to that amount of the active ingredient sufficient to ameliorate the symptoms or condition. Therapeutic efficacy and toxicity of such compounds can be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between therapeutic and toxic effects is the therapeutic index, and it can be expressed as the ratio, $LD_{50}/ED_{50}$. Preferably, the therapeutic agent in the composition is present in an amount sufficient to restore or preserve normal behavior and/or cognitive properties in case of amyotrophic lateral sclerosis, Alzheimer's disease (AD), amyotrophic lateral sclerosis/parkinsonism-dementia complex (ALS-PDC), Down's syndrome or Parkinson's disease, for example.

From the foregoing, it is evident that the present invention encompasses any use of an SOD1 binding molecule comprising at least one CDR of the above described antibody, in particular for diagnosing and/or treatment of a disease related to misfolded/aggregated SOD1 as mentioned above, particularly amyotrophic lateral sclerosis (ALS). Preferably, said binding molecule is an antibody of the present invention or an immunoglobulin chain thereof. In addition, the present invention relates to anti-idiotypic antibodies of any one of the mentioned antibodies described hereinbefore. These are antibodies or other binding molecules which bind to the unique antigenic peptide sequence located on an antibody's variable region near the antigen-binding site and are useful, e.g., for the detection of anti-SOD1 antibodies in sample of a subject.

In another embodiment the present invention relates to a diagnostic composition comprising any one of the above described SOD1 binding molecules, antibodies, antigen-binding fragments, polynucleotides, vectors or cells of the invention and optionally suitable means for detection such as reagents conventionally used in immuno- or nucleic acid-based diagnostic methods. The antibodies of the invention are, for example, suited for use in immunoassays in which they can be utilized in liquid phase or bound to a solid phase carrier. Examples of immunoassays which can utilize the antibody of the invention are competitive and non-competitive immunoassays in either a direct or indirect format. Examples of such immunoassays are the radioimmunoassay (MA), the sandwich (immunometric assay), flow cytometry and the Western blot assay. The antigens and antibodies of the invention can be bound to many different carriers and used to isolate cells specifically bound thereto. Examples of well-known carriers include glass, polystyrene, polyvinyl chloride, polypropylene, polyethylene, polycarbonate, dextran, nylon, amyloses, natural and modified celluloses, polyacrylamides, agaroses, and magnetite. The nature of the carrier can be either soluble or insoluble for the purposes of the invention. There are many different labels and methods of labeling known to those of ordinary skill in the art. Examples of the types of labels which can be used in the present invention include enzymes, radioisotopes, colloidal metals, fluorescent compounds, chemiluminescent compounds, and bioluminescent compounds; see also the embodiments discussed hereinabove.

By a further embodiment, the SOD1 binding molecules, in particular antibodies of the present invention may also be used in a method for the diagnosis of a disorder in an individual by obtaining a body fluid sample from the tested individual which may be a blood sample, a lymph sample or any other body fluid sample and contacting the body fluid sample with an antibody of the instant invention under conditions enabling the formation of antibody-antigen complexes. The level of such complexes is then determined by methods known in the art, a level significantly higher than that formed in a control sample indicating the disease in the tested individual. In the same manner, the specific antigen bound by the antibodies of the invention may also be used. Thus, the present invention relates to an in vitro immunoassay comprising the binding molecule, e.g., antibody or antigen-binding fragment thereof of the invention.

In this context, the present invention also relates to means specifically designed for this purpose. For example, an antibody-based array may be used, which is for example loaded with antibodies or equivalent antigen-binding molecules of the present invention which specifically recognize SOD1. Design of microarray immunoassays is summarized in Kusnezow et al., Mol. Cell Proteomics 5 (2006), 1681-1696. Accordingly, the present invention also relates to microarrays loaded with SOD1 binding molecules identified in accordance with the present invention.

In one embodiment, the present invention relates to a method of diagnosing a disease related to misfolded/aggregated SOD1 in a subject, the method comprising determining the presence of SOD1 and/or misfolded and/or aggregated SOD1 in a sample from the subject to be diagnosed with at least one antibody of the present invention, an SOD1 binding fragment thereof or an SOD1-binding molecule having substantially the same binding specificities of any one thereof, wherein the presence of pathologically misfolded and/or aggregated SOD1 is indicative of a neurodegenerative disorder and an increase of the level of the pathologically misfolded and/or aggregated SOD1 in comparison to the level of the physiological SOD1 dimeric forms is indicative for progression of a neurodegenerative disorder in said subject.

The subject to be diagnosed may be asymptomatic or preclinical for the disease. Preferably, the control subject has a disease related to misfolded/aggregated SOD1, for example, amyotrophic lateral sclerosis, Alzheimer's disease (AD), amyotrophic lateral sclerosis/parkinsonism-dementia complex (ALS-PDC), Down's syndrome or Parkinson's disease, wherein a similarity between the level of pathologically misfolded and/or aggregated SOD1 and the reference standard indicates that the subject to be diagnosed has a neurodegenerative disease. Alternatively, or in addition as a second control the control subject does not have a neurodegenerative disease, wherein a difference between the level of physiological SOD1 dimers and/or of pathologically misfolded and/or aggregated SOD1 and the reference standard indicates that the subject to be diagnosed has a neurodegenerative disease. Preferably, the subject to be diagnosed and the control subject(s) are age-matched. The sample to be analyzed may be any body fluid suspected to contain pathologically misfolded and/or aggregated SOD1, for example a blood, CSF, or urine sample.

The level of physiological SOD1 dimers and/or of pathologically misfolded and/or aggregated SOD1 may be assessed by any suitable method known in the art comprising, e.g., analyzing SOD1 by one or more techniques chosen from Western blot, immunoprecipitation, enzyme-linked immunosorbent assay (ELISA), radioimmunoassay (MA), fluorescent activated cell sorting (FACS), two-dimensional gel electrophoresis, mass spectroscopy (MS), matrix-assisted laser desorption/ionization-time of flight-MS (MALDI-TOF), surface-enhanced laser desorption ionization-time of flight (SELDI-TOF), high performance liquid chromatography (HPLC), fast protein liquid chromatography (FPLC), multidimensional liquid chromatography (LC) followed by tandem mass spectrometry (MS/MS), and laser densitometry. Preferably, said in vivo imaging of SOD1 comprises positron emission tomography (PET), single photon emission tomography (SPECT), near infrared (NIR) optical imaging or magnetic resonance imaging (MM).

Antibody based methods for detection SOD1 and for diagnosing or monitoring the progression of a disease related to misfolded/aggregated SOD1 such as ALS, and monitoring the treatment of such a disease using antibodies and related means which may be adapted in accordance with the present invention are also described in international applications WO2007/098607 and WO2007/025385 the disclosure content of all being incorporated herein by reference. Those methods may be applied as described but with an SOD1 specific antibody, binding fragment, derivative or variant of the present invention.

VII. Peptides with Conformational Specific SOD1 Epitopes

In a further aspect the present invention relates to peptides having an epitope of SOD1 specifically recognized by any antibody of the present invention. Preferably, such peptide comprises or consists of an amino acid sequence as indicated in SEQ ID NO: 2, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58 or in SEQ ID NO: 59 or a modified sequence thereof in which one or more amino acids are substituted, deleted and/or added, wherein the peptide is recognized by any antibody of the present invention, preferably by antibody NI-204.10D12, NI-204.12G7, NI-204.10A8, NI-204.11F11, NI-204.6H1, NI-204.12G3, NI-204.7G5, NI-204.7B3, NI-204.34A3 respective by antibody NI-204.25H3.

In one embodiment of this invention such a peptide may be used for diagnosing a disease related to misfolded/aggregated SOD1 such as ALS in a subject, comprising a step of determining the presence of an antibody that binds to a peptide in a biological sample of said subject, and being used for diagnosis of such a disease in said subject by measuring the levels of antibodies which recognize the above described peptide of the present invention and comparing the measurements to the levels which are found in healthy subjects of comparable age and gender. An elevated level of measured antibodies specific for said peptide of the present invention would be indicative for diagnosing a disease related to misfolded/aggregated SOD1 in said subject. The peptide of the present invention may be formulated in an array, a kit and composition, respectively, as described hereinbefore.

These and other embodiments are disclosed and encompassed by the description and examples of the present invention. Further literature concerning any one of the materials, methods, uses and compounds to be employed in accordance with the present invention may be retrieved from public libraries and databases, using for example electronic devices. For example the public database "Medline" may be utilized, which is hosted by the National Center for Biotechnology Information and/or the National Library of Medicine at the National Institutes of Health. Further databases and web addresses, such as those of the European Bioinformatics Institute (EBI), which is part of the European Molecular Biology Laboratory (EMBL) are known to the person skilled in the art and can also be obtained using internet search engines. An overview of patent information in biotechnology and a survey of relevant sources of patent information useful for retrospective searching and for current awareness is given in Berks, TIBTECH 12 (1994), 352-364.

The above disclosure generally describes the present invention. Unless otherwise stated, a term as used herein is given the definition as provided in the Oxford Dictionary of Biochemistry and Molecular Biology, Oxford University Press, 1997, revised 2000 and reprinted 2003, ISBN 0 19 850673 2. Several documents are cited throughout the text of this specification. Full bibliographic citations may be found at the end of the specification immediately preceding the claims. The contents of all cited references (including literature references, issued patents, published patent applications as cited throughout this application and manufacturer's specifications, instructions, etc) are hereby expressly incorporated by reference; however, there is no admission that any document cited is indeed prior art as to the present invention.

A more complete understanding can be obtained by reference to the following specific examples which are provided herein for purposes of illustration only and are not intended to limit the scope of the invention.

EXAMPLES

The examples which follow further illustrate the invention, but should not be construed to limit the scope of the invention in any way. The following experiments in Examples 1 to 7 are illustrated and described with respect to antibodies NI-204.10D12, NI-204.12G7, NI-204.10A8, NI-204.9F6, NI-204.11F11, NI-204.67E12, NI-204.6H1, NI-204.12G3, NI-204.7G5, NI-204.7B3, NI-204.34A3 and NI-204.25H3 as cloned, i.e. the framework 1 (FR1) Ig-variable regions without being adjusted to the germ line (GL) sequences of human variable heavy and light chains; see FIG. 1.

Material and Methods

Detailed descriptions of conventional methods, such as those employed herein can be found in the cited literature; see also "The Merck Manual of Diagnosis and Therapy" Seventeenth Ed. edited by Beers and Berkow (Merck & Co., Inc. 2003).

The practice of the present invention will employ, unless otherwise indicated, conventional techniques of cell biology, cell culture, molecular biology, transgenic biology, microbiology, recombinant DNA, and immunology, which are within the skill of the art. For further elaboration of general techniques useful in the practice of this invention, the practitioner can refer to standard textbooks and reviews in cell biology and tissue culture; see also the references cited in the examples. General methods in molecular and cellular biochemistry can be found in such standard textbooks as Molecular Cloning: A Laboratory Manual, 3rd Ed. (Sambrook et al., Harbor Laboratory Press 2001); Short Protocols in Molecular Biology, 4th Ed. (Ausubel et al. eds., John Wiley & Sons 1999); DNA Cloning, Volumes I and II (Glover ed., 1985); Oligonucleotide Synthesis (Gait ed., 1984); Nucleic Acid Hybridization (Hames and Higgins eds. 1984); Transcription And Translation (Hames and Higgins eds. 1984); Culture Of Animal Cells (Freshney and Alan, Liss, Inc., 1987); Gene Transfer Vectors for Mammalian Cells (Miller and Calos, eds.); Current Protocols in Molecular Biology and Short Protocols in Molecular Biology, 3rd Edition (Ausubel et al., eds.); and Recombinant DNA Methodology (Wu, ed., Academic Press). Gene Transfer Vectors For Mammalian Cells (Miller and Calos, eds., 1987, Cold Spring Harbor Laboratory); Methods In Enzymology, Vols. 154 and 155 (Wu et al., eds.); Immobilized Cells And Enzymes (IRL Press, 1986); Perbal, A Practical Guide To Molecular Cloning (1984); the treatise, Methods In Enzymology (Academic Press, Inc., N.Y.); Immunochemical Methods In Cell And Molecular Biology (Mayer and Walker, eds., Academic Press, London, 1987); Handbook Of Experimental Immunology, Volumes I-IV (Weir and Blackwell, eds., 1986). Protein Methods (Bollag et al., John Wiley & Sons 1996); Non-viral Vectors for Gene Therapy (Wagner et al. eds., Academic Press 1999); Viral Vectors (Kaplitt & Loewy eds., Academic Press 1995); Immunology Methods Manual (Lefkovits ed., Academic Press 1997); and Cell and Tissue Culture: Laboratory Procedures in Biotechnology (Doyle & Griffiths, John Wiley & Sons 1998). Reagents, cloning vectors and kits for genetic manipulation referred to in this disclosure are available from commercial vendors such as BioRad, Stratagene, Invitrogen, Sigma-Aldrich, and ClonTech. General techniques in cell culture and media collection are outlined in Large Scale Mammalian Cell Culture (Hu et al., Curr. Opin. Biotechnol. 8 (1997), 148); Serum-free Media (Kitano, Biotechnology 17 (1991), 73); Large Scale Mammalian Cell Culture (Curr. Opin. Biotechnol. 2 (1991), 375); and Suspension Culture of Mammalian Cells (Birch et al., Bioprocess Technol. 19 (1990), 251); Extracting information from cDNA arrays, Herzel et al., CHAOS 11 (2001), 98-107.

Methods of Identification of SOD1-Specific B-Cells and Cloning of the Respective Antibodies Unless indicated otherwise below, identification of SOD1-specific B cells and molecular cloning of anti-SOD1 antibodies displaying specificity of interest as well as their recombinant expression and functional characterization has been or can be generally performed as described in the Examples and Supplementary Methods section of international application PCT/EP2008/000053 published as WO2008/081008, the disclosure content of which is incorporated herein by reference in its entirety. A new method for identification of SOD1-specific B cells and molecular cloning of SOD1 antibodies displaying specificity of interest as well as their recombinant expression and functional characterization is provided within this application. As described above in one embodiment of the present invention cultures of single or oligoclonal B-cells are cultured and the supernatant of the culture, which contains antibodies produced by said B-cells, is screened for presence and affinity of new anti-SOD1 antibodies therein. The screening process comprises the steps of a sensitive tissue amyloid plaque immunoreactivity (TAPIR) assay as described in WO2004/095031, the disclosure content of which is incorporated herein by reference in its entirety; screen on spinal cord tissues of transgenic mouse expressing mutated human SOD1-forms for pathological aggregates of SOD1 as described in Example 4 and shown in FIG. 6; screening for binding of a peptide derived from SOD1 of the amino acid sequence represented by SEQ ID NO: 1 as analogously described in Example 5 and shown in FIG. 7 with peptides due to the epitope confirmation experiments for antibody NI-204.10D12; a screen for binding of full-length SOD1 of the amino acid sequence represented by SEQ ID NO: 1 and isolating the antibody for which binding is detected or the cell producing said antibody as described in international patent WO2008/081008 and as described in Example 1 and shown in FIGS. 2, 5 and 7.

SOD1 Antigens

Recombinant human SOD1 was purchased from biomol (Hamburg, Germany). Wild type SOD1 from human erythrocytes (physiological dimers) and all of the other reagents were purchased from Sigma-Aldrich (Buchs, Switzerland) if not mentioned otherwise.

Human SOD1 Antibody Screening

ELISA:

96 well microplates (Corning) were coated either with recombinant human SOD1 (biomol, Hamburg, Germany) or with BSA (Sigma-Aldrich, Buchs, Switzerland) diluted to a concentration of 3.3 µg/ml or 5 µg/ml in coating buffer (15 mM $Na_2CO_3$, 35 mM $NaHCO_3$, pH 9.42, pH 9.6) overnight at 4° C. Alternatively, 96 well microplates (Corning) are used coated with in vitro oxidized human SOD1 at a concentration of 34 µg/ml in coating buffer (15 mM $Na_2CO_3$, 35 mM $NaHCO_3$, pH 9.42). Plates were washed in PBS-T pH 7.6 and non-specific binding sites were blocked for 1 hr at RT with PBS/0.1% Tween-20 containing 2% BSA (Sigma-Aldrich, Buchs, Switzerland). B cell conditioned medium was transferred from memory B cell culture plates to ELISA plates and incubated for one hour at RT. ELISA plates were washed in PBS-T and binding was determined using horseradish peroxidase (HRP)-conjugated anti-human immunoglobulins polyclonal antibodies (Jackson ImmunoResearch, Newmarket, UK) followed by measurement of HRP activity in a standard colorimetric assay. Only B cell cultures which have shown binding of the antibodies contained in the medium to recombinant SOD1 but not to BSA were subjected to antibody cloning.

MULTI-ARRAY® Microplate Screening

Standard 96 well 10-Spot MULTI-SPOT plates (Meso Scale Discovery, USA) were coated with 30 ug/ml SOD1 (biomol, Hamburg, Germany) in PBS. Non-specific binding sites were blocked for 1 hr at RT with PBS-T containing 3% BSA followed by incubation with B cell conditioned medium for 1 hr at RT. Plates were washed in PBS-T and then incubated with SULFO-Tag conjugated anti-human polyclonal antibody (Meso Scale Discovery, USA). After washing with PBS-T, bound of antibody was detected by electrochemiluminescence measurement using a SECTOR Imager 6000 (Meso Scale Discovery, USA).

Molecular Cloning of SOD1 Antibodies

Samples containing memory B cells were obtained from healthy human subjects. Living B cells of selected memory B cell cultures are harvested and mRNA is prepared. Immunoglobulin heavy and light chain sequences are then obtained using a nested PCR approach.

A combination of primers representing all sequence families of the human immunoglobulin germline repertoire are used for the amplifications of leader peptides, V-segments and J-segments. The first round amplification is performed using leader peptide-specific primers in 5'-end and constant region-specific primers in 3'-end (Smith et al., Nat Protoc. 4 (2009), 372-384). For heavy chains and kappa light chains, the second round amplification is performed using V-segment-specific primers at the 5'-end and J-segment-specific primers at the 3'end. For lambda light chains, the second round amplification is performed using V-segment-specific primers at the 5'-end and a C-region-specific primer at the 3'end (Marks et al., Mol. Biol. 222 (1991), 581-597; de Haard et al., J. Biol. Chem. 26 (1999), 18218-18230).

Identification of the antibody clone with the desired specificity is performed by re-screening on ELISA upon recombinant expression of complete antibodies. Recombinant expression of complete human IgG1 antibodies or chimeric IgG2a antibodies is achieved upon insertion of the variable heavy and light chain sequences "in the correct reading frame" into expression vectors that complement the variable region sequence with a sequence encoding a leader peptide at the 5'-end and at the 3'-end with a sequence encoding the appropriate constant domain(s). To that end the primers contained restriction sites designed to facilitate cloning of the variable heavy and light chain sequences into antibody expression vectors. Heavy chain immunoglobulins are expressed by inserting the immunoglobulin heavy chain RT-PCR product in frame into a heavy chain expression vector bearing a signal peptide and the constant domains of human immunoglobulin gamma 1 or mouse immunoglobulin gamma 2a. Kappa light chain immunoglobulins are expressed by inserting the kappa light chain RT-PCR-product in frame into a light chain expression vector providing a signal peptide and the constant domain of human kappa light chain immunoglobulin Lambda light chain immunoglobulins are expressed by inserting the lambda light chain RT-PCR-product in frame into a lambda light chain expression vector providing a signal peptide and the constant domain of human or mouse lambda light chain immunoglobulin.

Functional recombinant monoclonal antibodies are obtained upon co-transfection into HEK293 or CHO cells (or any other appropriate recipient cell line of human or mouse origin) of an Ig-heavy-chain expression vector and a kappa or lambda Ig-light-chain expression vector. Recombinant human monoclonal antibody is subsequently purified from the conditioned medium using a standard Protein A column purification. Recombinant human monoclonal antibody can produced in unlimited quantities using either transiently or stably transfected cells. Cell lines producing recombinant human monoclonal antibody can be established either by using the Ig-expression vectors directly or by re-cloning of Ig-variable regions into different expression vectors. Derivatives such as F(ab), F(ab)$_2$ and scFv can also be generated from these Ig-variable regions.

Antibodies

Mouse monoclonal anti-SOD1 antibody 72B1 (Santa Cruz Biotechnology, Santa Cruz, USA) and rabbit monoclonal anti-SOD1 antibody EPR1726 (Epitomics, Burlingame, USA) were used according to manufacturer's protocol. Recombinant human or chimeric SOD1 antibodies NI-204.10D12, NI-204.10A8, NI-204.12G7, NI-204.9F6, NI-204.11F11, NI-204.67E12, NI-204.6H1, NI-204.12G3, NI-204.7G5, NI-204.7B3, NI-204.34A3 and NI-204.25H3 are antibodies of this invention. They were expressed in HEK293 or CHO cells, purified from conditioned media and were directly used in subsequent applications unless otherwise stated. In Examples 1 to 4 purified recombinant antibodies of the present invention were used.

Direct ELISA 96 well microplates (Costar, Corning, USA) were coated with recombinant SOD1 protein (biomol, Hamburg, Germany) diluted to a concentration of 3.3 µg/ml in carbonate ELISA coating buffer (15 mM Na$_2$CO$_3$, 35 mM NaHCO$_3$, pH 9.42) at 4° C. over night. Non-specific binding sites were blocked for 2 hr at RT with PBS containing 2% BSA (Sigma-Aldrich, Buchs, Switzerland) and 0.5% Tween20. Binding of human antibodies of the present invention (NI-204.10D12, NI-204.9F6, NI-204.12G7 and NI-204.10A8) was determined using a donkey anti-human IgGγ antibody conjugated with HRP (Jackson immunoResearch, Newmarket, UK), followed by measurement of HRP activity in a standard colorimetric assay. EC$_{50}$ values were estimated by a non-linear regression using GraphPad Prism software (San Diego, USA).

Transgenic Mice

The B6.Cg-Tg(SOD1*G93A)1Gur/J transgenic mouse line is used to validate the SOD1 antibodies (and molecules with the binding specificities thereof) of the present invention.

Said transgenic mouse line is a very well established and characterized mouse model for ALS. Neuropathological hallmarks in the spinal cord of this ALS mouse models are the presence of neurofilament-rich spheroids, similar to those seen in human amyotrophic lateral sclerosis, that are more frequently found in the anterior horn and in the anterior and lateral columns of the white matter than in the posterior horn, the presence of thickened dystrophic neurites filled with immunoreactive neurofilament-rich inclusions, motor neuron degeneration characterized by the presence of perikaryal vacuoles, gliosis and astrocytosis. Intracellular dispersed inclusions, Lewy body-like inclusions and extracellular aggregates, which mainly consist of abnormal aggregates of the superoxide dismutase 1 protein, are additional neuropathological hallmarks.

Example 1

Validation of Target and Binding Specificity of Human SOD1-Antibodies

To validate SOD1 as a recognized target of isolated antibodies direct ELISA assays were performed as described above. For the exemplary recombinant human NI-204.10D12, NI-204.12G7, NI-204.9F6 and NI-204.10A8 antibodies, 96 well microplates (Costar, Corning, USA) were coated with recombinant human SOD1 (biomol, Hamburg, Germany) or with BSA (Sigma-Aldrich, Buchs, Switzerland) diluted to a concentration of 3.3 µg/ml in carbonate ELISA coating buffer (15 mM $Na_2CO_3$, 35 mM $NaHCO_3$, pH 9.42) and binding efficiency of the antibody was tested. The exemplary NI-204.10D12, NI-204.12G7, NI-204.9F6 and NI-204.10A8 antibodies specifically bind to human SOD1 by ELISA. No binding is observed to BSA; see FIG. 2.

For a determination of the half maximal effective concentration ($EC_{50}$) of the exemplary antibodies NI-204.10D12, NI-204.12G7, NI-204.9F6 and NI-204.10A8 additional direct ELISA experiments with varying antibody concentrations were performed. 96 well microplates (Costar, Corning, USA) were coated with recombinant human SOD1 (biomol, Hamburg, Germany) diluted to a concentration of 3.3 µg/ml in carbonate ELISA coating buffer (15 mM $Na_2CO_3$, 35 mM $NaHCO_3$, pH 9.42) and binding efficiency of the antibody was tested. Binding was determined using a donkey anti-human IgGγ antibody (Jackson immunoResearch, Newmarket, UK) conjugated with HRP, followed by measurement of HRP activity in a standard colorimetric assay.

The $EC_{50}$ values were estimated by a non-linear regression using GraphPad Prism (San Diego, USA) software. Recombinant human-derived antibodies NI-204.10D12, NI-204.10A8 and NI-204.12G7 bind with a high affinity to recombinant human superoxide dismutase 1 with an $EC_{50}$ of 10.0 nM, of 2.7 nM and 0.4 nM, respectively. Antibody NI-204.9F6 binds with to recombinant human superoxide dismutase 1 with an $EC_{50}$ in the nanomolar range (104.8 nM); see FIG. 3. The NI-204.10D12, NI-204.12G7, NI-204.10A8 and NI-204.9F6 antibodies are therefore suitable human-derived drug candidates for familial ALS and can be studied in established transgenic mouse models overexpressing superoxide dismutase 1 mutants.

Example 2

$EC_{50}$ Analysis for Increasing Coating Concentrations of Human Superoxide Dismutase 1 (SOD1) Thus Preferring the Formation of Conformational Epitopes To determine the binding capacity of NI-204.10D12, the NI-204.10A8 the NI-204.12G7 and the NI-204.9F6 to conformational epitopes direct ELISA experiments were performed with human recombinant SOD1 (biomol, Hamburg, Germany) at four different coating concentrations (0.1; 1; 10 or 30 µg/ml) in coating buffer. Primary antibodies human NI-204.10D12, human NI-204.10A8, human NI-204.9F6 and murine monoclonal antibody SOD-1 72B1 (Santa Cruz Biotechnology, Santa Cruz, USA) were diluted to the indicated concentrations (FIG. 4) and incubated 1 hr at RT. Binding was determined using either a goat anti-mouse IgG antibody (Jackson immunoResearch, Newmarket, UK) or a donkey anti-human IgGγ (Jackson immunoResearch, Newmarket, UK) antibody conjugated with HRP, followed by measurement of HRP activity in a standard colorimetric assay. The $EC_{50}$ values were estimated by a non-linear regression using GraphPad Prism (San Diego, USA) software.

The half maximal effective concentration ($EC_{50}$) indicating the potency of an antibody was determined for low and high coating concentrations of human recombinant SOD1 using a direct SOD1 ELISA. High affinity binding of recombinant NI-204.10D12 with an $EC_{50}$ of 24 nM was observed for high coating densities of human SOD1 protein (10 or 30 µg/ml) (FIGS. 4A and F). At lower coating concentrations of human SOD1, a substantial drop in affinity was observed, with a corresponding increase of the $EC_{50}$ by close to 25 fold for NI-204.10D12 (FIGS. 4A and F). Very high affinity binding of recombinant NI-204.12G7 with an $EC_{50}$ of 0.4 nM was observed for high coating densities of human SOD1 protein (10 or 30 µg/ml) (FIGS. 4D and F). At lower coating concentrations of human SOD1, a substantial drop in affinity was observed, with a corresponding increase of the $EC_{50}$ by close to 195 fold for NI-204.12G7 (FIGS. 4D and F). In contrast, the NI-204.10A8 antibody binds with high affinity already at low coating densities (0.1 and 1 µg/ml) of human SOD1 protein, with an $EC_{50}$ of 96 nM and 19 nM, respectively (FIGS. 4B and F). At 10 µg/ml coating density of human SOD1 protein, a further increase in binding affinity of NI-204.10A8 was observed, the $EC_{50}$ decreasing to 2 nM (FIGS. 4B and F). The NI-204.9F6 antibody shows binding properties to recombinant human SOD1 protein that are very similar to these of the NI-204.10A8 antibody (FIG. 4C). However, NI-204.9F6 binding affinities are much lower of these determined for the NI-204.10A8 antibody (FIGS. 4B, C and F).

The commercially available SOD-1 72B1 antibody, showed no strong decrease in binding affinity at lower coating densities of human SOD1 (FIG. 4D).

$EC_{50}$ analysis of the NI-204.10D12 antibody with increasing human superoxide dismutase 1 coating concentrations revealed a strong gain in affinity at high coating concentrations of SOD1. While a 24 nM $EC_{50}$ was measured at 10 µg/ml coating, this value increased close to 25-fold for low density (0.1 µg/ml) SOD1 coating suggesting a considerable drop in affinity. Similarly to NI-204.10D12, the $EC_{50}$ analysis of the NI-204.12G7 antibody revealed a very strong gain in affinity at high coating concentrations of SOD1. While a 0.4 nM $EC_{50}$ was measured at 10 µg/ml coating, this value increased close to 195-fold for low density (0.1 µg/ml) SOD1 coating suggesting a considerable drop in affinity. These findings are likely explained by the possible spontaneous aggregation of recombinant human SOD1 at high local concentrations on the ELISA plate and point to epitopes of the NI-204.10D12 and NI-204.12G7 antibodies that are exposed upon SOD1 misfolding or aggregate formation. In contrast, high affinity binding at low density coating (0.1 µg/ml) with gain in affinity at high coating concentrations (10 µg/ml) of SOD1 of NI-204.10A8 antibody indicates that this antibody may recognize an epitope of human SOD1 that is present in the physiological protein conformation. NI-204.9F6 shows lower binding affinities at all concentrations of SOD1 then NI-204.10A8 with a slight gain in affinity in high coating concentrations suggesting that this antibody may also recognize an epitope of human SOD1 present in the physiological conformation.

Example 3

Binding Analysis to Physiological SOD1 Dimers and to In Vitro Misfolded/Aggregated SOD1

Metal-catalyzed oxidation reaction was used to induce in vitro superoxide dismutase 1 aggregation (according to Rakhit et al., J Biol Chem. 279 (2004), 15499-504). Wild type SOD1 from human erythrocytes (dimers) and all of the other reagents were purchased from Sigma-Aldrich (Sigma-Aldrich, Buchs, Switzerland). For aggregation, 10 µM human SOD1 were incubated in 10 mM Tris acetate buffer, pH 7.0, containing 4 mM ascorbic acid and 0.2 mM $CuCl_2$ for 48 hours at 37° C. As control, 10 µM human SOD1 were incubated in 10 mM Tris acetate buffer, pH 7.0, for 48 hours at 37° C.

96 well microplates (Corning) were coated with either physiological human SOD1 dimers or with in vitro aggregated human SOD1 dimers at a concentration of 34 µg/ml in coating buffer (15 mM $Na_2CO_3$, 35 mM $NaHCO_3$, pH 9.42). Non-specific binding sites were blocked for 1 hr at RT with PBS/0.1% Tween®-20 containing 2% BSA (Sigma-Aldrich, Buchs, Switzerland). Primary antibodies human NI-204.10D12, NI-204.12G7, NI-204.10A8, NI-204.9F6 and murine monoclonal antibody SOD-1 72B1 (Santa Cruz Biotechnology, Santa Cruz, USA) were diluted to the indicated concentrations and incubated 1 hr at RT. Binding was determined using either a goat anti-mouse IgG antibody (Jackson immunoResearch, Newmarket, UK) or a donkey anti-human IgGγ antibody (Jackson immunoResearch, Newmarket, UK) conjugated with HRP, followed by measurement of HRP activity in a standard colorimetric assay. $EC_{50}$ values were estimated by a non-linear regression using GraphPad Prism software (San Diego, USA).

Human NI-204.10D12 (FIG. 5A) and NI-204.12G7 (FIG. 5C) antibody preferentially binds to misfolded/aggregated human SOD1 with an $EC_{50}$ of 15 nM and of 3.6 nM, respectively. Human NI-204.9F6 (FIG. 5D) antibody binds slightly preferentially to misfolded/aggregated human superoxide dismutase 1 with an $EC_{50}$ of 127 nM. These findings suggest that NI-204.10D12, NI-204.12G7 and NI-204.9F6 antibodies preferentially target epitopes of human SOD1 that are exposed in pathologically relevant conformations of misfolded/aggregated but not in physiological forms of human superoxide dismutase 1.

In contrast, the NI-204.10A8 antibody binds with equal affinity human physiological SOD1 dimers and misfolded/aggregated human SOD1 (FIG. 5B) with an $EC_{50}$ of 19.1 nM and 29.5 nM, respectively. These findings suggest that NI-204.10A8 antibody targets an epitope of human SOD1 that is exposed both in pathologically relevant conformations of misfolded/aggregated and physiological forms of human superoxide dismutase 1.

The commercially available SOD-1 72B1 antibody binds with almost equal affinity human physiological SOD1 dimers and misfolded/aggregated human SOD1; see FIG. 5E.

Metal-catalyzed oxidation-induced SOD1 aggregates possess identical properties with ALS in vivo superoxide dismutase 1 aggregates. NI-204.10D12 (FIG. 5A) and NI-204.12G7 (FIG. 5C) show prominent binding to therapeutically relevant pathological forms of human SOD1 such as misfolded/aggregated SOD1. Binding to SOD1 aggregates seems to be preferred over physiological dimers. NI-204.9F6 (FIG. 5D) shows a slightly preferential binding to therapeutically relevant pathological forms of human superoxide dismutase 1. However, the binding affinity of the NI-204.9F6 antibody for misfolded/aggregated SOD1 is lower than the affinities determined for the NI-204.10D12 and NI-204.12G7 antibodies.

Interestingly, the NI-204.10A8 antibody (FIG. 5B), in contrast to the NI-204.10D12, NI-204.12G7 and NI-204.9F6 antibodies, does not show preferential binding to SOD1 aggregates over physiological dimers. This antibody binds both SOD1 species with high affinity in the low nanomolar range.

These findings highlight the therapeutically attractive profile of the human-derived NI-204.10D12 and NI-204.12G7 antibodies which are targeted against pathologically relevant conformations of the SOD1 protein and that the NI-204.10A8 antibody possesses biochemical properties that differ from these of the NI-204.10D12 and NI-204.12G7 antibodies. Therefore the human-derived NI-204.10A8 represents a potential therapeutic antibody for ALS with distinct properties from these of the molecules NI-204.10D12 and NI-204.12G7.

These findings are furthermore in agreement with the binding analysis with increasing coating concentrations of human superoxide dismutase 1.

Example 4

Assessment of the Binding of NI-204.10D12, NI-204.12G7, NI-204.10A8 and NI-204.9F6 Binding to Pathological Aggregates of SOD1 in Transgenic Mouse Spinal Cord Tissues Spinal cords of B6.Cg-Tg(SOD1*G93A)1Gur/J transgenic mice at the terminal stage of disease were fixed in phosphate-buffered 4% paraformaldehyde solution, paraffin-embedded, and cut into 5-µm sections. After formic acid pretreatment, sections were incubated with different anti-superoxide dismutase 1 antibodies: chimeric NI-204.10D12 (50 nM), human NI204-10A8 (50 nM), human NI-204.12G7 (20 nM) human NI-204.9F6 (50 nM) and EPR1726 anti-SOD1 (Epitomics, 1:10000) followed by incubation with either biotinylated donkey-anti-mouse or biotinylated donkey-anti-human or biotinylated donkey-anti-rabbit secondary antibody (Jackson ImmunoResearch Europe Ltd; 1:250). Antibody signal was amplified with the Vectastain ABC kit (Vector Laboratories) and detected with diaminobenzidine (Dako).

Binding of NI-204.10D12, NI-204.12G7, NI-204.10D12 and of NI-204.9F6 to superoxide dismutase 1 was characterized by immunohistochemical analysis of spinal cord sections from B6.Cg-Tg(SOD1*G93A)1Gur/J transgenic mice at the terminal stage of disease.

NI-204.10D12 shows mainly a diffuse staining of SOD1 pathology as well as intracellular dispersed inclusions; see FIG. 6A.

NI-204.12G7 shows prominent staining of SOD1 pathology including cytoplasmatic SOD1 inclusions, mainly in motor neurons, and extracellular SOD1 aggregates (FIG. 6C).

NI-204.10A8 shows prominent staining of SOD1 pathology including cytoplasmatic SOD1 inclusions, mainly in motor neurons, and extracellular SOD1 aggregates (FIG. 6B). Furthermore, this antibody seems to recognize also physiological SOD1 with high sensitivity, as shown by the intense diffuse staining of the spinal cord tissue (FIG. 6B).

These findings are in accordance with the biochemical binding properties of the three antibodies: the NI-204.10D12 and NI-204.12G7 antibodies showing strong binding preference to misfolded/aggregated SOD1 and the NI-204.10A8 antibody showing equal binding affinity to physiological SOD1 dimers and misfolded/aggregated SOD1.

The NI-204-9F6 antibody, under the tested staining conditions, reacts very weakly and detects mainly intracellular SOD1 and intracellular dispersed SOD1 inclusions; see FIG. 6D.

The commercially available EPR1726 anti SOD-1 antibody, which detects specifically human but not murine SOD1, binds both to physiological SOD1 as well to pathological SOD1 aggregates with high sensitivity; see FIG. 6E.

To test all of the antibodies of the present invention the above described experiment has been repeated. As shown in FIG. 9, human-derived SOD1-specific antibodies revealed distinct patterns of SOD1 pathology, such as dispersed, intracellular inclusions, cytoplasmic inclusions and larger, mostly extracellular SOD1 aggregates, in the lumbar spinal cord of B6.Cg-Tg(SOD1*G93A)1Gur/J transgenic mice.

All antibodies shown in FIG. 9 show staining of intracellular dispersed inclusions, diffuse cytoplasmic structures and vacuolar structures if the appropriate concentration of antibody is used. Staining of the larger aggregates comparable to reference antibody B8H10 (FIG. 9M) divides the antibodies of the present invention into two groups: Antibodies NI-204.12G7 (FIG. 9B), NI-204.11F11 (FIG. 9C), NI-204.6H1 (FIG. 9F), NI-204.12G3 (FIG. 9G), NI-204.7G5 (FIG. 9H), NI-204.25H3 (FIG. 9I), NI-204.34A3 (FIG. 9J) and NI-204.7B3 (FIG. 9K) stain these aggregates in the ventral horn of the spinal cord whereas NI-204.10D12 (FIG. 9A), NI-204.10A8 (FIG. 9D), NI-204.67E12 (FIG. 9E) do not stain these structures, similar to reference antibody C4F6 ((FIG. 9L) which is specific for soluble, misfolded forms of mutant human SOD1 (Bosco et al, 2010, Nat Neuroscience 13(11); 1396-1403). In addition, antibodies NI-204.10D12, NI-204.6H1 and NI-204.7G5 show diffuse staining in the substantia gelatinosa in the dorsal horn of the spinal cord sections.

Furthermore, some of the antibodies seem to recognize also physiological SOD1 with high sensitivity, as shown by the intense diffuse staining of the spinal cord tissues (NI-204.10D12 (FIG. 9A), NI-204.10A8 (FIG. 9D) and NI-204.67E12 (FIG. 9E)).

The commercially available C4F6 (MediMabs, Canada; #MM-0070-2) and B8H10 (MediMabs, Canada; #MM-0070) antibodies were used as control antibiodies. Incubation with C4F6 antibody or B8H10 antibody was followed by incubation with biotinylated horse-anti-mouse secondary antibody (Vector Laboratories; 1:250). Antibody signal was amplified with the Vectastain ABC kit (Vector Laboratories) and detected with diaminobenzidine (Dako). This staining revealed two different staining patterns: the C46A antibody showed a punctate/diffuse staining (FIG. 9L) whereas the B8H10 antibody mainly stained granular SOD1 inclusions and SOD1 aggregates (FIG. 9M).

Conclusions

These data demonstrate that NI-204 antibodies recognize pathological superoxide dismutase 1 structures in B6.Cg-Tg (SOD1*G93A)1Gur/J transgenic mouse model.

Example 5

NI-204 Antibodies Epitope Mapping

Scans of overlapping peptides were used for epitope mapping. The entire sequence of human superoxide dismutase 1 was synthesized as a total of 36 linear 15-meric peptides with 11 aa overlap between individual peptides (JPT Peptide Technologies, Berlin, Germany) and spotted onto nitrocellulose membranes. The membrane was activated for 5 min in methanol and then washed at RT in TBS for 10 min. Non-specific binding sites were blocked for 2 hours at RT with Roti®-Block (Carl Roth GmbH+Co. KG, Karlsruhe, Germany). Human NI-204.10D12, NI-204.10A8, NI-204.12G7, NI-204.11F11, NI-204.6H1, NI-204.12G3, NI-204.7G5, NI-204.7B3, NI-204.34A3 respective NI-204.25H3 antibodies (1 µg/ml) were incubated for 3 hours at RT in Roti®-Block. Binding of primary antibody was determined using HRP conjugated donkey-anti human IgGγ secondary antibody. Blots were developed using ECL and ImageQuant 350 detection (GE Healthcare, Otelfingen, Switzerland)

To map the epitope within the superoxide dismutase 1 protein that is recognized by the NI-204.10D12, NI-204.10A8, NI-204.12G7, NI-204.11F11, NI-204.6H1, NI-204.12G3, NI-204.7G5, NI-204.7B3, NI-204.34A3 respective by the NI-204.25H3 antibody, a pepscan membrane with 36 15aa peptides (11 amino acid overlap between peptides) covering the entire superoxide dismutase 1 protein sequence was used. As shown exemplary in FIG. 7, prominent binding of NI-204.10D12 is observed to peptides number 22, 23 and 24 indicating that the epitope recognized by this antibody is localized to the central domain of SOD1. The NI-204.10D12 binding epitope is therefore predicted to be localized within SOD1 amino acids 93-99. NI-204.10D12 binds to the central domain comprised of the fat and underlined amino acids 93-99 of the sequence DGVADVS (SEQ ID NO: 2). The analogously identified binding epitopes for human-derived SOD1-specific antibodies NI-204.10D12, NI-204.10A8, NI-204.12G7, NI-204.11F11, NI-204.6H1, NI-204.12G3, NI-204.7G5, NI-204.7B3, NI-204.34A3 and NI-204.25H3 of the present invention are summarized in Table IV below.

TABLE IV

Identified binding epitopes of the different human-derived SOD1-specific antibodies within the indicated amino acids of the human SOD1 protein sequence.

| Antibody | Binding epitope | SEQ ID NO |
|---|---|---|
| NI-204.10D12 | 93-DGVADVS-99 | SEQ ID NO: 2 |
| NI-204.12G7 | 73-GGPKDEERHVG-83 | SEQ ID NO: 51 |
| NI-204.10A8 | N-Terminal: 9-LKGDGPVQGIINFEQKESNG PVKVWGSIKGLTEGLHGFHVHE FGDNT-55 | SEQ ID NO: 52 |
| NI-204.9F6 | ND | |
| NI-204.11F11 | 113-IIGRTLV-119 | SEQ ID NO: 53 |
| NI-204.67E12 | ND | |
| NI-204.6H1 | 85-LGNVTADKDGV-95 | SEQ ID NO: 54 |
| NI-204.12G3 | 121-HEKADDLGKGGNEES-135 | SEQ ID NO: 55 |
| NI-204.7G5 | 101-EDSVISL-107 | SEQ ID NO: 56 |
| NI-204.7B3 | 137-KTGNAGS-143 | SEQ ID NO: 57 |
| NI-204.34A3 | 85-LGNVTADKDGV-95 | SEQ ID NO: 58 |
| NI-204.25H3 | 73-GGPKDEE-79 | SEQ ID NO: 59 |

ND: No identification of binding epitope by the use of The PepSpot technology

Example 6

NI-204.10D12 Binding to Wild Type, G93A Mutant and Murine SOD1 Derived Peptides

Streptavidin-coated 96 well microplates (Fischer Scientific) were coated with biotinylated peptides (JPT Peptide Technologies, Berlin, Germany) covering the putative NI-204.10D12 binding epitope of superoxide dismutase 1 protein at a concentration of 50 µg/ml in PBS at 4° C. overnight. Non-specific binding sites were blocked for 1 hr at RT with PBS/0.1% Tween-20 containing 2% BSA (Sigma-Aldrich, Buchs, Switzerland). Primary antibody chimeric NI-204.10D12 was diluted to the indicated concentrations and incubated 1 hr at RT. Binding was determined using a goat anti-mouse IgG antibody conjugated with HRP (Jackson immunoResearch, Newmarket, UK), followed by measurement of HRP activity in a standard colorimetric assay.

Figure 8:
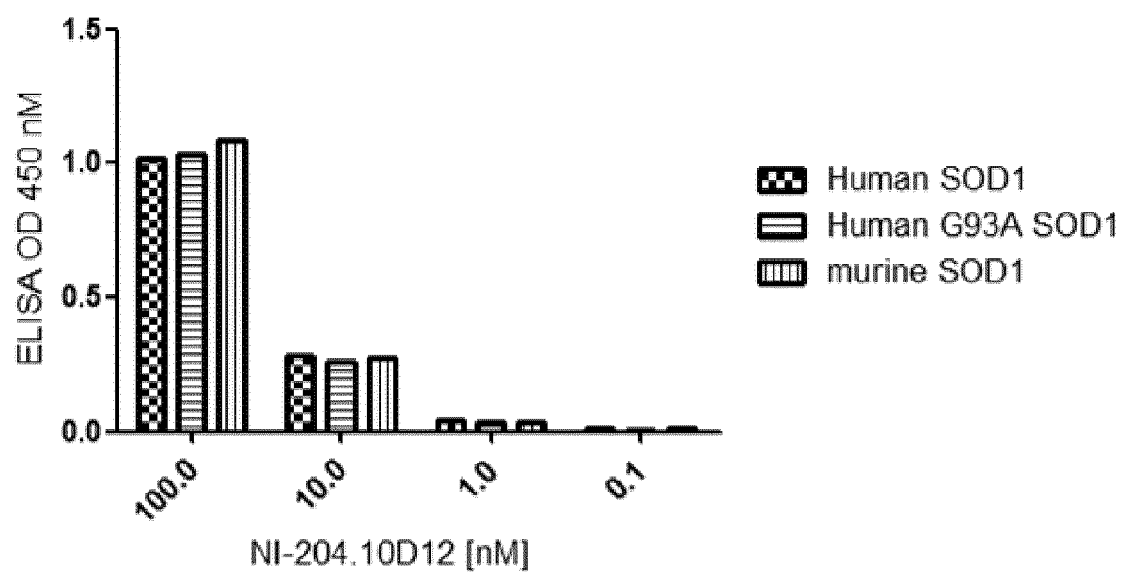
FIG. 8: Recombinant human-derived antibody NI-204.10D12 binds with equal affinity to SOD1 synthetic peptides having the amino acid sequence derived from wild type human, G93A human mutant and wild type murine SOD1 proteins. These synthetic peptides cover the identified NI-204.10D12 binding epitope.

Chimeric recombinant NI-204.10D12 antibody binds in a concentration dependent manner to synthetic peptides having the amino acid sequence covering the identified NI-204.10D12 binding epitope derived from wild type human, G93A human and murine superoxide dismutase 1 proteins (FIG. 8). NI-204.10D12 binds to the three different SOD1 species with equal affinity. The amino acid exchange at position 93 located within the NI-204.10D12 epitope in human superoxide dismutase 1 is linked to a familial form of ALS. These findings indicate that the NI-204.10D12 antibody is a suitable drug candidate for the treatment of sporadic and familiar ALS.

Example 7

In Vivo Tests of the Antibodies of the Present Invention

As already described above, studies in transgenic mouse lines using a passive immunization approach based on direct intraventricular infusion of anti-human SOD1 antibodies have shown such treatment capable of alleviating disease in SOD1 fALS mouse models by prolonging the lifespan and attenuating motor neuron loss (Urushtani et al., Proc. Natl. Acad. Sci. USA. 104 (2007), 2495-2500; Gros-Louis et al., J. Neurochem. (2010) 113, 1188-1199). An active vaccination approach in contrast, has failed to confer significant protection (Urushtani et al., Proc. Natl. Acad. Sci. USA. 104 (2007), 2495-2500). However, active vaccination may not be particularly useable in humans because a significant fraction of the elderly population is expected to be non-responders to vaccination. Furthermore, the potential side effects associated with an SOD1-directed immune response can be difficult to control. SOD1 binding molecules of the present invention may be reasonably expected to achieve similar reductions in brain levels of SOD1 aggregates as described above for the mouse antibodies, because of their similar binding specificities against pathologically misfolded/aggregated SOD1 species.

However, because of the evolutionarily optimization and affinity maturation within the human immune system antibodies of the present invention provide a valuable therapeutic tool due to being isolated from healthy human subjects with high probability for excellent safety profile and lack of immunogenicity. Confirmation of these expected therapeutic effects may be provided by test methods as described in the above mentioned publications with human instead of mouse antibodies. In particular, the antibodies to be screened may be applied on diverse possible routes to the animals such as intraperitoneal antibody injection, intracranial injection, intraventricular brain infusion and tested for treatment effects.

Coexpression of Aβ and SOD1(G93A) mutant leads to an elevation of buffer-insoluble SOD1 aggregates in a double transgenic mice suggesting a potential role of Aβ in ALS development (Li at al., Aging Cell. 5 (2006), 153-165). Either of the above mentioned application possibilities may be also used after prior brain injection of beta-amyloid preparations into the brain of SOD1 transgenic mice to evaluate treatment effects on Aβ-induced SOD1 pathology.

Evaluation and confirmation of the therapeutic effects of the antibodies of the present invention may be performed by monitoring the bodyweight changes due to the onset of muscle atrophy and the overall survival time of the animals. Before the onset of muscle atrophy diverse motor impairments either in coordination as in performance may be tested for delayed occurrence as a result of treatment. This may be performed by standard behavioral tests such as the rotarod, grip-strength testing, extension reflex testing, paw grip endurance testing, Y maze, novel object recognition testing or open field activity, for example (Crawley, J. N. (2000) What's Wrong with My Mouse?: Behavioral Phenotyping of Transgenic and Knockout Mice. Wiley-Liss, New York).

Further, histochemical methods may be used comprising monitoring the formation of toxic intracellular inclusions, staining and counting of motor neurons on spinal cord sections, total human SOD1 staining and/or a biochemical determination of spinal cord soluble and insoluble SOD1 levels upon sequential spinal cord extraction (Urushtani et al., Proc. Natl. Acad. Sci. USA. 104 (2007), 2495-2500).

Example 8

Binding Analysis to Native SOD1 Dimers, Denatured/Oxidized SOD1 and Recombinant SOD1

Methods
In Vitro Superoxide Dismutase 1 Aggregation

Metal-catalyzed oxidation reaction was used to induce in vitro superoxide dismutase 1 aggregation (according to Rakhit et al., J. Biol. Chem. 279 (2004), 15499-15504). Native SOD1 from human erythrocytes (dimers) and all of the other reagents were purchased from Sigma-Aldrich (Sigma-Aldrich, Buchs, Switzerland). For aggregation, 10 µM human SOD1 were incubated in 10 mM Tris acetate buffer, pH 7.0, containing 4 mM ascorbic acid and 0.2 mM $CuCl_2$ for 48 hours at 37° C. As control, 10 µM human SOD1 were incubated in 10 mM Tris acetate buffer, pH 7.0, for 48 hours at 37° C.

In Vitro Superoxide Dismutase 1 Denaturation

Superoxide dismutase 1 denaturation reaction was performed according to Zetterström et al., J Neurochem. 117 (2011), 91-99. Native SOD1 from human erythrocytes (dimers) and all of the other reagents were purchased from Sigma-Aldrich (Sigma-Aldrich, Buchs, Switzerland). For denaturation, 23 µM human SOD1 was incubated in 3.5 M guanidinium chloride and 25 mM EDTA, pH 7.0, for 4 hours at 22° C. Denaturation solutions were then dialyzed against PBS containing 5 mM EDTA, pH 7.0, centrifuged at 20,000 g to remove SOD1 aggregates, and denatured SOD-containing supernatants collected.

Direct ELISA 96 well microplates (Corning) were coated with either native human SOD1 dimers or with in vitro denatured/oxidized human SOD1 or with recombinant SOD1 (Biomol, Germany) at a concentration of 20 µg/ml in coating buffer (15 mM $Na_2CO_3$, 35 mM $NaHCO_3$, pH 9.42). Non-specific binding sites were blocked for 1 h at RT with PBS/0.1% Tween®-20 containing 2% BSA (Sigma-Aldrich, Buchs, Switzerland). Primary antibodies were diluted to the indicated concentrations and incubated 1 h at RT. Binding was determined using either a donkey anti-human IgG Fcγ-specific antibody conjugated with HRP or a goat anti-mouse IgG (H+L)-specific antibody conjugated with HRP, followed by measurement of HRP activity in a standard colorimetric assay.

$EC_{50}$ Determination $EC_{50}$ values were estimated by a non-linear regression using GraphPad Prism software (San Diego, USA).

Results

The $EC_{50}$ of the different human-derived SOD1-specific antibodies for native human SOD1 dimers, denatured/oxidized human SOD1 and recombinant SOD1 was determined by direct ELISA with coating of the different SOD1 species at 20 μg/ml concentration. The determined binding affinities of the human-derived SOD1-specific antibodies for the different SOD1 species are summarized in Table III below.

TABLE III

Binding affinity of the different human-derived SOD1-specific antibodies for different SOD1 species.

| Antibody | Native SOD1 $EC_{50}$ [nM] | Denatured SOD1 $EC_{50}$ [nM] | Oxidized SOD1 $EC_{50}$ [nM] | Recombinant SOD1 $EC_{50}$ [nM] |
|---|---|---|---|---|
| NI-204.10D12 | >100 | 5 | 6 | 7 |
| NI-204.12G7 | >40 | 0.07 | 0.6 | 0.06 |
| NI-204.11F11 | 50 | 0.3 | 0.4 | 0.5 |
| NI-204.10A8 | >100 | >100 | >100 | 1 |
| NI-204.67E12 | 0.1 | 0.08 | 0.06 | 0.2 |
| NI-204.6H1 | >100 | 5 | 4 | 2 |
| NI-204.12G3 | 21 | 0.2 | 1 | 0.6 |
| NI-204.7G5 | >100 | 60 | 5 | 13 |
| NI-204.7B3 | >100 | 50 | >100 | 42 |
| NI-204.34A3 | >100 | 10 | 12 | 2 |
| NI-204.25H3 | >100 | 4 | 2 | 1 |
| NI-204.9F6 | >100 | ND | >100 | >100 |

ND: not determined

Human SOD1-specific antibodies preferentially bind to recombinant and denatured/aggregated human superoxide dismutase 1 with $EC_{50}$ ranging from picomolar to low nanomolar values. These findings suggest that most of the NI-204 antibodies preferentially target epitopes of human SOD1 which are exposed in pathologically relevant misfolded conformations of denatured/oxidized but not native forms of human superoxide dismutase 1. Only antibodies NI-204.67E12, NI-204.10A8 and NI-204.9F6 do not discriminate the different SOD1 species, with high overall binding affinities of the NI-204.67E12 antibody in the picomolar, and affinities of the antibodies NI-204.10A8 and NI-204.9F6 in nanomolar range.

Conclusions

Metal-catalyzed oxidation-induced superoxide dismutase 1 aggregates and unfolded SOD1 possess similar or identical properties to ALS associated, in vivo superoxide dismutase 1 aggregates. Several human-derived SOD1-specific antibodies show prominent binding to therapeutically relevant misfolded forms of human superoxide dismutase 1 such as unfolded/oxidized SOD1. Binding to unfolded/oxidized superoxide dismutase 1 seems to be preferred over native dimers. These findings highlight the therapeutically attractive profile of the human-derived SOD-1 antibodies of the present invention that are targeted against pathologically relevant conformations of the superoxide dismutase 1 protein.

Examples 3 and 8 have been performed subsequently with a delay of several months in-between. During this time, antibodies NI-204.10D12, NI-204.12G7, NI-204.10A8 and NI-204.9F6 have been stored at 4° C., or preferably at −20° C., or −80° C. in small aliquots in Phosphate buffered saline without $CaCl_2$ and $MgCl_2$, pH 7.4 (Invitrogen) as to minimize damage due to freezing and thawing for several months.

Wherein in general similar data concerning binding affinities have been obtained in both experiments, antibody NI-204.10A8 showed a significant loss of binding affinity for physiological and for aggregated SOD-1 as well from 20 nM, respective 30 nM as calculated in Example 3 to over 100 nM for both forms of SOD-1 as indicated in Table III.

Proteins are known to undergo ice-water surface denaturation, cryoconcentration, and cold denaturation during freezing which may lead to such a loss of stability, see, e.g., Kolhe and Badkar, *Biotechnology Progress* 27 (2011), 494-504; Hawe et al., *Eur J Pharm Sci.* 38 (2009), 79-87; Lu Y et al., J Pharm Sci. 97 (2008), 1801-1812; and Glick S M, J Clin Endocrinol Metab. 37 (1973), 461-462. In this respect, the antibodies provided by the present invention show different stability profiles, wherein some of the antibodies (e.g., NI-204.10D12 and NI-204.12G7) may be stored for a prolonged time period of at least several months before usage, wherein others (e.g., NI-204.10A8) should be used without freezing steps after their production.

Example 9

NI-204.10D12 Therapeutic Efficacy: In Vivo Proof-of-Concept

Studies in transgenic mouse lines using a passive immunization approach based on direct intraventricular infusion of anti-human SOD1 antibodies have shown such treatment capable of alleviating disease in SOD1 fALS mouse models by prolonging the lifespan and attenuating motor neuron loss (Urushtani et al., Proc. Natl. Acad. Sci. USA. 104 (2007), 2495-2500; Gros-Louis et al., J. Neurochem. (2010) 113, 1188-1199).

The B6.Cg-Tg(SOD1*G93A)1Gur/J transgenic mouse line was used for the evaluation of therapeutic efficacy of human-derived SOD-1 antibodies. This transgenic mouse line is a well-established and characterized mouse model for ALS. Evaluation and confirmation of the therapeutic effects of the NI-204.10D12 antibody was performed by monitoring the bodyweight changes due to the onset of muscle atrophy and the overall survival time of the animals. Before the onset of muscle atrophy, motor impairments in performance were tested for delayed occurrence as a result of treatment by paw grip endurance testing. Further, histochemical methods were used for staining and counting of motor neurons on spinal cord sections for assessing NI-204.10D12-mediated attenuation of motor neuron loss. In order to avoid mouse-anti-human antibody responses during the chronic treatment regimen, a chimeric version of the NI-204.10D12 antibody was used in the study consisting of the NI-204.10D12 human variable domains fused to mouse Ig2a constant domains.

Methods

Surgical Implantation of Alzet® Osmotic Minipumps for Brain Infusion 60 day old B6.Cg-Tg(SOD1*G93A)1Gur/J transgenic mice were deeply anaesthetized (fentanyl/midazolam/medetomidin), a small midline incision was made to expose the skull, and a subcutaneous pocket was prepared in the midscapular area of the back of the mice so that a sterile Alzet® minipump (ALZET Osmotic Pumps; Cupertino, Calif., USA, model 1004, 1.5 cm in length, 0.6 cm in diameter and weighing 0.4 g empty weight) filled with antibody solution or PBS could be inserted. Mice were then head fixed within a stereotaxic apparatus and the bone suture junction bregma was used as a reference point to drill a hole in the skull and lower an Alzet® Brain infusion kit 3 cannula into the left lateral ventricle; coordinates according to bregma; AP, −0.2 mm; ML, 0.9 mm; and DV, 2.5 mm. Following the placement of the cannula, two small screws were placed within the skull and dental cement applied to firmly attach to the skull. Naloxon (56952 (Swissmedic), OrPha Swiss GmbH, Küsnacht, Switzerland), flumazenill (48280 (Swissmedic), Roche Pharma (Schweiz), Reinach, Switzerland)/atipamezol (60562 (Swissmedic), Dr. E. Graub A G, Bern, Switzerland) and metacam (Boehringer Ingelheim, Germany) was given subcutaneously as an antidote and post-operative analgesic, with further metacam and buprenorphine (41931, 44100 (Swissmedic), Reckitt Benckiser Healthcare, UK)/phenylbutazon (42726 (Swissmedic), Streuli Pharma AG, Uznach, Switzerland)/aminophenazon/benzylpenicillin (56271 (Swissmedic), Grunenthal Pharma AG, Glarus; Switzerland)/dihydrostreptomycin (42790 (Swissmedic), Streuli Pharma AG, Uznach, Switzerland) provided within the drinking water for 1 week as an analgesic/antibiotic. Post-operatively, mice were housed for three days on heat pads and moist food placed at the floor of the cage to promote recovery and to reduce drop-outs.

The Alzet® osmotic minipump model 1004 pumps antibody or PBS solution into the lateral ventricle at a constant infusion rate of 0.11 µl per hour=2.64 µl per day over a total duration of 28 days. Concentration of antibody solution in pump was chosen to equal 0.1 mg/kg body weight per day.

Pump Change

Every 28 days the osmotic minipumps were exchanged. The B6.Cg-Tg(SOD1*G93A)1Gur/J transgenic mice were deeply anaesthetized by inhalation anesthesia (3.5% Sevofluran (53211 (Swissmedic), Abbott A G, Baar, Switzerland)) and a small incision was made above the pump, the pump was disconnected from the brain infusion cannula and taken out. A freshly filled pump was inserted, connected to the infusion cannula and wound clips were used to close the incision site.

Grip Strength Analysis

A Grip strength meter apparatus (Ugo Basile, Comero, Italy; Cat. No.: 47106) was used to measure the gripping strength of mice. The system is supplied with a grid which connects to a sensor. Animals were lowered down until all four paws grasped the grid and then gently pulled back until the grip was released. The maximal force achieved by the animal was recorded electronically over three trials.

Clinical End Point

The clinical end point of severe disabling motor neuron disease was defined by the inability of mice to right themselves within 15 seconds from lying laterally on the side. The probability of survival was tested by Kaplan-Meier survival analyses of mice having not reached, at any given point in time of the experiment, the defined clinical endpoint of motor neuron disease.

Immunohistochemistry and Motor Neuron Count

Spinal cord of B6.Cg-Tg(SOD1*G93A)1Gur/J transgenic mice at the terminal stage of disease were fixed in phosphate-buffered 4% paraformaldehyde solution, paraffin-embedded, and cut into 5-µm sections. For Nissl staining (0.5% Cresyl-violet solution (Sigma-Aldrich, C5042)), sections were stained in Nissl solution for 3' at RT and then washed in distilled water for 3 min. Sections were further processed according standard protocol. For NeuN staining, after formic acid pretreatment sections were incubated with monoclonal NeuN antibody, 1:1000 dilution (MAB377; Milipore). Antibody signal was amplified with standard DAB detection system. NeuN staining was performed with automated Leica BondMax™ staining system (Leica, Wetzlar, Germany).

Nissl- or NeuN-positive neurons having a diameter >of 30 µm were counted in both ventral horns of 8 lumbar spinal cord sections per animal, each section spaced 100 µm apart.

Results

Figure 10:
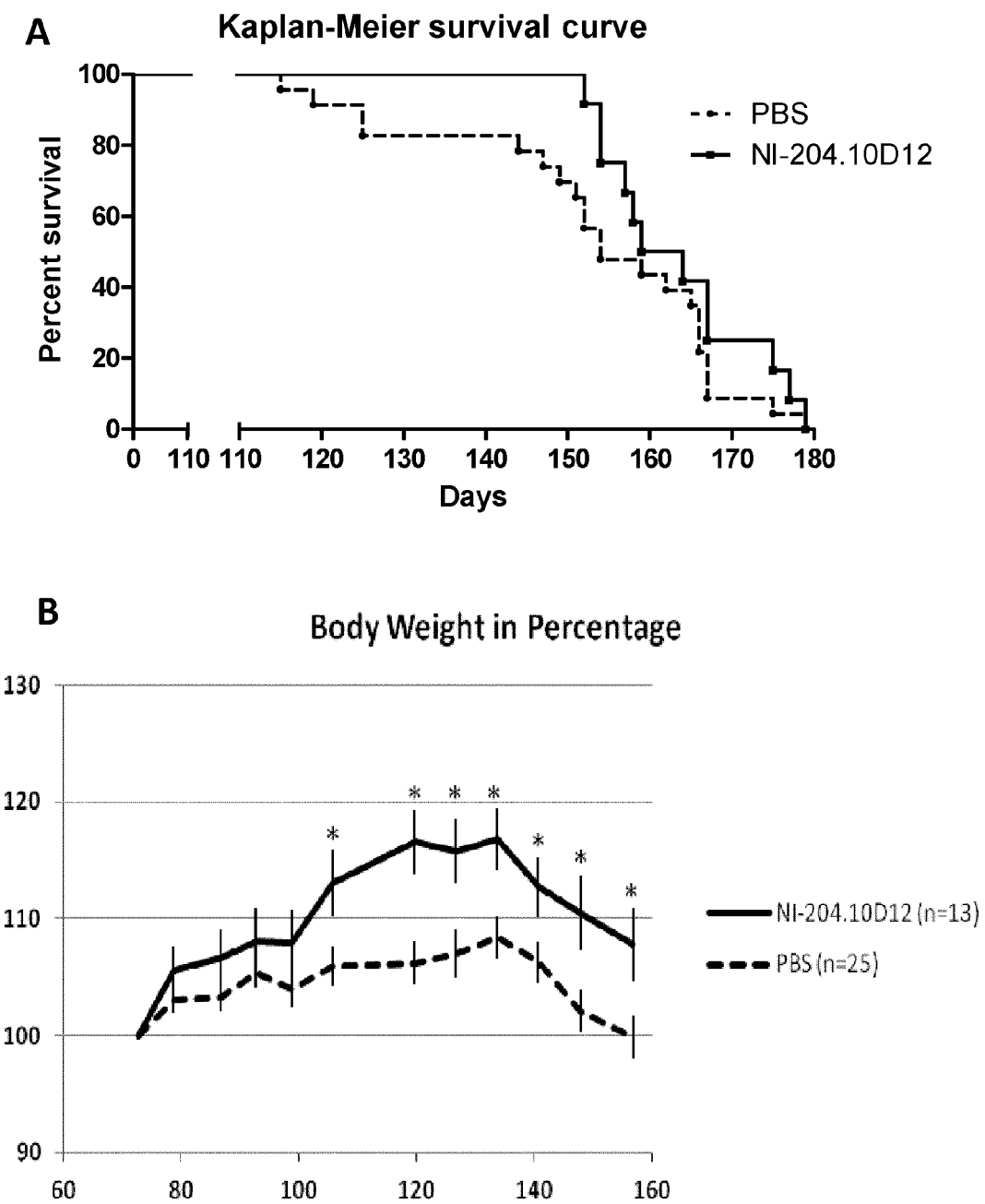
FIG. 10: (A) Kaplan-Meier survival curve of B6.Cg-Tg (SOD1*G93A)1Gur/J transgenic mice passively immunized with NI-204.10D12 antibody. Kaplan-Meier survival curve of B6.Cg-Tg(SOD1*G93A)1Gur/J transgenic mice treated intraventricularly either with PBS (●) or NI-204.10D12 SOD1-specific antibody (■)

To assess the pharmacological treatment effects of human-derived antibodies targeting SOD1, NI-204.10D12 antibody was administered chronically for three months by direct intraventricular brain infusion in B6.Cg-Tg(SOD1*G93A)1Gur/J transgenic mice starting at 60 days of age. Chronic 204.10D12 antibody treatment significantly extended the lifespan of SOD1 transgenic animals by 11 days with an average survival time of 164±3 days in mice receiving chronic NI-204.10D12 infusions vs. 153±4 days in the vehicle-treated group (p<0.05; FIG. 10(A)). Furthermore, chronic NI-204.10D12 treatment of B6.Cg-Tg(SOD1*G93A)1Gur/J transgenic mice led to a significant delay in the loss of body weight throughout the entire disease-course as compared to the PBS-treated control group (FIG. 10(B)). The severe progressive motor impairments observed during disease progression in the SOD1 transgenic mice were ameliorated by the NI-204.10D12 treatment as evident by improved grip strength performance in the antibody treated group compared to vehicle controls (FIG. 11). Quantitative analysis of the complement of motor neurons in the ventral horn of the lumbar spinal cord revealed a significant attenuation of the loss of motor neurons in animals treated with NI-204.10D12 as compared to vehicle treated animals, suggesting that NI-204.10D12 treatment can protect from the degeneration of motor neurons mediated by mutant SOD-1 overexpression (FIG. 12). These findings highlight the profound therapeutic effects of human-derived SOD1-specific antibodies which upon chronic administration can delay the disease onset, prolong survival, improve body weight and motor performance and ameliorate neuronal degeneration. Human-derived SOD1-specific antibodies are therefore promising novel drug candidates for the treatment of ALS.

Example 10

IgG Germ Line Family Classification of the SOD1 Antibodies

Sequence analysis of the variable regions of the different human SOD1 specific antibodies allows classification of the NI-204 antibodies into germ line IgG families (Table V).

In order to provide classification of the human NI-204 antibodies into germ line V segment families, nucleotide sequences of the original variable region were aligned with the human germ line sequences in the database Vbase (http://vbase.mrc-cpe.cam.ac.uk/) hosted by the MRC Centre for Protein Engineering (Cambridge, UK). The germ lines have been specified by their loci for heavy chains and by their Vbase entry numbers for the light chains (see Table V below).

TABLE V

NI-204 antibody family classification according to germline immunoglobulin sequence comparison (last character in the names of the antibodies indicates their type: H—heavy, K—kappa, L—lambda)

| Antibody | V-segment germline family classification |
|---|---|
| NI-204.10D12H | VH 3-74 |
| NI-204.10D12K | DPK24 |
| NI-204.12G7H | VH 1-46 |
| NI-204.12G7L | 3a.119B4/V2-11+ |
| NI-204.11F11H | VH 3-15 |
| NI-204.11F11K | Vg/38K |
| NI-204.10A8H | VH 1-69 |
| NI-204.10A8K | DPK9/012 |
| NI-204.67E12H | VH 3-23 |
| NI-204.67E12K | HK102/V1+ |
| NI-204.6H1H | VH 4-34 |
| NI-204.6H1L | V2-17+ |
| NI-204.12G3H | VH 3-33 |
| NI-204.12G3H | IGGLL150/V2-17+ |
| NI-204.7G5H | VH 3-30/3-30.5 |
| NI-204.7G5L | 3p.81A4/V2-7+ |
| NI-204.7B3H | VH 3-74 |
| NI-204.7B3L | V2-17+ |
| NI-204.34A3H | LSG6.1 (V3-15) |
| NI-204.34A3L | 3p.81A4/V2-7+ |
| NI-204.25H3H | VH 4-59 |
| NI-204.25H3L | 1b.366F5/DPL5 |
| NI-204.9F6H | VH 3-23 |
| NI-204.9F6L | 3r.9C5/DPL23 |

The invention claimed is:

1. A cDNA molecule encoding a human anti-SOD1 antibody or an antigen-binding fragment thereof capable of binding to misfolded or aggregated SOD1; wherein the encoded antibody or antigen-binding fragment thereof comprises in its variable region the complementarity determining regions (CDRs) depicted in any one of FIGS. 1A-1L, and wherein the encoded antibody
   (i) binds to physiological SOD1 dimers
   (ii) preferentially recognizes the misfolded or aggregated SOD1 over physiological SOD1 dimers, or
   (iii) does not substantially recognize physiological SOD1 dimers.

2. The cDNA of claim 1, wherein the antibody or antigen binding fragment thereof selectively binds to human wildtype and murine SOD1.

3. The cDNA of claim 1, wherein the antibody or antigen binding fragment thereof which binds to physiological SOD1, specifically binds an SOD1 epitope comprising or consisting of an amino acid sequence selected from the group consisting of:

GGPKDEERHVG, (SEQ ID NO: 51)

IIGRTLV, (SEQ ID NO: 53)

or

HEKADDLGKGGNEES. (SEQ ID NO: 55)

4. The cDNA of claim 1, wherein the antibody or antigen binding fragment thereof which preferentially recognizes misfolded or aggregated SOD1 over physiological SOD1 dimers, or which does not substantially recognize physiological SOD1 dimers, specifically binds an SOD1 epitope comprising or consisting of an amino acid sequence selected from the group consisting of:

DGVADVS, (SEQ ID NO: 2)

GGPKDEERHVG, (SEQ ID NO: 51)

IIGRTLV, (SEQ ID NO: 53)

LGNVTADKDGV, (SEQ ID NO: 54)

HEKADDLGKGGNEES, (SEQ ID NO: 55)

EDSVISL, (SEQ ID NO: 56)

KTGNAGS, (SEQ ID NO: 57)

LGNVTADKDGV, (SEQ ID NO: 58)
or

GGPKDEE. (SEQ ill NO: 59)

5. The cDNA of claim 1, which is derived from mRNA obtained from a human memory B-cell.

6. The cDNA of claim 5, wherein the antibody or antigen binding fragment thereof further comprises a polypeptide sequence which is heterologous to at least one CDR.

7. The cDNA of claim 6, wherein the human constant domain is of the IgG-type.

8. The cDNA of claim 5, wherein the antibody or antigen-binding fragment thereof comprises in its variable region a set of complementarity determining regions (CDRs) selected from:
  (i) VHCDR1: positions 31-35 of SEQ ID NO:60,
  VHCDR2: positions 50-66 of SEQ ID NO:60,
  VHCDR3: positions 99-115 of SEQ ID NO:60,
  VKCDR1: positions 24-38 of SEQ ID NO:61,
  VKCDR2: positions 54-60 of SEQ ID NO:61,
  VKCDR3: positions 93-101 of SEQ ID NO:61;
  (ii) VHCDRI: positions 31-35 of SEQ ID NO:62,
  VHCDR2: positions 50-66 of SEQ ID NO:62,
  VHCDR3: positions 109-132 of SEQ ID NO:62
  VLCDRI: positions 23-33 of SEQ ID NO:63,
  VLCDR2: positions 49-55 of SEQ ID NO:63,
  VLCDR3: LSADSSGTWV positions 89-98 of SEQ ID NO:63;
  (iii) VHCDRI: positions 31-35 of SEQ ID NO:64,
  VHCDR2: positions 50-66 of SEQ ID NO:64,
  VHCDR3: positions 99-110 of SEQ ID NO:64,
  VKCDR1: positions 24-34 of SEQ ID NO:65,
  VKCDR2: positions 50-56 of SEQ ID NO:65,
  VKCDR3: positions 89-97 of SEQ ID NO:65;
  (iv) VHCDRI: positions 31-35 of SEQ ID NO:66,
  VHCDR2: positions 50-66 of SEQ ID NO:66,
  VHCDR3: positions 100-115 of SEQ ID NO:66,
  VLCDRI: positions 22-33 of SEQ ID NO:67,
  VLCDR2: positions 49-55 of SEQ ID NO:67,
  VLCDR3: positions 89-99 of SEQ ID NO:67;
  (v) VHCDRI: positions 31-35 of SEQ ID NO:68,
  VHCDR2: positions 50-66 of SEQ ID NO:68,
  VHCDR3: positions 102-117 of SEQ ID NO:68,
  VLCDR1: positions 24-33 of SEQ ID NO:69,
  VLCDR2: positions 50-56 of SEQ ID NO:69,
  VLCDR3: positions 90-98 of SEQ ID NO:69;
  (vi) VHCDRI: positions 31-35 of SEQ ID NO:70,
  VHCDR2: positions 50-66 of SEQ ID NO:70,
  VHCDR3: positions 100-114 of SEQ ID NO:70,
  VLCDR1: positions 24-34 of SEQ ID NO:71,
  VLCDR2: positions 50-56 of SEQ ID NO:71,
  VLCDR3: positions 90-98 of SEQ ID NO:71;
  (vii) VHCDRI: positions 31-35 of SEQ ID NO:72,
  VHCDR2: positions 50-60 of SEQ ID NO:72,
  VHCDR3: positions 98-111 of SEQ ID NO:72,
  VLCDRI: positions 23-33 of SEQ ID NO:73,
  VLCDR2: positions 49-55 of SEQ ID NO:73,
  VLCDR3: positions 88-98 of SEQ ID NO:73;
  (viii) VHCDRI: positions 31-35 of SEQ ID NO:74,
  VHCDR2: positions 50-66 of SEQ ID NO:74,
  VHCDR3: positions 99-110 of SEQ ID NO:74,
  VLCDRI: positions 23-33 of SEQ ID NO:75,
  VLCDR2: positions 49-55 of SEQ ID NO:75,
  VLCDR3: positions 88-97 of SEQ ID NO:75;
  (ix) VHCDRI: positions 31-35 of SEQ ID NO:76,
  VHCDR2: positions 50-66 of SEQ ID NO:76,
  VHCDR3: positions 99-119 of SEQ ID NO:76
  VLCDR1: positions 23-33 of SEQ ID NO:77,
  VLCDR2: positions 49-55 of SEQ ID NO:77,
  VLCDR3: positions 88-98 of SEQ ID NO:77;
  (x) VHCDRI: positions 31-35 of SEQ ID NO:78,
  VHCDR2: positions 50-66 of SEQ ID NO:78,
  VHCDR3: positions 99-103 of SEQ ID NO:78,
  VLCDRI: positions 23-33 of SEQ ID NO:79,
  VLCDR2: positions 49-55 of SEQ ID NO:79,
  VLCDR3: positions 88-97 of SEQ ID NO:79;
  (xi) VHCDRI: positions 31-35 of SEQ ID NO:80,
  VHCDR2: positions 50-68 of SEQ ID NO:80,
  VHCDR3: positions 101-111 of SEQ ID NO:80,
  VLCDR1: positions 23-33 of SEQ ID NO:81,
  VLCDR2: positions 49-55 of SEQ ID NO:81,
  VLCDR3: positions 88-98 of SEQ ID NO:81; or
  (xii) VHCDRI: positions 31-35 of SEQ ID NO:82,
  VHCDR2: positions 49-65 of SEQ ID NO:82,
  VHCDR3: positions 98-108 of SEQ ID NO:82,
  VLCDR1: positions 23-35 of SEQ ID NO:83,
  VLCDR2: positions 51-57 of SEQ ID NO:83,
  VLCDR3: positions 90-100 of SEQ ID NO:83.

9. The cDNA of claim 1, wherein the antibody is selected from the group consisting of a chimeric murine-human or a murinized antibody.

10. The cDNA of claim 1, wherein the antibody comprises a heterologous human constant region compared to the natural occurring antibody.

11. The cDNA of claim 1, wherein the antibody is selected from the group consisting of a single chain Fv fragment (scFv), an F(ab') fragment, an F(ab) fragment, and an F(ab')$_2$ fragment.

12. The cDNA of claim 1, wherein the antibody or antigen binding fragment thereof further comprises a polypeptide sequence which is heterologous to the $V_H$ and $V_L$ region.

13. The cDNA of claim 12, wherein the human constant region is of the IgG-type.

14. A method of producing an isolated monoclonal anti-SOD1 antibody or antigen-binding fragment thereof, comprising:
  using an expression vector comprising the cDNA of any one of claims 1, 2, 3, 4, 5 and 8-12 operatively-linked to a promoter to express anti-SOD1 antibodies or antigen-binding fragments thereof, in a host cell to obtain an isolated anti-SOD1 antibody or antigen-binding fragment thereof.

15. The method of claim 14, wherein the anti-SOD1 antibody is detectably labeled.

16. The method of claim 15, wherein the detectable label is selected from the group consisting of an enzyme, a radioisotope, a fluorophore and a heavy metal.

17. The method of claim 14, wherein the antibody is attached to a drug.

18. A vector comprising the cDNA of claim 1.

19. The vector of claim 18, which is an expression vector comprising the cDNA operably linked to expression control sequences.

20. An isolated host cell comprising the vector of claim 18 or 19.

21. A method of producing an isolated anti-SOD1 antibody comprising culturing the isolated host cell of claim 20 under conditions allowing for expression of the anti-SOD1 antibody or antigen-binding fragment thereof and isolating the antibody or antigen-binding fragment thereof from the culture.

* * * * *

SEQUENCE LISTING

<160> NUMBER OF SEQ ID NOS: 83

<210> SEQ ID NO 1
<211> LENGTH: 154
<212> TYPE: PRT
<213> ORGANISM: Homo sapiens
<220> FEATURE:
<221> NAME/KEY: PEPTIDE
<222> LOCATION: (1)..(154)
<223> OTHER INFORMATION: amino acid sequence of human SOD1
<300> PUBLICATION INFORMATION:
<301> AUTHORS: Kajihara J., Enomoto M., Nishijima K., Yabuuchi M.,
    Katoh K.
<302> TITLE: Comparison of properties between human recombinant and
    placental copper-zinc SOD.
<303> JOURNAL: Journal of Biochemistry
<304> VOLUME: 104
<305> ISSUE: 5
<306> PAGES: 851-854
<307> DATE: 1988-11-01
<308> DATABASE ACCESSION NUMBER: PubMed/2853161
<309> DATABASE ENTRY DATE: 1988-11-01
<300> PUBLICATION INFORMATION:
<308> DATABASE ACCESSION NUMBER: SODC_HUMAN/P00441
<309> DATABASE ENTRY DATE: 2010-11-30
<313> RELEVANT RESIDUES IN SEQ ID NO: (1)..(154)

<400> SEQUENCE: 1

```
Met Ala Thr Lys Ala Val Cys Val Leu Lys Gly Asp Gly Pro Val Gln
1               5                   10                  15

Gly Ile Ile Asn Phe Glu Gln Lys Glu Ser Asn Gly Pro Val Lys Val
            20                  25                  30

Trp Gly Ser Ile Lys Gly Leu Thr Glu Gly Leu His Gly Phe His Val
        35                  40                  45

His Glu Phe Gly Asp Asn Thr Ala Gly Cys Thr Ser Ala Gly Pro His
    50                  55                  60

Phe Asn Pro Leu Ser Arg Lys His Gly Gly Pro Lys Asp Glu Glu Arg
65                  70                  75                  80

His Val Gly Asp Leu Gly Asn Val Thr Ala Asp Lys Asp Gly Val Ala
                85                  90                  95

Asp Val Ser Ile Glu Asp Ser Val Ile Ser Leu Ser Gly Asp His Cys
            100                 105                 110

Ile Ile Gly Arg Thr Leu Val Val His Glu Lys Ala Asp Asp Leu Gly
        115                 120                 125
```

```
            Lys Gly Gly Asn Glu Glu Ser Thr Lys Thr Gly Asn Ala Gly Ser Arg
                130                 135                 140

Leu Ala Cys Gly Val Ile Gly Ile Ala Gln
            145                 150

<210> SEQ ID NO 2
<211> LENGTH: 7
<212> TYPE: PRT
<213> ORGANISM: Artificial Sequence
<220> FEATURE:
<223> OTHER INFORMATION: Epitope recognized by NI-204.10D12 antibody
<220> FEATURE:
<221> NAME/KEY: PEPTIDE
<222> LOCATION: (1)..(7)
<223> OTHER INFORMATION: Epitope of NI-204.10D12 antibody

<400> SEQUENCE: 2

Asp Gly Val Ala Asp Val Ser
1               5

<210> SEQ ID NO 3
<211> LENGTH: 378
<212> TYPE: DNA
<213> ORGANISM: Homo sapiens
<220> FEATURE:
<221> NAME/KEY: CDS
<222> LOCATION: (1)..(378)
<223> OTHER INFORMATION: NI-204.10D12-VH variable heavy chain (VH)
      sequence
<220> FEATURE:
<221> NAME/KEY: V_region
<222> LOCATION: (91)..(105)
<223> OTHER INFORMATION: complementarity determining region (CDR)
      VH-CDR1
<220> FEATURE:
<221> NAME/KEY: V_region
<222> LOCATION: (148)..(198)
<223> OTHER INFORMATION: complementarity determining region (CDR)
      VH-CDR2
<220> FEATURE:
<221> NAME/KEY: V_region
<222> LOCATION: (295)..(345)
<223> OTHER INFORMATION: complementarity determining region (CDR)
      VH-CDR3

<400> SEQUENCE: 3 gag gtg cag ctg gtg gag tct ggg gga gac tta gtt cgc cct ggg ggg        48
Glu Val Gln Leu Val Glu Ser Gly Gly Asp Leu Val Arg Pro Gly Gly
1               5                   10                  15 tcc ctg aga ctc tcc tgt gtc gcc tct gga ttc acc ttc agc aac tac        96
Ser Leu Arg Leu Ser Cys Val Ala Ser Gly Phe Thr Phe Ser Asn Tyr
            20                  25                  30 tgg atg cac tgg gtc cgc caa gct cca ggg cag cgg ccg gtg tgg gtc       144
Trp Met His Trp Val Arg Gln Ala Pro Gly Gln Arg Pro Val Trp Val
        35                  40                  45 tca cgt act aat act gat ggc cgt aac aca gcc tac gcg gac tac gcg       192
Ser Arg Thr Asn Thr Asp Gly Arg Asn Thr Ala Tyr Ala Asp Tyr Ala
    50                  55                  60 aag ggc cga ttc acc atc tcc aga gac aat gcc aag agc acg ctg tat       240
Lys Gly Arg Phe Thr Ile Ser Arg Asp Asn Ala Lys Ser Thr Leu Tyr
65                  70                  75                  80 ctg caa ctg aac agt ctg aga gcc gaa gac acg gct gtg tac ttc tgt       288
Leu Gln Leu Asn Ser Leu Arg Ala Glu Asp Thr Ala Val Tyr Phe Cys
                85                  90                  95 gca agg ctg cga aga aac gtc gcc gac caa atc act cac aac tac tac       336
Ala Arg Leu Arg Arg Asn Val Ala Asp Gln Ile Thr His Asn Tyr Tyr
            100                 105                 110
```

```
atg gac gtc tgg ggc aaa ggc acc ctg gtc acc gtc tcc tcg        378
Met Asp Val Trp Gly Lys Gly Thr Leu Val Thr Val Ser Ser
        115                 120                 125

<210> SEQ ID NO 4
<211> LENGTH: 126
<212> TYPE: PRT
<213> ORGANISM: Homo sapiens

<400> SEQUENCE: 4

Glu Val Gln Leu Val Glu Ser Gly Gly Asp Leu Val Arg Pro Gly Gly
1               5                   10                  15

Ser Leu Arg Leu Ser Cys Val Ala Ser Gly Phe Thr Phe Ser Asn Tyr
            20                  25                  30

Trp Met His Trp Val Arg Gln Ala Pro Gly Gln Arg Pro Val Trp Val
        35                  40                  45

Ser Arg Thr Asn Thr Asp Gly Arg Asn Thr Ala Tyr Ala Asp Tyr Ala
    50                  55                  60

Lys Gly Arg Phe Thr Ile Ser Arg Asp Asn Ala Lys Ser Thr Leu Tyr
65                  70                  75                  80

Leu Gln Leu Asn Ser Leu Arg Ala Glu Asp Thr Ala Val Tyr Phe Cys
                85                  90                  95

Ala Arg Leu Arg Arg Asn Val Ala Asp Gln Ile Thr His Asn Tyr Tyr
            100                 105                 110

Met Asp Val Trp Gly Lys Gly Thr Leu Val Thr Val Ser Ser
        115                 120                 125

<210> SEQ ID NO 5
<211> LENGTH: 333
<212> TYPE: DNA
<213> ORGANISM: Homo sapiens
<220> FEATURE:
<221> NAME/KEY: CDS
<222> LOCATION: (1)..(333)
<223> OTHER INFORMATION: NI-204.10D12-VL variable light chain (VL)
      sequence
<220> FEATURE:
<221> NAME/KEY: V_region
<222> LOCATION: (70)..(114)
<223> OTHER INFORMATION: complementarity determining region (CDR)
      VL-CDR1
<220> FEATURE:
<221> NAME/KEY: V_region
<222> LOCATION: (160)..(180)
<223> OTHER INFORMATION: complementarity determining region (CDR)
      VL-CDR2
<220> FEATURE:
<221> NAME/KEY: V_region
<222> LOCATION: (277)..(303)
<223> OTHER INFORMATION: complementarity determining region (CDR)
      VL-CDR3

<400> SEQUENCE: 5 gaa att gtg ctg act cag tct cca ggc tcc ctg gct gtg tct ctg ggc    48
Glu Ile Val Leu Thr Gln Ser Pro Gly Ser Leu Ala Val Ser Leu Gly
1               5                   10                  15 gag agg gcc acc atc aac tgc aag tcc agc cag act gtt tta tac aat    96
Glu Arg Ala Thr Ile Asn Cys Lys Ser Ser Gln Thr Val Leu Tyr Asn
            20                  25                  30 aat aag aac tat tta gct tgg tac cag cag aaa cca gga cag cct ccg   144
Asn Lys Asn Tyr Leu Ala Trp Tyr Gln Gln Lys Pro Gly Gln Pro Pro
        35                  40                  45 aag ttg ctc att tcc tgg gca tct tcc cga gaa tcc ggg gtc cct gac   192
Lys Leu Leu Ile Ser Trp Ala Ser Ser Arg Glu Ser Gly Val Pro Asp
    50                  55                  60
```

```
cgg ttc agt ggc agc ggg tct ggg aca gat ttc act ctc acc atc agc        240
Arg Phe Ser Gly Ser Gly Ser Gly Thr Asp Phe Thr Leu Thr Ile Ser
 65              70                  75                  80 agc ctg cag gct gaa gat gtg gca gtt tat tac tgt cag cac tat tat        288
Ser Leu Gln Ala Glu Asp Val Ala Val Tyr Tyr Cys Gln His Tyr Tyr
                 85                  90                  95 ggt act cct gtc act ttc ggc gga ggg acc aag gtg gaa atc aaa            333
Gly Thr Pro Val Thr Phe Gly Gly Gly Thr Lys Val Glu Ile Lys
            100                 105                 110

<210> SEQ ID NO 6
<211> LENGTH: 111
<212> TYPE: PRT
<213> ORGANISM: Homo sapiens

<400> SEQUENCE: 6

Glu Ile Val Leu Thr Gln Ser Pro Gly Ser Leu Ala Val Ser Leu Gly
 1               5                  10                  15

Glu Arg Ala Thr Ile Asn Cys Lys Ser Ser Gln Thr Val Leu Tyr Asn
             20                  25                  30

Asn Lys Asn Tyr Leu Ala Trp Tyr Gln Gln Lys Pro Gly Gln Pro Pro
         35                  40                  45

Lys Leu Leu Ile Ser Trp Ala Ser Ser Arg Glu Ser Gly Val Pro Asp
 50                  55                  60

Arg Phe Ser Gly Ser Gly Ser Gly Thr Asp Phe Thr Leu Thr Ile Ser
 65              70                  75                  80

Ser Leu Gln Ala Glu Asp Val Ala Val Tyr Tyr Cys Gln His Tyr Tyr
                 85                  90                  95

Gly Thr Pro Val Thr Phe Gly Gly Gly Thr Lys Val Glu Ile Lys
            100                 105                 110

<210> SEQ ID NO 7
<211> LENGTH: 369
<212> TYPE: DNA
<213> ORGANISM: Homo sapiens
<220> FEATURE:
<221> NAME/KEY: CDS
<222> LOCATION: (1)..(369)
<223> OTHER INFORMATION: NI-104.12G7-VH variable heavy chain (VH)
      sequence, wherein Glu at positions 1 and 6 of the amino acid
      sequence can also be Gln
<220> FEATURE:
<221> NAME/KEY: V_region
<222> LOCATION: (91)..(105)
<223> OTHER INFORMATION: complementarity determining region (CDR)
      VH-CDR1
<220> FEATURE:
<221> NAME/KEY: V_region
<222> LOCATION: (148)..(198)
<223> OTHER INFORMATION: complementarity determining region (CDR)
      VH-CDR2
<220> FEATURE:
<221> NAME/KEY: V_region
<222> LOCATION: (295)..(336)
<223> OTHER INFORMATION: complementarity determining region (CDR)
      VH-CDR3

<400> SEQUENCE: 7 gag gtg cag ctg gtg gag tct ggg gct gag gtg aag aag cct ggg gcc         48
Glu Val Gln Leu Val Glu Ser Gly Ala Glu Val Lys Lys Pro Gly Ala
 1               5                  10                  15 tca gtg aca ctg tcc tgc aag gca tct gga tac acc ttc acc gcc tac         96
Ser Val Thr Leu Ser Cys Lys Ala Ser Gly Tyr Thr Phe Thr Ala Tyr
             20                  25                  30
```

```
tat ata cac tgg gtg cga cag gcc cga gaa caa ggg ctt gag tgg atg      144
Tyr Ile His Trp Val Arg Gln Ala Arg Glu Gln Gly Leu Glu Trp Met
        35                  40                  45 ggc gta atc aac cct agt act gga acc aca ttt tac gca cag aac ttc      192
Gly Val Ile Asn Pro Ser Thr Gly Thr Thr Phe Tyr Ala Gln Asn Phe
    50                  55                  60 ccg gac aga gtc tcc gtg acc agg gac acg tcc acg agt aca gtc ttc      240
Pro Asp Arg Val Ser Val Thr Arg Asp Thr Ser Thr Ser Thr Val Phe
65                  70                  75                  80 atg gag ctg cac aac ctg aaa tct gag gac acg gcc gta tat tac tgt      288
Met Glu Leu His Asn Leu Lys Ser Glu Asp Thr Ala Val Tyr Tyr Cys
                85                  90                  95 gcg aga gca atc agt gag cat ggt tca ggg agt tat tca cct tat tac      336
Ala Arg Ala Ile Ser Glu His Gly Ser Gly Ser Tyr Ser Pro Tyr Tyr
            100                 105                 110 tgg ggc cag ggc acc ctg gtc acc gtc tcc tcg                          369
Trp Gly Gln Gly Thr Leu Val Thr Val Ser Ser
        115                 120

<210> SEQ ID NO 8
<211> LENGTH: 123
<212> TYPE: PRT
<213> ORGANISM: Homo sapiens

<400> SEQUENCE: 8

Glu Val Gln Leu Val Glu Ser Gly Ala Glu Val Lys Lys Pro Gly Ala
1               5                   10                  15

Ser Val Thr Leu Ser Cys Lys Ala Ser Gly Tyr Thr Phe Thr Ala Tyr
            20                  25                  30

Tyr Ile His Trp Val Arg Gln Ala Arg Glu Gln Gly Leu Glu Trp Met
        35                  40                  45

Gly Val Ile Asn Pro Ser Thr Gly Thr Thr Phe Tyr Ala Gln Asn Phe
    50                  55                  60

Pro Asp Arg Val Ser Val Thr Arg Asp Thr Ser Thr Ser Thr Val Phe
65                  70                  75                  80

Met Glu Leu His Asn Leu Lys Ser Glu Asp Thr Ala Val Tyr Tyr Cys
                85                  90                  95

Ala Arg Ala Ile Ser Glu His Gly Ser Gly Ser Tyr Ser Pro Tyr Tyr
            100                 105                 110

Trp Gly Gln Gly Thr Leu Val Thr Val Ser Ser
        115                 120

<210> SEQ ID NO 9
<211> LENGTH: 321
<212> TYPE: DNA
<213> ORGANISM: Homo sapiens
<220> FEATURE:
<221> NAME/KEY: CDS
<222> LOCATION: (1)..(321)
<223> OTHER INFORMATION: NI-204.12G7-VL variable light chain (VL)
      sequence, wherein Val at position 3 of the amino acid sequence can
      also be Glu
<220> FEATURE:
<221> NAME/KEY: V_region
<222> LOCATION: (67)..(99)
<223> OTHER INFORMATION: complementarity determining region (CDR)
      VL-CDR1
<220> FEATURE:
<221> NAME/KEY: V_region
<222> LOCATION: (145)..(165)
<223> OTHER INFORMATION: complementarity determining region (CDR)
      VL-CDR2
<220> FEATURE:
<221> NAME/KEY: V_region
```

<222> LOCATION: (262)..(291)
<223> OTHER INFORMATION: complementarity determining region (CDR)
      VL-CDR3

<400> SEQUENCE: 9

```
tcc tat gtg ctg act cag cca ccc tcg gtg tca gtg tcc cta gga cag    48
Ser Tyr Val Leu Thr Gln Pro Pro Ser Val Ser Val Ser Leu Gly Gln
1               5                   10                  15 atg gcc gcg atc acc tgc tct gga gag gca ttg cca aaa aag tat ggt    96
Met Ala Ala Ile Thr Cys Ser Gly Glu Ala Leu Pro Lys Lys Tyr Gly
            20                  25                  30 tat tgg tac cag cag aag cca ggc cag gtc cct gtt ctg cta att tat   144
Tyr Trp Tyr Gln Gln Lys Pro Gly Gln Val Pro Val Leu Leu Ile Tyr
        35                  40                  45 aga gac gtc gag agg ccc tca ggg gtc cct gac cga ttc tct ggc tcc   192
Arg Asp Val Glu Arg Pro Ser Gly Val Pro Asp Arg Phe Ser Gly Ser
    50                  55                  60 agc tca ggg aca atg gtc aca ttg acc atc agt gga gtc cag gca gag   240
Ser Ser Gly Thr Met Val Thr Leu Thr Ile Ser Gly Val Gln Ala Glu
65                  70                  75                  80 gac gag gct gac tat tac tgt ctc tca gca gac agc agt ggt act tgg   288
Asp Glu Ala Asp Tyr Tyr Cys Leu Ser Ala Asp Ser Ser Gly Thr Trp
                85                  90                  95 gtg ttc ggc gga ggg acc aag ctg acc gtc cta                       321
Val Phe Gly Gly Gly Thr Lys Leu Thr Val Leu
            100                 105
```

<210> SEQ ID NO 10
<211> LENGTH: 107
<212> TYPE: PRT
<213> ORGANISM: Homo sapiens

<400> SEQUENCE: 10

```
Ser Tyr Val Leu Thr Gln Pro Pro Ser Val Ser Val Ser Leu Gly Gln
1               5                   10                  15

Met Ala Ala Ile Thr Cys Ser Gly Glu Ala Leu Pro Lys Lys Tyr Gly
            20                  25                  30

Tyr Trp Tyr Gln Gln Lys Pro Gly Gln Val Pro Val Leu Leu Ile Tyr
        35                  40                  45

Arg Asp Val Glu Arg Pro Ser Gly Val Pro Asp Arg Phe Ser Gly Ser
    50                  55                  60

Ser Ser Gly Thr Met Val Thr Leu Thr Ile Ser Gly Val Gln Ala Glu
65                  70                  75                  80

Asp Glu Ala Asp Tyr Tyr Cys Leu Ser Ala Asp Ser Ser Gly Thr Trp
                85                  90                  95

Val Phe Gly Gly Gly Thr Lys Leu Thr Val Leu
            100                 105
```

<210> SEQ ID NO 11
<211> LENGTH: 363
<212> TYPE: DNA
<213> ORGANISM: Homo sapiens
<220> FEATURE:
<221> NAME/KEY: CDS
<222> LOCATION: (1)..(363)
<223> OTHER INFORMATION: NI-204.10A8-VH variable heavy chain (VH)
      sequence, wherein Glu at positions 1 and 6 of the amino acid
      sequence can also be Gln
<220> FEATURE:
<221> NAME/KEY: V_region
<222> LOCATION: (91)..(105)
<223> OTHER INFORMATION: complementarity determining region (CDR)
      VH-CDR1

```
<220> FEATURE:
<221> NAME/KEY: V_region
<222> LOCATION: (148)..(198)
<223> OTHER INFORMATION: complementarity determining region (CDR)
      VH-CDR2
<220> FEATURE:
<221> NAME/KEY: V_region
<222> LOCATION: (295)..(330)
<223> OTHER INFORMATION: complementarity determining region (CDR)
      VH-CDR3

<400> SEQUENCE: 11 gag gtg cag ctg gtg gag tct ggg gct gag gtg aag gag cct ggg tcg      48
Glu Val Gln Leu Val Glu Ser Gly Ala Glu Val Lys Glu Pro Gly Ser
1               5                   10                  15 tcg gtg agg gtc tcc tgc aag act tct gga ggc tcc ttc aac aga cat      96
Ser Val Arg Val Ser Cys Lys Thr Ser Gly Gly Ser Phe Asn Arg His
            20                  25                  30 gtt atc acc tgg gtg cga cag gcc cct gga caa ggg ctt gag tgg atg     144
Val Ile Thr Trp Val Arg Gln Ala Pro Gly Gln Gly Leu Glu Trp Met
        35                  40                  45 ggc gag atc atc cct ttc ttt ggt aca cca aag tat gca ccg aag ttc     192
Gly Glu Ile Ile Pro Phe Phe Gly Thr Pro Lys Tyr Ala Pro Lys Phe
50                  55                  60 cag ggc aga gtc acc att atc gcc gac gcg tcc acg agc aca ttc ttc     240
Gln Gly Arg Val Thr Ile Ile Ala Asp Ala Ser Thr Ser Thr Phe Phe
65                  70                  75                  80 ttg gac gtg aag agc ctg aca tct gag gac acg gcc ctg tat ttc tgt     288
Leu Asp Val Lys Ser Leu Thr Ser Glu Asp Thr Ala Leu Tyr Phe Cys
                85                  90                  95 tgg att gtt gtg gtg tct gtt gtt cag cga agg gag gac ttc tgg ggc     336
Trp Ile Val Val Val Ser Val Val Gln Arg Arg Glu Asp Phe Trp Gly
                100                 105                 110 cag gga atc ctg gtc acc gtc tcc tcg                                 363
Gln Gly Ile Leu Val Thr Val Ser Ser
        115                 120

<210> SEQ ID NO 12
<211> LENGTH: 121
<212> TYPE: PRT
<213> ORGANISM: Homo sapiens

<400> SEQUENCE: 12

Glu Val Gln Leu Val Glu Ser Gly Ala Glu Val Lys Glu Pro Gly Ser
1               5                   10                  15

Ser Val Arg Val Ser Cys Lys Thr Ser Gly Gly Ser Phe Asn Arg His
            20                  25                  30

Val Ile Thr Trp Val Arg Gln Ala Pro Gly Gln Gly Leu Glu Trp Met
        35                  40                  45

Gly Glu Ile Ile Pro Phe Phe Gly Thr Pro Lys Tyr Ala Pro Lys Phe
50                  55                  60

Gln Gly Arg Val Thr Ile Ile Ala Asp Ala Ser Thr Ser Thr Phe Phe
65                  70                  75                  80

Leu Asp Val Lys Ser Leu Thr Ser Glu Asp Thr Ala Leu Tyr Phe Cys
                85                  90                  95

Trp Ile Val Val Val Ser Val Val Gln Arg Arg Glu Asp Phe Trp Gly
                100                 105                 110

Gln Gly Ile Leu Val Thr Val Ser Ser
        115                 120

<210> SEQ ID NO 13
```

```
<211> LENGTH: 321
<212> TYPE: DNA
<213> ORGANISM: Homo sapiens
<220> FEATURE:
<221> NAME/KEY: CDS
<222> LOCATION: (1)..(321)
<223> OTHER INFORMATION: NI-204.10A8-VL variable light chain (VL)
      sequence, wherein Glu at position 1 of the amino acid sequence can
      also be Asp and Val-Leu at positions 3 to 4 can also be  Gln-Met
<220> FEATURE:
<221> NAME/KEY: V_region
<222> LOCATION: (70)..(102)
<223> OTHER INFORMATION: complementarity determining region (CDR)
      VL-CDR1
<220> FEATURE:
<221> NAME/KEY: V_region
<222> LOCATION: (148)..(168)
<223> OTHER INFORMATION: complementarity determining region (CDR)
      VL-CDR2
<220> FEATURE:
<221> NAME/KEY: V_region
<222> LOCATION: (265)..(291)
<223> OTHER INFORMATION: complementarity determining region (CDR)
      VL-CDR3

<400> SEQUENCE: 13 gaa att gtg ttg acg cag tct cca tcg tcc ctg tct gca tct gtt gga      48
Glu Ile Val Leu Thr Gln Ser Pro Ser Ser Leu Ser Ala Ser Val Gly
1               5                   10                  15 gac aca gtc acc atc act tgc cgg tca agt cag aac atc agc aac tat      96
Asp Thr Val Thr Ile Thr Cys Arg Ser Ser Gln Asn Ile Ser Asn Tyr
            20                  25                  30 ctg agt tgg ttt cag cat aag cca ggc aag gcc cct aga atc ctg gtc     144
Leu Ser Trp Phe Gln His Lys Pro Gly Lys Ala Pro Arg Ile Leu Val
        35                  40                  45 tat gct gca tcc act ttg cag act ggg gtc ccg tca agg ttc agt ggc     192
Tyr Ala Ala Ser Thr Leu Gln Thr Gly Val Pro Ser Arg Phe Ser Gly
    50                  55                  60 aga gga tct ggg aca att ttc act ctt tcc atc acc agt cta caa tcc     240
Arg Gly Ser Gly Thr Ile Phe Thr Leu Ser Ile Thr Ser Leu Gln Ser
65                  70                  75                  80 gag gat tat gca act tac tac tgt caa cag aat gac aaa att ccc cga     288
Glu Asp Tyr Ala Thr Tyr Tyr Cys Gln Gln Asn Asp Lys Ile Pro Arg
                85                  90                  95 acg ttc ggc caa ggg acc aag gtg gaa atc aaa                         321
Thr Phe Gly Gln Gly Thr Lys Val Glu Ile Lys
            100                 105

<210> SEQ ID NO 14
<211> LENGTH: 107
<212> TYPE: PRT
<213> ORGANISM: Homo sapiens

<400> SEQUENCE: 14

Glu Ile Val Leu Thr Gln Ser Pro Ser Ser Leu Ser Ala Ser Val Gly
1               5                   10                  15

Asp Thr Val Thr Ile Thr Cys Arg Ser Ser Gln Asn Ile Ser Asn Tyr
            20                  25                  30

Leu Ser Trp Phe Gln His Lys Pro Gly Lys Ala Pro Arg Ile Leu Val
        35                  40                  45

Tyr Ala Ala Ser Thr Leu Gln Thr Gly Val Pro Ser Arg Phe Ser Gly
    50                  55                  60

Arg Gly Ser Gly Thr Ile Phe Thr Leu Ser Ile Thr Ser Leu Gln Ser
65                  70                  75                  80

Glu Asp Tyr Ala Thr Tyr Tyr Cys Gln Gln Asn Asp Lys Ile Pro Arg
```

```
                    85                  90                  95
Thr Phe Gly Gln Gly Thr Lys Val Glu Ile Lys
            100                 105

<210> SEQ ID NO 15
<211> LENGTH: 375
<212> TYPE: DNA
<213> ORGANISM: Homo sapiens
<220> FEATURE:
<221> NAME/KEY: CDS
<222> LOCATION: (1)..(375)
<223> OTHER INFORMATION: NI-204.9F6-VH variable heavy chain (VH)
      sequence, wherein Val at position 5 of the amino acid sequence can
      also be Leu
<220> FEATURE:
<221> NAME/KEY: V_region
<222> LOCATION: (91)..(105)
<223> OTHER INFORMATION: complementarity determining region (CDR)
      VH-CDR1
<220> FEATURE:
<221> NAME/KEY: V_region
<222> LOCATION: (148)..(198)
<223> OTHER INFORMATION: complementarity determining region (CDR)
      VH-CDR2
<220> FEATURE:
<221> NAME/KEY: V_region
<222> LOCATION: (295)..(342)
<223> OTHER INFORMATION: complementarity determining region (CDR)
      VH-CDR3

<400> SEQUENCE: 15 gag gtg cag ctg gtg gag tct ggg gga ggc ctg gtc cag ccg ggg ggg        48
Glu Val Gln Leu Val Glu Ser Gly Gly Gly Leu Val Gln Pro Gly Gly
1               5                   10                  15 tcc cta aga ctc tcc tgt gcg gtc tct gga ttc acc ttt gac acc ttt        96
Ser Leu Arg Leu Ser Cys Ala Val Ser Gly Phe Thr Phe Asp Thr Phe
                20                  25                  30 gcc atg agt tgg gtc cgc cag gct cca ggg aag ggt ctg gag tgg gtc       144
Ala Met Ser Trp Val Arg Gln Ala Pro Gly Lys Gly Leu Glu Trp Val
            35                  40                  45 tcg gca att act gcc agt tct tct aag acg tac tac gcc gac tcc gtg       192
Ser Ala Ile Thr Ala Ser Ser Ser Lys Thr Tyr Tyr Ala Asp Ser Val
        50                  55                  60 aag ggc cgc ttc acc atc tcc aga gac aat tcc agg aat acg gtg tat       240
Lys Gly Arg Phe Thr Ile Ser Arg Asp Asn Ser Arg Asn Thr Val Tyr
65                  70                  75                  80 ctg cgc ctg agc agt ctg aga gcc gac gac acg gcc gtt tat ttc tgt       288
Leu Arg Leu Ser Ser Leu Arg Ala Asp Asp Thr Ala Val Tyr Phe Cys
                85                  90                  95 gcg agg ccg aaa ggg gca cac agt ggc ctc tac ata gaa agc gct ttt       336
Ala Arg Pro Lys Gly Ala His Ser Gly Leu Tyr Ile Glu Ser Ala Phe
            100                 105                 110 gat ctg tgg ggc cca ggg aca atg gtc acc gtc tct tcg                   375
Asp Leu Trp Gly Pro Gly Thr Met Val Thr Val Ser Ser
        115                 120                 125

<210> SEQ ID NO 16
<211> LENGTH: 125
<212> TYPE: PRT
<213> ORGANISM: Homo sapiens

<400> SEQUENCE: 16

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Thr Phe Asp Thr Phe
                20                  25                  30
```

```
Ala Met Ser Trp Val Arg Gln Ala Pro Gly Lys Gly Leu Glu Trp Val
        35                  40                  45

Ser Ala Ile Thr Ala Ser Ser Lys Thr Tyr Tyr Ala Asp Ser Val
 50                  55                  60

Lys Gly Arg Phe Thr Ile Ser Arg Asp Asn Ser Arg Asn Thr Val Tyr
 65                  70                  75                  80

Leu Arg Leu Ser Ser Leu Arg Ala Asp Asp Thr Ala Val Tyr Phe Cys
                 85                  90                  95

Ala Arg Pro Lys Gly Ala His Ser Gly Leu Tyr Ile Glu Ser Ala Phe
                100                 105                 110

Asp Leu Trp Gly Pro Gly Thr Met Val Thr Val Ser Ser
            115                 120                 125

<210> SEQ ID NO 17
<211> LENGTH: 324
<212> TYPE: DNA
<213> ORGANISM: Homo sapiens
<220> FEATURE:
<221> NAME/KEY: CDS
<222> LOCATION: (1)..(324)
<223> OTHER INFORMATION: NI-204.9F6-VL variable light chain (VL)
      sequence, wherein Val at position 3 of the amino acid sequence can
      also be Glu
<220> FEATURE:
<221> NAME/KEY: V_region
<222> LOCATION: (67)..(99)
<223> OTHER INFORMATION: complementarity determining region (CDR)
      VL-CDR1
<220> FEATURE:
<221> NAME/KEY: V_region
<222> LOCATION: (145)..(165)
<223> OTHER INFORMATION: complementarity determining region (CDR)
      VL-CDR2
<220> FEATURE:
<221> NAME/KEY: V_region
<222> LOCATION: (262)..(294)
<223> OTHER INFORMATION: complementarity determining region (CDR)
      VL-CDR3

<400> SEQUENCE: 17 tcc tat gtg ctg act cag cca ccc tca gtg tcc gtg tcc gca gga cag     48
Ser Tyr Val Leu Thr Gln Pro Pro Ser Val Ser Val Ser Ala Gly Gln
 1               5                  10                  15 aca gcc tcc atc acc tgt tct gca gat atg ttg ggg gac aca tat gtt     96
Thr Ala Ser Ile Thr Cys Ser Ala Asp Met Leu Gly Asp Thr Tyr Val
             20                  25                  30 tcc tgg tat cag aag agg cca ggc cag tcc cct gtc ctg ctc atc tat    144
Ser Trp Tyr Gln Lys Arg Pro Gly Gln Ser Pro Val Leu Leu Ile Tyr
         35                  40                  45 cag gat tcc aag agg ccc tca gag atc cct gag cga ttc tct ggc tcc    192
Gln Asp Ser Lys Arg Pro Ser Glu Ile Pro Glu Arg Phe Ser Gly Ser
     50                  55                  60 agc tct gag gac aca gct act ctg acc att acc ggg acc cag gct ctc    240
Ser Ser Glu Asp Thr Ala Thr Leu Thr Ile Thr Gly Thr Gln Ala Leu
 65                  70                  75                  80 gat gag gct gcc tat tac tgt caa gtg tgg gac agg cgc act aca aca    288
Asp Glu Ala Ala Tyr Tyr Cys Gln Val Trp Asp Arg Arg Thr Thr Thr
                 85                  90                  95 tat gtc ttc gga cct ggg acc gag gtc acc gtc ctg                    324
Tyr Val Phe Gly Pro Gly Thr Glu Val Thr Val Leu
            100                 105

<210> SEQ ID NO 18
<211> LENGTH: 108
```

```
<212> TYPE: PRT
<213> ORGANISM: Homo sapiens

<400> SEQUENCE: 18

Ser Tyr Val Leu Thr Gln Pro Pro Ser Val Ser Val Ser Ala Gly Gln
1               5                   10                  15

Thr Ala Ser Ile Thr Cys Ser Ala Asp Met Leu Gly Asp Thr Tyr Val
            20                  25                  30

Ser Trp Tyr Gln Lys Arg Pro Gly Gln Ser Pro Val Leu Leu Ile Tyr
        35                  40                  45

Gln Asp Ser Lys Arg Pro Ser Glu Ile Pro Glu Arg Phe Ser Gly Ser
    50                  55                  60

Ser Ser Glu Asp Thr Ala Thr Leu Thr Ile Thr Gly Thr Gln Ala Leu
65                  70                  75                  80

Asp Glu Ala Ala Tyr Tyr Cys Gln Val Trp Asp Arg Arg Thr Thr Thr
                85                  90                  95

Tyr Val Phe Gly Pro Gly Thr Glu Val Thr Val Leu
            100                 105

<210> SEQ ID NO 19
<211> LENGTH: 381
<212> TYPE: DNA
<213> ORGANISM: Homo sapiens
<220> FEATURE:
<221> NAME/KEY: CDS
<222> LOCATION: (1)..(381)
<223> OTHER INFORMATION: NI-204.11F11-VH variable heavy chain (VH)
      sequence
<220> FEATURE:
<221> NAME/KEY: V_region
<222> LOCATION: (91)..(105)
<223> OTHER INFORMATION: complementarity determining region (CDR)
      VH-CDR1
<220> FEATURE:
<221> NAME/KEY: V_region
<222> LOCATION: (148)..(204)
<223> OTHER INFORMATION: complementarity determining region (CDR)
      VH-CDR2
<220> FEATURE:
<221> NAME/KEY: V_region
<222> LOCATION: (301)..(348)
<223> OTHER INFORMATION: complementarity determining region (CDR)
      VH-CDR3

<400> SEQUENCE: 19 gag gtg cag ctg gtg gag tct ggg gga ggc ttg gtt aag ccg ggg ggg     48
Glu Val Gln Leu Val Glu Ser Gly Gly Gly Leu Val Lys Pro Gly Gly
1               5                   10                  15 tcc ctt aga ctc tcc tgt gca gcc tct gga ttg cct ttc agc aag gcc     96
Ser Leu Arg Leu Ser Cys Ala Ala Ser Gly Leu Pro Phe Ser Lys Ala
            20                  25                  30 tgg atg agc tgg gtc cgc cag gct cca ggg aag ggg ctg gag tgg gtc    144
Trp Met Ser Trp Val Arg Gln Ala Pro Gly Lys Gly Leu Glu Trp Val
        35                  40                  45 ggc cgt atc aaa agt caa gct gat ggt ggg gca ata gac tac gct aca    192
Gly Arg Ile Lys Ser Gln Ala Asp Gly Gly Ala Ile Asp Tyr Ala Thr
    50                  55                  60 tcc gtg aat ggc aga ttc acc atc aca aga gat gat tca aaa aat acg    240
Ser Val Asn Gly Arg Phe Thr Ile Thr Arg Asp Asp Ser Lys Asn Thr
65                  70                  75                  80 ctg tat ctg caa atg acc agc ctg aaa acc gag gac aca gcc gtg tat    288
Leu Tyr Leu Gln Met Thr Ser Leu Lys Thr Glu Asp Thr Ala Val Tyr
                85                  90                  95 tac tgt acc ccg ggg ata ata tta cga ttt ttg gag ggc acc ctt cgg    336
```

```
Tyr Cys Thr Pro Gly Ile Ile Leu Arg Phe Leu Glu Gly Thr Leu Arg
            100                 105                 110 gga atg gac gtc tgg ggc caa ggg acc acg gtc acc gtc tcc tcg          381
Gly Met Asp Val Trp Gly Gln Gly Thr Thr Val Thr Val Ser Ser
        115                 120                 125
```

<210> SEQ ID NO 20
<211> LENGTH: 127
<212> TYPE: PRT
<213> ORGANISM: Homo sapiens

<400> SEQUENCE: 20

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Leu Pro Phe Ser Lys Ala
            20                  25                  30

Trp Met Ser Trp Val Arg Gln Ala Pro Gly Lys Gly Leu Glu Trp Val
        35                  40                  45

Gly Arg Ile Lys Ser Gln Ala Asp Gly Gly Ala Ile Asp Tyr Ala Thr
    50                  55                  60

Ser Val Asn Gly Arg Phe Thr Ile Thr Arg Asp Asp Ser Lys Asn Thr
65                  70                  75                  80

Leu Tyr Leu Gln Met Thr Ser Leu Lys Thr Glu Asp Thr Ala Val Tyr
                85                  90                  95

Tyr Cys Thr Pro Gly Ile Ile Leu Arg Phe Leu Glu Gly Thr Leu Arg
            100                 105                 110

Gly Met Asp Val Trp Gly Gln Gly Thr Thr Val Thr Val Ser Ser
        115                 120                 125
```

<210> SEQ ID NO 21
<211> LENGTH: 321
<212> TYPE: DNA
<213> ORGANISM: Homo sapiens
<220> FEATURE:
<221> NAME/KEY: CDS
<222> LOCATION: (1)..(321)
<223> OTHER INFORMATION: NI-204.11F11-VL variable light chain (VL)
      sequence
<220> FEATURE:
<221> NAME/KEY: V_region
<222> LOCATION: (70)..(102)
<223> OTHER INFORMATION: complementarity determining region (CDR)
      VL-CDR1
<220> FEATURE:
<221> NAME/KEY: V_region
<222> LOCATION: (148)..(168)
<223> OTHER INFORMATION: complementarity determining region (CDR)
      VL-CDR2
<220> FEATURE:
<221> NAME/KEY: V_region
<222> LOCATION: (265)..(291)
<223> OTHER INFORMATION: complementarity determining region (CDR)
      VL-CDR3

<400> SEQUENCE: 21

```
gaa att gtg ctg act cag tct cca ccc acc ctg tct ttg tct cca ggg       48
Glu Ile Val Leu Thr Gln Ser Pro Pro Thr Leu Ser Leu Ser Pro Gly
1               5                   10                  15 gaa aga gcc acc ctc tcc tgc agg gcc agt cag act gtt agt aag tac       96
Glu Arg Ala Thr Leu Ser Cys Arg Ala Ser Gln Thr Val Ser Lys Tyr
            20                  25                  30 tta gcc tgg tac caa cag aag cct ggc cag gct ccc agg ctc ctc gtc      144
Leu Ala Trp Tyr Gln Gln Lys Pro Gly Gln Ala Pro Arg Leu Leu Val
        35                  40                  45
```

```
tat gat aca tcc aac agg gcc att ggc atc cca ccc agg ttc agt ggc    192
Tyr Asp Thr Ser Asn Arg Ala Ile Gly Ile Pro Pro Arg Phe Ser Gly
 50                  55                  60 agt ggg tct ggg aca gac ttc act ctc acc atc agc acc cta gag cct    240
Ser Gly Ser Gly Thr Asp Phe Thr Leu Thr Ile Ser Thr Leu Glu Pro
 65                  70                  75                  80 gag gat ttc gca ctt tat tat tgt cag cag cgt agc aac tgg cct ccg    288
Glu Asp Phe Ala Leu Tyr Tyr Cys Gln Gln Arg Ser Asn Trp Pro Pro
                 85                  90                  95 acc ttc ggc caa ggg aca cga ctg gag att aaa                        321
Thr Phe Gly Gln Gly Thr Arg Leu Glu Ile Lys
                100                 105
```

```
<210> SEQ ID NO 22
<211> LENGTH: 107
<212> TYPE: PRT
<213> ORGANISM: Homo sapiens

<400> SEQUENCE: 22

Glu Ile Val Leu Thr Gln Ser Pro Pro Thr Leu Ser Leu Ser Pro Gly
 1               5                  10                  15

Glu Arg Ala Thr Leu Ser Cys Arg Ala Ser Gln Thr Val Ser Lys Tyr
                20                  25                  30

Leu Ala Trp Tyr Gln Gln Lys Pro Gly Gln Ala Pro Arg Leu Leu Val
            35                  40                  45

Tyr Asp Thr Ser Asn Arg Ala Ile Gly Ile Pro Pro Arg Phe Ser Gly
 50                 55                  60

Ser Gly Ser Gly Thr Asp Phe Thr Leu Thr Ile Ser Thr Leu Glu Pro
 65                 70                  75                  80

Glu Asp Phe Ala Leu Tyr Tyr Cys Gln Gln Arg Ser Asn Trp Pro Pro
                 85                  90                  95

Thr Phe Gly Gln Gly Thr Arg Leu Glu Ile Lys
                100                 105
```

```
<210> SEQ ID NO 23
<211> LENGTH: 372
<212> TYPE: DNA
<213> ORGANISM: Homo sapiens
<220> FEATURE:
<221> NAME/KEY: CDS
<222> LOCATION: (1)..(372)
<223> OTHER INFORMATION: NI-204.67E12-VH variable heavy chain (VH)
      sequence
<220> FEATURE:
<221> NAME/KEY: V_region
<222> LOCATION: (1)..(102)
<223> OTHER INFORMATION: complementarity determining region (CDR)
      VH-CDR1
<220> FEATURE:
<221> NAME/KEY: V_region
<222> LOCATION: (148)..(198)
<223> OTHER INFORMATION: complementarity determining region (CDR)
      VH-CDR2
<220> FEATURE:
<221> NAME/KEY: V_region
<222> LOCATION: (294)..(339)
<223> OTHER INFORMATION: complementarity determining region (CDR)
      VH-CDR3

<400> SEQUENCE: 23 gag gtg cag ctg ttg gag tct ggg gga ggc tta atc cgg cct ggg ggg    48
Glu Val Gln Leu Leu Glu Ser Gly Gly Gly Leu Ile Arg Pro Gly Gly
 1               5                  10                  15 tcc ctg aga ctc tcc tgt gca gcc tct gga ttc acc ttc agt aac tat    96
Ser Leu Arg Leu Ser Cys Ala Ala Ser Gly Phe Thr Phe Ser Asn Tyr
```

```
                20                  25                  30
gcc atg ggc tgg gtc cgc cag gct cca ggg aag ggg ctg gag tgg gtc      144
Ala Met Gly Trp Val Arg Gln Ala Pro Gly Lys Gly Leu Glu Trp Val
        35                  40                  45 tca gcc atc agt ggc aat ggt gga agc acc tat tat gga ggc tcc gtg      192
Ser Ala Ile Ser Gly Asn Gly Gly Ser Thr Tyr Tyr Gly Gly Ser Val
 50                  55                  60 aag ggc cgg ttc acc atc tcc aga gac aag tcc aag aat acc ctg tat      240
Lys Gly Arg Phe Thr Ile Ser Arg Asp Lys Ser Lys Asn Thr Leu Tyr
 65                  70                  75                  80 cta caa atg aac aac ttg aga gcc gac gac acg gcc gtt tac ttt tgt      288
Leu Gln Met Asn Asn Leu Arg Ala Asp Asp Thr Ala Val Tyr Phe Cys
                 85                  90                  95 gcg aaa tta gag gcc gta gcc ccc act ttg aca ttg cga tac ttc aag      336
Ala Lys Leu Glu Ala Val Ala Pro Thr Leu Thr Leu Arg Tyr Phe Lys
            100                 105                 110 cac tgg ggc aag ggc acc ctg gtc acc gtc tcc tcg                      372
His Trp Gly Lys Gly Thr Leu Val Thr Val Ser Ser
            115                 120
```

<210> SEQ ID NO 24
<211> LENGTH: 124
<212> TYPE: PRT
<213> ORGANISM: Homo sapiens

<400> SEQUENCE: 24

```
Glu Val Gln Leu Leu Glu Ser Gly Gly Gly Leu Ile Arg Pro Gly Gly
 1               5                  10                  15

Ser Leu Arg Leu Ser Cys Ala Ala Ser Gly Phe Thr Phe Ser Asn Tyr
            20                  25                  30

Ala Met Gly Trp Val Arg Gln Ala Pro Gly Lys Gly Leu Glu Trp Val
        35                  40                  45

Ser Ala Ile Ser Gly Asn Gly Gly Ser Thr Tyr Tyr Gly Gly Ser Val
 50                  55                  60

Lys Gly Arg Phe Thr Ile Ser Arg Asp Lys Ser Lys Asn Thr Leu Tyr
 65                  70                  75                  80

Leu Gln Met Asn Asn Leu Arg Ala Asp Asp Thr Ala Val Tyr Phe Cys
                 85                  90                  95

Ala Lys Leu Glu Ala Val Ala Pro Thr Leu Thr Leu Arg Tyr Phe Lys
            100                 105                 110

His Trp Gly Lys Gly Thr Leu Val Thr Val Ser Ser
            115                 120
```

<210> SEQ ID NO 25
<211> LENGTH: 321
<212> TYPE: DNA
<213> ORGANISM: Homo sapiens
<220> FEATURE:
<221> NAME/KEY: CDS
<222> LOCATION: (1)..(321)
<223> OTHER INFORMATION: NI-204.67E12-VL variable light chain (VL)
      sequence
<220> FEATURE:
<221> NAME/KEY: V_region
<222> LOCATION: (70)..(102)
<223> OTHER INFORMATION: complementarity determining region (CDR)
      VL-CDR1
<220> FEATURE:
<221> NAME/KEY: V_region
<222> LOCATION: (148)..(168)
<223> OTHER INFORMATION: complementarity determining region (CDR)
      VL-CDR2
<220> FEATURE:

```
<221> NAME/KEY: V_region
<222> LOCATION: (265)..(291)
<223> OTHER INFORMATION: complementarity determining region (CDR)
      VL-CDR3

<400> SEQUENCE: 25 gac atc cag atg acc cag tct cca tcc acc ctg tct gca tct gta gga      48
Asp Ile Gln Met Thr Gln Ser Pro Ser Thr Leu Ser Ala Ser Val Gly
1               5                   10                  15 gac aga gtc acc atc act tgt cgg gcc agt cag agt att agc agg tgg      96
Asp Arg Val Thr Ile Thr Cys Arg Ala Ser Gln Ser Ile Ser Arg Trp
            20                  25                  30 ttg gcc tgg tat caa cag aga cca ggt aga gcc cct gac ctc ctg atc     144
Leu Ala Trp Tyr Gln Gln Arg Pro Gly Arg Ala Pro Asp Leu Leu Ile
        35                  40                  45 tat gat gcc tcc aac ttg gaa agt ggg gtc cca tca agg ttc agc ggc     192
Tyr Asp Ala Ser Asn Leu Glu Ser Gly Val Pro Ser Arg Phe Ser Gly
    50                  55                  60 agt gga tct ggg aca gag ttc act ctc acc atc agt agc ctg cag cct     240
Ser Gly Ser Gly Thr Glu Phe Thr Leu Thr Ile Ser Ser Leu Gln Pro
65                  70                  75                  80 ggt gat ttc gca act tat tac tgt caa caa tat tat agt tat gtt tac     288
Gly Asp Phe Ala Thr Tyr Tyr Cys Gln Gln Tyr Tyr Ser Tyr Val Tyr
                85                  90                  95 act ttt ggc cag ggg acc aag ctg gag atc aaa                         321
Thr Phe Gly Gln Gly Thr Lys Leu Glu Ile Lys
            100                 105

<210> SEQ ID NO 26
<211> LENGTH: 107
<212> TYPE: PRT
<213> ORGANISM: Homo sapiens

<400> SEQUENCE: 26

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Arg Trp
            20                  25                  30

Leu Ala Trp Tyr Gln Gln Arg Pro Gly Arg Ala Pro Asp Leu Leu Ile
        35                  40                  45

Tyr Asp Ala Ser Asn Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Gly Asp Phe Ala Thr Tyr Tyr Cys Gln Gln Tyr Tyr Ser Tyr Val Tyr
                85                  90                  95

Thr Phe Gly Gln Gly Thr Lys Leu Glu Ile Lys
            100                 105

<210> SEQ ID NO 27
<211> LENGTH: 366
<212> TYPE: DNA
<213> ORGANISM: Homo sapiens
<220> FEATURE:
<221> NAME/KEY: CDS
<222> LOCATION: (1)..(366)
<223> OTHER INFORMATION: NI-204.6H1-VH variable heavy chain (VH)
      sequence
<220> FEATURE:
<221> NAME/KEY: V_region
<222> LOCATION: (91)..(105)
<223> OTHER INFORMATION: complementarity determining region (CDR)
      VH-CDR1
```

```
<220> FEATURE:
<221> NAME/KEY: V_region
<222> LOCATION: (148)..(195)
<223> OTHER INFORMATION: complementarity determining region (CDR)
       VH-CDR2
<220> FEATURE:
<221> NAME/KEY: V_region
<222> LOCATION: (292)..(333)
<223> OTHER INFORMATION: complementarity determining region (CDR)
       VH-CDR3

<400> SEQUENCE: 27 cag gtg cag cta cag cag tgg ggc gca gga cgg ctg agg cct tcg gag     48
Gln Val Gln Leu Gln Gln Trp Gly Ala Gly Arg Leu Arg Pro Ser Glu
1               5                   10                  15 acc ctg tcc ctc acc tgc gct gtc tat ggt ggg tcc ttc aat ggt tac     96
Thr Leu Ser Leu Thr Cys Ala Val Tyr Gly Gly Ser Phe Asn Gly Tyr
            20                  25                  30 gcc agg acc tgg atc cgc cag ccc ccg ggg aag ggg ctg gag tgg att    144
Ala Arg Thr Trp Ile Arg Gln Pro Pro Gly Lys Gly Leu Glu Trp Ile
        35                  40                  45 ggg gaa atc gat cat agg gaa aac acc aac tac aac ccg tcc ctc aag    192
Gly Glu Ile Asp His Arg Glu Asn Thr Asn Tyr Asn Pro Ser Leu Lys
    50                  55                  60 agt cga gtc acc atg tca gta gac acg tcc aag aat cag ttc tcc ctg    240
Ser Arg Val Thr Met Ser Val Asp Thr Ser Lys Asn Gln Phe Ser Leu
65                  70                  75                  80 agg ctg aac tct gtg acc gcc gcg gac acg gct gtt tat ttc tgt gcg    288
Arg Leu Asn Ser Val Thr Ala Ala Asp Thr Ala Val Tyr Phe Cys Ala
                85                  90                  95 aga ggc caa aag aac gcg aag gat caa cac gag ggt ttt cgc tac tgg    336
Arg Gly Gln Lys Asn Ala Lys Asp Gln His Glu Gly Phe Arg Tyr Trp
            100                 105                 110 ggc cgg gga acc ctg gtc acc gtc tcc tcg                            366
Gly Arg Gly Thr Leu Val Thr Val Ser Ser
        115                 120

<210> SEQ ID NO 28
<211> LENGTH: 122
<212> TYPE: PRT
<213> ORGANISM: Homo sapiens

<400> SEQUENCE: 28

Gln Val Gln Leu Gln Gln Trp Gly Ala Gly Arg Leu Arg Pro Ser Glu
1               5                   10                  15

Thr Leu Ser Leu Thr Cys Ala Val Tyr Gly Gly Ser Phe Asn Gly Tyr
            20                  25                  30

Ala Arg Thr Trp Ile Arg Gln Pro Pro Gly Lys Gly Leu Glu Trp Ile
        35                  40                  45

Gly Glu Ile Asp His Arg Glu Asn Thr Asn Tyr Asn Pro Ser Leu Lys
    50                  55                  60

Ser Arg Val Thr Met Ser Val Asp Thr Ser Lys Asn Gln Phe Ser Leu
65                  70                  75                  80

Arg Leu Asn Ser Val Thr Ala Ala Asp Thr Ala Val Tyr Phe Cys Ala
                85                  90                  95

Arg Gly Gln Lys Asn Ala Lys Asp Gln His Glu Gly Phe Arg Tyr Trp
            100                 105                 110

Gly Arg Gly Thr Leu Val Thr Val Ser Ser
        115                 120

<210> SEQ ID NO 29
```

-continued

```
<211> LENGTH: 324
<212> TYPE: DNA
<213> ORGANISM: Homo sapiens
<220> FEATURE:
<221> NAME/KEY: CDS
<222> LOCATION: (1)..(324)
<223> OTHER INFORMATION: NI-204.6H1-VL variable light chain (VL)
      sequence
<220> FEATURE:
<221> NAME/KEY: V_region
<222> LOCATION: (67)..(99)
<223> OTHER INFORMATION: complementarity determining region (CDR)
      VL-CDR1
<220> FEATURE:
<221> NAME/KEY: V_region
<222> LOCATION: (145)..(165)
<223> OTHER INFORMATION: complementarity determining region (CDR)
      VL-CDR2
<220> FEATURE:
<221> NAME/KEY: V_region
<222> LOCATION: (262)..(294)
<223> OTHER INFORMATION: complementarity determining region (CDR)
      VL-CDR3

<400> SEQUENCE: 29 tcc tat gag ctg act cag cca ccc tcg gtg tca gtg tcc cca gga cag    48
Ser Tyr Glu Leu Thr Gln Pro Pro Ser Val Ser Val Ser Pro Gly Gln
1               5                   10                  15 acg gcc agg atc acc tgt tct gga gat gca ttg cca aag caa ttt gct    96
Thr Ala Arg Ile Thr Cys Ser Gly Asp Ala Leu Pro Lys Gln Phe Ala
                20                  25                  30 tat tgg tac cag cag aag tca ggc cag gcc cct aaa ttg gtg atc ttt   144
Tyr Trp Tyr Gln Gln Lys Ser Gly Gln Ala Pro Lys Leu Val Ile Phe
            35                  40                  45 aaa gac act gag agg ccc tca ggg atc cct gag cga ttc tct gcc tcc   192
Lys Asp Thr Glu Arg Pro Ser Gly Ile Pro Glu Arg Phe Ser Ala Ser
        50                  55                  60 agc tca ggt aca aaa gcc acg ttg acc atc agt gga gtc cag gca gag   240
Ser Ser Gly Thr Lys Ala Thr Leu Thr Ile Ser Gly Val Gln Ala Glu
65                  70                  75                  80 gat gag gct gac tat tac tgt caa tca gcg gac aga act gct act tct   288
Asp Glu Ala Asp Tyr Tyr Cys Gln Ser Ala Asp Arg Thr Ala Thr Ser
                85                  90                  95 tgg gtg ttc ggc gga ggg acc aag ctg acc gtc cta                   324
Trp Val Phe Gly Gly Gly Thr Lys Leu Thr Val Leu
                100                 105

<210> SEQ ID NO 30
<211> LENGTH: 108
<212> TYPE: PRT
<213> ORGANISM: Homo sapiens

<400> SEQUENCE: 30

Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Pro Lys Gln Phe Ala
                20                  25                  30

Tyr Trp Tyr Gln Gln Lys Ser Gly Gln Ala Pro Lys Leu Val Ile Phe
            35                  40                  45

Lys Asp Thr Glu Arg Pro Ser Gly Ile Pro Glu Arg Phe Ser Ala Ser
        50                  55                  60

Ser Ser Gly Thr Lys Ala Thr Leu Thr Ile Ser Gly Val Gln Ala Glu
65                  70                  75                  80

Asp Glu Ala Asp Tyr Tyr Cys Gln Ser Ala Asp Arg Thr Ala Thr Ser
                85                  90                  95
```

```
<210> SEQ ID NO 31
<211> LENGTH: 363
<212> TYPE: DNA
<213> ORGANISM: Homo sapiens
<220> FEATURE:
<221> NAME/KEY: CDS
<222> LOCATION: (1)..(363)
<223> OTHER INFORMATION: NI-204.12G3-VH variable heavy chain (VH)
      sequence
<220> FEATURE:
<221> NAME/KEY: V_region
<222> LOCATION: (91)..(105)
<223> OTHER INFORMATION: complementarity determining region (CDR)
      VH-CDR1
<220> FEATURE:
<221> NAME/KEY: V_region
<222> LOCATION: (148)..(198)
<223> OTHER INFORMATION: complementarity determining region (CDR)
      VH-CDR2
<220> FEATURE:
<221> NAME/KEY: V_region
<222> LOCATION: (295)..(330)
<223> OTHER INFORMATION: complementarity determining region (CDR)
      VH-CDR3

<400> SEQUENCE: 31
```

```
cag gtg cag ctg gtg gag tct ggg gga ggc gtg gtc cag cct ggg agg      48
Gln Val Gln Leu Val Glu Ser Gly Gly Gly Val Val Gln Pro Gly Arg
1               5                   10                  15 tcc ctc aga ctc tcc tgt gca gcc tct gga tac atc ttc agt agc ttt      96
Ser Leu Arg Leu Ser Cys Ala Ala Ser Gly Tyr Ile Phe Ser Ser Phe
            20                  25                  30 ggc atg cac tgg gtc cgc cag act cca ggc aag ggg ctg gag tgg gtg     144
Gly Met His Trp Val Arg Gln Thr Pro Gly Lys Gly Leu Glu Trp Val
        35                  40                  45 gca ctc att tgg tat gat gga agt cgt cag tcc tat gcg gac tct gtg     192
Ala Leu Ile Trp Tyr Asp Gly Ser Arg Gln Ser Tyr Ala Asp Ser Val
    50                  55                  60 agg ggc cgg ttc acc atc tcc aga gac aat tct aag aac acg gtg ttt     240
Arg Gly Arg Phe Thr Ile Ser Arg Asp Asn Ser Lys Asn Thr Val Phe
65                  70                  75                  80 ttg caa atg aac agc ctg aga ggc gag gac acg gct gta tat cac tgt     288
Leu Gln Met Asn Ser Leu Arg Gly Glu Asp Thr Ala Val Tyr His Cys
                85                  90                  95 gcg aga acg ggc tac gat gac aaa cgc ggt ggt ttt gat act tgg ggc     336
Ala Arg Thr Gly Tyr Asp Asp Lys Arg Gly Gly Phe Asp Thr Trp Gly
            100                 105                 110 caa ggg aca atg gtc acc gtc tct tcg                                  363
Gln Gly Thr Met Val Thr Val Ser Ser
        115                 120
```

```
<210> SEQ ID NO 32
<211> LENGTH: 121
<212> TYPE: PRT
<213> ORGANISM: Homo sapiens

<400> SEQUENCE: 32
```

Gln Val Gln Leu Val Glu Ser Gly Gly Gly Val Val Gln Pro Gly Arg
1               5                   10                  15

Ser Leu Arg Leu Ser Cys Ala Ala Ser Gly Tyr Ile Phe Ser Ser Phe
            20                  25                  30

Gly Met His Trp Val Arg Gln Thr Pro Gly Lys Gly Leu Glu Trp Val

```
                    35                  40                  45
Ala Leu Ile Trp Tyr Asp Gly Ser Arg Gln Ser Tyr Ala Asp Ser Val
         50                  55                  60

Arg Gly Arg Phe Thr Ile Ser Arg Asp Asn Ser Lys Asn Thr Val Phe
 65                  70                  75                  80

Leu Gln Met Asn Ser Leu Arg Gly Glu Asp Thr Ala Val Tyr His Cys
                 85                  90                  95

Ala Arg Thr Gly Tyr Asp Asp Lys Arg Gly Gly Phe Asp Thr Trp Gly
            100                 105                 110

Gln Gly Thr Met Val Thr Val Ser Ser
            115                 120

<210> SEQ ID NO 33
<211> LENGTH: 321
<212> TYPE: DNA
<213> ORGANISM: Homo sapiens
<220> FEATURE:
<221> NAME/KEY: CDS
<222> LOCATION: (1)..(321)
<223> OTHER INFORMATION: NI-204.12G3-VL variable light chain (VL)
      sequence
<220> FEATURE:
<221> NAME/KEY: V_region
<222> LOCATION: (67)..(99)
<223> OTHER INFORMATION: complementarity determining region (CDR)
      VL-CDR1
<220> FEATURE:
<221> NAME/KEY: V_region
<222> LOCATION: (145)..(165)
<223> OTHER INFORMATION: complementarity determining region (CDR)
      VL-CDR2
<220> FEATURE:
<221> NAME/KEY: V_region
<222> LOCATION: (262)..(291)
<223> OTHER INFORMATION: complementarity determining region (CDR)
      VL-CDR3

<400> SEQUENCE: 33 tcc tat gag ctg act cag cca ccc tcg gtg tca gtg tcc cca gga cag      48
Ser Tyr Glu Leu Thr Gln Pro Pro Ser Val Ser Val Ser Pro Gly Gln
 1               5                  10                  15 acg gct agg atc acc tgc tct gga gat gca ttg gca aag caa tat tct      96
Thr Ala Arg Ile Thr Cys Ser Gly Asp Ala Leu Ala Lys Gln Tyr Ser
             20                  25                  30 tat tgg tac cag cat aag cca ggc cag gcc cct gtg atg gtg atg tat     144
Tyr Trp Tyr Gln His Lys Pro Gly Gln Ala Pro Val Met Val Met Tyr
         35                  40                  45 aaa gac aga gag agg ccc tca ggg atc cct gag cga ttc tct ggc tcc     192
Lys Asp Arg Glu Arg Pro Ser Gly Ile Pro Glu Arg Phe Ser Gly Ser
     50                  55                  60 agt tca ggg aca aca gtc acg ttg acc atc agt gca gtc cag gcc gaa     240
Ser Ser Gly Thr Thr Val Thr Leu Thr Ile Ser Ala Val Gln Ala Glu
 65                  70                  75                  80 gac gag gct gac tat tac tgt caa tca aca ggc acc gat agt cct tat     288
Asp Glu Ala Asp Tyr Tyr Cys Gln Ser Thr Gly Thr Asp Ser Pro Tyr
                 85                  90                  95 atc ttc gga act ggg acc aag gtc acc gtc tta                         321
Ile Phe Gly Thr Gly Thr Lys Val Thr Val Leu
            100                 105

<210> SEQ ID NO 34
<211> LENGTH: 107
<212> TYPE: PRT
<213> ORGANISM: Homo sapiens
```

-continued

<400> SEQUENCE: 34

Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Ala Lys Gln Tyr Ser
            20                  25                  30

Tyr Trp Tyr Gln His Lys Pro Gly Gln Ala Pro Val Met Val Met Tyr
        35                  40                  45

Lys Asp Arg Glu Arg Pro Ser Gly Ile Pro Glu Arg Phe Ser Gly Ser
    50                  55                  60

Ser Ser Gly Thr Thr Val Thr Leu Thr Ile Ser Ala Val Gln Ala Glu
65                  70                  75                  80

Asp Glu Ala Asp Tyr Tyr Cys Gln Ser Thr Gly Thr Asp Ser Pro Tyr
                85                  90                  95

Ile Phe Gly Thr Gly Thr Lys Val Thr Val Leu
            100                 105

<210> SEQ ID NO 35
<211> LENGTH: 390
<212> TYPE: DNA
<213> ORGANISM: Homo sapiens
<220> FEATURE:
<221> NAME/KEY: CDS
<222> LOCATION: (1)..(390)
<223> OTHER INFORMATION: NI-204.7G5-VH variable heavy chain (VH)
      sequence, wherein Glu in position 1 of the amino acid sequence can
      also be Gln
<220> FEATURE:
<221> NAME/KEY: V_region
<222> LOCATION: (91)..(105)
<223> OTHER INFORMATION: complementarity determining region (CDR)
      VH-CDR1
<220> FEATURE:
<221> NAME/KEY: V_region
<222> LOCATION: (148)..(198)
<223> OTHER INFORMATION: complementarity determining region (CDR)
      VH-CDR2
<220> FEATURE:
<221> NAME/KEY: V_region
<222> LOCATION: (295)..(357)
<223> OTHER INFORMATION: complementarity determining region (CDR)
      VH-CDR3

<400> SEQUENCE: 35 gag gtg cag ctg gtg gag tct ggg gga ggc gtg gtc cag gct ggg ggg      48
Glu Val Gln Leu Val Glu Ser Gly Gly Gly Val Val Gln Ala Gly Gly
1               5                   10                  15 tcc ctg aga ctc tcc tgt gta gcc tct gga ctc acc ttc agt tcc tat      96
Ser Leu Arg Leu Ser Cys Val Ala Ser Gly Leu Thr Phe Ser Ser Tyr
            20                  25                  30 ggc atg cac tgg gtc cgc cag gct cca ggc aag ggg ctg gag tgg gtg     144
Gly Met His Trp Val Arg Gln Ala Pro Gly Lys Gly Leu Glu Trp Val
        35                  40                  45 gca gtc att tca tat gat gga aga agt aaa ttc tat gca gac tcc gtg     192
Ala Val Ile Ser Tyr Asp Gly Arg Ser Lys Phe Tyr Ala Asp Ser Val
    50                  55                  60 aag ggc cga ttc acc atc tcc aga gac aat tcc aag aac acg ttg tat     240
Lys Gly Arg Phe Thr Ile Ser Arg Asp Asn Ser Lys Asn Thr Leu Tyr
65                  70                  75                  80 ctc caa atg aac agc ctg aga gct gag gac gcg gct gtg tat tac tgt     288
Leu Gln Met Asn Ser Leu Arg Ala Glu Asp Ala Ala Val Tyr Tyr Cys
                85                  90                  95 gcg aac gca cgc gtc cgt gac gct tgt tct ggt acc aga tgc gat aaa     336
Ala Asn Ala Arg Val Arg Asp Ala Cys Ser Gly Thr Arg Cys Asp Lys
            100                 105                 110

```
ttt ggc ttc tac atg gac gtc tgg ggc aaa ggg acc acg gtc acc gtc      384
Phe Gly Phe Tyr Met Asp Val Trp Gly Lys Gly Thr Thr Val Thr Val
        115                 120                 125 tcc tcg                                                              390
Ser Ser
    130

<210> SEQ ID NO 36
<211> LENGTH: 130
<212> TYPE: PRT
<213> ORGANISM: Homo sapiens

<400> SEQUENCE: 36

Glu Val Gln Leu Val Glu Ser Gly Gly Gly Val Val Gln Ala Gly
1               5                   10                  15

Ser Leu Arg Leu Ser Cys Val Ala Ser Gly Leu Thr Phe Ser Ser Tyr
                20                  25                  30

Gly Met His Trp Val Arg Gln Ala Pro Gly Lys Gly Leu Glu Trp Val
            35                  40                  45

Ala Val Ile Ser Tyr Asp Gly Arg Ser Lys Phe Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Ala Ala Val Tyr Tyr Cys
                85                  90                  95

Ala Asn Ala Arg Val Arg Asp Ala Cys Ser Gly Thr Arg Cys Asp Lys
            100                 105                 110

Phe Gly Phe Tyr Met Asp Val Trp Gly Lys Gly Thr Thr Val Thr Val
        115                 120                 125

Ser Ser
    130

<210> SEQ ID NO 37
<211> LENGTH: 324
<212> TYPE: DNA
<213> ORGANISM: Homo sapiens
<220> FEATURE:
<221> NAME/KEY: CDS
<222> LOCATION: (1)..(324)
<223> OTHER INFORMATION: NI-204.7G5-VL variable light chain (VL)
      sequence, wherein Val in position 3 of the amino acid sequence can
      also be Glu
<220> FEATURE:
<221> NAME/KEY: V_region
<222> LOCATION: (67)..(99)
<223> OTHER INFORMATION: complementarity determining region (CDR)
      VL-CDR1
<220> FEATURE:
<221> NAME/KEY: V_region
<222> LOCATION: (145)..(165)
<223> OTHER INFORMATION: complementarity determining region (CDR)
      VL-CDR2
<220> FEATURE:
<221> NAME/KEY: V_region
<222> LOCATION: (262)..(294)
<223> OTHER INFORMATION: complementarity determining region (CDR)
      VL-CDR3

<400> SEQUENCE: 37 tcc tat gtg ctg act cag cca ccc tcg gtg tca gtg tcc cca gga caa      48
Ser Tyr Val Leu Thr Gln Pro Pro Ser Val Ser Val Ser Pro Gly Gln
1               5                   10                  15 acg gcc agg atc acc tgc tct gga gat gca ttg cca aag aaa tat gct      96
Thr Ala Arg Ile Thr Cys Ser Gly Asp Ala Leu Pro Lys Lys Tyr Ala
```

```
                20                  25                  30
tat tgg tac cag cag aag tca ggc cag gcc cct gtg ctg gtc atc tat    144
Tyr Trp Tyr Gln Gln Lys Ser Gly Gln Ala Pro Val Leu Val Ile Tyr
         35                  40                  45 gag gac atc aag cga ccc tcc ggg atc cct gag aga ttc tct ggc tcc    192
Glu Asp Ile Lys Arg Pro Ser Gly Ile Pro Glu Arg Phe Ser Gly Ser
 50                  55                  60 agc tca ggg aca atg gcc acc ttg act atc agt ggg gcc cag gtg gag    240
Ser Ser Gly Thr Met Ala Thr Leu Thr Ile Ser Gly Ala Gln Val Glu
 65                  70                  75                  80 gat gaa ggt gac tat tat tgt tac tca gca gac aga agt gga aat cgc    288
Asp Glu Gly Asp Tyr Tyr Cys Tyr Ser Ala Asp Arg Ser Gly Asn Arg
                 85                  90                  95 tgg gcg ttc ggc gga ggg acc aag ctg acc gtc cta                    324
Trp Ala Phe Gly Gly Gly Thr Lys Leu Thr Val Leu
            100                 105
```

<210> SEQ ID NO 38
<211> LENGTH: 108
<212> TYPE: PRT
<213> ORGANISM: Homo sapiens

<400> SEQUENCE: 38

```
Ser Tyr Val Leu Thr Gln Pro Pro Ser Val Ser Val Ser Pro Gly Gln
 1               5                  10                  15

Thr Ala Arg Ile Thr Cys Ser Gly Asp Ala Leu Pro Lys Lys Tyr Ala
             20                  25                  30

Tyr Trp Tyr Gln Gln Lys Ser Gly Gln Ala Pro Val Leu Val Ile Tyr
         35                  40                  45

Glu Asp Ile Lys Arg Pro Ser Gly Ile Pro Glu Arg Phe Ser Gly Ser
 50                  55                  60

Ser Ser Gly Thr Met Ala Thr Leu Thr Ile Ser Gly Ala Gln Val Glu
 65                  70                  75                  80

Asp Glu Gly Asp Tyr Tyr Cys Tyr Ser Ala Asp Arg Ser Gly Asn Arg
                 85                  90                  95

Trp Ala Phe Gly Gly Gly Thr Lys Leu Thr Val Leu
            100                 105
```

<210> SEQ ID NO 39
<211> LENGTH: 342
<212> TYPE: DNA
<213> ORGANISM: Homo sapiens
<220> FEATURE:
<221> NAME/KEY: CDS
<222> LOCATION: (1)..(342)
<223> OTHER INFORMATION: NI-204.7B3-VH variable heavy chain (VH)
      sequence, wherein Gln at position 6 of the amino acid sequence can
      also be Glu
<220> FEATURE:
<221> NAME/KEY: V_region
<222> LOCATION: (91)..(105)
<223> OTHER INFORMATION: complementarity determining region (CDR)
      VH-CDR1
<220> FEATURE:
<221> NAME/KEY: V_region
<222> LOCATION: (148)..(198)
<223> OTHER INFORMATION: complementarity determining region (CDR)
      VH-CDR2
<220> FEATURE:
<221> NAME/KEY: V_region
<222> LOCATION: (295)..(309)
<223> OTHER INFORMATION: complementarity determining region (CDR)
      VH-CDR3

<400> SEQUENCE: 39

```
gag gtg cag ctg gtg cag tct ggg gga gac atc gtt cag tcg gga ggg         48
Glu Val Gln Leu Val Gln Ser Gly Gly Asp Ile Val Gln Ser Gly Gly
1               5                   10                  15 tcc ctg aga ctc tcc tgt gca gcc tct gga ttc gtc ttc agt agc aac         96
Ser Leu Arg Leu Ser Cys Ala Ala Ser Gly Phe Val Phe Ser Ser Asn
                20                  25                  30 tgg atg cac tgg gtc cgc caa cgt cca ggg aag gga ctg gag tgg atc        144
Trp Met His Trp Val Arg Gln Arg Pro Gly Lys Gly Leu Glu Trp Ile
            35                  40                  45 tca ctt att aat gtc gat ggg cga acc aca aag tat gcg gac tcc gtg        192
Ser Leu Ile Asn Val Asp Gly Arg Thr Thr Lys Tyr Ala Asp Ser Val
        50                  55                  60 aag ggc cga ttc acc att tcc aga gac aac gcc aag aaa aca gtg tat        240
Lys Gly Arg Phe Thr Ile Ser Arg Asp Asn Ala Lys Lys Thr Val Tyr
65                  70                  75                  80 ctg cag atg gac agt ctg aga gcc gaa gac acg gcc gtg tat tac tgt        288
Leu Gln Met Asp Ser Leu Arg Ala Glu Asp Thr Ala Val Tyr Tyr Cys
                85                  90                  95 gtg aaa gtg gag gga ttg aac tgg ggc ccg gga acc ctg gtc acc gtc        336
Val Lys Val Glu Gly Leu Asn Trp Gly Pro Gly Thr Leu Val Thr Val
            100                 105                 110 tcc tcg                                                                 342
Ser Ser <210> SEQ ID NO 40
<211> LENGTH: 114
<212> TYPE: PRT
<213> ORGANISM: Homo sapiens

<400> SEQUENCE: 40

Glu Val Gln Leu Val Gln Ser Gly Gly Asp Ile Val Gln Ser Gly Gly
1               5                   10                  15

Ser Leu Arg Leu Ser Cys Ala Ala Ser Gly Phe Val Phe Ser Ser Asn
                20                  25                  30

Trp Met His Trp Val Arg Gln Arg Pro Gly Lys Gly Leu Glu Trp Ile
            35                  40                  45

Ser Leu Ile Asn Val Asp Gly Arg Thr Thr Lys Tyr Ala Asp Ser Val
        50                  55                  60

Lys Gly Arg Phe Thr Ile Ser Arg Asp Asn Ala Lys Lys Thr Val Tyr
65                  70                  75                  80

Leu Gln Met Asp Ser Leu Arg Ala Glu Asp Thr Ala Val Tyr Tyr Cys
                85                  90                  95

Val Lys Val Glu Gly Leu Asn Trp Gly Pro Gly Thr Leu Val Thr Val
            100                 105                 110

Ser Ser

<210> SEQ ID NO 41
<211> LENGTH: 321
<212> TYPE: DNA
<213> ORGANISM: Homo sapiens
<220> FEATURE:
<221> NAME/KEY: CDS
<222> LOCATION: (1)..(321)
<223> OTHER INFORMATION: NI-204.7B3-VL variable light chain (VL)
      sequence, wherein Leu-Pro-Val at positions 1-3 of the of the amino
      acid sequence can also be Ser-Glu-Tyr
<220> FEATURE:
<221> NAME/KEY: V_region
<222> LOCATION: (67)..(99)
<223> OTHER INFORMATION: complementarity determining region (CDR)
      VL-CDR1
```

<220> FEATURE:
<221> NAME/KEY: V_region
<222> LOCATION: (145)..(165)
<223> OTHER INFORMATION: complementarity determining region (CDR) VL-CDR2
<220> FEATURE:
<221> NAME/KEY: V_region
<222> LOCATION: (262)..(291)
<223> OTHER INFORMATION: complementarity determining region (CDR) VL-CDR3

<400> SEQUENCE: 41

```
ctg cct gtg ctg act cag cca ccc tcg gtg tca gtg tcc cca gga cag      48
Leu Pro Val Leu Thr Gln Pro Pro Ser Val Ser Val Ser Pro Gly Gln
1               5                   10                  15 acg gcc agg atc acc tgc tct gga gac gag ttg tca aaa caa tat gct      96
Thr Ala Arg Ile Thr Cys Ser Gly Asp Glu Leu Ser Lys Gln Tyr Ala
            20                  25                  30 tat tgg tac cag aag aag tca ggc cag gcc cct gtg atg gtg gtg aat     144
Tyr Trp Tyr Gln Lys Lys Ser Gly Gln Ala Pro Val Met Val Val Asn
        35                  40                  45 gaa gac act aag agg ccc ccg ggg att cct gaa cgg ttt tct ggt tcc     192
Glu Asp Thr Lys Arg Pro Pro Gly Ile Pro Glu Arg Phe Ser Gly Ser
    50                  55                  60 agt tca ggg aca aca agc aca ttg acc atc agt gga gtc cag gcg gaa     240
Ser Ser Gly Thr Thr Ser Thr Leu Thr Ile Ser Gly Val Gln Ala Glu
65                  70                  75                  80 gat gag gct gac tat tat tgt caa tca gca gac ata acc ggt tct tgg     288
Asp Glu Ala Asp Tyr Tyr Cys Gln Ser Ala Asp Ile Thr Gly Ser Trp
                85                  90                  95 gtg ttt ggc gga ggg acc aaa ttg acc gtc cta                         321
Val Phe Gly Gly Gly Thr Lys Leu Thr Val Leu
                100                 105
```

<210> SEQ ID NO 42
<211> LENGTH: 107
<212> TYPE: PRT
<213> ORGANISM: Homo sapiens

<400> SEQUENCE: 42

```
Leu Pro Val Leu Thr Gln Pro Pro Ser Val Ser Val Ser Pro Gly Gln
1               5                   10                  15

Thr Ala Arg Ile Thr Cys Ser Gly Asp Glu Leu Ser Lys Gln Tyr Ala
            20                  25                  30

Tyr Trp Tyr Gln Lys Lys Ser Gly Gln Ala Pro Val Met Val Val Asn
        35                  40                  45

Glu Asp Thr Lys Arg Pro Pro Gly Ile Pro Glu Arg Phe Ser Gly Ser
    50                  55                  60

Ser Ser Gly Thr Thr Ser Thr Leu Thr Ile Ser Gly Val Gln Ala Glu
65                  70                  75                  80

Asp Glu Ala Asp Tyr Tyr Cys Gln Ser Ala Asp Ile Thr Gly Ser Trp
                85                  90                  95

Val Phe Gly Gly Gly Thr Lys Leu Thr Val Leu
                100                 105
```

<210> SEQ ID NO 43
<211> LENGTH: 366
<212> TYPE: DNA
<213> ORGANISM: Homo sapiens
<220> FEATURE:
<221> NAME/KEY: CDS
<222> LOCATION: (1)..(366)
<223> OTHER INFORMATION: NI-204.34A3-VH variable heavy chain (VH)

```
        sequence
<220> FEATURE:
<221> NAME/KEY: V_region
<222> LOCATION: (91)..(105)
<223> OTHER INFORMATION: complementarity determining region (CDR)
      VH-CDR1
<220> FEATURE:
<221> NAME/KEY: V_region
<222> LOCATION: (148)..(204)
<223> OTHER INFORMATION: complementarity determining region (CDR)
      VH-CDR2
<220> FEATURE:
<221> NAME/KEY: V_region
<222> LOCATION: (301)..(333)
<223> OTHER INFORMATION: complementarity determining region (CDR)
      VH-CDR3

<400> SEQUENCE: 43 gag gtg cag ctg gtg gag tct ggg gga ggc ctg gtg aag ccg ggg ggg      48
Glu Val Gln Leu Val Glu Ser Gly Gly Gly Leu Val Lys Pro Gly Gly
1               5                   10                  15 tcc cta aga gtc tcc tgt gac gtc tct ggg cag aga ctt tct aag gct      96
Ser Leu Arg Val Ser Cys Asp Val Ser Gly Gln Arg Leu Ser Lys Ala
            20                  25                  30 tgg atg aac tgg gtc cgc caa act cca acg agg gga ctg gag tgg gtc     144
Trp Met Asn Trp Val Arg Gln Thr Pro Thr Arg Gly Leu Glu Trp Val
        35                  40                  45 ggc cta att aag aga gat gca gat gga ggg acc aca gaa ttc gct gca     192
Gly Leu Ile Lys Arg Asp Ala Asp Gly Gly Thr Thr Glu Phe Ala Ala
    50                  55                  60 ccc gtg gag gga cgg ttc act att tca agg gat gac ata caa aac acc     240
Pro Val Glu Gly Arg Phe Thr Ile Ser Arg Asp Asp Ile Gln Asn Thr
65                  70                  75                  80 atg act ctg cat atg acc agg ctg aga gtc gac gac acg ggc gtg tat     288
Met Thr Leu His Met Thr Arg Leu Arg Val Asp Asp Thr Gly Val Tyr
                85                  90                  95 tac tgt gtc gca gga gat atc ggc tgc att aaa gag aat tgc cgt tgg     336
Tyr Cys Val Ala Gly Asp Ile Gly Cys Ile Lys Glu Asn Cys Arg Trp
            100                 105                 110 ggc gag ggg acc acg gtc acc gtc tcc tcg                             366
Gly Glu Gly Thr Thr Val Thr Val Ser Ser
        115                 120

<210> SEQ ID NO 44
<211> LENGTH: 122
<212> TYPE: PRT
<213> ORGANISM: Homo sapiens

<400> SEQUENCE: 44

Glu Val Gln Leu Val Glu Ser Gly Gly Gly Leu Val Lys Pro Gly Gly
1               5                   10                  15

Ser Leu Arg Val Ser Cys Asp Val Ser Gly Gln Arg Leu Ser Lys Ala
            20                  25                  30

Trp Met Asn Trp Val Arg Gln Thr Pro Thr Arg Gly Leu Glu Trp Val
        35                  40                  45

Gly Leu Ile Lys Arg Asp Ala Asp Gly Gly Thr Thr Glu Phe Ala Ala
    50                  55                  60

Pro Val Glu Gly Arg Phe Thr Ile Ser Arg Asp Asp Ile Gln Asn Thr
65                  70                  75                  80

Met Thr Leu His Met Thr Arg Leu Arg Val Asp Asp Thr Gly Val Tyr
                85                  90                  95

Tyr Cys Val Ala Gly Asp Ile Gly Cys Ile Lys Glu Asn Cys Arg Trp
            100                 105                 110
```

```
<210> SEQ ID NO 45
<211> LENGTH: 324
<212> TYPE: DNA
<213> ORGANISM: Homo sapiens
<220> FEATURE:
<221> NAME/KEY: CDS
<222> LOCATION: (1)..(324)
<223> OTHER INFORMATION: NI-204.34A3-VL variable light chain (VL)
      sequence
<220> FEATURE:
<221> NAME/KEY: V_region
<222> LOCATION: (67)..(99)
<223> OTHER INFORMATION: complementarity determining region (CDR)
      VL-CDR1
<220> FEATURE:
<221> NAME/KEY: V_region
<222> LOCATION: (145)..(165)
<223> OTHER INFORMATION: complementarity determining region (CDR)
      VL-CDR2
<220> FEATURE:
<221> NAME/KEY: V_region
<222> LOCATION: (262)..(294)
<223> OTHER INFORMATION: complementarity determining region (CDR)
      VL-CDR3

<400> SEQUENCE: 45 tcc tat gag ctg act cag cca ccc tcg gtg tca gtg tcc cca gga caa      48
Ser Tyr Glu Leu Thr Gln Pro Pro Ser Val Ser Val Ser Pro Gly Gln
1               5                   10                  15 acg gcc agg atc acc tgc tct gga gac gcg ttg cca aca aaa ttt gct      96
Thr Ala Arg Ile Thr Cys Ser Gly Asp Ala Leu Pro Thr Lys Phe Ala
            20                  25                  30 ttt tgg tat caa caa aaa tca ggc cag gcc cct gtc ttg gtc atc tat     144
Phe Trp Tyr Gln Gln Lys Ser Gly Gln Ala Pro Val Leu Val Ile Tyr
        35                  40                  45 gag gac gac aaa cga cct tcc ggg att cct cag aga ttc tct ggc tcc     192
Glu Asp Asp Lys Arg Pro Ser Gly Ile Pro Gln Arg Phe Ser Gly Ser
 50                  55                  60 agt tct ggg aca acg gcc acc ctg act atc agt ggg gcc cag gag gaa     240
Ser Ser Gly Thr Thr Ala Thr Leu Thr Ile Ser Gly Ala Gln Glu Glu
65                  70                  75                  80 gat gac gct gat tac tat tgt tat tca aaa gac agc act aat gtt gaa     288
Asp Asp Ala Asp Tyr Tyr Cys Tyr Ser Lys Asp Ser Thr Asn Val Glu
                85                  90                  95 cga gtc ttc gga aca ggg acc aag ctc tcc gtc ctg                     324
Arg Val Phe Gly Thr Gly Thr Lys Leu Ser Val Leu
            100                 105

<210> SEQ ID NO 46
<211> LENGTH: 108
<212> TYPE: PRT
<213> ORGANISM: Homo sapiens

<400> SEQUENCE: 46

Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Pro Thr Lys Phe Ala
            20                  25                  30

Phe Trp Tyr Gln Gln Lys Ser Gly Gln Ala Pro Val Leu Val Ile Tyr
        35                  40                  45

Glu Asp Asp Lys Arg Pro Ser Gly Ile Pro Gln Arg Phe Ser Gly Ser
 50                  55                  60
```

```
Gly Glu Gly Thr Thr Val Thr Val Ser Ser
            115                 120
```

```
Ser Ser Gly Thr Thr Ala Thr Leu Thr Ile Ser Gly Ala Gln Glu Glu
65                  70                  75                  80

Asp Asp Ala Asp Tyr Tyr Cys Tyr Ser Lys Asp Ser Thr Asn Val Glu
                85                  90                  95

Arg Val Phe Gly Thr Gly Thr Lys Leu Ser Val Leu
            100                 105

<210> SEQ ID NO 47
<211> LENGTH: 357
<212> TYPE: DNA
<213> ORGANISM: Homo sapiens
<220> FEATURE:
<221> NAME/KEY: CDS
<222> LOCATION: (1)..(357)
<223> OTHER INFORMATION: NI-204.25H3-VH variable heavy chain (VH)
      sequence
<220> FEATURE:
<221> NAME/KEY: V_region
<222> LOCATION: (91)..(105)
<223> OTHER INFORMATION: complementarity determining region (CDR)
      VH-CDR1
<220> FEATURE:
<221> NAME/KEY: V_region
<222> LOCATION: (148)..(195)
<223> OTHER INFORMATION: complementarity determining region (CDR)
      VH-CDR2
<220> FEATURE:
<221> NAME/KEY: V_region
<222> LOCATION: (292)..(324)
<223> OTHER INFORMATION: complementarity determining region (CDR)
      VH-CDR3

<400> SEQUENCE: 47 cag gtg cag ctg cag gag tcg ggc cca gga ctg gtg aag ccc tcg gag      48
Gln Val Gln Leu Gln Glu Ser Gly Pro Gly Leu Val Lys Pro Ser Glu
1               5                   10                  15 acc ctg tcc ctc acc tgc act gtc tct ggt ggc tcc atc agt agt tct      96
Thr Leu Ser Leu Thr Cys Thr Val Ser Gly Gly Ser Ile Ser Ser Ser
            20                  25                  30 tac tgg agt tgg atc cgg cag ccc cca ggg cag gga ctg gag tgg att     144
Tyr Trp Ser Trp Ile Arg Gln Pro Pro Gly Gln Gly Leu Glu Trp Ile
        35                  40                  45 ggg tat atc tat tac agc gga aac acc tac tac aac ccc tcc ctc aag     192
Gly Tyr Ile Tyr Tyr Ser Gly Asn Thr Tyr Tyr Asn Pro Ser Leu Lys
    50                  55                  60 agt cga gtc acc ata tca ata gac acg tcc aag acc cag ttc tcc ctg     240
Ser Arg Val Thr Ile Ser Ile Asp Thr Ser Lys Thr Gln Phe Ser Leu
65                  70                  75                  80 aac ctg acc tct gtg agc gct gcg gac acg gcc gtg tat tac tgt gcg     288
Asn Leu Thr Ser Val Ser Ala Ala Asp Thr Ala Val Tyr Tyr Cys Ala
                85                  90                  95 aga gat ggc ata cca gga gcc ata ggt atg gac gtc tgg ggc caa ggg     336
Arg Asp Gly Ile Pro Gly Ala Ile Gly Met Asp Val Trp Gly Gln Gly
            100                 105                 110 acc acg gtc acc gtc tcc tcg                                         357
Thr Thr Val Thr Val Ser Ser
        115

<210> SEQ ID NO 48
<211> LENGTH: 119
<212> TYPE: PRT
<213> ORGANISM: Homo sapiens

<400> SEQUENCE: 48

Gln Val Gln Leu Gln Glu Ser Gly Pro Gly Leu Val Lys Pro Ser Glu
```

```
     1               5                  10                 15
Thr Leu Ser Leu Thr Cys Thr Val Ser Gly Gly Ser Ile Ser Ser Ser
                20                 25                 30

Tyr Trp Ser Trp Ile Arg Gln Pro Gly Gln Gly Leu Glu Trp Ile
            35                 40                 45

Gly Tyr Ile Tyr Tyr Ser Gly Asn Thr Tyr Tyr Asn Pro Ser Leu Lys
        50                 55                 60

Ser Arg Val Thr Ile Ser Ile Asp Thr Ser Lys Thr Gln Phe Ser Leu
65                  70                 75                 80

Asn Leu Thr Ser Val Ser Ala Ala Asp Thr Ala Val Tyr Tyr Cys Ala
                85                 90                 95

Arg Asp Gly Ile Pro Gly Ala Ile Gly Met Asp Val Trp Gly Gln Gly
                100                105                110

Thr Thr Val Thr Val Ser Ser
        115

<210> SEQ ID NO 49
<211> LENGTH: 330
<212> TYPE: DNA
<213> ORGANISM: Homo sapiens
<220> FEATURE:
<221> NAME/KEY: CDS
<222> LOCATION: (1)..(330)
<223> OTHER INFORMATION: NI-204.25H3-VL variable light chain (VL)
      sequence
<220> FEATURE:
<221> NAME/KEY: V_region
<222> LOCATION: (67)..(105)
<223> OTHER INFORMATION: complementarity determining region (CDR)
      VL-CDR1
<220> FEATURE:
<221> NAME/KEY: V_region
<222> LOCATION: (151)..(171)
<223> OTHER INFORMATION: complementarity determining region (CDR)
      VL-CDR2
<220> FEATURE:
<221> NAME/KEY: V_region
<222> LOCATION: (268)..(300)
<223> OTHER INFORMATION: complementarity determining region (CDR)
      VL-CDR3

<400> SEQUENCE: 49 cag tct gtg ttg acg cag ccg ccc tca gtg tct gcg gcc cca gga cag      48
Gln Ser Val Leu Thr Gln Pro Pro Ser Val Ser Ala Ala Pro Gly Gln
1               5                  10                 15 aag gtc aac atc tcc tgc tct gga agc agc tcc aac att ggg aat aat      96
Lys Val Asn Ile Ser Cys Ser Gly Ser Ser Ser Asn Ile Gly Asn Asn
                20                 25                 30 tat gta tcc tgg tac cag cga ctc cca gga aca gcc ccc aaa ctc ctc     144
Tyr Val Ser Trp Tyr Gln Arg Leu Pro Gly Thr Ala Pro Lys Leu Leu
            35                 40                 45 att tat gac aat aat aaa cga ccc tca ggg att cct gac cga ttc tct     192
Ile Tyr Asp Asn Asn Lys Arg Pro Ser Gly Ile Pro Asp Arg Phe Ser
        50                 55                 60 ggc tcc aag tct ggc acg tca gcc acc ctg ggc atc acc gga ctc cag     240
Gly Ser Lys Ser Gly Thr Ser Ala Thr Leu Gly Ile Thr Gly Leu Gln
65                  70                 75                 80 act ggg gac ggg gcc gat tat tac tgc gca act tgg gat aaa agc ctg     288
Thr Gly Asp Gly Ala Asp Tyr Tyr Cys Ala Thr Trp Asp Lys Ser Leu
                85                 90                 95 att gct gtg gtg ttc ggc gga ggg acc aag ctg acc gtc tta             330
Ile Ala Val Val Phe Gly Gly Gly Thr Lys Leu Thr Val Leu
                100                105                110
```

```
<210> SEQ ID NO 50
<211> LENGTH: 110
<212> TYPE: PRT
<213> ORGANISM: Homo sapiens

<400> SEQUENCE: 50

Gln Ser Val Leu Thr Gln Pro Pro Ser Val Ser Ala Ala Pro Gly Gln
1               5                   10                  15

Lys Val Asn Ile Ser Cys Ser Gly Ser Ser Ser Asn Ile Gly Asn Asn
            20                  25                  30

Tyr Val Ser Trp Tyr Gln Arg Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Gly Ala Asp Tyr Tyr Cys Ala Thr Trp Asp Lys Ser Leu
                85                  90                  95

Ile Ala Val Val Phe Gly Gly Gly Thr Lys Leu Thr Val Leu
            100                 105                 110

<210> SEQ ID NO 51
<211> LENGTH: 11
<212> TYPE: PRT
<213> ORGANISM: Artificial Sequence
<220> FEATURE:
<223> OTHER INFORMATION: Epitope recognized by NI-204.12G7 antibody
<220> FEATURE:
<221> NAME/KEY: PEPTIDE
<222> LOCATION: (1)..(11)
<223> OTHER INFORMATION: Epitope recognized by NI-204.12G7 antibody

<400> SEQUENCE: 51

Gly Gly Pro Lys Asp Glu Glu Arg His Val Gly
1               5                   10

<210> SEQ ID NO 52
<211> LENGTH: 47
<212> TYPE: PRT
<213> ORGANISM: Artificial Sequence
<220> FEATURE:
<223> OTHER INFORMATION: Epitope recognized by NI-204.10A8 antibody
<220> FEATURE:
<221> NAME/KEY: PEPTIDE
<222> LOCATION: (1)..(47)
<223> OTHER INFORMATION: Epitope recognized by NI-204.10A8 antibody

<400> SEQUENCE: 52

Leu Lys Gly Asp Gly Pro Val Gln Gly Ile Ile Asn Phe Glu Gln Lys
1               5                   10                  15

Glu Ser Asn Gly Pro Val Lys Val Trp Gly Ser Ile Lys Gly Leu Thr
            20                  25                  30

Glu Gly Leu His Gly Phe His Val His Glu Phe Gly Asp Asn Thr
        35                  40                  45

<210> SEQ ID NO 53
<211> LENGTH: 7
<212> TYPE: PRT
<213> ORGANISM: Artificial Sequence
<220> FEATURE:
<223> OTHER INFORMATION: Epitope recognized by NI-204.11F11 antibody
<220> FEATURE:
<221> NAME/KEY: PEPTIDE
<222> LOCATION: (1)..(7)
```

```
<223> OTHER INFORMATION: Epitope recognized by NI-204.11F11 antibody

<400> SEQUENCE: 53

Ile Ile Gly Arg Thr Leu Val
1               5

<210> SEQ ID NO 54
<211> LENGTH: 11
<212> TYPE: PRT
<213> ORGANISM: Artificial Sequence
<220> FEATURE:
<223> OTHER INFORMATION: Epitope recognized by NI-204.6H1 antibody
<220> FEATURE:
<221> NAME/KEY: PEPTIDE
<222> LOCATION: (1)..(11)
<223> OTHER INFORMATION: Epitope recognized by NI-204.6H1 antibody

<400> SEQUENCE: 54

Leu Gly Asn Val Thr Ala Asp Lys Asp Gly Val
1               5                   10

<210> SEQ ID NO 55
<211> LENGTH: 15
<212> TYPE: PRT
<213> ORGANISM: Artificial Sequence
<220> FEATURE:
<223> OTHER INFORMATION: Epitope recognized by NI-204.12G3 antibody
<220> FEATURE:
<221> NAME/KEY: PEPTIDE
<222> LOCATION: (1)..(15)
<223> OTHER INFORMATION: Epitope recognized by NI-204.12G3 antibody

<400> SEQUENCE: 55

His Glu Lys Ala Asp Asp Leu Gly Lys Gly Gly Asn Glu Glu Ser
1               5                   10                  15

<210> SEQ ID NO 56
<211> LENGTH: 7
<212> TYPE: PRT
<213> ORGANISM: Artificial Sequence
<220> FEATURE:
<223> OTHER INFORMATION: Epitope recognized by NI-204.7G5 antibody
<220> FEATURE:
<221> NAME/KEY: PEPTIDE
<222> LOCATION: (1)..(7)
<223> OTHER INFORMATION: Epitope recognized by NI-204.7G5 antibody

<400> SEQUENCE: 56

Glu Asp Ser Val Ile Ser Leu
1               5

<210> SEQ ID NO 57
<211> LENGTH: 7
<212> TYPE: PRT
<213> ORGANISM: Artificial Sequence
<220> FEATURE:
<223> OTHER INFORMATION: Epitope recognized by NI-204.7B3 antibody
<220> FEATURE:
<221> NAME/KEY: PEPTIDE
<222> LOCATION: (1)..(7)
<223> OTHER INFORMATION: Epitope recognized by NI-204.7B3 antibody

<400> SEQUENCE: 57

Lys Thr Gly Asn Ala Gly Ser
1               5

<210> SEQ ID NO 58
<211> LENGTH: 11
<212> TYPE: PRT
```

```
<213> ORGANISM: Artificial Sequence
<220> FEATURE:
<223> OTHER INFORMATION: Epitope recognized by NI-204.34A3 antibody
<220> FEATURE:
<221> NAME/KEY: PEPTIDE
<222> LOCATION: (1)..(11)
<223> OTHER INFORMATION: Epitope recognized by NI-204.34A3 antibody

<400> SEQUENCE: 58

Leu Gly Asn Val Thr Ala Asp Lys Asp Gly Val
1               5                   10

<210> SEQ ID NO 59
<211> LENGTH: 7
<212> TYPE: PRT
<213> ORGANISM: Artificial Sequence
<220> FEATURE:
<223> OTHER INFORMATION: Epitope recognized by NI-204.25H3 antibody
<220> FEATURE:
<221> NAME/KEY: PEPTIDE
<222> LOCATION: (1)..(7)
<223> OTHER INFORMATION: Epitope recognized by NI-204.25H3 antibody

<400> SEQUENCE: 59

Gly Gly Pro Lys Asp Glu Glu
1               5

<210> SEQ ID NO 60
<211> LENGTH: 126
<212> TYPE: PRT
<213> ORGANISM: Homo sapiens

<400> SEQUENCE: 60

Glu Val Gln Leu Val Glu Ser Gly Gly Asp Leu Val Arg Pro Gly Gly
1               5                   10                  15

Ser Leu Arg Leu Ser Cys Val Ala Ser Gly Phe Thr Phe Ser Asn Tyr
            20                  25                  30

Trp Met His Trp Val Arg Gln Ala Pro Gly Gln Arg Pro Val Trp Val
        35                  40                  45

Ser Arg Thr Asn Thr Asp Gly Arg Asn Thr Ala Tyr Ala Asp Tyr Ala
    50                  55                  60

Lys Gly Arg Phe Thr Ile Ser Arg Asp Asn Ala Lys Ser Thr Leu Tyr
65                  70                  75                  80

Leu Gln Leu Asn Ser Leu Arg Ala Glu Asp Thr Ala Val Tyr Phe Cys
                85                  90                  95

Ala Arg Leu Arg Arg Asn Val Ala Asp Gln Ile Thr His Asn Tyr Tyr
            100                 105                 110

Met Asp Val Trp Gly Lys Gly Thr Leu Val Thr Val Ser Ser
        115                 120                 125

<210> SEQ ID NO 61
<211> LENGTH: 111
<212> TYPE: PRT
<213> ORGANISM: Homo sapiens

<400> SEQUENCE: 61

Glu Ile Val Leu Thr Gln Ser Pro Gly Ser Leu Ala Val Ser Leu Gly
1               5                   10                  15

Glu Arg Ala Thr Ile Asn Cys Lys Ser Ser Gln Thr Val Leu Tyr Asn
            20                  25                  30

Asn Lys Asn Tyr Leu Ala Trp Tyr Gln Gln Lys Pro Gly Gln Pro Pro
        35                  40                  45
```

```
Lys Leu Leu Ile Ser Trp Ala Ser Ser Arg Glu Ser Gly Val Pro Asp
 50                  55                  60

Arg Phe Ser Gly Ser Gly Ser Gly Thr Asp Phe Thr Leu Thr Ile Ser
 65                  70                  75                  80

Ser Leu Gln Ala Glu Asp Val Ala Val Tyr Tyr Cys Gln His Tyr Tyr
                 85                  90                  95

Gly Thr Pro Val Thr Phe Gly Gly Gly Thr Lys Val Glu Ile Lys
                100                 105                 110

<210> SEQ ID NO 62
<211> LENGTH: 123
<212> TYPE: PRT
<213> ORGANISM: Homo sapiens

<400> SEQUENCE: 62

Gln Val Gln Leu Val Gln Ser Gly Ala Glu Val Lys Lys Pro Gly Ala
 1               5                  10                  15

Ser Val Thr Leu Ser Cys Lys Ala Ser Gly Tyr Thr Phe Thr Ala Tyr
                 20                  25                  30

Tyr Ile His Trp Val Arg Gln Ala Arg Glu Gln Gly Leu Glu Trp Met
             35                  40                  45

Gly Val Ile Asn Pro Ser Thr Gly Thr Thr Phe Tyr Ala Gln Asn Phe
 50                  55                  60

Pro Asp Arg Val Ser Val Thr Arg Asp Thr Ser Thr Ser Thr Val Phe
 65                  70                  75                  80

Met Glu Leu His Asn Leu Lys Ser Glu Asp Thr Ala Val Tyr Tyr Cys
                 85                  90                  95

Ala Arg Ala Ile Ser Glu His Gly Ser Gly Ser Tyr Ser Pro Tyr Tyr
                100                 105                 110

Trp Gly Gln Gly Thr Leu Val Thr Val Ser Ser
            115                 120

<210> SEQ ID NO 63
<211> LENGTH: 107
<212> TYPE: PRT
<213> ORGANISM: Homo sapiens

<400> SEQUENCE: 63

Ser Tyr Glu Leu Thr Gln Pro Pro Ser Val Ser Val Ser Leu Gly Gln
 1               5                  10                  15

Met Ala Ala Ile Thr Cys Ser Gly Glu Ala Leu Pro Lys Lys Tyr Gly
                 20                  25                  30

Tyr Trp Tyr Gln Gln Lys Pro Gly Gln Val Pro Val Leu Leu Ile Tyr
             35                  40                  45

Arg Asp Val Glu Arg Pro Ser Gly Val Pro Asp Arg Phe Ser Gly Ser
 50                  55                  60

Ser Ser Gly Thr Met Val Thr Leu Thr Ile Ser Gly Val Gln Ala Glu
 65                  70                  75                  80

Asp Glu Ala Asp Tyr Tyr Cys Leu Ser Ala Asp Ser Ser Gly Thr Trp
                 85                  90                  95

Val Phe Gly Gly Gly Thr Lys Leu Thr Val Leu
                100                 105

<210> SEQ ID NO 64
<211> LENGTH: 121
<212> TYPE: PRT
<213> ORGANISM: Homo sapiens
```

<400> SEQUENCE: 64

Gln Val Gln Leu Val Gln Ser Gly Ala Glu Val Lys Glu Pro Gly Ser
1               5                   10                  15

Ser Val Arg Val Ser Cys Lys Thr Ser Gly Gly Ser Phe Asn Arg His
            20                  25                  30

Val Ile Thr Trp Val Arg Gln Ala Pro Gly Gln Gly Leu Glu Trp Met
        35                  40                  45

Gly Glu Ile Ile Pro Phe Phe Gly Thr Pro Lys Tyr Ala Pro Lys Phe
    50                  55                  60

Gln Gly Arg Val Thr Ile Ile Ala Asp Ala Ser Thr Ser Thr Phe Phe
65                  70                  75                  80

Leu Asp Val Lys Ser Leu Thr Ser Glu Asp Thr Ala Leu Tyr Phe Cys
                85                  90                  95

Trp Ile Val Val Ser Val Val Gln Arg Arg Glu Asp Phe Trp Gly
            100                 105                 110

Gln Gly Ile Leu Val Thr Val Ser Ser
        115                 120

<210> SEQ ID NO 65
<211> LENGTH: 107
<212> TYPE: PRT
<213> ORGANISM: Homo sapiens

<400> SEQUENCE: 65

Asp Ile Gln Met Thr Gln Ser Pro Ser Ser Leu Ser Ala Ser Val Gly
1               5                   10                  15

Asp Thr Val Thr Ile Thr Cys Arg Ser Ser Gln Asn Ile Ser Asn Tyr
            20                  25                  30

Leu Ser Trp Phe Gln His Lys Pro Gly Lys Ala Pro Arg Ile Leu Val
        35                  40                  45

Tyr Ala Ala Ser Thr Leu Gln Thr Gly Val Pro Ser Arg Phe Ser Gly
    50                  55                  60

Arg Gly Ser Gly Thr Ile Phe Thr Leu Ser Ile Thr Ser Leu Gln Ser
65                  70                  75                  80

Glu Asp Tyr Ala Thr Tyr Tyr Cys Gln Gln Asn Asp Lys Ile Pro Arg
                85                  90                  95

Thr Phe Gly Gln Gly Thr Lys Val Glu Ile Lys
            100                 105

<210> SEQ ID NO 66
<211> LENGTH: 125
<212> TYPE: PRT
<213> ORGANISM: Homo sapiens

<400> SEQUENCE: 66

Glu Val Gln Leu Leu Glu Ser Gly Gly Gly Leu Val Gln Pro Gly Gly
1               5                   10                  15

Ser Leu Arg Leu Ser Cys Ala Val Ser Gly Phe Thr Phe Asp Thr Phe
            20                  25                  30

Ala Met Ser Trp Val Arg Gln Ala Pro Gly Lys Gly Leu Glu Trp Val
        35                  40                  45

Ser Ala Ile Thr Ala Ser Ser Lys Thr Tyr Tyr Ala Asp Ser Val
    50                  55                  60

Lys Gly Arg Phe Thr Ile Ser Arg Asp Asn Ser Arg Asn Thr Val Tyr
65                  70                  75                  80

Leu Arg Leu Ser Ser Leu Arg Ala Asp Asp Thr Ala Val Tyr Phe Cys

```
                    85                  90                  95
Ala Arg Pro Lys Gly Ala His Ser Gly Leu Tyr Ile Glu Ser Ala Phe
            100                 105                 110

Asp Leu Trp Gly Pro Gly Thr Met Val Thr Val Ser Ser
            115                 120                 125

<210> SEQ ID NO 67
<211> LENGTH: 108
<212> TYPE: PRT
<213> ORGANISM: Homo sapiens

<400> SEQUENCE: 67

Ser Tyr Glu Leu Thr Gln Pro Pro Ser Val Ser Val Ser Ala Gly Gln
1               5                   10                  15

Thr Ala Ser Ile Thr Cys Ser Ala Asp Met Leu Gly Asp Thr Tyr Val
            20                  25                  30

Ser Trp Tyr Gln Lys Arg Pro Gly Gln Ser Pro Val Leu Leu Ile Tyr
        35                  40                  45

Gln Asp Ser Lys Arg Pro Ser Glu Ile Pro Glu Arg Phe Ser Gly Ser
    50                  55                  60

Ser Ser Glu Asp Thr Ala Thr Leu Thr Ile Thr Gly Thr Gln Ala Leu
65                  70                  75                  80

Asp Glu Ala Ala Tyr Tyr Cys Gln Val Trp Asp Arg Arg Thr Thr Thr
                85                  90                  95

Tyr Val Phe Gly Pro Gly Thr Glu Val Thr Val Leu
            100                 105

<210> SEQ ID NO 68
<211> LENGTH: 127
<212> TYPE: PRT
<213> ORGANISM: Homo sapiens

<400> SEQUENCE: 68

Glu Val Gln Leu Val Glu Ser Gly Gly Gly Leu Val Lys Pro Gly Gly
1               5                   10                  15

Ser Leu Arg Leu Ser Cys Ala Ala Ser Gly Leu Pro Phe Ser Lys Ala
            20                  25                  30

Trp Met Ser Trp Val Arg Gln Ala Pro Gly Lys Gly Leu Glu Trp Val
        35                  40                  45

Gly Arg Ile Lys Ser Gln Ala Asp Gly Gly Ala Ile Asp Tyr Ala Thr
    50                  55                  60

Ser Val Asn Gly Arg Phe Thr Ile Thr Arg Asp Asp Ser Lys Asn Thr
65                  70                  75                  80

Leu Tyr Leu Gln Met Thr Ser Leu Lys Thr Glu Asp Thr Ala Val Tyr
                85                  90                  95

Tyr Cys Thr Pro Gly Ile Ile Leu Arg Phe Leu Glu Gly Thr Leu Arg
            100                 105                 110

Gly Met Asp Val Trp Gly Gln Gly Thr Thr Val Thr Val Ser Ser
            115                 120                 125

<210> SEQ ID NO 69
<211> LENGTH: 107
<212> TYPE: PRT
<213> ORGANISM: Homo sapiens

<400> SEQUENCE: 69

Glu Ile Val Leu Thr Gln Ser Pro Pro Thr Leu Ser Leu Ser Pro Gly
1               5                   10                  15
```

-continued

Glu Arg Ala Thr Leu Ser Cys Arg Ala Ser Gln Thr Val Ser Lys Tyr
            20                  25                  30

Leu Ala Trp Tyr Gln Gln Lys Pro Gly Gln Ala Pro Arg Leu Leu Val
        35                  40                  45

Tyr Asp Thr Ser Asn Arg Ala Ile Gly Ile Pro Pro Arg Phe Ser Gly
    50                  55                  60

Ser Gly Ser Gly Thr Asp Phe Thr Leu Thr Ile Ser Thr Leu Glu Pro
65                  70                  75                  80

Glu Asp Phe Ala Leu Tyr Tyr Cys Gln Gln Arg Ser Asn Trp Pro Pro
                85                  90                  95

Thr Phe Gly Gln Gly Thr Arg Leu Glu Ile Lys
            100                 105

<210> SEQ ID NO 70
<211> LENGTH: 124
<212> TYPE: PRT
<213> ORGANISM: Homo sapiens

<400> SEQUENCE: 70

Glu Val Gln Leu Leu Glu Ser Gly Gly Gly Leu Ile Arg Pro Gly Gly
1               5                   10                  15

Ser Leu Arg Leu Ser Cys Ala Ala Ser Gly Phe Thr Phe Ser Asn Tyr
            20                  25                  30

Ala Met Gly Trp Val Arg Gln Ala Pro Gly Lys Gly Leu Glu Trp Val
        35                  40                  45

Ser Ala Ile Ser Gly Asn Gly Gly Ser Thr Tyr Tyr Gly Gly Ser Val
    50                  55                  60

Lys Gly Arg Phe Thr Ile Ser Arg Asp Lys Ser Lys Asn Thr Leu Tyr
65                  70                  75                  80

Leu Gln Met Asn Asn Leu Arg Ala Asp Asp Thr Ala Val Tyr Phe Cys
                85                  90                  95

Ala Lys Leu Glu Ala Val Ala Pro Thr Leu Thr Leu Arg Tyr Phe Lys
            100                 105                 110

His Trp Gly Lys Gly Thr Leu Val Thr Val Ser Ser
        115                 120

<210> SEQ ID NO 71
<211> LENGTH: 107
<212> TYPE: PRT
<213> ORGANISM: Homo sapiens

<400> SEQUENCE: 71

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Arg Trp
            20                  25                  30

Leu Ala Trp Tyr Gln Gln Arg Pro Gly Arg Ala Pro Asp Leu Leu Ile
        35                  40                  45

Tyr Asp Ala Ser Asn Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Gly Asp Phe Ala Thr Tyr Tyr Cys Gln Gln Tyr Tyr Ser Tyr Val Tyr
                85                  90                  95

Thr Phe Gly Gln Gly Thr Lys Leu Glu Ile Lys
            100                 105

```
<210> SEQ ID NO 72
<211> LENGTH: 122
<212> TYPE: PRT
<213> ORGANISM: Homo sapiens

<400> SEQUENCE: 72

Gln Val Gln Leu Gln Gln Trp Gly Ala Gly Arg Leu Arg Pro Ser Glu
1               5                   10                  15

Thr Leu Ser Leu Thr Cys Ala Val Tyr Gly Gly Ser Phe Asn Gly Tyr
            20                  25                  30

Ala Arg Thr Trp Ile Arg Gln Pro Pro Gly Lys Gly Leu Glu Trp Ile
        35                  40                  45

Gly Glu Ile Asp His Arg Glu Asn Thr Asn Tyr Asn Pro Ser Leu Lys
    50                  55                  60

Ser Arg Val Thr Met Ser Val Asp Thr Ser Lys Asn Gln Phe Ser Leu
65                  70                  75                  80

Arg Leu Asn Ser Val Thr Ala Ala Asp Thr Ala Val Tyr Phe Cys Ala
                85                  90                  95

Arg Gly Gln Lys Asn Ala Lys Asp Gln His Glu Gly Phe Arg Tyr Trp
            100                 105                 110

Gly Arg Gly Thr Leu Val Thr Val Ser Ser
        115                 120

<210> SEQ ID NO 73
<211> LENGTH: 108
<212> TYPE: PRT
<213> ORGANISM: Homo sapiens

<400> SEQUENCE: 73

Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Pro Lys Gln Phe Ala
            20                  25                  30

Tyr Trp Tyr Gln Gln Lys Ser Gly Gln Ala Pro Lys Leu Val Ile Phe
        35                  40                  45

Lys Asp Thr Glu Arg Pro Ser Gly Ile Pro Glu Arg Phe Ser Ala Ser
    50                  55                  60

Ser Ser Gly Thr Lys Ala Thr Leu Thr Ile Ser Gly Val Gln Ala Glu
65                  70                  75                  80

Asp Glu Ala Asp Tyr Tyr Cys Gln Ser Ala Asp Arg Thr Ala Thr Ser
                85                  90                  95

Trp Val Phe Gly Gly Gly Thr Lys Leu Thr Val Leu
            100                 105

<210> SEQ ID NO 74
<211> LENGTH: 121
<212> TYPE: PRT
<213> ORGANISM: Homo sapiens

<400> SEQUENCE: 74

Gln Val Gln Leu Val Glu Ser Gly Gly Gly Val Val Gln Pro Gly Arg
1               5                   10                  15

Ser Leu Arg Leu Ser Cys Ala Ala Ser Gly Tyr Ile Phe Ser Ser Phe
            20                  25                  30

Gly Met His Trp Val Arg Gln Thr Pro Gly Lys Gly Leu Glu Trp Val
        35                  40                  45
```

```
Ala Leu Ile Trp Tyr Asp Gly Ser Arg Gln Ser Tyr Ala Asp Ser Val
 50                  55                  60

Arg Gly Arg Phe Thr Ile Ser Arg Asp Asn Ser Lys Asn Thr Val Phe
 65                  70                  75                  80

Leu Gln Met Asn Ser Leu Arg Gly Glu Asp Thr Ala Val Tyr His Cys
                 85                  90                  95

Ala Arg Thr Gly Tyr Asp Asp Lys Arg Gly Gly Phe Asp Thr Trp Gly
            100                 105                 110

Gln Gly Thr Met Val Thr Val Ser Ser
            115                 120

<210> SEQ ID NO 75
<211> LENGTH: 107
<212> TYPE: PRT
<213> ORGANISM: Homo sapiens

<400> SEQUENCE: 75

Ser Tyr Glu Leu Thr Gln Pro Pro Ser Val Ser Val Ser Pro Gly Gln
 1               5                  10                  15

Thr Ala Arg Ile Thr Cys Ser Gly Asp Ala Leu Ala Lys Gln Tyr Ser
                20                  25                  30

Tyr Trp Tyr Gln His Lys Pro Gly Gln Ala Pro Val Met Val Met Tyr
            35                  40                  45

Lys Asp Arg Glu Arg Pro Ser Gly Ile Pro Glu Arg Phe Ser Gly Ser
 50                  55                  60

Ser Ser Gly Thr Thr Val Thr Leu Thr Ile Ser Ala Val Gln Ala Glu
 65                  70                  75                  80

Asp Glu Ala Asp Tyr Tyr Cys Gln Ser Thr Gly Thr Asp Ser Pro Tyr
                 85                  90                  95

Ile Phe Gly Thr Gly Thr Lys Val Thr Val Leu
            100                 105

<210> SEQ ID NO 76
<211> LENGTH: 130
<212> TYPE: PRT
<213> ORGANISM: Homo sapiens

<400> SEQUENCE: 76

Gln Val Gln Leu Val Glu Ser Gly Gly Val Val Gln Ala Gly Gly
 1               5                  10                  15

Ser Leu Arg Leu Ser Cys Val Ala Ser Gly Leu Thr Phe Ser Ser Tyr
                20                  25                  30

Gly Met His Trp Val Arg Gln Ala Pro Gly Lys Gly Leu Glu Trp Val
            35                  40                  45

Ala Val Ile Ser Tyr Asp Gly Arg Ser Lys Phe Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Ala Ala Val Tyr Tyr Cys
                 85                  90                  95

Ala Asn Ala Arg Val Arg Asp Ala Cys Ser Gly Thr Arg Cys Asp Lys
            100                 105                 110

Phe Gly Phe Tyr Met Asp Val Trp Gly Lys Gly Thr Thr Val Thr Val
            115                 120                 125

Ser Ser
130
```

<210> SEQ ID NO 77
<211> LENGTH: 108
<212> TYPE: PRT
<213> ORGANISM: Homo sapiens

<400> SEQUENCE: 77

```
Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Pro Lys Lys Tyr Ala
            20                  25                  30

Tyr Trp Tyr Gln Gln Lys Ser Gly Gln Ala Pro Val Leu Val Ile Tyr
        35                  40                  45

Glu Asp Ile Lys Arg Pro Ser Gly Ile Pro Glu Arg Phe Ser Gly Ser
    50                  55                  60

Ser Ser Gly Thr Met Ala Thr Leu Thr Ile Ser Gly Ala Gln Val Glu
65                  70                  75                  80

Asp Glu Gly Asp Tyr Tyr Cys Tyr Ser Ala Asp Arg Ser Gly Asn Arg
                85                  90                  95

Trp Ala Phe Gly Gly Gly Thr Lys Leu Thr Val Leu
            100                 105
```

<210> SEQ ID NO 78
<211> LENGTH: 114
<212> TYPE: PRT
<213> ORGANISM: Homo sapiens

<400> SEQUENCE: 78

```
Glu Val Gln Leu Val Glu Ser Gly Gly Asp Ile Val Gln Ser Gly Gly
1               5                   10                  15

Ser Leu Arg Leu Ser Cys Ala Ala Ser Gly Phe Val Phe Ser Ser Asn
            20                  25                  30

Trp Met His Trp Val Arg Gln Arg Pro Gly Lys Gly Leu Glu Trp Ile
        35                  40                  45

Ser Leu Ile Asn Val Asp Gly Arg Thr Thr Lys Tyr Ala Asp Ser Val
    50                  55                  60

Lys Gly Arg Phe Thr Ile Ser Arg Asp Asn Ala Lys Lys Thr Val Tyr
65                  70                  75                  80

Leu Gln Met Asp Ser Leu Arg Ala Glu Asp Thr Ala Val Tyr Tyr Cys
                85                  90                  95

Val Lys Val Glu Gly Leu Asn Trp Gly Pro Gly Thr Leu Val Thr Val
            100                 105                 110

Ser Ser
```

<210> SEQ ID NO 79
<211> LENGTH: 107
<212> TYPE: PRT
<213> ORGANISM: Homo sapiens

<400> SEQUENCE: 79

```
Ser Glu Tyr Leu Thr Gln Pro Pro Ser Val Ser Val Ser Pro Gly Gln
1               5                   10                  15

Thr Ala Arg Ile Thr Cys Ser Gly Asp Glu Leu Ser Lys Gln Tyr Ala
            20                  25                  30

Tyr Trp Tyr Gln Lys Lys Ser Gly Gln Ala Pro Val Met Val Val Asn
        35                  40                  45

Glu Asp Thr Lys Arg Pro Pro Gly Ile Pro Glu Arg Phe Ser Gly Ser
    50                  55                  60
```

```
Ser Ser Gly Thr Thr Ser Thr Leu Thr Ile Ser Gly Val Gln Ala Glu
 65                  70                  75                  80

Asp Glu Ala Asp Tyr Tyr Cys Gln Ser Ala Asp Ile Thr Gly Ser Trp
                 85                  90                  95

Val Phe Gly Gly Gly Thr Lys Leu Thr Val Leu
            100                 105
```

<210> SEQ ID NO 80
<211> LENGTH: 122
<212> TYPE: PRT
<213> ORGANISM: Homo sapiens

<400> SEQUENCE: 80

```
Glu Val Gln Leu Val Glu Ser Gly Gly Leu Val Lys Pro Gly Gly
 1               5                  10                  15

Ser Leu Arg Val Ser Cys Asp Val Ser Gly Gln Arg Leu Ser Lys Ala
                 20                  25                  30

Trp Met Asn Trp Val Arg Gln Thr Pro Thr Arg Gly Leu Glu Trp Val
                 35                  40                  45

Gly Leu Ile Lys Arg Asp Ala Asp Gly Gly Thr Thr Glu Phe Ala Ala
             50                  55                  60

Pro Val Glu Gly Arg Phe Thr Ile Ser Arg Asp Asp Ile Gln Asn Thr
 65                  70                  75                  80

Met Thr Leu His Met Thr Arg Leu Arg Val Asp Asp Thr Gly Val Tyr
                 85                  90                  95

Tyr Cys Val Ala Gly Asp Ile Gly Cys Ile Lys Glu Asn Cys Arg Trp
                100                 105                 110

Gly Glu Gly Thr Thr Val Thr Val Ser Ser
            115                 120
```

<210> SEQ ID NO 81
<211> LENGTH: 108
<212> TYPE: PRT
<213> ORGANISM: Homo sapiens

<400> SEQUENCE: 81

```
Ser Tyr Glu Leu Thr Gln Pro Pro Ser Val Ser Val Ser Pro Gly Gln
 1               5                  10                  15

Thr Ala Arg Ile Thr Cys Ser Gly Asp Ala Leu Pro Thr Lys Phe Ala
                 20                  25                  30

Phe Trp Tyr Gln Gln Lys Ser Gly Gln Ala Pro Val Leu Val Ile Tyr
                 35                  40                  45

Glu Asp Asp Lys Arg Pro Ser Gly Ile Pro Gln Arg Phe Ser Gly Ser
             50                  55                  60

Ser Ser Gly Thr Thr Ala Thr Leu Thr Ile Ser Gly Ala Gln Glu Glu
 65                  70                  75                  80

Asp Asp Ala Asp Tyr Tyr Cys Tyr Ser Lys Asp Ser Thr Asn Val Glu
                 85                  90                  95

Arg Val Phe Gly Thr Gly Thr Lys Leu Ser Val Leu
                100                 105
```

<210> SEQ ID NO 82
<211> LENGTH: 119
<212> TYPE: PRT
<213> ORGANISM: Homo sapiens

<400> SEQUENCE: 82

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Tyr Trp Ser Trp Ile Arg Gln Pro Pro Gly Gln Gly Leu Glu Trp Ile
        35                  40                  45

Gly Tyr Ile Tyr Tyr Ser Gly Asn Thr Tyr Tyr Asn Pro Ser Leu Lys
    50                  55                  60

Ser Arg Val Thr Ile Ser Ile Asp Thr Ser Lys Thr Gln Phe Ser Leu
65                  70                  75                  80

Asn Leu Thr Ser Val Ser Ala Ala Asp Thr Ala Val Tyr Tyr Cys Ala
            85                  90                  95

Arg Asp Gly Ile Pro Gly Ala Ile Gly Met Asp Val Trp Gly Gln Gly
            100                 105                 110

Thr Thr Val Thr Val Ser Ser
        115

<210> SEQ ID NO 83
<211> LENGTH: 110
<212> TYPE: PRT
<213> ORGANISM: Homo sapiens

<400> SEQUENCE: 83

Gln Ser Val Leu Thr Gln Pro Pro Ser Val Ser Ala Ala Pro Gly Gln
1               5                   10                  15

Lys Val Asn Ile Ser Cys Ser Gly Ser Ser Ser Asn Ile Gly Asn Asn
            20                  25                  30

Tyr Val Ser Trp Tyr Gln Arg Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Gly Ala Asp Tyr Tyr Cys Ala Thr Trp Asp Lys Ser Leu
            85                  90                  95

Ile Ala Val Val Phe Gly Gly Gly Thr Lys Leu Thr Val Leu
            100                 105                 110
```